(12) United States Patent
Baum et al.

(10) Patent No.: US 7,175,849 B2
(45) Date of Patent: Feb. 13, 2007

(54) NECTIN POLYPEPTIDES

(75) Inventors: Peter R Baum, Seattle, WA (US); William C Fanslow, III, Normandy Park, WA (US); Timothy E Lofton, Marysville, WA (US); Eric A Sorensen, Lynnwood, WA (US); Adel Youakim, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 09/972,268

(22) Filed: Oct. 5, 2001

(65) Prior Publication Data

US 2003/0044893 A1 Mar. 6, 2003

Related U.S. Application Data

(60) Provisional application No. 60/238,557, filed on Oct. 5, 2000.

(51) Int. Cl.
*A61K 39/00* (2006.01)
*A61K 38/04* (2006.01)
*C07K 14/00* (2006.01)

(52) U.S. Cl. .................. 424/185.1; 530/324; 530/350

(58) Field of Classification Search ................ 530/350, 530/300, 324; 424/185.1
See application file for complete search history.

(56) References Cited

U.S. PATENT DOCUMENTS 6,362,371 B1 * 3/2002 Moran et al.
6,472,520 B2 * 10/2002 Fisher
2003/0008334 A1 1/2003 Takai et al.

FOREIGN PATENT DOCUMENTS

EP 1 179 592 A1 2/2002
WO WO 01/66736 A1 9/2001

OTHER PUBLICATIONS

Ottenwelder et al, GenBank Accession No. T08732, 1999.*
Attwood TK. Genomics. The Babel of bioinformatics. Science. 290(5491):471-473, 2000.*
Skolnick et al. From genes to protein structure and function: novel applications of computational approaches in the genomic era. Trends Biotechnol. 18(1):34-9, 2000.*
Metzler et al. Solution structure of human CTLA-4 and delineation of a CD80/CD86 binding site conserved in CD28. Nat Struc Biol. 4(7):527-531, 1997.*
Martinez and Spear. Structural features of nectin-2 (HveB) required for herpes simplex virus entry. J Virol. 75(22):11185-11195, 2001.*
Reymond N, et al "Human nectin3PRR3: a novel member of the PRV/PRR/nectin family that interacts with afadin," *Gene* 255(2):347-355, Sep. 2000.

Sakisaka T et al. "Requirement of Interaction of Nectin-1α/HveC with Afadin for Efficient Cell-Cell Spread of Herpes Simplex Virus Type I," *J. Virology* 75(10):4734-4743. May 2001.
Bouchard MJ et al. "Defects in Nuclear and Cytoskeletal Morphology and Mitochondrial Localization in Spermatozoa of Mice Lacking Nectin-2, a Component of Cell-Cell Adherens Junctions," *Molecular and Cellular Biology* 20(8):2865-2873, Apr. 2000.
Takahashi K et al. "Nectin/PRR: A An Immunoglobulin-like Cell Adhesion Molecule Recruited to Cadherin-based Adherens Junctions through Interaction with Afadin, a PDZ Domain-containing Protein," *J. Cell Biology* 145:539-549, 1999.
Cocchi F et al. "Cell-to-Cell Spread of Wild-Type Herpes Simplex Virus Type 1, but Not of Syncytial Strains, Is Mediated by the Immunoglobulin-Like Receptors That Mediate Virion Entry, Nectin 1 (PRR1/HveC/HigR) and Nectin2 (PRR2/HveB)," *J. Virology* 74(8):3909-3917, Apr. 2000.
Lopez M et al. "Novel, Soluble Isoform of the Herpes Simplex Virus (HSV) Receptor Nectin1 (or PRR1-HIgR-HveC) Modulates Positively and Negatively Susceptibility to HSV Infection," *J. Virology* 75(12):5684-5691, Jun. 2001.
Lopez M et al. "Nectin2α (PRR2α or HveB) and Nectin2δ Are Low-Efficiency Mediators for Entry of Herpes Simplex Virus Mutants Carrying the Leu25Pro Substitution in Glycoprotein D," *J. Virology* 74(3):1267-1274, Feb. 2000.
Menotti L. et al. "Comparison of Murine and Human Nectin1 Binding to Herpes Simplex Virus Glycoprotein D (gD) Reveals a Weak Interaction of Murine Nectin1 to gD and a gD-Dependent Pathway of Entry," *Virology* 282:256-266, 2001.
Reymond N. et al. "Nectin4:/PRR4: A new afadin-associated member of the nectin family that trans-interacts with nectin1/PRR1 through V domain interaction," *American Soc for Biochem and Molecular Bio, JBC Papers in Press*. Pub Sep. 5, 2001, #M103810200, 2001.
Satoh-Horikawa K et al. Nectin-3, a New Member of Immunoglobulin-like Cell Adhesion Molecules That Shows Homophilic and Heterophilic Cell-Cell Adhesion Activities, *J. Biological Chemistry* 275(14):10291-10299, Apr. 2000.
Lopez M et al. "Complementary DNA characterization and chromsomal localization of a human gene related to the poliovirus receptor-encoding gene," *Gene* 155:261-265, 1995.
Lopez M et al. "The Human Poliovirus Receptor Related 2 Protein Is a New Hematopoietic/Endothelial Homophilic Adhesion Molecule," *Blood* 92(12)4602-4611, Dec. 1998.
Menotti L et al. "The murine homolog of human Nectin1δ serves as a species nonspecific mediator for entry of human and animal αherpesviruses in a pathway independent of a detectable binding to gD," *PNAS* 97(9):4867-4872, Apr. 2000.

(Continued)

*Primary Examiner*—Maher M. Haddad
(74) *Attorney, Agent, or Firm*—Joseph R. Baker; Suzanne A. Sprunger; Susan E. Lingenfelter

(57) ABSTRACT

This invention relates to nectin polypeptides and polynucleotides, to methods of making such polypeptides and polynucleotides, and to methods of using such polypeptides and polynucleotides to modulate cell adhesion, cell migration, and angiogenesis, to treat conditions related to cell adhesion including endothelial and epithelial cell proliferation, migration, and barrier function, and to identify agents that alter nectin polypeptide activities.

32 Claims, 4 Drawing Sheets

OTHER PUBLICATIONS

Friestadt MS and Eberle KE, "Physical Association Between CD155 and CD44 in Human Monocytes," *Molecular Immunology* 34(18):1247-1257, 1997.

Kikyo M et al., "Cell-cell adhesion-mediated tyrosine phosphorylation of nectin-2δ, an immunoglobulin-like cell adhesion molecule at adherens junctions," *Oncogene* 19:4022-4028, 2000.

Lopez M et al., "Complementary DNA characterization and chromosomal localization of a human gene related to the poliovirus receptor-encoding gene," *Gene* 155:261-265, 1995.

Miyahara M et al., "Interaction of Nectin with Afadin Is Necessary for Its Clustering at Cell-Cell Contact Sites but Not for Its *cis* Dimerization or *trans* Interaction," *J. Biological Chemistry* 275(1):613-618, Jan. 2000.

Takahashi K et al., "Nectin/PRR: An Immunoglobulin-like Cell Adhesion Molecule Recruited to Cadherin-based Adherens Junctions through Interaction with Afadin, a PDZ Domain-containing Protein," *J Cell Biology* 14(3):539-549, May 1999.

Satoh-Horikawa K et al., GenBank Accession No. NP_067471, Mar. 2001.

NCBI Annotation Project, GenBank Accession No. XP_011079, Aug. 2001.

Strausberg R. GenBank Accession No. AAH01336, Jul. 2001.

Tao Q et al., GenBank Accession No. AAF82399, Jul. 2000.

Strausberg R. GenBank Accession No. AAH10423, Jul. 2001.

Isogai T et al., GenBank Accession No. BAB55344, May 2001.

Carninci P and Hayashizaki Y, GenBank Accession No. BAB23592, Jul. 2001.

Satoh-Horikawa K et al., GenBank Accession No. NP_067472, Mar. 2001.

Satoh-Horikawa K et al., GenBank Accession No. NP_067470, Feb. 2001.

Satoh-Horikawa K et al., GenBank Accession No. AF195833, Apr. 2000.

Reymond N. et al., EMBL Database Accession No. Q9NQS3, Oct. 1, 2000.

Satoh-Horikawa K. et al., EMBL Database Accession No. Q9JLB7, Oct. 1, 2000.

Cocchi F et al., "The V domain of herpesvirus Ig-like receptor (HIgR) contains a major functional region in herpes simplex virus-1 entry into cells and interacts physically with the viral glycoprotein D," *Proc. Natl. Acad. Sci. USA*, 95:15700-15705; 1998.

*EMBL* Database accession No. AF195835, "*Mus musculus* cell adhesion molecule nectin-3 gamma mRNA, complete cds.," Apr. 14, 2000.

*EMBL* Database accession No. AF282874, "*Homo sapiens* nectin 3 mRNA, complete cds.," Aug. 7, 2000.

Lopez M et al., "Nectin2α (PRR2α or HveB) and Nectin2δ Are Low-Efficiency Mediators for Entry of Herpes Simplex Virus Mutants Carrying the Leu25Pro Substitution in Glycoprotein D," *J. Virol.* 74:1267-1274; 2000.

Lopez M et al., "Novel, Soluble Isoform of the Herpes Simplex Virus (HSV) Receptor Nectin1 (or PRR1-HIgR-HveC) Modulates Positively and Negatively Susceptibility to HSV Infection," *J. Virol.* 75:5684-5691, 2001.

*UniProt* Database accession No. Q9JLB8, "Cell adhesion molecule nectin-3 beta," Oct. 1, 2000.

\* cited by examiner

NECTIN POLYPEPTIDES

CROSS REFERENCE TO RELATED APPLICATIONS

This application claims priority under 35 U.S.C. §119 to U.S. Provisional Application Ser. No. 60/238,557, filed Oct. 5, 2000, the disclosure of which is incorporated herein by references.

FIELD OF THE INVENTION

This invention relates to nectin polypeptides, polynucleotides encoding such polypeptides, methods of making nectin polypeptides, and methods of using nectin polypeptides in the modulation of cell adhesion and migration activities, and to methods of making such polypeptides.

BACKGROUND

Nectin proteins are a related group of immunoglobulin-like cell adhesion molecules involved in cell-cell interactions. Nectin proteins are expressed in a wide variety of cell types including epithelial and endothelial cells and hematopoietic cells. The nectin proteins include nectin-1 and nectin-2, which are also referred to as poliovirus receptor related (PRR) proteins 1 and 2 and Herpesvirus entry (Hve) proteins C and B, respectively. Multiple forms of nectin-1 and nectin-2 resulting from alternative splicing have been identified. Another polypeptide related by significant sequence similarity to these nectin polypeptides is the poliovirus receptor (PVR), also called CD155 protein.

In order to develop more effective treatments for conditions and diseases involving cell-cell interactions or the binding of herpesviruses to cells, information is needed about the biological roles and activities of nectin polypeptides, and about the characteristics of previously unidentified members of the nectin polypeptide family in particular.

SUMMARY OF THE INVENTION

The invention provides nectin-3 and nectin-4 polypeptides, polynucleotides, methods of making and use thereof.

Accordingly, the invention provides a substantially purified polypeptide comprising a sequence that is at least 80% identical to a sequence selected from the group consisting of SEQ ID NO:2, 4, 6, 8, 10, 12, 24, 31, 34, 37–39, and fragments thereof, wherein the polypeptide binds to nectin-1.

The invention further provides a substantially purified soluble polypeptide comprising a sequence that is at least 80% identical to the extracellular domain of SEQ ID NO:2, 4, 6, 8, 10, 12, 24, 31, 34, 37–39 and fragments thereof, wherein the polypeptide binds to nectin-1 and/or inhibits endothelial cell migration.

The invention also provides soluble polypeptide according to above which further comprise an Fc polypeptide domain, a leucine zipper domain and/or a peptide linker domain. In one embodiment, the fusion construct comprises a sequence $Z_1$-X-$Z_2$, wherein $Z_1$ and $Z_2$ are each individually a soluble polypeptide comprising a sequence selected from the group consisting of: from about $x_1$ to 404 of SEQ ID NO:4 or 6 wherein $x_1$ is an amino acid between 1 and 39, from about amino acid 58 to 152 of SEQ ID NO:4 or 6, from about amino acid 58 to 250 of SEQ ID NO:4 or 6, from about amino acid 58 to 342 of SEQ ID NO:4 or 6, from about amino acid 58 to 404 of SEQ ID NO:4 or 6, from about amino acid 74 to 152 of SEQ ID NO:4 or 6, from about amino acid 74 to 250 of SEQ ID NO:4 or 6, from about amino acid 74 to 342 of SEQ ID NO:4 or 6, from about amino acid 74 to 404 of SEQ ID NO:4 or 6, from about amino acid 189 to 250 of SEQ ID NO:4 or 6, from about amino acid 189 to 342 of SEQ ID NO:4 or 6, from about amino acid 189 to 404 of SEQ ID NO:4 or 6, from about amino acid 287 to 342 of SEQ ID NO:4 or 6, from about amino acid 287 to 404 of SEQ ID NO:4 or 6, from about $x_1$ to 365 of SEQ ID NO:10 or 12 wherein $x_1$ is an amino acid between 1 and 39, from about amino acid 58 to 152 of SEQ ID NO:10 or 12, from about amino acid 58 to 250 of SEQ ID NO:10 or 12, from about amino acid 58 to 342 of SEQ ID NO:10 or 12, from about amino acid 58 to 365 of SEQ ID NO:10 or 12, from about amino acid 74 to 152 of SEQ ID NO:10 or 12, from about amino acid 74 to 250 of SEQ ID NO:10 or 12, from about amino acid 74 to 342 of SEQ ID NO:10 or 12, from about amino acid 74 to 365 of SEQ ID NO:10 or 12, from about amino acid 189 to 250 of SEQ ID NO:10 or 12, from about amino acid 189 to 342 of SEQ ID NO:10 or 12, from about amino acid 189 to 365 of SEQ ID NO:10 or 12, from about amino acid 287 to 342 of SEQ ID NO:10 or 12, from about amino acid 287 to 365 of SEQ ID NO: 10 or 12, from about $x_2$ to 349 of SEQ ID NO:24 or 34 where $x_2$ is an amino acid between 1 and 16, from about amino acid 27 to 350 of SEQ ID NO:36, from about amino acid 44 to 362 of SEQ ID NO:37, from about amino acid 39 to 242 of SEQ ID NO:38, from about amino acid 44 to 363 of SEQ ID NO:39; and fragments of any of the forgoing sequences that provides a polypeptide that binds to nectin-1 and/or inhibits endothelial cell migration, and wherein X is a peptide linker.

The invention further provides composition comprising a polypeptide of the invention and a pharmaceutically acceptable carrier.

The invention yet further provides an isolated polynucleotide encoding a polypeptide of the invention. In one embodiment, the polynucleotide comprises a sequence selected from SEQ ID NO:1, 3, 5, 7, 9, 11, 30, 32, 33, or 35; a polynucleotide comprising a sequence selected from the group consisting of: from about nucleotide $x_1$ to 1212 of SEQ ID NO:3 or 5 wherein $x_1$ is a nucleotide between 1 and 115, from about nucleotide 172 to 456 of SEQ ID NO:3 or 5, from about nucleotide 172 to 750 of SEQ ID NO:3 or 5, from about nucleotide 172 to 1026 of SEQ ID NO:3 or 5, from about nucleotide 172 to 1212 of SEQ ID NO:3 or 5, from about nucleotide 222 to 456 of SEQ ID NO:3 or 5, from about nucleotide 222 to 750 of SEQ ID NO:3 or 5, from about nucleotide 222 to 1026 of SEQ ID NO:3 or 5, from about nucleotide 222 to 1212 of SEQ ID NO:3 or 5, from about nucleotide 567 to 750 of SEQ ID NO:3 or 5, from about nucleotide 567 to 1026 of SEQ ID NO:3 or 5, from about nucleotide 567 to 1212 of SEQ ID NO:3 or 5, from about nucleotide 861 to 1026 of SEQ ID NO:3 or 5, and from about nucleotide 861 to 1212 of SEQ ID NO:3 or 5; a polynucleotide comprising a sequence selected from the group consisting of: from about nucleotide $x_1$ to 1098 of SEQ ID NO:9 or 11 wherein $x_1$ is a nucleotide between 1 and 115, from about nucleotide 172 to 456 of SEQ ID NO:9 or 11, from about nucleotide 172 to 750 of SEQ ID NO:9 or 11, from about nucleotide 172 to 1026 of SEQ ID NO:9 or 11, from about nucleotide 172 to 1098 of SEQ ID NO:9 or 11, from about nucleotide 222 to 456 of SEQ ID NO:9 or 11, from about nucleotide 222 to 750 of SEQ ID NO:9 or 11, from about nucleotide 222 to 1026 of SEQ ID NO:9 or 11, from about nucleotide 222 to 1098 of SEQ ID NO:9 or 11, from about nucleotide 567 to 750 of SEQ ID NO:9 or 11, from about nucleotide 567 to 1026 of SEQ ID NO:9 or 11, from about nucleotide 567 to 1098 of SEQ ID NO:9 or 11, from about nucleotide 861 to 1026 of SEQ ID NO:9 or 11, and from about nucleotide 861 to 1098 of SEQ ID NO:9 or 11; a polynucleotide comprising a sequence from about nucleotide 79 to 1047 of SEQ ID NO:32 or 33; and a polynucleotide that hybridizes under moderate to highly stringent conditions to a polynucleotide comprising the sequence of (a), (b), (c), or (d) and encoding a polypeptide that binds to nectin-1.

Expression vectors and host cells comprising a polynucleotide of the invention is also provided by the present invention.

The invention further provides a method for producing a polypeptide, comprising culturing a host cell comprising a polynucleotide of the invention under conditions such that the polypeptide is expressed.

The invention provides a polypeptide produced by culturing a host cell of the invention comprising a polynucleotide of the invention under conditions to promote expression of the polypeptide.

The invention additionally provides a substantially purified antibody that specifically binds to a nectin polypeptide of the invention.

Also provided by the invention is a method of designing an inhibitor or binding agent of a nectin polypeptide of the invention, comprising determining the three-dimensional structure of the polypeptide, analyzing the three-dimensional structure for binding sites of substrates or ligands, designing a molecule that is predicted to interact with the polypeptide, and determining the inhibitory or binding activity of the molecule.

The invention further provides a method for identifying an agent that modulates an activity of a nectin polypeptide of the invention. The method includes contacting the agent with a polypeptide of the invention under conditions such that the agent and polypeptide interact and determining an activity of the polypeptide in the presence of the agent compared to a control, wherein a change in activity is indicative of an agent that modulates the polypeptide's activity. The agent can be an antibody, a small molecule, a peptide, or a peptidomimetic.

In yet a further aspect, the invention provides a method of modulating an activity of a nectin-1 polypeptide, comprising contacting the nectin-1 polypeptide with a nectin-3 or nectin-4 polypeptide or soluble domain thereof.

In addition, the invnetion provides a method of identifying an agent that modulates binding between a nectin-1 polypeptide and a nectin-3 and/or -4 polypeptide of the invention, comprising contacting a sample containing the nectin-1 polypeptide with the agent and measuring the interaction of the nectin-1 polypeptide with the polypeptide compared to a control sample, wherein a change in the binding between the nectin-1 polypeptide and the polypeptide compared to the control is indicative of an agent that modulates binding.

Also provided is a method of modulating cellular proliferation or migration, comprising contacting a cell with an agent that modulates nectin-1 activity or expression under conditions such that the cell and the agent interact.

The invention further provides a method of inhibiting angiogenesis in a mammal in need of such treatment, comprising administering to the mammal an inhibition-effective amount of a nectin-3 and/or -4 polypeptide or soluble polypeptide thereof.

The invention provides a method for treating an endothelial proliferation, migration, angiogenic condition or viral infection comprising contacting a tissue or subject in need of such treatment with a nectin-3 and/or nectin-4 polypeptide or soluble polypeptides thereof.

DETAILED DESCRIPTION OF THE INVENTION

Figure 1:
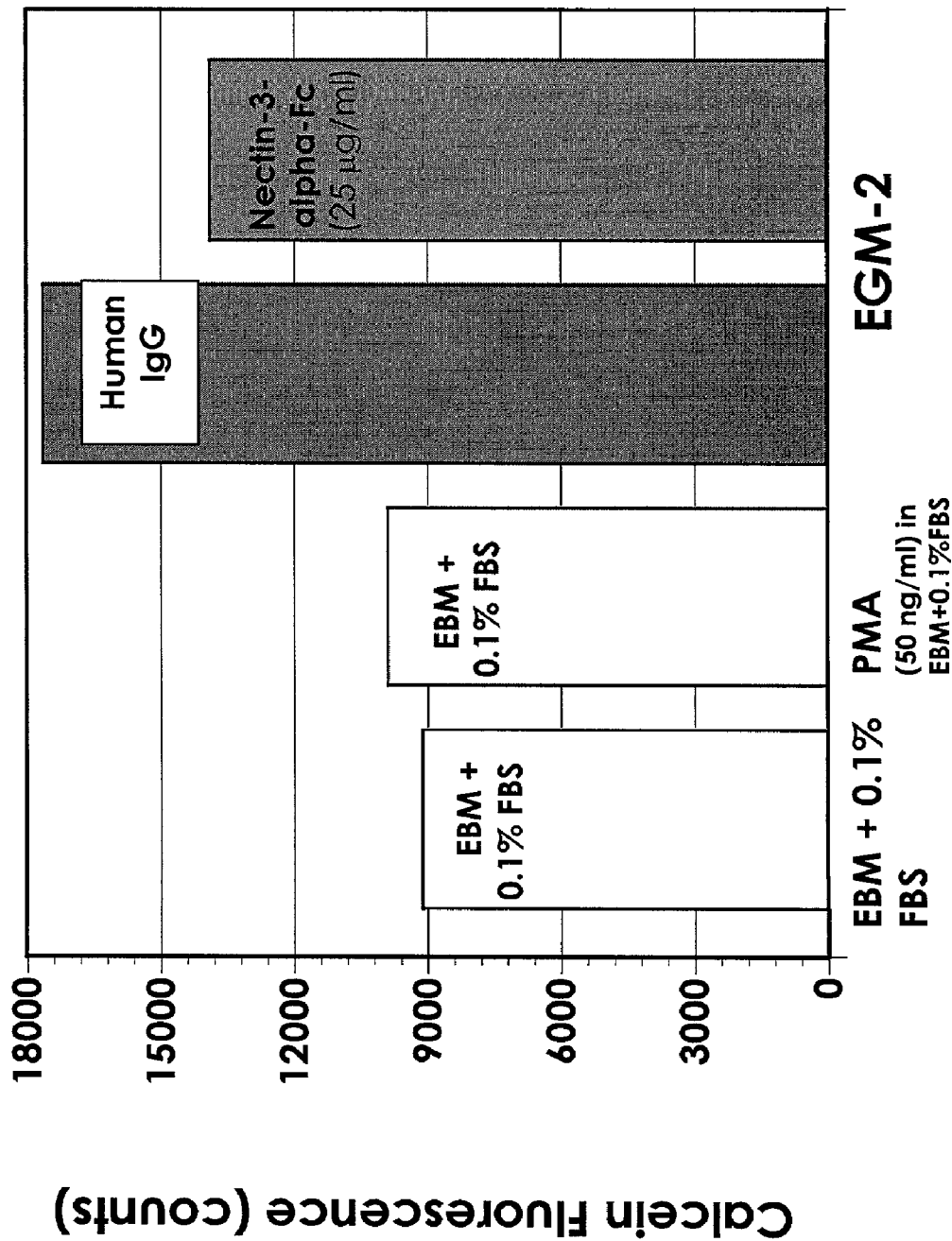
FIG. 1 shows that a soluble form of nectin-3, nectin-3α-Fc, inhibits endothelial cell migration.

The present invention provides nectin-3α, nectin-3β, nectin-3γ, and nectin-4 polypeptides, members of the family of nectin polypeptides, polynucleotides encoding such polypeptides and methods of making and using such polypeptides and agonists and antagonists thereof.

A common structural feature of nectin and nectin-related polypeptides is a set of three extracellular immunoglobulin (Ig) domains. The N-terminal Ig domain of nectin-1 and nectin-2 is a V-type Ig domain, while the two C-terminal Ig domains are C2-type domains. The N-terminal Ig domain of this family of molecules has been shown to be required for binding in trans to other nectin molecules on adjacent cells in a hetero- or homotypic fashion. The third Ig domain appears to be involved in a cis homodimerization function. The extracellular domain of nectin-1 and nectin-2 is involved in binding to viruses such as herpes simplex virus and is believed to associate with cadherin molecules in adherens junctions (AJs). It has also been shown that CD155 (nectin-5), a nectin-related poliovirus receptor, is in close proximity on monocytes to CD44, a protein involved in cell-cell and cell-matrix interactions.

Another common feature of nectin polypeptides is an intracellular C-terminus comprising a consensus amino acid sequence that has been shown to bind the PDZ domain of afadin proteins present at AJs. Variations in this C-terminal sequence are believed to affect the type of PDZ domain to which the intracellular domain binds. Variants of nectin polypeptides that do not have this sequence or a related sequence are predicted to lack a PDZ-domain-binding function.

The functions of nectin polypeptides include a role in the formation and maintenance of cadherin-based AJs. AJs are adhesive contact points between cells that play an important role in tissue organization during development and maintenance of tissue structures in adults. In addition to basic adhesive functions, AJs provide a variety of more specialized functions in different cell types, including linking cytoskeletal force generation to sites on the cell surface and the mediation of intercellular signaling. For example, in epithelial sheets and endothelium, AJs form a circumferential belt around the cells and separate their apical and basal surfaces; tight junction formation between epithelial cells is also related to the presence of E-cadherin, a component of AJs. AJs and tight junctions are needed to create the functional barrier between the two surfaces of an epithelial sheet or the endothelium so that differing physiological environments can be maintained on each side of the barrier, and the movement of cells and molecules across this barrier can be regulated. In cardiac myocytes, the AJs (also called contractile disks) anchor contractile filaments to the plasma membrane. In the nervous system, AJs hold synaptic cell surfaces together to form the synaptic junction, and are present between layers of a myelin cell to shape the myelin cell membrane into the paranodal loops of the myelin sheath that encloses the axon.

Polynucleotides that encode nectin-3α, β, and γ polypeptides are shown in SEQ ID Nos:5, 11, and 30, respectively. Polynucleotides that encode nectin-4 are shown in SEQ ID Nos:32 and 33. The corresponding amino acid sequences of nectin-3α, β, and γ are SEQ ID Nos:6, 12, and 31, respectively. The corresponding amino acid sequences of nectin-4 are SEQ ID Nos:24 and 34, respectively. The polypeptides comprising SEQ ID Nos:2, 4, 6, 8, 10, 12, 24, 31, and 34, are encoded by the polynucleotides comprising SEQ ID Nos: 1, 3, 5, 7, 9, 11, 32, 30, and 33.

Nectin-3α, β, and γ are related to each other as the products of alternative splicing: the N-terminal 356 amino acids of the full-length amino acid sequences of these polypeptides are identical. The signal sequence for nectin-3α, β, or γ is located and begins between about amino acid 1 to 39 and extends to about amino acid 57 (e.g., from $x_1$ to about 57, wherein $x_1$ is an amino acid between 1 and 39) of SEQ ID Nos: 6, 12, and 31, with the mature polypeptide formed by cleavage following the signal sequence. Typically the signal sequence is cleaved following amino acid 50, 55, or 57, depending upon factors such as the host cell used. Accordingly, the mature polypeptide comprises an amino acid sequence starting at an amino acid between, and including, residue 51 and 58 (e.g., at amino acid 51, 52, 53, 54, 55, 56, 57, or 58; ) of SEQ ID Nos: 6, 12, and 31. Three extracellular Ig domains, common to members of the nectin polypeptide family, are located at about amino acids 74 through about 152, about amino acids 189 through about 250, and about amino acids 287 through about 342 for nectin-3α (SEQ ID NO:6), β (SEQ ID NO:12), and γ (SEQ ID NO:31). The portion of the extracellular domain common to the nectin-3α, β, and γ also contains six predicted sites for N-linked glycosylation, at the asparagine ("Asn" or "N") residues located at positions 73, 83, 125, 186, 222, and 331 of SEQ ID NO:6, 12, and 31. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets can prevent attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in polypeptides include those described in U.S. Pat. No. 5,071,972 and EP 276,846. The transmembrane domain of nectin-3α is predicted to include the amino acids from about amino acid 405 through amino acid 424 of SEQ ID NO:6; therefore, the extracellular domain of nectin-3α (including the signal sequence) extends from an amino acid between 1 and 39 through approximately amino acid 404 of SEQ ID NO:6 (e.g., from about $x_1$ to 404, wherein $x_1$ is an amino acid between 1 and 39). The transmembrane domain of nectin-3β and γ is predicted to include the amino acids approximately from amino acid 366 through amino acid 385 of SEQ ID NO:12 or 31, respectively; therefore, the extracellular domain of nectin-3β and γ (including the signal sequence) extends from an amino acid between 1 and 39 through approximately amino acid 365 of SEQ ID NO:12 or 31(e.g., from about $x_1$ to 365, wherein $x_1$ is an amino acid between 1 and 39). The nectin-3α and β forms have intracellular C-terminal domains of similar size but different overall amino acid sequence (approximately amino acids 425 through 549 of SEQ ID NO:6 and approximately amino acids 386 through 510 of SEQ ID NO:12, respectively), but the very C-terminal amino acid sequences of these two nectins are similar: ISRREWYV (amino acids 542 through 549 of SEQ ID NO:6) and IDPREHYV (amino acids 503 through 510 of SEQ ID NO:12). Nectin-3γ has a intracellular domain from about 386 to 437 of SEQ ID NO:31. The C-termini of nectin proteins bind PDZ-domain containing proteins, and the C-terminus of at least one splice variant of each related group of nectin polypeptides (e.g. human nectin-1ot, human nectin-2α, and murine nectin-3α and β) contain a sequence with a high degree of similarity to an "ISRREWYV" consensus amino acid sequence (see, e.g., Table 1). Human nectin-3γ is predicted to lack a PDZ domain.

TABLE 1

C-terminal sequence of the nectin family members

| | | | | | | | | | | | |
|---|---|---|---|---|---|---|---|---|---|---|---|
| Consensus | – | – | I | S | R | R | E | W | Y | V | (SEQ ID NO:17 from aa 542 to 549) |
| Human Nectin 1α | S | F | I | S | K | K | E | W | Y | V | (SEQ ID NO:20 from aa 508 to 517) |
| Human Nectin 1β | V | R | T | T | E | P | R | G | E | C | (SEQ ID NO:21 from aa 448 to 457) |
| Human Nectin 2α | S | L | I | S | R | R | A | V | Y | V | (SEQ ID NO:22 from aa 470 to 479) |
| Human Nectin 2δ | G | F | V | M | S | R | A | M | Y | V | (SEQ ID NO:23 from aa 529 to 538) |
| Murine Nectin 3α | S | V | I | S | R | R | E | W | Y | V | (SEQ ID NO:17 from aa 540 to 549) |
| Murine Nectin 3β | L | Y | I | N | P | R | E | H | Y | V | (SEQ ID NO:18 from aa 501 to 510) |
| Murine Nectin 3γ | L | G | Q | V | R | A | L | E | D | T | (SEQ ID No:19 from aa 429 to 438) |
| Human Nectin 3α | S | V | I | S | R | R | E | W | Y | V | (SEQ ID NO:6 from aa 540 to 549) |
| Human Nectin 3β | V | Y | I | D | P | R | E | H | Y | V | (SEQ ID NO:12 from aa 501 to 510) |
| Human Nectin 3γ | L | F | Q | V | C | V | H | E | Y | T | (SEQ ID NO:31 from aa 428 to 437) |

Nectin-4 (e.g., SEQ ID NO:24 or 34) comprises a signal sequence beginning between about amino acid 1 and 16 and extending to amino acid 31 (e.g., from about $x_2$ to 31, wherein $x_2$ is an amino acid between 1 and 16 of SEQ ID NO:24 or 34), with the mature polypeptide formed by cleavage following the signal sequence. Typically cleavage of the signal sequence will occur following amino acid 26, 28 or 31, depending upon such factor as the cell type used for expression. Accordingly, the mature polypeptide comprises an amino acid sequence beginning between, and including, residue 22 and 32 (e.g., at amino acid 22, 23, 24, 25, 26, 27, 28, 29, 30, 31, 32, or 33; the N-terminal amino acid may vary depending upon host cell types used for expression) of SEQ ID NO:24 or 34. Three Ig domains, common to members of the nectin polypeptide family, are found between about amino acids 27 and 349 of SEQ ID NO:24 or 34 (e.g., 27–349, 28–349, 29–349, 31–349, or 32–349). The transmembrane domain of nectin-4 is predicted to include the amino acids from about amino acid 350 through amino acid 372 of SEQ ID NO:24 or 34; therefore, the extracellular domain of nectin-4 (including the signal sequence) extends from an amino acid between 1 and 16 through approximately amino acid 349 (e.g., from about $x_2$ to 349, wherein $x_2$ is an amino acid between 1 and 16) of SEQ ID NO:24 or 34.

Particularly conserved regions and amino acid residues common to nectin polypeptides were identified by aligning nectin polypeptide sequences with each other and additional closely-related members of the nectin-Ig superfamily of proteins. The amino acid sequence of nectin-3α and nectin-4 (SEQ ID Nos: 6 and 24) were compared with the amino acid sequences of other nectin and Ig family members (SEQ ID NO:20, 22, and 25), using a multiple sequence alignment program. The alignment of these sequences is shown in Table 2, and includes consensus residues (capitalized), which are identical among at least a majority [(three)] of the [five] amino acid sequences in the alignment. [In addition, lower case residues are shown on a separate line of Table 2 and represent residues that are not consensus residues, but are identical between human nectin-3α and human nectin-4 (SEQ ID Nos: 6 and 24).]

Amino acid substitutions and other alterations (deletions, insertions, and the like) to the nectin amino acid sequences (e.g., SEQ ID Nos:6, 12, or 24) are predicted to be more likely to alter or disrupt nectin polypeptide activities if they result in changes to the consensus residues of the amino acid sequences shown in Table 2, and particularly if those changes do not substitute an amino acid of similar structure (e.g., such as substitution of any one of the aliphatic residues—Ala, Gly, Leu, Ile, or Val—for another aliphatic residue), or a residue present in other nectin polypeptides at that conserved position. Conversely, if a change is made to a nectin-3 (α, β, or γ) or nectin-4 polypeptide resulting in substitution of a residue at a position in the alignment that is not conserved from one of the other nectin and nectin-like sequences in Table 2, it is less likely that such an alteration will affect the function of the altered nectin-3 (α, β, or γ) or nectin-4 polypeptide. For example, the consensus residue at position 98 in Table 2 is arginine, and some of the nectins have an lysine at that position. Accordingly, substitution of an lysine or the chemically similar histidine for arginine at that position are less likely to alter the function of the polypeptide than substitution of tryptophan or tyrosine. The invention provides nectin polypeptides and fragments of nectin polypeptides, preferably nectin-3α, nectin-3β, nectin-3γ, and nectin-4 polypeptides, comprising altered amino acid sequences. Altered nectin-3 (α, β, or γ) polypeptide sequences share at least 30% to 70%, or more preferably at least 75% to 80%, or more preferably at least 85% to 90%, or more preferably at least 95% to 97.5%, or more preferably at least 99%, or most preferably at least 99.5% amino acid identity with one or more of the nectin-3 amino acid sequences provided herein. Examples of nectin-3 polypeptides that contain such alterations include SEQ ID NO:4 and SEQ ID NO:10. These polypeptides have the N-terminal 6–7 amino acids of murine nectin-3 added to the N-terminus of SEQ ID NO:2 or 8, respectively. The result is the substitution of Pro for Leu at residue 5 and Gly for Arg at residue 6 of the nectin-3α and β polypeptides (SEQ ID NO:6 and 12). The fusion polypeptides of SEQ ID Nos:13–16 also have this alteration at positions 5 and 6 of the amino acid sequence. Polypeptides having the amino acid sequences of SEQ ID NO:4, 13, and 15, were expressed and the N-terminal signal sequences were functional for secretion of these polypeptides.

TABLE 2

Conserved Nectin Amino Acids

| | | | | | | |
|---|---|---|---|---|---|---|
| HUNECTIN2 (SEQ ID NO:22) | ~~~~~~~ | ~~~~~~~ | MARAAALLPS | RSPPTPLLWP | LLLLLLL... | |
| HUCK155 (SEQ ID NO:25) | ~~~~~~~ | ~~~~~~~ | ~~~~~~~ | MARAMAAAWP | LLLVALLVLS | |
| HUNECTIN1 (SEQ ID NO:20) | ~~~~~~~ | ~~~~~~~ | ~~~~MARMG | LAGAAGRWWG | L...ALGLTA | |
| HUNECTIN3 (SEQ ID NO:6) | MARTLRPSPL | CPGGGKAQLS | SASLLGAGLL | LQPPTPPPLL | LLLFPLLLFS | |
| HUNECTIN4 (SEQ ID NO:24) | ~~~~~~~ | ~~~~~~~ | ~~~~MPLSLG | AEMWGPEAWL | LLLLLLASFT | |
| consensus | | | | | LLL  LL | |

| | 51 | | | | | 100 |
|---|---|---|---|---|---|---|
| HUNECTIN2 | ..ETGAQDVR | VQVLPEVRGQ | LGGTVELPCH | L.LPPVPGLY | ISLVTWQRPD | |
| HUCD155 | WPPPGTGDVV | VQAPTQVPGF | LGDSVTLPCY | LQVPNMEVTH | VSQLTWAR.. | |
| HUNECTIN1 | FFLPGVHSQV | VQVNDSMYGF | IGTDVVLHCS | FANP.LPSVK | ITQVTWQK.S | |
| HUNECTIN3 | RLCGALAGP. | IIVEPHVTAV | WGKNVSLKCL | I..EV..NET | ITQISWEKIH | |
| HUNECTIN4 | GRCP..AGE. | LETSDVVTVV | LGQDAKLPCF | YRGDS..GEQ | VGQVAWARVD | |
| | cPG ag | VQV   VtGv | LG  V LPC | P      e | I QV W R | |

| | 101 | | | | | 150 |
|---|---|---|---|---|---|---|
| HUNECTIN2 | APANHQNVAA | FHPKMGPSFP | SPKPGSERLS | FVSAKQSTGQ | DTEAELQDAT | |
| HUCD155 | .HGESGSMAV | FHQTQGPSYS | E....SKRLE | FVAARLG... | ...AELRNAS | |
| HUNECTIN1 | TNGSKQNVAI | YNPSMGVSV. | .LAPYRERVE | FL........ | ..RPSFTDGT | |
| HUNECTIN3 | .GKSSQTVAV | HHPQYGFSVQ | ..GEYQGRVL | FKNYSLN... | .......DAT | |
| HUNECTIN4 | AGEGAQELAL | LHSKYGLHVS | ..PAYEGRVE | QPPPPRNPL. | .......DGS | |
| | g    Q  A | H  yG SV | Y gRVE | F      n | DAT | |

TABLE 2-continued

Conserved Nectin Amino Acids

```
             151                                                              200
HUNECTIN2    LALHGLTVED  EGNYTCEFAT  FPKGSVRGMT  WLRVIAKPKN  QAEAQKVTF.
HUCD155      LRMFGLRVED  EGNYTCLFVT  FPQGSRSVDI  WLRVLAKPQN  TAEVQKVQL.
HUNECTIN1    IRLSRLELED  EGVYICEFAT  FPTGNRESQL  NLTVMAKPTN  WIEGTQAVLR
HUNECTIN3    ITLHNIGFSD  SGKYICKAVT  FPLGNAQSST  TVTVLVEPTV  SLIKGPDSLI
HUNECTIN4    VLLRNAVQAD  EGEYECRVST  FPAGSFQARL  RLRVLVPPLP  SLNPGP.ALE
               L nL ED    EG Y C F T   FP GS q      LRVLAKP N   s E     L 201                                                              250
HUNECTIN2    ....SQDPTT  VALCISKEGR  PPARISWLSS  LDWEAKETQV  SGTLAGTVTV
HUCD155      ....TGEPVP  MARCVSTGGR  PPAQITWHSD  LGGMPNTSQV  PGFLSGTVTV
HUNECTIN1    AKKGQDDKVL  VATCTSANGK  PPSVVSWETR  LKGEARVPGD  SGTPMAPVTV
HUNECTIN3    DGGNE...TV  AAICIAATGK  PVAHIDWEGD  LGEM...ESTT TSFPNETATI
HUNECTIN4    EGQGL...TL  AASC.TAEGS  PAPSVTWDTE  VKGT..TSSR  SFKHSRSAAV
                g     T    aA C Sa G   PPA I W      L G    S   SG   TVTV 251                                                              300
HUNECTIN2    TSRFTLVPSG  RADGVTVTCK  VEH..ESFEE  PALIPVTLSV  RYPPEVSISG
HUCD155      TSLWILVPSS  QVDGKNVTCK  VEH..ESFEK  PQLLTVNLTV  YYPPEVSISG
HUNECTIN1    ISRYRLVPSR  EAHQQSLACI  VNYHMDRFKE  ....SLTLNV  QYEPEVTIEG
HUNECTIN3    ISQYKLFPTR  FARGRRITCV  VKHP..ALEK  DIRYSFILDI  QYAPEVSVTG
HUNECTIN4    TSEFHLVPSR  SMNGQPLTCV  VSHP..GLLQ  DQRITHILHV  SFLAEASVRG
               TS   LVPSR   A G    TC   V Hp   FE   d r   iL V   Y PEVSI G 301                                                              350
HUNECTIN2    Y.DDN.WYLG  RTDATLSCDV  RSNPEPTGYD  WSTTSGTFPT  SAVAQGSQLV
HUCD155      Y.DNN.WYLG  QNEATLTCDA  RSNPEPTGYN  WSTTMGPLPP  FAVAQGAQLL
HUNECTIN1    F.DGN.WYLQ  RMDVKLTCKA  DANPPATEYH  WTTLNGSLPK  GVEAQNRTLF
HUNECTIN3    Y.DGN.WFVG  RKGVNLKCNA  DANPPPFKSV  WSRLDGQWPD  GLLASDNTLH
HUNECTIN4    LEDQNLWHIG  REGAMLKCLS  EGQPPPSYN.  WTRLDGPLPS  GVRVDGDTLG
               Y D N WYLG   R gA LkC A    NPPPTY     WStLdG LP    G  AQG TL 351                                                              400
HUNECTIN2    IH.AVDSLFN  TTFVCTVTNA  VGMGRAEQVI  FVRETP....  ..........
HUCD155      IR.PVDKPIN  TTLICNVTNA  LGARQAELTV  QVKEGP....  ..........
HUNECTIN1    FKGPINYSLA  GTYICEATNP  IGTRSGQVEV  NITEFPYTPS  ..........
HUNECTIN3    FVHPLTFNYS  GVYICKVTNS  LGQRSDQKVI  YISDPPTTTT  LQPTIQWHPS
HUNECTIN4    F.PPLTTEHS  GIYVCHVSNE  FSSRDSQVTV  DVLDPQEDSG  KQ........
               F  Plt    s   G YIC VTN    G R  Q  V      EpP         q 401                                                              450
HUNECTIN2    ..........  .......RAS  P...RDV..G  PLVWGAVGGT  LLVLLLLAGG
HUCD155      ..........  .......PSE  H...SGISRN  AIIFLVLG..  ILVFLILLGI
HUNECTIN1    ..........  .......PPE  HGRRAGPVPT  AIIGGVAGSI  LLVLIVVGGI
HUNECTIN3    TADIEDLATE  PKKLPFPLST  LATIKDDTIA  TIIASVVGGA  LFIVLVSVLA
HUNECTIN4    ....VDLV..  ..........  .......SAS  VVVVGVIAAL  LFCLLVVVVV
                 d                                 II GV G     LLVLLV vG 451                                                              500
HUNECTIN2    SLAFILLRVR  RR.....RKS  .PGGAGGGAS  GDGGFYDPKA  QVLGNGDPVF
HUCD155      GIYFYWSKCS  REVLWHCHLC  .PSSEHHQSC  RN~~~~~~~   ~~~~~~~~~~
HUNECTIN1    VVALRRRRHT  FKGDYSTKKH  .VYGNGYSKA  GIPQHHPPMA  QNLQYPDDSD
HUNECTIN3    GIFCYRRRRT  FRGDYFAKNY  IPPSDMQKES  QIDVLQQDEL  D..SYP.DSV
HUNECTIN4    LMSRYHRR..  .KAQQMTQKY  EEELTLTREN  SIRRLHSHHT  DPRSQPEESV
               y RR        y         P     e      I  lH       d Ls PD Sv 501                                                              550
HUHECTIN2    WTPVVPGPME  P.DGKDEEEE  EEEEKAEKGL  MLPPPPALED  DMESQLDGSL
HUCD155      ~~~~~~~~~~  ~~~~~~~~~~  ~~~~~~~~~~  ~~~~~~~~~~  ~~~~~~~~~~
HUNECTIN1    .DEKKAGPLG  G.SSYEEEEE  EEEGGGGGER  KVGGPHPKYD  EDAKRPYFTV
HUNECTIN3    .KKENKNP..  .VNNLIRKDY  LEEPEKTQWN  NVENLNRFER  PMDYYEDLKM
HUNECTIN4    GLRAEGHPDS  LKDNSSCSVM  SEEPEGRSYS  TLTTVREIET  QT...ELLSP
                  p           n         Eepe         e           l 551                                           597
HUNECTIN2    ISRRAVYV~~  ~~~~~~~~~~  ~~~~~~~~~~  ~~~~~~~~~~  ~~~~~~
HUCD155      ~~~~~~~~~~  ~~~~~~~~~~  ~~~~~~~~~~  ~~~~~~~~~~  ~~~~~~
HUNECTIN1    DEAEARQDGY  GDRTLGYQYD  PEQLDLAENM  VSQNDGSFIS  KKEWYV~
HUNECTIN3    GM.KFVSDEH  YDENEDDLVS  HV...DGSVI  SR...REWYV  ~~~~~~
HUNECTIN4    GSGRAEEEED  QDEGIKQAMN  HFVQENGTLR  AKPTGNGIYI  NGRGHLV
                g   A  E    DE I         H   g                y
```

(Hs = *Homo sapiens*)
(Mus = Murine)

In addition to the nectin-4 polypeptide show in SEQ ID NO:24, variants of nectin-4 are also provided by the present invention. For example, the nectin-4 polypeptides of the invention comprise the variants having the amino acid alterations as shown in the pileup in Table 3. In Table 3, the boxed region at the N-terminal end of SEQ ID NO:24 is indicative of the signal sequence and the boxed region towards the C-terminal end is indicative of the transmembrane domain. The underlined region of SEQ ID NO:36 is indicative of the Fc domain of this fusion construct. Of particular interest is the variant SEQ ID NO:38, which lacks the first Ig domain typical of the nectin family of proteins. This form would not bind to, for example, nectin-1 but would be capable of forming homodimers with other nectin-4 forms and would bind to afadin. Accordingly, the polypeptide comprising SEQ ID NO:38 would not be activated by, and can block activation of, for example, nectin-1.

TABLE 3

```
                 1                                                                          50
SEQ ID NO:34                                         M P L  S L G A E M W G P E  A W L L P L L L L A
SEQ ID NO:37     - - - - - - - - - - - - - - - E L Q K R  W A V C L S T M P L  S L G A E M W G P E  A W L L L L L L L A
SEQ ID NO:38     - - - - - - - - - - - - - - - E L Q K R  W A V C L S T M P L  S L G A E M W G P E  A W L L L L L L L A
SEQ ID NO:39     - - - - - - - - - - - - - - - E L Q K R  W A V C L S T M P L  S L G A E M W G P E  A W L L L L L L L A
SEQ ID NO:24                                         M P L  S L G A E M W G P E  A W L L L L L L L A
SEQ ID NO:36                                         M P L  S L G A E M W G P E  A W L L P L L L L A 51                                                                          100
SEQ ID NO:34     S F T G R C P A G E  L E T S D V V T V V  L G Q D A K L P C F  Y R G D S G E Q V G  Q V A W A R V D A G
SEQ ID NO:37     S F T G R C P A G E  L E T S D V V T V V  L G Q D A K L P C F  Y R G D S G E Q V G  Q V A W A R V D A G
SEQ ID NO:38     S F T . . . . . . .  . . . . . . . . . .  . . . . . . . . . .  . . . . . . . . . .  . . . . . . . . . .
SEQ ID NO:39     S F A G R C P A G E  L E T S D V V T V V  L G Q D A K L P C F  Y R G D S G E Q V G  Q V A W A R V D A G
SEQ ID NO:24     S F T G R C P A G E  L E T S D V V T V V  L G Q D A K L P C F  Y R G D S G E Q V G  Q V A W A R V D A G
SEQ ID NO:36     S F T G R C P A G E  L E T S D V V T V V  L G Q D A K L P C F  Y R G D S G E Q V G  Q V A W A R V D A G 101                                                                         150
SEQ ID NO:34     E G A Q E L A L L H  S K Y G L H V S P A  Y E G R V E Q P P P  P R N P L D G S V L  L R N A V Q A D E G
SEQ ID NO:37     E G A Q E L A L L H  S K Y G L H V S P A  Y E G R V E Q P P P  P R N P L D G S V L  L R N A V Q A D E G
SEQ ID NO:38     . . . . . . . . . .  . . . . . . . . . .  . . . . . . . . . .  . . . . . . . . . .  . . . . . . . . . .
SEQ ID NO:39     E G A Q E L A L L H  S K Y G L H V S P A  Y E G R V E Q P P P  P R N L L D G S V L  L R N A V Q A D E G
SEQ ID NO:24     E G A Q E L A L L H  S K Y G L H V S P A  Y E G R V E Q P P P  P R N P L D G S V L  L R N A V Q A D E G
SEQ ID NO:36     E G A Q E L A L L H  S K Y G L H V S P A  Y E G R V E Q P P P  P R N P L D G S V L  L R N A V Q A D E G 151                                                                         200
SEQ ID NO:34     E Y E C R V S T F P  A G S F Q A R L R L  R V L V P P L P S L  N P G P A L E E G Q  G L T L A A S C T A
SEQ ID NO:37     E Y E C R V S T F P  A G S F Q A R L R L  R V L V P P L P S L  N P G P A L E E G Q  G L T L A A S C T A
SEQ ID NO:38     . . . . . . . . . .  . . . . . . . . . .  . . . V P P L P S L  N P G P A L E E G Q  G L T L A A S C T A
SEQ ID NO:39     E Y E C R V S T F P  A G S F Q A R L R L  R V L V P P L P S L  N P G P A L E E G Q  G L T L A A S C T A
SEQ ID NO:24     E Y E C R V S T F P  A G S F Q A R L R L  R V L V P P L P S L  N P G P A L E E G Q  G L T L A A S C T A
SEQ ID NO:36     E Y E C R V S T F P  A G S F Q A R L R L  R V L V P P L P S L  N P G P A L E E G Q  G L T L A A S C T A 201                                                                         250
SEQ ID NO:34     E G S P A P S V T W  D T E V K G T T S S  R S F K H S R S A A  V T S E F H L V P S  R S M N G Q P L T C
SEQ ID NO:37     E G S P A P S V T W  D T E V K G T T S S  R S F K H S R S A A  V T S E F H L V P S  R S M N G Q P L T C
SEQ ID NO:38     E G S P A P S V T W  D T E V K G T T S S  R S F K H S R S A A  V T S E F H L V P S  R S M N G Q P L T C
SEQ ID NO:39     E G S P A P S V T W  D T E V K G T T S S  R S F K H S R S A A  V T S E F H L V P S  R S M N G Q P L T C
SEQ ID NO:24     E G S P A P S V T W  D T E V K G T T S S  R S F K H S R S A A  V T S E F H L V P S  R S M N G Q P L T C
SEQ ID NO:36     E G S P A P S V T W  D T E V K G T T S S  R S F K H S R S A A  V T S E F H L V P S  R S M N G Q P L T C 251                                                                         300
SEQ ID NO:34     V V S H P G L L Q D  Q R I T H I L H V S  F L A E A S V R G L  E D Q N L W H I G R  E G A M L K C L S E
SEQ ID NO:37     V V S H P G L L Q D  Q R I T H I L H V S  F L A E A S V R G L  E D Q N L W H I G R  E G A M L K C L S E
SEQ ID NO:38     V V S H P G L L Q D  Q R I T H I L H V S  F L A E A S V R G L  E D Q N L W H I G R  E G A M L K C L S E
SEQ ID NO:39     V V S H P G L L Q D  Q R I T H I L H V S  F L A E A S V R G L  E D Q N L W H I G R  E G A M L K C L S E
SEQ ID NO:24     V V S H P G L L Q D  Q R I T H I L H V S  F L A E A S V R G L  E D Q N L W H I G R  E G A M L K C L S E
SEQ ID NO:36     V V S H P G L L Q D  Q R I T H I L H V S  F L A E A S V R G L  E D Q N L W H I G R  E G A M L K C L S E 301                                                                         350
SEQ ID NO:34     G Q P P P S Y N W T  R L D G P L P S G V  R V D G D T L G F P  P L T T E H S G I Y  V C H V S N E F S S
SEQ ID NO:37     G Q P P P S Y N W T  R L D G P L P S G V  R V D G D T L G F P  P L T T E H S G I Y  V C H V S N E F S S
SEQ ID NO:38     G Q P P P S Y N W T  R L D G P L P S G V  R V D G D T L G F P  P L T T E H S G I Y  V C H V S N E F S S
SEQ ID NO:39     G Q P P P S Y N W T  R L D G P L P S G V  R V D G D T L G F P  P L T T E H S G I Y  V C H V S N E F S S
SEQ ID NO:24     G Q P P P S Y N W T  R L D G P L P S G V  R V D G D T L G F P  P L T T E H S G I Y  V C H V S N E F S S
SEQ ID NO:36     G Q P P P S Y N W T  R L D G P L P S G V  R V D G D T L G F P  P L T T E H S G I Y  V C H V S N E F S S 351                                                                         400
SEQ ID NO:34     R D S Q V T V D V L  A D P Q E D S G K Q  V D L V S A S V V V  V G V I A A L L F C  L L V V V V L M S
SEQ ID NO:37     R D S Q V T V D V L  . D P Q E D S G K Q  V D L V S A S V V V  V G V I A A L L F C  L L V V V V L M S
SEQ ID NO:38     R D S Q V T V D V L  . D P Q E D S G K Q  V D L V S A S V V V  V G V I A A L L F C  L L V V V V L M S
SEQ ID NO:39     R D S Q V T V D V L  A D P Q E D S G K Q  V D L V S A S V V V  V G V I A A L L F C  L L V V V V L M S
SEQ ID NO:24     R D S Q V T V D V L  . D P Q E D S G K Q  V D L V S A S V V V  V G V I A A L L F C  L L V V V V L M S
SEQ ID NO:36     R D S Q V T V D V L  A D P Q E D S G K Q  V D L V S A S R S C  D K T H T C P P C P  A P E A E G A P S V
```

TABLE 3-continued

```
              401                                                              450
SEQ ID NO:34  R Y H R R K A Q Q M  T Q K Y E E E L T L  T R E N S I R R L H  S H H T D P R S Q P  E E S V G L R A E G
SEQ ID NO:37  R Y H R R K A Q Q M  T Q K Y E E E L T L  T R E N S I R R L H  S H H T D P R S Q .  . . . . . . . . . . .
SEQ ID NO:38  R Y H R R K A Q Q M  T Q K Y E E E L T L  T R E N S I R R L H  S H H T D P R S Q P  E E S V G L R A E G
SEQ ID NO:39  R Y H R R K A Q Q M  T Q K Y E E E L T L  T R E N S I R R L H  S H H T D P R S Q .  . . . . . . . . . . .
SEQ ID NO:24  R Y H R R K A Q Q M  T Q K Y E E E L T L  T R E N S I R R L H  S H H T D P R S Q P  E E S V G L R A E G
SEQ ID NO:36  F L F P P K P K D T  L M I S R T P E V T  C V V V D V S H E D  P E V K F N W Y V D  G V E V H N A K T K 451                                                              500
SEQ ID NO:34  H P D S L K D N S S  C S V M S E E P E G  R S Y S T L T T V R  E I E T Q T E L L S  P G S G R A E E E E
SEQ ID NO:37  . . . . . . . . . .  . . . . S E E P E G  R S Y S T L T T V R  E I E T Q T E L L S  P G S G R A E E E E
SEQ ID NO:38  H P D S L K D N S S  C S V M S E E P E G  R S Y S T L T T V R  E I E T Q T E L L S  P G S G R A E E E E
SEQ ID NO:39  . . . . . . . . . .  . . . . S E E P E G  R S Y S T L T T V R  E I E T Q T E L L S  P G S G R A E E E E
SEQ ID NO:24  H P D S L K D N S S  C S V M S E E P E G  R S Y S T L T T V R  E I E T Q T E L L S  P G S G R A E E E E
SEQ ID NO:36  P R E E Q Y N S T Y  R V V S V L T V L H  Q D W L N G K E Y K  C K V S N K A L P A  P I E K T I S K A K 501                                                              550
SEQ ID NO:34  D Q D E G I K Q A M  N H F V Q E N G T L  R A K P T G N G I Y  I N G R G H L V *
SEQ ID NO:37  D Q D E G I K Q A M  N H F V Q E N G T L  R A K P T G N G I Y  I N G R G H L V *
SEQ ID NO:38  D Q D E G I K Q A M  N H F V Q E N G T L  R A K P T G N G I Y  I N G R G H L V *
SEQ ID NO:39  D Q D E G I K Q A M  N H F V Q E N G T L  R A K P T G N G I Y  I N G R G H L V *
SEQ ID NO:24  D Q D E G I K Q A M  N H F V Q E N G T L  R A K P T G N G I Y  I N G R G H L V *
SEQ ID NO:36  G Q P R E P Q V Y T  L P P S R E E M T K  N Q V S L T C L V K  G F Y P S D I A V E  W E S N G Q P E N N 551                                                              600
SEQ ID NO:36  Y K T T P P V L D S  D G S F F L Y S K L  T V D K S R W Q Q G  N V F S C S V M H E  A L H N H Y T Q K S 601         608
SEQ ID NO:36  L S L S P G K *
```

The present invention provides active fragments, soluble polypeptides, and useful distinct domains of the sequence set forth in Table 3. A signal sequence is present in SEQ ID Nos:24, 34, and 36–39. For example, the relative domains of SEQ ID Nos:24, 34, and 36–39 are as follows:

| Amino acids: | Signal sequence | Soluble/Extra-cellular Domain | Trans-membrane Domain |
|---|---|---|---|
| SEQ ID NO: 24 | aa between 1 and 16 to ~26 | ~27 to between 349 and 351 | between 350 and 352 to 372 |
| SEQ ID NO: 34 | aa between 1 and 16 to ~26 | ~27 to between 350 and 352 | between 351 and 353 to 373 |
| SEQ ID NO: 36 | aa between 1 and 16 to ~26 | ~27 to 580 (incl. Fc domain) | NONE |
| SEQ ID NO: 37 | aa between 13 and 28 to ~43 | ~44 to between 362 and 364 | between 363 and 365 to 384 |
| SEQ ID NO: 38 | aa between 13 and 28 to ~38 | ~39 to between 242 and 244 | between 243 and 244 to 264 |
| SEQ ID NO: 39 | aa between 13 and 28 to ~43 | ~44 to between 363 and 364 | between 363 and 365 to 385 |

Polypeptides of the nectin family are expressed in most cell types including epithelial, hematopoietic, and vascular endothelial and smooth muscle cells. Typical biological activities or functions associated with this family of polypeptides include AJ activity, viral protein binding, and PDZ domain binding. Nectins are associated with the actin cytoskeleton through afadin, an F-actin-binding protein. Nectin polypeptides having cell adhesion activity associated with AJ function bind to other nectin polypeptides in a homotypic or heterotypic fashion and/or modulate cadherin polypeptides. This AJ cell adhesion activity is associated with the extracellular domain of nectin polypeptides, and particularly with the N-terminal V-type Ig domain. Thus, for modulating (e.g., promoting or inhibiting) cell adhesion activity, preferred nectin polypeptides include those having the N-terminal Ig domain and exhibiting nectin- and/or cadherin-binding activity. Preferred nectin polypeptides further include oligomers or fusion polypeptides comprising at least one extracellular or Ig domain portion of one or more nectin polypeptides, and fragments of any of these polypeptides that are capable of modulating cell adhesion activity. Preferably, the nectin domain is a soluble domain comprising the extracellular domain of a nectin molecule. Although the applicants are under no duty or obligation to explain the mechanism by which the invention works, the activity of soluble polypeptide domains of a nectin polypeptide may modulate cellular adhesion and migration by modulating intracellular signaling. For example, soluble nectin may modulate the activity of native nectins present in the AJs thereby modulating cytoskeletal functions of a cell.

The cell adhesion activity of nectin polypeptides may be determined, for example, in an assay that measures binding between normally non-adhesive cells (such as L cells) that have been altered to express one or more nectin polypeptides and optionally one or more cadherin polypeptides (see, e.g., Satoh-Horikawa et al., 2000, J Biol Chem. 275(14):10291–10299). Alternatively, the activity of the polypeptide can be determined by endothelial migration assays in the presence of phorbol mysteric acid (PMA), EGF, or VEGF/FGF.

The viral protein binding activity of nectin polypeptides is associated with the extracellular domain of these polypeptides. Thus, to modulate viral protein binding activity, preferred nectin polypeptides include those having the extracellular domain, and in particular the N-terminal V-type Ig domain, and exhibiting the ability to bind viral proteins. Preferred nectin polypeptides further include oligomers or fusion polypeptides comprising at least one extracellular domain of one or more nectin polypeptides, and fragments of any of these polypeptides that have viral protein binding activity. The viral protein binding activity of nectin polypeptides may be determined, for example, in an assay that measures viral infection of nectin-expressing cells through β-galactosidase staining in cells exposed to recombinant viruses expressing LacZ protein, or by immunohistochemical staining of cells exposed to virus particles (see, e.g., Menotti et al., 2000, *Proc. Natl. Acad. Sci. USA* 97(9): 4867–4872).

The binding of nectin polypeptides to the PDZ domain of certain polypeptides such as afadin is associated with the intracellular domain of these polypeptides, and particularly with the C-terminal portion of the polypeptides. Therefore, for uses requiring PDZ domain-binding activity preferred nectin polypeptides include those having the intracellular domain and exhibiting the ability to bind polypeptides comprising one or more PDZ domains. Preferred nectin polypeptides further include oligomers or fusion polypeptides comprising at least one intracellular domain of one or more nectin polypeptides, and fragments of any of these polypeptides that have PDZ domain binding activity. The PDZ domain binding activity of nectin polypeptides may be determined, for example, in a yeast two-hybrid assay or by affinity chromatography (see Takahashi et al., 1999, *J Cell Biol.* 145(3):539–549), or in a competitive binding assay as described herein.

One aspect of the biological activity of nectin polypeptides is the ability of members of this polypeptide family to bind particular binding partners such as nectin polypeptides, afadin polypeptides, α-catenin, and viral proteins via their extracellular domain, and to bind polypeptides comprising PDZ domains via their intracellular domain. Nectin polypeptides also interact with cadherins via afadin and α-catenin via their intracellular domain. For example, nectin-3 interacts with nectin-1 and/or nectin 2, and nectin-4 interacts with nectin-1. Accordingly, a preferred use of the nectin-3 and 4 polypeptides includes blocking the interaction of nectin-1 with its cognate such as, for example, a nectin-3 or 4. In this embodiment, soluble extracellular domains of nectin-3 or -4 are used to modulate the biological activity of nectin-1. Without wishing to be bound to a theory, soluble domains of nectin-3 and -4 are believed to work by preventing the interaction of a native nectin-3 or -4 with nectin-1 or, alternatively, by modulating the activity of nectin-1 on intracellular communication. Human nectin-1 sequences are known and have GenBank accession nos. X76400, AF060231, NM_002855, AY029539, and AF110314, each of which is incorporated herein by references. In addition, human nectin-2 sequences are known and have GenBank accession nos. AF058448, BC003091, and X80038, each of which is incorporated herein by references. Murine nectin-1 sequences and nectin-2 sequence can be identified using the above-identified accession numbers and include GenBank accession nos. D26107 and M80206, each of which is incorporated herein by references.

At least some nectin polypeptides may also be associated with members of the CD44 family or other cell-matrix adhesion molecules. The term "binding partner," as used herein, includes ligands, receptors, substrates, antibodies, other nectin polypeptides, the same nectin polypeptide (in the case of homotypic interactions), and other molecules that interacts with a nectin polypeptide through contact or proximity between particular portions of the binding partner and the nectin polypeptide. Binding partners for nectin polypeptides are expressed by epithelial and endothelial cells as well as other cell types including neural and cardiac cells and are associated with these cell types due to their role in the function of AJs that connect cells to each other. Because the extracellular domain of nectin polypeptides binds to binding partners such as nectins and viral proteins, the extracellular domain, when expressed as a separate fragment from the rest of a nectin polypeptide, or as a soluble polypeptide fused, for example, to an immunoglobulin Fc domain, is expected to disrupt the binding of nectin polypeptides to their binding partners. Thus, such soluble nectins are capable of modulating the function of native nectin molecules. By binding to one or more binding partners, the separate extracellular domain polypeptide prevents binding by the native nectin polypeptide(s), and so acts in a dominant negative fashion to inhibit the biological activities—cell adhesion and virus receptor functions, for example—mediated via binding of nectin polypeptides to their binding partners. Alternatively, such soluble nectin-3 or -4 domains may bind to their cognate and stimulate activity. For example, soluble nectin-3 molecules interact with nectin-1 and can promote nectin-1 activity, as discussed more fully herein.

The soluble nectin-3 and/or nectin-4 polypeptides of the invention can be used, without limitation, to modulate the nectin-1 activity (e.g., the interaction of nectin-1 with cognate(s)), cell adhesion activity; AJ activity; endothelial or epithelial cell barrier activity, proliferative activity, migration activity, immune cell activity, and virus receptor activity. These activities can be determined by standard assay methods, such as those disclosed herein, and those of skill in the art will readily understand that additional types of similar assays can be used to measure nectin biological activities.

Uses of nectin-3 (α, β, or γ) and nectin-4 polypeptides including fragments having nectin-3 or -4 activity include, but are not limited to, the following: purifying polypeptides and measuring the activity thereof; delivery agents; therapeutic and research reagents; molecular weight and isoelectric focusing markers; controls for peptide fragmentation; identification of unknown polypeptides; and preparation of antibodies.

Of particular interest are soluble nectin-3 (α, β, or γ) polypeptides comprising the extracellular domain or a fragment thereof ("solNectin-3") or the extracellular domain or fragment thereof of nectin-4 ("solNectin-4"). A solNectin-3 or solNectin-4 polypeptide may comprise the V-Ig domain, either of the C-Ig domains or a combination of V-Ig domain and C-Ig domain of a nectin-3 or nectin-4 polypeptide. Such solNectin-3 polypeptides and solNectin-4 polypeptides preferably retain a biological activity of a native extracellular domain of nectin-3 or -4 (e.g., the ability to interact with its binding partner). In one embodiment, solNectin-3 polypeptides are capable of interacting with nectin-1, nectin-2 and associated molecules. Similarly, in one embodiment, solNectin-4 is capable of interacting with nectin-1. In addition, such solNectin-3 or solNectin-4 polypeptides preferentially interact with a nectin-3 or -4 binding partner thereby inhibiting or preventing binding of native nectin-3 or -4 with the binding partner, respectively. Soluble nectin-3 or solNectin-4 polypeptides may be fused to polypeptides of interest (e.g., Fc or leucine-zipper polypeptides) to provide for the formation of oligomers comprising one or more solNectin-3 or solNectin-4 polypeptides. Such solNectin-3 and/or solNectin4 polypeptides, fusion polypeptides, and oligomers thereof can play a role that includes, for example, inhibition of endothelial cell migration and/or angiogenesis. Antibodies to a nectin-3 polypeptide of the invention can also be used as antagonists and inhibit endothelial cell migration and/or angiogenesis. It is also contemplated, as discussed more fully below that agonistic antibodies can be designed that bind to nectin-3 or nectin-4 binding partners (e.g., nectin-1) and modulate the activity of the binding partner.

Because of their roles in mediation of cell-cell interactions such as AJ function, nectin polypeptides are associated with conditions relating to normal cell adhesion activity, as well as pathological or disease conditions that result from malfunction or misregulation of cell adhesion. As one example, interaction of nectin polypeptides via their extracellular domains is involved in the movement or migration of epithelial and endothelial cells both in normal wound healing and in abnormal conditions such as restenosis. As another example, human nectin-3α is expressed on peripheral blood cells including, for example, T cells and antigen-presenting dendritic cells (see Example 2 below). Nectin-3α has a structure similar to the B7 family of immune cell adhesion and signaling molecules, with nectins having three Ig domains and B7 family members having two Ig domains. Levels of human nectin-3 mRNA molecules increase in stimulated dendritic cells and T cells. Thus, nectin is likely to be involved in interactions between dendritic cells and T cells. Therefore, nectin polypeptides are involved in diseases or conditions that share as a common feature cell-cell interaction or cell adhesion activity (or the misregulation thereof) in their etiology. More specifically, the conditions shown in Table 4 are some of those that are known or are likely to involve the biological activities of nectin polypeptides. Because a wide variety of cells express nectins, these polypeptides are involved in a broad spectrum of biological functions or activities, and conditions related to such biological activities. Given the many cell types in which nectin polypeptides are expressed including, for example, neural, stromal, dendritic, leukocyte, and cardiac cells, those of skill in the art will recognize that there are innumerable other biological functions and conditions related to nectin polypeptides in addition to those shown in Table 4.

TABLE 4

Selected Biological Functions of Nectin Polypeptides and Related Conditions

| | Biological Activity | Related Conditions |
| --- | --- | --- |
| ACTIVITIES COMMON TO MANY CELL TYPES: | VIRAL PROTEIN BINDING | Herpesvirus infections |
| ENDOTHELIAL/ EPITHELIAL CELL FUNCTIONS: | DEVELOPMENT BARRIER FUNCTIONS | Cleft palate formation Inflammation Inflammatory bowel disease Asthma Allergy Paracellular ion transport Edema Vascular leakage Allograft rejection due to vascular defects Transendothelial or transepithelial cell migration Metastasis |
| | ENDOTHIELIAL ACTIVATION, PROLIFERATION, OR MIGRATION | Reperfusion injury, ischemia Stroke, thrombosis Restenosis, vascular remodeling Angiogenesis or vasculogenesis Tumour growth, metastasis Wound closure Diabetic retinopathy Athlerosclerotic ischemia |

TABLE 4-continued

Selected Biological Functions of Nectin Polypeptides and Related Conditions

| | Biological Activity | Related Conditions |
| --- | --- | --- |
| IMMUNE CELL FUNCTIONS: | DENDRITIC CELL FUNCTIONS | T cell binding, antigen presentation |

Blocking or inhibiting the interactions between members of the nectin polypeptide family and their substrates, ligands, receptors, binding partners, and/or other interacting polypeptides is an aspect of the invention and provides methods for treating or ameliorating these diseases and conditions through the use of inhibitors of nectin polypeptide activity. Examples of such inhibitors include solNectin-3 or solNectin-4 that bind to a nectin-3 or nectin-4 cognate, and antagonistic antibodies that specifically bind nectin-3 (α, β, or γ) or nectin-4. For certain conditions involving too little nectin-3 (α, β, or γ) polypeptide activity, methods of treating or ameliorating these conditions comprise increasing the amount or activity of a nectin-3 (α, β, or γ) polypeptide by providing an isolated nectin-3 (α, β, or γ) polypeptide or active fragment or fusion polypeptide thereof, or by providing agents (agonists) that activate endogenous or exogenous nectin-3 polypeptides. Examples of activators of nectin-1 include solNectin-3 and solNectin-4 polypeptides, fusion constructs and oligomers.

In another aspect of the invention, an agent which upregulates expression of a nectin-3 or nectin-4 can be used to induce wound closure or tissue repair and regeneration by promoting endothelial and epithelial cells to migrate to the site of injury. The agent can be provided to the site of injury in any number of ways including on biodegradable sponges, matrices, and scaffolds. Accordingly, the invention provides methods of tissue engineering, wound repair, and regeneration.

A nectin-3 or nectin-4 polypeptide of the invention includes a polypeptide that shares a sufficient degree of amino acid identity or similarity to nectin-3α (SEQ ID NO:6), β (SEQ ID NO:12), or γ (SEQ ID NO:31) or to nectin-4 (e.g., SEQ ID NO:24, 34, 37, 38, and 39) to be identified by those of skill in the art as a polypeptide likely to share particular structural domains, have biological activities in common with nectin-3 or nectin-4 polypeptides, and/or bind to antibodies that also specifically bind to nectin-3 or nectin-4 polypeptides, respectively. The nectin-3 and nectin-4 polypeptides of the invention may be isolated from naturally occurring sources. Alternatively, the nectin polypeptides may be recombinantly produced and have the same structure as naturally occurring nectin polypeptides, or may be produced to have structures that differ from naturally occurring nectin-3 or -4 polypeptides. Polypeptides derived from any nectin polypeptide of the invention by any type of alteration (for example, but not limited to, insertions, deletions, or substitutions of amino acids, changes in glycosylation of the polypeptide, refolding or isomerization to change its three-dimensional structure or self-association state, and changes to its association with other polypeptides or molecules) are also nectin polypeptides for the purposes of the invention. Therefore, the polypeptides provided by the invention include polypeptides characterized by amino acid sequences similar to those of the nectin-3 polypeptides or similar to nectin-4 polypeptides described herein, but into which modifications are naturally provided or deliberately engineered. A polypeptide that shares biological activities in common with members of the nectin-3 polypeptide family is a polypeptide having nectin-3 polypeptide activity. Similarly, a polypeptide that shares biological activities in common with members of the nectin-4 polypeptide family is a polypeptide having nectin-4 polypeptide activity.

The invention provides both full-length and mature forms of nectin-3 ($\alpha$, $\beta$, or $\gamma$) and nectin-4 polypeptides. "Full-length" polypeptides are those having the complete primary amino acid sequence of the polypeptide as initially translated. The amino acid sequences of full-length polypeptides can be obtained, for example, by translation of the complete open reading frame ("ORF") of a cDNA molecule. Several full-length polypeptides may be encoded by a single genetic locus if multiple mRNA forms are produced from that locus by alternative splicing or by the use of multiple translation initiation sites. An example of a full length polypeptide of the invention includes the sequence as set forth in SEQ ID NO:6, 12, 24, 31 and 34. The "mature form" of a polypeptide refers to a polypeptide that has undergone post-translational processing steps such as cleavage of the signal sequence or proteolytic cleavage to remove a prodomain. Multiple mature forms of a particular full-length polypeptide may be produced, for example by cleavage of the signal sequence at multiple sites, or by differential regulation of proteases that cleave the polypeptide. The mature form(s) of such polypeptide may be obtained by expression, in a suitable mammalian cell or other host cell, of a polynucleotide that encodes the full-length polypeptide. The sequence of the mature form of the polypeptide may also be determinable from the amino acid sequence of the full-length form, through identification of signal sequences or protease cleavage sites. Examples of mature forms of polypeptides of the invention are SEQ ID NO:6 from amino acid residue $x_1$ to amino acid residue 549, SEQ ID NO:12 from amino acid residue $x_1$ to amino acid residue 510, and SEQ ID NO:31 from amino acid residue $x_1$ to amino acid residue 437, wherein $x_1$ is an amino acid between and including residues 51 to 58. The nectin polypeptides of the invention also include those that result from post-transcriptional or post-translational processing events such as alternate mRNA processing which can yield a truncated but biologically active polypeptide, for example, a naturally occurring soluble form of the polypeptide. Also encompassed within the invention are variations attributable to proteolysis such as differences in the N- or C-termini upon expression in different types of host cells, due to proteolytic removal of one or more terminal amino acids from the polypeptide (generally from about 1 to 5 terminal amino acids).

The invention further includes nectin-3 ($\alpha$, $\beta$, and $\gamma$) and nectin-4 polypeptides with or without associated native-pattern glycosylation. Polypeptides expressed in yeast or mammalian expression systems (e.g., COS-1 or CHO cells) can be similar to or significantly different from a native polypeptide in molecular weight and glycosylation pattern, depending upon the choice of expression system. Expression of polypeptides of the invention in bacterial expression systems, such as *E. coli*, typically provides non-glycosylated molecules. Further, a given preparation can include multiple differentially glycosylated species of the polypeptide. Glycosyl groups can be removed through conventional methods, in particular those utilizing glycopeptidase (Boehringer Mannheim).

Species homologues of nectin-3 ($\alpha$, $\beta$, and $\gamma$) and nectin-4 polypeptides and polynucleotides are also provided by the invention. As used herein, a "species homologue" is a polypeptide or polynucleotide with a different species of origin from that of a given polypeptide or polynucleotide, but with significant sequence similarity to the given polypeptide or polynucleotide. Species homologues may be isolated and identified by making suitable probes or primers from polynucleotides encoding the nectin-3 ($\alpha$, $\beta$, or $\gamma$) and nectin-4 polypeptides provided herein and screening a suitable nucleic acid source from the desired species. Alternatively, homologues may be identified by screening a genome database containing sequences from one or more species utilizing a sequence (e.g., nucleic acid or amino acid) of a nectin molecule of the invention. Such genome databases are readily available for a number of species (e.g., on the world wide web (www) at tigr.org/tdb; genetics.wisc.edu; stanford.edu/~ball; hiv-web.lan1.gov; ncbi.nlm.nig.gov; and ebi.ac.uk; pasteur.fr/other/biology). Use computer algorithms, which connects two proteins through one or more intermediate sequences, can be used to identify closely related as well as distant homologs. For example, an algorithm that repetitively uses the results of the previous query as new search seeds such as Saturated BLAST can be used. Starting with a protein sequence, Saturated BLAST runs a BLAST search and identifies representative sequences for the next generation of searches. The procedure is run until convergence or until some predefined criteria are met. Saturated BLAST is available on the world wide web (www) at: bioinformatics.burnham-inst.org/xblast (see also, Li et al. Bioinformatics 16(12):1105–1110, 2000).

The invention also encompasses allelic variants of nectin-3 ($\alpha$, $\beta$, or $\gamma$) and nectin-4 polypeptides and polynucleotides; that is, naturally-occurring forms of such polypeptides and polynucleotides in which differences in amino acid or nucleotide sequence are attributable to genetic polymorphism.

Fragments of the nectin polypeptides of the invention are encompassed by the invention and may be in linear form or cyclized using known methods, for example, as described in H. U. Saragovi, et al., Bio/Technology 10:773–778 (1992) and in R. S. McDowell, et al., J. Amer. Chem. Soc. 114: 9245–9253 (1992). Nectin-3 ($\alpha$, $\beta$, or $\gamma$) or nectin-4 polypeptides and fragments thereof, and the polynucleotides encoding them, include amino acid or nucleotide sequence lengths that are at least 25% (more preferably at least 50%, 60%, 70%, and most preferably at least 80%) of the length of a nectin-3 ($\alpha$, $\beta$, or $\gamma$) or nectin-4 polypeptide or polynucleotide and have at least 60% sequence identity (more preferably at least 70%, 75%, 80%, 85%, 90%, 95%, 97.5%, or at least 99%, and most preferably at least 99.5%) with that nectin-3 ($\alpha$, $\beta$, or $\gamma$) or nectin-4 polypeptide or polynucleotide, where sequence identity is determined by comparing the amino acid or nucleotide sequences when aligned so as to maximize overlap and identity while minimizing sequence gaps. Also included in the invention are polypeptides and fragments, and polynucleotides encoding them, that contain or encode a segment preferably comprising at least 8, or at least 10, or preferably at least 15, or more preferably at least 20, or still more preferably at least 30, or most preferably at least 40 contiguous amino acids. Such polypeptides and fragments may also contain a segment that shares at least 70% sequence identity (more preferably at least 75%, 80%, 85%, 90%, 95%, 97.5%, or at least 99%, and most preferably at least 99.5%) with any such segment of any of the nectin polypeptides or polynucleotides, where sequence identity is determined by comparing the sequences of the polypeptide or polynucleotide when aligned so as to maximize overlap and identity while minimizing sequence gaps.

The percent identity can be determined by visual inspection and mathematical calculation. The percent identity of two amino acid sequences or two polynucleotide sequences can be determined by comparing sequence information using the GAP computer program, version 6.0 described by Devereux et al. (*Nucl. Acids Res.* 12:387, 1984) and available from the University of Wisconsin Genetics Computer Group. The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Polypeptide Sequence and Structure*, National Biomedical Research Foundation, pp. 353–358, 1979; (2) a penalty of 3.0 for each gap and an additional 0.10 penalty for each symbol in each gap; and (3) no penalty for end gaps. Other programs used by those skilled in the art of sequence comparison may also be used, such as, for example, the BLASTN program version 2.0.9, available for use via the National Library of Medicine website: www.ncbi.nlm.nih.gov/gorf/wblast2.cgi, or the UW-BLAST 2.0 algorithm. Standard default parameter settings for UW-BLAST 2.0 are described at the following Internet webpage: blast.wustl.edu/blast/README.html# References. In addition, the BLAST algorithm preferably uses the BLOSUM62 amino acid scoring matrix, and optional parameters that may be used are as follows: (A) inclusion of a filter to mask segments of the query sequence that have low compositional complexity (as determined by the SEG program of Wootton & Federhen (Computers and Chemistry, 1993); also see Wootton and Federhen, *Methods Enzymol.* 266:554–71, 1996) or segments consisting of short-periodicity internal repeats (as determined by the XNU program of Claverie & States, Computers and Chemistry, 1993), and (B) a statistical significance threshold for reporting matches against database sequences, or E-score (the expected probability of matches being found merely by chance, according to the stochastic model of Karlin and Altschul (1990); if the statistical significance ascribed to a match is greater than this E-score threshold, the match will not be reported.); preferred E-score threshold values are 0.5, or in order of increasing preference, 0.25, 0.1, 0.05, 0.01, 0.001, 0.0001, $10^{-5}$, $10^{-10}$, $10^{-15}$, $10^{-20}$, $10^{-25}$, $10^{-30}$, $10^{-40}$, $10^{-50}$, $10^{-75}$, $10^{-100}$. The percent identify for human nectins is provided in Table 5 and were determined with the use of the GAP algorithm.

TABLE 5

Identities For Human Nectins

| MOLECULE | Nectin 1 α | Nectin 2 α | Nectin 3 α | Nectin 4 | Nectin 5 α |
|---|---|---|---|---|---|
| Nectin 1 α | — | 37% | 36% | 29% | 35% |
| Nectin 2 α | 37% | — | 29% | 25% | 48% |
| Nectin 3 α | 36% | 29% | — | 32% | 31% |
| Nectin 4 | 29% | 25% | 32% | — | 28% |
| Nectin 5 α | 35% | 48% | 31% | 28% | — |

The invention also provides for soluble forms of nectin-3 (α, β, and γ) and nectin-4 polypeptides comprising certain fragments or domains of these polypeptides, and particularly those comprising the extracellular domain or one or more fragments of the extracellular domain so long as the fragment retains a nectin-3 or nectin-4 polypeptide activity. Soluble polypeptides are polypeptides that are capable of being secreted from the cells in which they are expressed. In such forms part or all of the intracellular and transmembrane domains of the polypeptide are deleted such that the polypeptide is fully secreted from the cell in which it is expressed. The intracellular and transmembrane domains of polypeptides of the invention can be identified in accordance with known techniques for determination of such domains from sequence information. Soluble nectin-3 (α, β, or γ) polypeptides (solNectin-3) and soluble nectin-4 polypeptides (solNectin4) also include those polypeptides which include part of the transmembrane region, provided that the soluble nectin polypeptide is capable of being secreted from a cell, and preferably retains nectin polypeptide activity. Soluble nectin polypeptides further include oligomers or fusion polypeptides comprising the extracellular portion of at least one nectin-3 (α, β, or γ) and/or one nectin-4 polypeptide, and fragments of any of these polypeptides that have nectin polypeptide activity. A secreted soluble polypeptide may be identified (and distinguished from its non-soluble membrane-bound counterparts) by separating intact cells which express the desired polypeptide from the culture medium, e.g., by centrifugation, and assaying the medium (supernatant) for the presence of the desired polypeptide (e.g., solNectin-3 and/or solNectin-4). The presence of the desired polypeptide in the medium indicates that the polypeptide was secreted from the cells and thus is a soluble form of the polypeptide. The use of soluble nectin-3 (α, β, or γ) and/or soluble nectin-4 polypeptides are advantageous for many applications. Purification of the polypeptides from recombinant host cells is facilitated, since the soluble polypeptides are secreted from the cells. Moreover, soluble polypeptides are generally more suitable than membrane-bound forms for parenteral administration and for many enzymatic procedures. Examples of soluble forms of nectin-3 and nectin-4 polypeptides are provided herein. SEQ ID Nos:13 and 14 are the amino acid sequences of the extracellular domains of nectin-3α and nectin-3β, respectively, fused at their C termini to the Fc domain of an IgG1 molecule. SEQ ID Nos: 15 and 16 are the amino acid sequences of the extracellular domains of nectin-3α and nectin-3β, respectively, fused at their C termini to a FLAG® peptide sequence (amino acids 405 through 420 of SEQ ID NO:15 and amino acids 366 through 381 of SEQ ID NO:16) and a C-terminal polyHis stretch of six histidine residues. Additional examples of preferred soluble nectin polypeptides comprise amino acids 27 through 349 of SEQ ID NO:24, 34, or 36, or Ig domain containing fragments thereof.

The soluble nectin-3 and/or soluble nectin-4 polypeptides can be employed in inhibiting a biological activity of nectin-3 or -4 in in vitro or in vivo procedures. Accordingly, the soluble/extracellular domains of nectin-3 (α, β, and/or γ) and soluble nectin-4 polypeptides and fragments thereof that act as "dominant negative" inhibitors of native nectin-3 or -4 polypeptide function when expressed as fragments or as components of fusion polypeptides. For example, a purified polypeptide domain of the invention can be used to inhibit binding of nectin-3 and/or nectin-4 polypeptides to endogenous binding partners. Such use effectively would block nectin polypeptide interactions and inhibit nectin polypeptide activities. In still another aspect of the invention, a soluble form of a nectin-binding partner (e.g., a nectin-1, -2, or cadherin polypeptide) is used to bind to and competitively inhibit activation of the endogenous nectin-3 and/or nectin-4 polypeptide. Alternatively, purified and modified nectin-3 and/or -4 polypeptides can be administered to modulate interactions between nectin-3 and/or -4 polypeptides and their binding partners that are not membrane-bound. Such an approach will allow an alternative method for the modification of nectin-influenced bioactivity.

In another aspect, the invention provides polypeptides comprising various combinations of polypeptide domains from different nectin polypeptides, such as the extracellular domain (or a portion thereof such as the N-terminal V-type Ig domain) from one nectin and the intracellular domain from a different nectin. Accordingly, polypeptides or polynucleotides of the invention include those comprising or encoding two or more copies of a domain such as the N-terminal Ig domain, two or more copies of a domain such as either of the C-type Ig domains, or at least one copy of each domain, wherein at least one domain is derived from a nectin-3 ($\alpha$, $\beta$, or $\gamma$) and/or nectin-4 polypeptide and these domains may be presented in any order within such polypeptides. In one embodiment, a fusion construct comprising at least one nectin-4 extracellular domain and at least one nectin-3 extracellular domain are linked via a peptide linker. As indicated below, both nectin-4 and nectin-3 demonstrate interactions with nectin-1. A combination of soluble domains of both nectin-4 and nectin-3 would thus increase the modulatory activity of the soluble domains on nectin-1.

Additional variants within the scope of the invention include polypeptides that can be modified to create derivatives thereof by forming covalent or aggregative conjugates with other chemical moieties, such as glycosyl groups, lipids, phosphate, acetyl groups and the like. Covalent derivatives can be prepared by linking the chemical moieties to functional groups on amino acid side chains or at the N-terminus or C-terminus of a polypeptide. Conjugates comprising diagnostic (e.g., detectable) or therapeutic agents attached thereto are contemplated herein. Preferably, such alteration, substitution, replacement, insertion or deletion retains the desired activity of the polypeptide or a substantial equivalent thereof.

Other derivatives include covalent or aggregative conjugates of the polypeptides with other polypeptides, such as by synthesis in recombinant culture as N-terminal or C-terminal fusion polypeptides. Examples of fusion polypeptides are discussed herein in connection with oligomers. Further, fusion polypeptides can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, which is highly antigenic and provides an epitope reversibly bound by a specific monoclonal antibody, enabling rapid assay and facile purification of expressed recombinant polypeptide. A murine hybridoma designated 4E11 produces a monoclonal antibody that binds the FLAG® peptide in the presence of certain divalent metal cations, as described in U.S. Pat. No. 5,011,912. The 4E11 hybridoma cell line is available from the American Type Culture Collection under accession no. HB9259. Monoclonal antibodies that bind the FLAG® peptide are available from Eastman Kodak Co., Scientific Imaging Systems Division, New Haven, Conn.

As used herein, a "chimeric polypeptide" or "fusion polypeptide" comprises a nectin-3 and/or nectin-4 (including fragments) amino acid sequence of the invention operatively linked to a second polypeptide. The second polypeptide can be any polypeptide of interest having an activity or function independent of or related to the function of a nectin-3 ($\alpha$, $\beta$, or $\gamma$) or nectin-4 polypeptide. For example, the second polypeptide can have a related activity to a nectin-3 ($\alpha$, $\beta$, or $\gamma$) polypeptide and can be a domain of a related but distinct member of the nectin family of proteins such as, for example, an extracellular, cytoplasmic or transmembrane domain of a related nectin polypeptide. In one embodiment, a nectin-3 polypeptide is operatively linked to a nectin-4 polypeptide, preferably the nectin-3 and nectin-4 polypeptides are extracellular/soluble domains of the molecules. Within the fusion polypeptide, the term "operatively linked" is intended to indicate that a nectin polypeptide sequence and the second polypeptide sequence are fused in-frame to each other. The second polypeptide can be fused to the N-terminus or C-terminus of a nectin sequence of the invention. Additional examples of polypeptides of interest include peptide linkers, Fc polypeptides, leucine zipper polypeptides, and the like.

Encompassed by the invention are oligomers or fusion polypeptides that contain a nectin-3 ($\alpha$, $\beta$, or $\gamma$) polypeptide, one or more fragments of nectin-3 ($\alpha$, $\beta$, or $\gamma$) polypeptides, or any of the derivative or variant forms thereof as disclosed herein. Also encompassed are oligomers or fusion polypeptides that contain a nectin-4 polypeptide, one or more fragments of nectin-4 polypeptides, or any of the derivative or variant forms thereof as disclosed herein. In particular embodiments, the oligomers comprise soluble nectin polypeptides. Oligomers can be in the form of covalently linked or non-covalently-linked multimers, including dimers, trimers, or higher oligomers. In one aspect of the invention, the oligomers maintain the binding ability of the polypeptide components and have multivalent (e.g., bivalent, trivalent) binding sites. In an another embodiment, the invention provides oligomers comprising multiple nectin polypeptides joined via covalent or non-covalent interactions between peptide moieties fused to the polypeptides, such peptides having the property of promoting oligomerization. Leucine zippers and polypeptides derived from antibodies are among the peptides that can promote oligomerization of the polypeptides attached thereto, as described in more detail below.

In embodiments where variants of the nectin-3 ($\alpha$, $\beta$, or $\gamma$) polypeptides are constructed to include a membrane-spanning domain, they will form a Type I membrane polypeptide. Membrane-spanning nectin-3 polypeptides can be fused with extracellular domains of receptor polypeptides for which the ligand is known. Such fusion polypeptides can then be manipulated to control the intracellular signaling pathways triggered by the membrane-spanning nectin polypeptide. Nectin-3 polypeptides that span the cell membrane can also be fused with agonists or antagonists of cell-surface receptors, or cellular adhesion molecules to further modulate nectin-3 intracellular effects. For example, interleukins can be situated between the nectin-3 polypeptide and other fusion domains.

The polypeptides of the invention or fragments thereof may be fused to molecules such as peptide linkers or immunoglobulins for purposes including increasing the valency of polypeptide binding sites. For example, fragments of a nectin-3 or nectin-4 polypeptide, preferably soluble fragments (e.g., solNectin-3 or solNectin-4) may be fused directly or through linker sequences to the Fc portion of an immunoglobulin. For a bivalent form of the polypeptide, such a fusion comprises an Fc portion of an IgG molecule. Other immunoglobulin isotypes may also be used to generate such fusions. For example, a polypeptide-IgM fusion would generate a decavalent form of the polypeptide of the invention. The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Preferred Fc polypeptides comprise an Fc polypeptide derived from a human IgG1 antibody. Preparation of fusion polypeptides comprising certain heterologous polypeptides fused to various portions of antibody-derived polypeptides (including the Fc domain) has been described (see, e.g., by Ashkenazi et al. *PNAS USA* 88:10535, 1991; Byrn et al. *Nature* 344:677, 1990; and Hollenbaugh and Aruffo, "Construction of Immunoglobulin Fusion Polypeptides", in *Current Protocols in Immunology*, Suppl. 4, pages 10.19.1–10.19.11, 1992). One embodiment of the invention is directed to a dimer comprising two fusion polypeptides created by fusing a polypeptide of the invention to an Fc polypeptide derived from an antibody. A gene fusion encoding the polypeptide/Fc fusion polypeptide is inserted into an appropriate expression vector. Polypeptide/Fc fusion polypeptides are expressed in host cells transformed with the recombinant expression vector, and allowed to assemble much like antibody molecules, whereupon interchain disulfide bonds form between the Fc moieties to yield divalent molecules. A suitable Fc polypeptide, described in PCT application WO 93/10151, is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J.* 13:3992–4001, 1994). The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. The above-described fusion polypeptides comprising Fc moieties (and oligomers formed therefrom) offer the advantage of facile purification by affinity chromatography over Polypeptide A or Polypeptide G columns. In other embodiments, the polypeptides of the invention can be substituted for the variable portion of an antibody heavy or light chain. If fusion polypeptides are made with both heavy and light chains of an antibody, it is possible to form an oligomer with as many as four nectin-3 extracellular regions. Examples of nectin-3/Fc fusion polypeptides are provided herein (see, e.g., SEQ ID Nos:13 and 14). SEQ ID Nos: 13 and 14 are the amino acid sequences of the extracellular domains of nectin-3α and nectin-3β, respectively, fused at their C termini to the Fc domain of an IgG1 molecule. An example of a nectin-4-Fc is provided by the polypeptide sequence comprising SEQ ID NO:36. The nectin-4-Fc of SEQ ID NO:36 is encoded by SEQ ID NO:35 and comprises the extracellular domain of the nectin-4 comprising SEQ ID NO:34 from about amino acid 1 to amino acid 350.

Alternatively, the oligomer is a fusion polypeptide comprising multiple nectin polypeptides, with or without peptide linkers (spacer peptides). Among the suitable peptide linkers are those described in U.S. Pat. Nos. 4,751,180 and 4,935,233. In some embodiments, a linker moiety separates the nectin polypeptide domain and the second polypeptide domain in a fusion polypeptide. Such linkers are operatively linked to the C- and the N-terminal amino acids, respectively, of the two polypeptides. Typically a linker will be a peptide linker moiety. The length of the linker moiety is chosen to optimize the biological activity of the soluble nectin (e.g., solNectin-3 and/or solNectin-4 polypeptide sequence) and can be determined empirically without undue experimentation. The linker moiety should be long enough and flexible enough to allow a nectin moiety to freely interact with a substrate or ligand. The preferred linker moiety is a peptide between about one and 30 amino acid residues in length, preferably between about two and 15 amino acid residues. One linker moiety is a —Gly-Gly—linker. The linker moiety can include flexible spacer amino acid sequences, such as those known in single-chain antibody research. Linking moieties are described, for example, in Huston, J. S., et al., PNAS 85:5879–5883 (1988), Whitlow, M., et al., Protein Engineering 6:989–995 (1993), and Newton, D. L., et al., Biochemistry 35:545–553 (1996). Other suitable peptide linkers are those described in U.S. Pat. Nos. 4,751,180 and 4,935,233, which are hereby incorporated by reference. A DNA sequence encoding a desired peptide linker can be inserted between, and in the same reading frame as, the heterologous sequences (e.g., a nectin sequence of the invention) and a second polypeptide sequence, using any suitable conventional technique. For example, a chemically synthesized oligonucleotide encoding the linker can be ligated between the sequences encoding a nectin polypeptide and a second polypeptide of interest. In particular embodiments, a fusion polypeptide comprises from two to four soluble nectin polypeptides (e.g., one or more soluble nectin-3 polypeptides and/or one or more soluble nectin-4 polypeptides) separated by peptide linkers.

Another method for preparing the oligomers of the invention involves use of a leucine zipper. Leucine zipper domains are peptides that promote oligomerization of the polypeptides in which they are found (Landschulz et al., *Science* 240:1759, 1988), and have since been found in a variety of different polypeptides. Among the known leucine zippers are naturally occurring peptides and derivatives thereof that dimerize or trimerize. The zipper domain or oligomer-forming domain comprises a repetitive heptad repeat, often with four or five leucine residues interspersed with other amino acids. Use of leucine zippers and preparation of oligomers using leucine zippers are known in the art.

Also encompassed within the invention are nectin-3 or -4 polypeptide variants with partner binding sites that have been altered in conformation so that (1) the nectin variant will still bind to its partner(s), but a specified small molecule will fit into the altered binding site and block that interaction, or (2) the nectin-3 or -4 variant will no longer bind to its partner(s) unless a specified small molecule is present (see, for example, Bishop et al., 2000, *Nature* 407:395). Polynucleotides encoding such altered nectin-3 or -4 polypeptides can be introduced into organisms according to methods described herein. Such methods allow for the interaction of nectin-3 or -4 with its binding partners to be regulated by administration of a small molecule compound to an organism, either systemically or in a localized manner.

The nectin-3 or -4 polypeptides can be employed in modulating a biological activity of nectin-3 or -4 in in vitro or in vivo procedures. Encompassed within the invention are extracellular domains of nectin-3 (α, β, and/or γ) polypeptides, as well as extracellular domains of nectin-4 polypeptides, and fragments thereof that act as "dominant negative" inhibitors of native nectin-3 and/or nectin-4 polypeptide function when expressed as fragments or as components of fusion polypeptides. For example, a purified soluble polypeptide domain of the invention can be used to inhibit binding of nectin-3 and/or nectin-4 polypeptides to endogenous binding partners. Such use effectively would block nectin-3 or nectin-4 polypeptide interactions and inhibit nectin-3 and/or nectin-4 polypeptide activities. In still another aspect of the invention, a soluble form of a nectin-binding partner (e.g., a nectin-1, or -2 polypeptide) is used to bind to and modulate endogenous nectin-3 polypeptide activity (e.g., inhibit or activate nectin-3 activity). Furthermore, antibodies which bind to nectin-3 or nectin-4 polypeptides are capable of inhibiting nectin-3 or nectin-4 polypeptide activity, respectively, and act as antagonists. For example, antibodies that specifically recognize one or more epitopes of a nectin polypeptide of the invention, or epitopes of conserved variants of nectin polypeptides, or peptide fragments of the nectin polypeptides of the invention can be used in the invention to inhibit nectin-3 and/or nectin-4 polypeptide activity. Such antibodies include but are not limited to polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above. Alternatively, purified and modified nectin-3 polypeptides can be administered to modulate interactions between nectin-3 polypeptides and nectin-3 binding partners that are not membrane-bound. Such an approach will allow an alternative method for the modification of nectin-influenced bioactivity. Similarly, purified and modified nectin-4 polypeptides can be administered to modulate interactions between nectin-4 polypeptides and nectin-4 binding partners that are not membrane-bound. Such an approach will allow an alternative method for the modification of nectin-influenced bioactivity.

A polypeptide of the invention may be prepared by culturing transformed and/or recombinant host cells under culture conditions suitable to express the recombinant polypeptide. The resulting expressed polypeptide may then be purified from such culture (i.e., from culture medium or cell extracts) using known purification processes, such as gel filtration and ion exchange chromatography. The purification of the polypeptide may also include an affinity column containing agents which will bind to the polypeptide; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography. Alternatively, the polypeptide of the invention may be expressed in a form that will facilitate purification. For example, it may be expressed as a fusion polypeptide comprising, for example, maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.) and InVitrogen, respectively. The polypeptide can also be tagged with an epitope and subsequently purified by using a specific antibody directed to such epitope. One such epitope ("FLAG®") is commercially available from Kodak (New Haven, Conn.). Finally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can be employed to provide a substantially purified homogeneous recombinant polypeptide. A nectin-3 or nectin-4 polypeptide thus purified is substantially free of other mammalian polypeptides and is defined in accordance with the invention as a "substantially purified polypeptide"; such purified polypeptides of the invention include purified antibodies that bind to a nectin-3 or a nectin-4 polypeptide, fragment, variant, binding partner and the like. A nectin-3 or nectin-4 polypeptide of the invention may also be expressed as a product of transgenic animals, e.g., as a component of the milk of transgenic cows, goats, pigs, or sheep which are characterized by somatic or germ cells containing a nucleotide sequence encoding the polypeptide.

It is also possible to utilize an affinity column comprising a polypeptide that binds a nectin-3 or a nectin-4 polypeptide of the invention, such as a monoclonal antibody generated against a nectin-3 or a nectin-4 polypeptide, to affinity-purify expressed polypeptides. Polypeptides can be removed from an affinity column using conventional techniques, e.g., in a high salt elution buffer and then dialyzed into a lower salt buffer or by changing pH or other components depending on the affinity matrix utilized, or be competitively removed using the naturally occurring substrate of the affinity moiety, such as a polypeptide derived from the invention. In this aspect of the invention, nectin-binding polypeptides, such as the anti-nectin-3 antibodies of the invention or other polypeptides that can interact with a nectin-3 polypeptide of the invention, can be bound to a solid phase support such as a column chromatography matrix or a similar substrate suitable for identifying, separating, or purifying cells that express polypeptides of the invention on their surface. Adherence of polypeptide-binding polypeptides of the invention to a solid phase contacting surface can be accomplished by any means; for example, magnetic microspheres can be coated with these polypeptide-binding polypeptides and held in the incubation vessel through a magnetic field. Suspensions of cell mixtures are contacted with the solid phase that has such nectin-binding polypeptides thereon. Cells having nectin-3 and/or nectin-4 polypeptides of the invention on their surface bind to the fixed nectin-binding polypeptide and unbound cells are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. Alternatively, mixtures of cells suspected of containing nectin-3 or nectin-4 expressing cells of the invention can be incubated with a biotinylated nectin-3 or nectin-4 binding polypeptide of the invention. Incubation periods are typically at least one hour in duration to ensure sufficient binding to polypeptides of the invention. The resulting mixture is then passed through a column packed with avidin-coated beads, whereby the high affinity of biotin for avidin provides the binding of the polypeptide-binding cells to the beads. Use of avidin-coated beads is known in the art (see Berenson, et al. J. Cell. Biochem., 10D:239 (1986).

The polypeptide may also be produced by known conventional chemical synthesis. Methods for constructing polypeptides by synthetic means are known in the art. The synthetically-constructed polypeptide sequences, by virtue of sharing primary, secondary or tertiary structural and/or conformational characteristics with nectin-3 or -4 polypeptides, may possess biological properties in common therewith, including nectin-3 or -4 activity. Thus, they may be employed as biologically active or immunological substitutes for natural, purified polypeptides in screening of therapeutic compounds and in immunological processes for the development of antibodies.

The desired degree of purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the art that multiple bands corresponding to the polypeptide can be visualized by SDS-PAGE, due to differential glycosylation, differential post-translational processing, and the like. Preferably, the polypeptide of the invention is purified to substantial homogeneity, as indicated by a single polypeptide band upon analysis by SDS-PAGE. The polypeptide band can be visualized by silver staining, Coomassie blue staining, or by autoradiography.

In an alternative aspect, the invention further encompasses the use of agonists of nectin-3 and/or nectin-4 polypeptide activity to treat or ameliorate the symptoms of a disease for which increased nectin-3 or -4 polypeptide activity is beneficial. Such diseases or conditions include, but are not limited to, inflammation, inflammatory bowel disease, vascular leakage, and edema. In a preferred aspect, the invention entails administering compositions comprising a nectin-3 and/or -4 polynucleotide or polypeptide to cells in vitro, to cells ex vivo, to cells in vivo, and/or to a multicellular organism. The therapeutic form of a nectin polypeptide of the invention may include one or more D-amino acids to confer increased stability. Preferred therapeutic forms are soluble forms. In still another aspect of the invention, the compositions comprise administering a nectin-3 and/or nectin-4 polynucleotide for expression of a nectin polypeptide in a host organism for treatment of disease. Particularly preferred in this regard is expression in a human subject for treatment of a dysfunction associated with aberrant (e.g., decreased) endogenous activity of a nectin polypeptide. Furthermore, the invention encompasses the administration to cells and/or organisms of compounds found to increase the endogenous activity of nectin-3 and/or nectin-4 polypeptides. One example of compounds that increase nectin-3 or -4 polypeptide activity are agonistic antibodies, preferably monoclonal antibodies, that bind to nectin-3 or -4 polypeptides or binding partners, which increase polypeptide activity by causing constitutive intracellular signaling (or "ligand mimicking"), or by preventing the binding of an inhibitor to a nectin-3 or -4 polypeptide.

Antibodies that are immunoreactive with a nectin-3 (α, β, or γ) or nectin-4 polypeptide are provided herein. Such antibody specifically bind to the polypeptide via the antigen-binding site of the antibody (as opposed to non-specific binding). In the invention, specifically binding anti-nectin-3 antibodies are those that will specifically recognize and bind with nectin-3 polypeptides, homologues, and variants, but not with other molecules. Similarly, specifically binding anti-nectin-4 antibodies are those that will specifically recognize and bind with nectin-4 polypeptides, homologues, and variants, but not with other molecules In one preferred embodiment, the antibodies are specific for a nectin-3 or nectin-4 polypeptide and do not cross-react with other polypeptides including related nectins. In this manner, the nectin polypeptides, fragments, variants, fusion polypeptides, and the like, as set forth above can be employed as "immunogens" in producing antibodies immunoreactive therewith.

The antigenic determinants or epitopes of nectin-3 or -4 used for immunization can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding (Janeway et al., *Immunobiology* 3:9 (Garland Publishing Inc., 2nd ed. 1996)). Because folded polypeptides have complex surfaces, the number of epitopes available is quite numerous; however, due to the conformation of the polypeptide and steric hinderances, the number of antibodies that actually bind to the epitopes is less than the number of available epitopes (Janeway et al., supra). Epitopes can be identified by methods known in the art. Thus, one aspect of the invention relates to the antigenic epitopes of nectin-3 or nectin-4 polypeptides. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques known in the art such as solid-phase synthesis, chemical or enzymatic cleavage of a polypeptide, or using recombinant DNA technology.

Both polyclonal and monoclonal antibodies (mABs) can be elicited by the epitopes of the polypeptides of the invention, whether the epitopes have been isolated or remain part of the polypeptides, by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow et al. (eds.), Cold Spring Harbor Laboratory Press, Cold Spring Harbor, N.Y., (1988); Kohler and Milstein, (U.S. Pat. No. 4,376,110); the human B-cell hybridoma technique (Kosbor et al., 1983, Immunology Today 4:72; Cole et al., 1983, Proc. Natl. Acad. Sci. USA 80:2026); and the EBV-hybridoma technique (Cole et al., 1985, Monoclonal Antibodies And Cancer Therapy, Alan R. Liss, Inc., pp. 77–96). Hybridoma cell lines that produce monoclonal antibodies specific for nectin-3 or nectin-4 polypeptides are also contemplated herein. Such hybridomas can be produced and identified by conventional techniques. The hybridoma producing the mAb of this invention may be cultivated in vitro or in vivo. Production of high titers of mAbs in vivo makes this the presently preferred method of production. One method for producing such a hybridoma cell line comprises immunizing an animal with a polypeptide of the invention or antigenic fragment thereof; harvesting spleen cells from the immunized animal; fusing said spleen cells to a myeloma cell line, thereby generating hybridoma cells; and identifying a hybridoma cell line that produces a monoclonal antibody that binds a polypeptide of the invention. For the production of antibodies, various host animals may be immunized by injection with one or more of the following: a nectin-3 or nectin-4 polypeptide, a fragment of a nectin-3 or nectin-4 polypeptide, a functional equivalent of a nectin-3 or nectin-4 polypeptide, or a mutant form of a nectin-3 or nectin-4 polypeptide. Such host animals include, but are not limited to, rabbits, mice, and rats. Various adjutants may be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjutants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD and any subclass thereof.

In addition, techniques developed for the production of "chimeric antibodies" (Takeda et al., 1985, Nature, 314:452)

by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a porcine mAb and a human immunoglobulin constant region. The monoclonal antibodies of the invention also include humanized versions of murine monoclonal antibodies. Such humanized antibodies can be prepared by known techniques and offer the advantage of reduced immunogenicity when the antibodies are administered to humans. In one embodiment, a humanized monoclonal antibody comprises the variable region of a murine antibody (or just the antigen-binding site thereof) and a constant region derived from a human antibody. Alternatively, a humanized antibody fragment can comprise the antigen-binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Biol/Technology* 7:934, 1989), and Winter et al. (*TIPS* 14:139, Can, 1993). Procedures to generate antibodies transgenically can be found in GB 2,272,440, U.S. Pat. Nos. 5,569,825 and 5,545,806, and related patents. Preferably, for use in humans, the antibodies are human or humanized; techniques for creating such human or humanized antibodies are known and are available from, for example, Medarex Inc. (Princeton, N.J.) and Abgenix Inc. (Fremont, Calif.).

Antigen-binding antibody fragments that recognize specific epitopes may be generated by known techniques. For example, such fragments include but are not limited to: the F(ab')2 fragments which can be produced by pepsin digestion of the antibody molecule and the Fab fragments which can be generated by reducing the disulfide bridges of the (ab')2 fragments. Alternatively, Fab expression libraries may be constructed (Huse et al., 1989, Science, 246:1275) to allow rapid and easy identification of monoclonal Fab fragments with the desired specificity. Techniques described for the production of single chain antibodies (U.S. Pat. No. 4,946,778; Bird, 1988, Science 242:423; Huston et al., 1988, Proc. Natl. Acad. Sci. USA 85:5879; and Ward et al., 1989, Nature 334:544) can also be adapted to produce single chain antibodies against nectin gene products. Single chain antibodies are formed by linking the heavy and light chain fragments of the Fv region via an amino acid bridge. In addition, antibodies to the nectin-3 or nectin-4 polypeptide can be utilized to generate anti-idiotype antibodies that "mimic" nectin-3 or nectin-4 polypeptide and that may bind to the nectin polypeptide using techniques known to those skilled in the art. (See, e.g., Greenspan et al., 1993, FASEB J 7(5):437; and Nissinoff, 1991, J. Immunol. 147(8):2429).

Screening procedures by which such antibodies can be identified are known, and can involve immunoaffinity chromatography, for example. Antibodies can be screened for agonistic (i.e., mimicking) properties. Such antibodies, upon binding to a cell surface nectin, induce biological effects (e.g., transduction of biological signals) similar to the biological effects induced when the nectin-binding partner binds to the cell surface nectin. Agonistic antibodies can be used to induce nectin-mediated co-stimulatory pathways or intercellular communication.

Those antibodies that can block binding of nectin-3 or nectin-4 polypeptides of the invention to a binding partner can be used to inhibit nectin-mediated intercellular communication or cell adhesion that results from such binding. Such blocking antibodies can be identified using any suitable assay procedure, such as by testing antibodies for the ability to inhibit binding of nectin-3 or nectin-4 to cells or viral particles expressing a nectin binding partner. Alternatively, blocking antibodies can be identified in assays for the ability to inhibit a biological effect that results from binding of nectin-3 or nectin-4 to target cells or ligands. Antibodies can be assayed for the ability to inhibit nectin binding partner-mediated co-stimulatory pathways, for example. Such an antibody can be employed in an in vitro procedure, or administered in vivo to inhibit a biological activity mediated by the entity that generated the antibody. Disorders caused or exacerbated (directly or indirectly) by the interaction of nectin-3 with a cell-surface binding partner thus can be treated. A therapeutic method involves in vivo administration of a blocking antibody to a mammal in an amount effective to inhibit nectin-3 binding partner-mediated biological activity. Monoclonal antibodies are generally preferred for use in such therapeutic methods. In one embodiment, an antigen-binding antibody fragment is employed. Compositions comprising an antibody that is directed against a nectin, and a physiologically acceptable diluent, excipient, or carrier, are provided herein. Suitable components of such compositions are described below.

Also provided herein are conjugates comprising a detectable (e.g., diagnostic) or therapeutic agent, attached to an antibody of the invention. Examples of such agents are described herein. The conjugates find use in in vitro or in vivo procedures. The antibodies of the invention can also be used in assays to detect the presence of the polypeptides or fragments of the invention, either in vitro or in vivo. The antibodies also can be employed in purifying polypeptides or fragments of the invention by immunoaffinity chromatography.

Also provided is rational drug designed using a nectin-3 or nectin-4, or a combination thereof, of the invention. Rational drug design is used to produce structural analogs of biologically active polypeptides of interest or of small molecules with which they interact, e.g., inhibitors, agonists, antagonists, and the like. Rational drug design can be used to fashion drugs that are more active or stable forms of the polypeptide or that enhance or interfere with the function of a polypeptide in vivo (Hodgson, 1991, Biotechnology 9:19). In one approach, the three-dimensional structure of a nectin-3 or nectin-4 polypeptide of the invention, or of a polypeptide-inhibitor complex, is determined by x-ray crystallography, by nuclear magnetic resonance, or by computer homology modeling or, most typically, by a combination of these approaches. Both the shape and charges of the polypeptide must be ascertained to elucidate the structure and to determine active/binding site(s) of the molecule. Less often, useful information regarding the structure of a polypeptide may be gained by modeling based on the structure of homologous polypeptides. In both cases, relevant structural information is used to design analogous nectin-like molecules, to identify efficient inhibitors, or to identify small molecules that may bind nectins. Combinations of a nectin-3 and nectin-4 three dimensional structural information may be utilized to design inhibitors or binding agents due to the similar structures and biological activity (e.g., binding to nectin-1) of nectin-3 and -4. Useful examples of rational drug design may include molecules which have improved activity or stability as shown by Braxton et al. (1992 Biochemistry 31:7796) or which act as inhibitors, agonists, or antagonists of native peptides as shown by Athauda et al. (1993 J Biochem 113:742). The use of nectin polypeptide structural information in molecular modeling software systems to assist in inhibitor design and inhibitor-nectin polypeptide interaction is also encompassed by the invention. A particular method of the invention comprises analyzing the three-dimensional structure of a nectin-3 or nectin-4 polypeptide for likely binding sites of substrates, synthesizing a new molecule that incorporates a predictive reactive site, and assaying the new molecule as described herein. Examples of algorithms, software, and methods for modeling substrates or binding agents based upon the three-dimensional structure of a protein are described in PCT publication WO107579A2, entitled "METHODS AND COMPOSITIONS FOR DETERMINING ENZYMATIC ACTIVITY," the disclosure of which is incorporated herein.

It is also possible to isolate a target-specific antibody, selected by functional assay, as described herein, and then to solve its crystal structure. This approach can yield a pharmacore upon which subsequent drug design can be based. It is possible to bypass polypeptide crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

The purified nectin polypeptides of the invention (including polypeptides, fragments, variants, oligomers, and other forms thereof) are useful in a variety of assays. For example, the nectin molecules of the invention can be used to identify binding partners of nectin polypeptides, which can also be used to modulate intercellular communication, cell adhesion, viral protein binding, or immune cell activity. Alternatively, they can be used to identify non-binding-partner molecules or substances that modulate intercellular communication, cell adhesion, viral protein binding, or immune cell activity.

The terms "polynucleotide" as used herein, refers to a polymeric form of nucleotides of at least 10 bases in length (smaller nucleotide sequences are typically referred to as oligonucleotides). The nucleotides can be ribonucleotides, deoxyribonucleotides, or modified forms of either type of nucleotide. The term includes single and double stranded forms of DNA or RNA. DNA includes, for example, cDNA, genomic DNA, chemically synthesized DNA, DNA amplified by PCR, and combinations thereof. The polynucleotides of the invention include full-length genes or cDNA molecules as well as a combination of fragments thereof. The polynucleotides of the invention are preferentially derived from human sources, but the invention includes those derived from non-human species, as well.

By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant polynucleotide molecule, which is incorporated into a vector, e.g., an expression vector; into an autonomously replicating plasmid or virus; or into the genomic DNA of a prokaryote or eukaryote, or which exists as a separate molecule (e.g., a cDNA) independent of other sequences.

A nectin-3 polynucleotide of the invention comprises (1) a polynucleotide that encodes a polypeptide comprising a sequence of SEQ ID NO:6, 12, or 31, or a fragment thereof; (2) a sequence as set forth in SEQ ID Nos:1, 3, 5, 7, 9, 11, 13, 15, 26, 27, 28, 29, or 30; (3) sequences complementary to a sequence as set forth in SEQ ID Nos:1, 3, 5, 7, 9, 11, 13, 15, 26, 27, 28, 29, or 30; (4) fragments of SEQ ID Nos:1, 3, 5, 7, 9, 11, 13, 15, 26, 27, 28, 29, or 30 or their complements that specifically hybridize to the polynucleotide of (2) or (3), above under moderate to highly stringent conditions; and (5) sequences of (2), (3), or (4) wherein T can also be U (e.g., RNA sequences). Also encompassed by the invention are homologues of a nectin-3 polynucleotide of the invention. Polynucleotide homologues can be identified in several ways, including isolation of genomic or cDNA molecules from a suitable source, or computer searches of available DNA sequence databases.

A nectin-4 polynucleotide of the invention comprises (1) a polynucleotide that encodes a polypeptide comprising a sequence of SEQ ID NO:24, 34, 37, 38, 39, or a fragment thereof; (2) a sequence as set forth in SEQ ID NO:32 or 33; (3) sequences complementary to a sequence as set forth in SEQ ID NO:32 or 33; (4) fragments of SEQ ID NO:32 or 33 or its complement that specifically hybridize to the polynucleotide of (2) or (3), above under moderate to highly stringent conditions; and (5) sequences of (2), (3), or (4) wherein T can also be U (e.g., RNA sequences). Also encompassed by the invention are homologues of a nectin-4 polynucleotide of the invention. Polynucleotide homologues can be identified in several ways, including isolation of genomic or cDNA molecules from a suitable source, or computer searches of available DNA sequence databases.

Polynucleotides corresponding to the amino acid sequences described herein, can be used as probes or primers for the isolation of nucleic acids or as query sequences for database searches. Such probes or primers can be obtained by "back-translation" from the amino acid sequences, or by identification of regions of amino acid identity with polypeptides for which the coding DNA sequence has been identified. The polymerase chain reaction (PCR) procedure can be employed to isolate and amplify a polynucleotide encoding a nectin-3 or nectin-4 polypeptide or a desired combination of nectin polypeptide fragments. Oligonucleotides that define the desired termini of a combination of DNA fragments are employed as 5' and 3' primers. The oligonucleotides can additionally contain recognition sites for restriction endonucleases to facilitate insertion of the amplified DNA fragments into an expression vector. PCR techniques are described in Saiki et al., *Science* 239:487 (1988); *Recombinant DNA Methodology*, Wu et al., eds., Academic Press, Inc., San Diego (1989), pp. 189–196; and *PCR Protocols: A Guide to Methods and Applications*, Innis et. al., eds., Academic Press, Inc. (1990). Preferred PCR primer sequences are presented in SEQ ID Nos:26–29. SEQ ID Nos:26 and 27 are forward and reverse primers, respectively, for amplifying the entire nectin-3α coding region including the initiation and termination codons; these primers have restriction sites at their 5' ends and SEQ ID NO:26 contains some nucleotides corresponding to codons for the N-terminal portion of mouse nectin-3α, but is capable of amplifying nectin-3α sequences at typical annealing temperatures. SEQ ID Nos:28 and 29 are forward and reverse 'α-specific' primers, respectively, for amplifying a portion of the nectin-3α coding region that encodes a part of the extracellular domain that is specific to the nectin-3α splice form. Primer pairs SEQ ID Nos: 26 and 29 and SEQ ID Nos: 27 and 28 can also be used to amplify nectin-3α sequences.

The invention also includes polynucleotides that hybridize under moderately stringent conditions, and more preferably highly stringent conditions, to polynucleotides encoding nectin-3 or nectin-4 polypeptides described herein. The basic parameters affecting the choice of hybridization conditions and guidance for devising suitable conditions are set forth by Sambrook et al. (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3–6.4), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55° C. (or other similar hybridization solutions, such as one containing about 50% formamide, with a hybridization temperature of about 42° C.), and washing conditions of about 60° C., in 0.5×SSC, 0.1% SDS. Generally, highly stringent conditions are defined as hybridization conditions as above, but with washing at approximately 68° C., 0.2×SSC, 0.1% SDS. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes were performed for 15 minutes after hybridization is complete. The wash temperature and wash salt concentration can be adjusted as necessary to achieve a desired degree of stringency by applying the basic principles that govern hybridization reactions and duplex stability, as known to those skilled in the art and described further below (see, e.g., Sambrook et al, 1989). When hybridizing a nucleic acid to a target nucleic acid of unknown sequence, the hybrid length is assumed to be that of the hybridizing nucleic acid. When nucleic acid of known sequences are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids above 18 base pairs in length, $T_m$ (° C.)=81.5+16.6($\log_{10}$[$Na^+$])+0.41(% G+C)−(600/N), where N is the number of bases in the hybrid, and [$Na^+$] is the concentration of sodium ions in the hybridization buffer ([$Na^+$] for 1×SSC=0.165M). Preferably, each such hybridizing nucleic acid molecule has a length that is at least 15 nucleotides (or more preferably at least 18 to about 20 nucleotides, or at least 25 to about 30 nucleotides, or at least 40 nucleotides, or most preferably at least 50 nucleotides), or at least 25% (more preferably at least 50%, or at least 60%, or at least 70%, and most preferably at least 80%) of the length of a polynucleotide of the invention to which it hybridizes, and has at least 60% sequence identity (more preferably at least 70% to about 75%, at least 80% to about 85%, at least 90% to about 95%, at least 97.5%, or at least 99%, and most preferably at least 99.5%) with a polynucleotide of the invention to which it hybridizes, where sequence identity is determined by comparing the sequences of the hybridizing nucleic acids when aligned so as to maximize overlap and identity while minimizing sequence gaps as described above.

The invention also provides genes corresponding to the polynucleotides disclosed herein. "Corresponding genes" are the regions of the genome that are transcribed to produce the mRNAs from which cDNA molecules are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. An "isolated gene" is a gene that has been separated from the adjacent coding sequences, if any, present in the genome of the organism from which the gene was isolated.

Methods for making nectin-3 and nectin-4 polypeptides are described below, with preferred methods for nectin-3 polypeptide expression and purification described in Example 3. Expression, isolation, and purification of the polypeptides and fragments of the invention can be accomplished by any suitable technique, including but not limited to the following methods.

An isolated polynucleotide of the invention may be operably linked to an expression control sequence such as the pDC412 or pDC314 vectors (Microbix Biosystems Inc., Toronto, Canada), or the pMT2 or pED expression vectors disclosed in Kaufman et al., Nucleic Acids Res. 19:4485–4490 (1991); and Pouwels et al. Cloning Vectors: A Laboratory Manual, Elsevier, N.Y., (1985), in order to produce the polypeptide recombinantly. Many suitable expression control sequences are known in the art. General methods of expressing recombinant polypeptides are also known and are exemplified in R. Kaufman, Methods in Enzymology 185, 537-566 (1990). As used herein "operably linked" means that a polynucleotide of the invention and an expression control sequence are situated within a construct, vector, or cell in such a way that the polypeptide encoded by a polynucleotide is expressed when appropriate molecules (such as polymerases) are present. In one embodiment, at least one expression control sequence is operably linked to a nectin-3 or nectin-4 polynucleotide of the invention in a recombinant host cell or progeny thereof, the polynucleotide and/or expression control sequence having been introduced into the host cell by transformation or transfection, for example, or by any other suitable method. In another embodiment, at least one expression control sequence is integrated into the genome of a recombinant host cell such that it is operably linked to a polynucleotide encoding a nectin-3 or nectin-4 polypeptide. In one embodiment of the invention, at least one expression control sequence is operably linked to a polynucleotide of the invention through the action of a trans-acting factor such as a transcription factor, either in vitro or in a recombinant host cell.

In addition, a polynucleotide encoding an appropriate signal peptide (native or heterologous) can be incorporated into expression vectors. The choice of signal sequence can depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., Nature 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846. A DNA sequence for a signal sequence (secretory leader) can be fused in frame to a polynucleotide of the invention so that the DNA is initially transcribed, and the mRNA translated, into a fusion polypeptide comprising the signal peptide. A signal peptide that is functional in the intended host cells promotes extracellular secretion of the polypeptide. The signal peptide is cleaved from the polypeptide upon secretion of polypeptide from the cell. The skilled artisan will also recognize that the position(s) at which the signal peptide is cleaved can differ from that predicted by computer program, and can vary according to such factors as the type of host cells employed in expressing a recombinant polypeptide. A polypeptide preparation can include a mixture of polypeptide molecules having different N-terminal amino acids, resulting from cleavage of the signal peptide at more than one site.

Established methods for introducing DNA into mammalian cells have been described (Kaufman, *Large Scale Mammalian Cell Culture*, 1990, pp. 15–69). Additional protocols using commercially available reagents, such as Lipofectamine lipid reagent (Gibco/BRL) or Lipofectamine-Plus lipid reagent, can be used to transfect cells (Felgner et al., *Proc. Natl. Acad. Sci. USA* 84:7413–7417, 1987). In addition, electroporation can be used to transfect mammalian cells using conventional procedures, such as those in Sambrook et al. (*Molecular Cloning: A Laboratory Manual*, 2 ed. Vol. 1–3, Cold Spring Harbor Laboratory Press, 1989). Selection of stable transformants can be performed using methods known in the art such as, for example, resistance to cytotoxic drugs. Kaufman et al., *Meth. in Enzymology* 185:487–511, 1990, describes several selection schemes, such as dihydrofolate reductase (DHFR) resistance. A suitable strain for DH selection can be CHO strain DX-B11, which is deficient in DHFR (Urlaub et al., *Proc. Natl. Acad. Sci. USA* 77:4216–4220, 1980). A plasmid expressing the DHFR cDNA can be introduced into strain DX-B11, and only cells that contain the plasmid can grow in the appropriate selective media. Examples of selectable markers that can be incorporated into expression vectors include cDNAs conferring resistance to antibiotics, such as G418 and hygromycin B. Cells having the vector can be selected based on resistance to such compounds.

Alternatively, gene products can be obtained via homologous recombination, or "gene targeting" techniques. Such techniques employ the introduction of exogenous transcription control elements (such as the CMV promoter or the like) in a particular predetermined site on the genome, to induce expression of an endogenous nectin-3 or nectin-4 of the invention. The location of integration into a host chromosome or genome can be determined by one of skill in the art, given the known location and sequence of the gene. In one embodiment, the invention contemplates the introduction of exogenous transcriptional control elements in conjunction with an amplifiable gene, to produce increased amounts of the gene product. The practice of homologous recombination or gene targeting is explained by Chappel in U.S. Pat. No. 5,272,071 (see also Schimke, et al. "*Amplification of Genes in Somatic Mammalian cells*," Methods in Enzymology 151:85 (1987), and by Capecchi, et al., "*The New Mouse Genetics: Altering the Genome by Gene Targeting*," TIG 5:70 (1989)).

A number of cell types may act as suitable host cells for expression of a polypeptide of the invention. Mammalian host cells include, for example, the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, BHK (ATCC CRL 10) cell lines, the CV1/EBNA cell line derived from the African green monkey kidney cell line CV1 (ATCC CCL 70) as described by McMahan et al. (*EMBO J*. 10: 2821, 1991), human kidney 293 cells, human epidermal A431 cells, human Colo205 cells, other transformed primate cell lines, normal diploid cells, cell strains derived from in vitro culture of primary tissue, primary explants, HL-60, U937, HaK or Jurkat cells. Alternatively, it may be possible to produce the polypeptide in lower eukaryotes such as yeast or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous polypeptides. Potentially suitable bacterial strains include *Escherichia coli, Bacillus subtilis, Salmonella typhimurium*, or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain the functional polypeptide. Such covalent attachments may be accomplished using known chemical or enzymatic methods. The polypeptides may also be produced by operably linking an isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), or as described in Summers and Smith, Texas Agricultural Experiment Station Bulletin No. 1555 (1987), and Luckow and Summers, *Bio/Technology* 6:47 (1988). As used herein, an host cell capable of expressing a polynucleotide of the invention is "transformed." Cell-free translation systems could also be employed to produce polypeptides using RNAs derived from polynucleotide constructs disclosed herein. A host cell that comprises an isolated polynucleotide of the invention, preferably operably linked to at least one expression control sequence, is a "recombinant host cell".

The polynucleotides encoding the nectin-3 and nectin-4 polypeptides of the invention can be used for numerous diagnostic or other useful purposes. The polynucleotides of the invention can be used to express recombinant polypeptides for analysis, characterization or therapeutic uses; as markers for tissues in which the corresponding polypeptide is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in subjects to identify potential genetic disorders; as probes to hybridize and thus discover novel, related nucleic acid molecules; as a source of information to derive PCR primers for genetic fingerprinting; as a probe to "subtract-out" known sequences in the process of discovering other novel nucleic acids; for selecting and making oligomers for attachment to a "gene chip" or other support, including for examination of expression patterns; to raise anti-polypeptide antibodies using DNA immunization techniques; as an antigen to raise anti-DNA antibodies or elicit another immune response, and for gene therapy. Any or all polynucleotides suitable for these uses are capable of being developed into reagent grade or kit format for commercialization as products. For example, a kit of the invention will include one or more containers being compartmentalized and designed to hold primers (e.g., SEQ ID Nos: 26 and 27 and/or 28 and 29 to amplify nectin-3α or β, respectively), antibodies, polypeptides and related reagents (e.g., Taq polymerase and the like). Methods for performing these uses are known in the art. References disclosing such methods include, without limitation, "Molecular Cloning: A Laboratory Manual", 2d ed., Cold Spring Harbor Laboratory Press, Sambrook et al. eds., 1989, and "Methods in Enzymology: Guide to Molecular Cloning Techniques", Academic Press, Berger and Kimmel eds., 1987.

Probes and Primers. Among the uses of the disclosed nectin-3 and nectin-4 polynucleotides, and combinations of fragments thereof, is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence. The basic parameters affecting the choice of hybridization conditions and guidance for devising suitable conditions are set forth by Sambrook et al., 1989 and are described herein. Using knowledge of the genetic code in combination with the amino acid sequences set forth above, sets of degenerate oligonucleotides can be prepared. Such oligonucleotides are useful as primers, e.g., in polymerase chain reactions (PCR). In certain embodiments, degenerate primers can be used as probes for non-human genetic libraries. Such libraries include, but are not limited to, cDNA libraries, genomic libraries, and even electronic EST (express sequence tag) or DNA libraries. Homologous sequences identified by this method would then be used as probes to identify non-human nectin-3 homologues.

Chromosome Mapping. The polynucleotides encoding nectin-3 and nectin-4 polypeptides, and the disclosed fragments and combinations of these polynucleotides, can be used by those skilled in the art using well-known techniques to identify the human chromosome to which these polynucleotides map. Useful techniques include, but are not limited to, using the sequence or portions, including oligonucleotides, as a probe in techniques such as radiation hybrid mapping (high resolution), in situ hybridization to chromosome spreads (moderate resolution), and Southern blot hybridization to hybrid cell lines containing individual human chromosomes (low resolution). For example, chromosomes can be mapped by radiation hybridization. First, PCR is performed using the Whitehead Institute/MIT Center for Genome Research Genebridge4 panel of 93 radiation hybrids:http://www-genome.wi.mit.edu/ftp/distribution/human_STS_releases/july97/rhmap/genebridge4.html. Primers are used which lie within a putative exon of the gene of interest and which amplify a product from human genomic DNA, but do not amplify hamster genomic DNA. The results of the PCRs are converted into a data vector that is submitted to the Whitehead/MIT Radiation Mapping site on the internet (http://www-seq.wi.mit.edu). The data is scored and the chromosomal assignment and placement relative to known Sequence Tag Site (STS) markers on the radiation hybrid map is provided. The following web site provides additional information about radiation hybrid mapping: www-genome.wi.mit.edu/ftp/distribution/human_STS_releases/july97/07-97.INTRO.html.

Diagnostics and Gene Therapy. The polynucleotides encoding nectin-3 and nectin-4 polypeptides, and the disclosed fragments and combinations of these polynucleotides can be used by one skilled in the art using known techniques to analyze abnormalities associated with the genes corresponding to these molecules. This enables one to distinguish conditions in which this marker is rearranged or deleted. In addition, polynucleotides of the invention or a fragment thereof can be used as a positional marker to map other genes of unknown location. The DNA can be used in developing treatments for any disorder mediated (directly or indirectly) by defective, or insufficient amounts of, the genes corresponding to the polynucleotides of the invention. The polynucleotides disclosed herein permit the detection of defective genes, and the replacement thereof with normal genes. Defective genes can be detected in in vitro diagnostic assays, and by comparison of a native nucleotide sequence disclosed herein with that of a gene derived from a person suspected of harboring a defect in this gene.

Any method that neutralizes nectin-3 and/or nectin-4 polypeptides or inhibits expression of the nectin-3 and/or nectin-4 genes of the invention (either transcription or translation) can be used to reduce the biological activities of the nectin polypeptides of the invention. In particular embodiments, antagonists inhibit the binding of, or interaction of, a nectin-3 and/or nectin-4 cognate with a nectin-3 and/or nectin-4 polypeptide, thereby inhibiting biological activities induced by the binding or interaction of such nectin polypeptides to the cells. In another embodiment of the invention, antagonists can be designed to reduce the level of endogenous nectin-3 and/or nectin-4 gene expression, e.g., using known antisense or ribozyme approaches to inhibit or prevent translation of nectin-3 and/or nectin-4 mRNA transcripts; triple helix approaches to inhibit transcription; or targeted homologous recombination to inactivate or "knock out" the nectin-3 and/or nectin-4 genes or their endogenous promoters or enhancer elements. Such antisense, ribozyme, and triple helix antagonists may be designed to reduce or inhibit either unimpaired, or if appropriate, mutant nectin gene activity.

Antisense RNA and DNA molecules act to directly block the translation of mRNA by hybridizing to targeted mRNA and preventing polypeptide translation. Antisense approaches involve the design of oligonucleotides (either DNA or RNA) that are complementary to a nectin-3 and/or nectin-4 mRNA. Absolute complementarity, although preferred, is not required. An oligonucleotide "complementary" to a portion of a nucleic acid, as referred to herein, means a sequence having sufficient complementarity to be able to hybridize with the nucleic acid, forming a stable duplex (or triplex, as appropriate). In the case of double-stranded antisense nucleic acids, a single strand of the duplex DNA may thus be tested, or triplex formation may be assayed. The ability to hybridize will depend on both the degree of complementarity and the length of the antisense nucleic acid. Oligonucleotides that are complementary to the 5' untranslated sequence up to and including the AUG initiation codon, should work most efficiently at inhibiting translation. However, oligonucleotides complementary to either the 5'- or 3'-non-translated, non-coding regions of the nectin-3 and/or nectin-4 gene transcript could be used in an antisense approach to inhibit translation of endogenous mRNA. Antisense nucleic acids should be at least six nucleotides in length, and are preferably oligonucleotides ranging from 6 to about 50 nucleotides in length. In specific aspects the oligonucleotide is at least 10, at least 17, at least 25 or at least 50 nucleotides in length. The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, and the like. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl.

Acad. Sci. 84:648–652; PCT Publication No. WO88/09810), or hybridization-triggered cleavage agents or intercalating agents. (See, e.g., Zon, 1988, Pharm. Res. 5:539–549). The antisense molecules are delivered to cells that express a nectin-3 and/or nectin-4 transcript in vivo. A number of methods have been developed for delivering antisense DNA or RNA to cells; e.g., antisense molecules can be injected directly into the tissue or cell derivation site or modified antisense molecules, designed to target the desired cells (e.g., antisense linked to peptides or antibodies that specifically bind receptors or antigens expressed on the target cell surface) can be administered systemically. A preferred approach utilizes a recombinant DNA construct in which the antisense oligonucleotide is placed under the control of a strong pol III or pol II promoter. The use of such a construct to transfect target cells in the subject will result in the transcription of sufficient amounts of single stranded RNAs that will form complementary base pairs with the endogenous nectin gene transcripts and thereby prevent translation of the mRNA. For example, a vector can be introduced in vivo such that it is taken up by a cell and directs the transcription of an antisense RNA. Such a vector can remain episomal or become chromosomally integrated so long as it can be transcribed to produce the desired antisense RNA. Such vectors can be constructed by recombinant DNA technology methods standard in the art. Vectors can be plasmid, viral, or others known in the art, used for replication and expression in mammalian cells.

Ribozyme molecules designed to catalytically cleave nectin-3 and/or nectin-4 mRNA transcripts can also be used to prevent translation of nectin-3 or -4 mRNA and expression of corresponding nectin polypeptides. (See, e.g., PCT International Publication WO90/11364; U.S. Pat. No. 5,824,519). The ribozymes that can be used in the invention include hammerhead ribozymes (Haseloff et al., 1988, Nature, 334: 585–591), RNA endoribonucleases ("Cech-type ribozymes") such as the one which occurs naturally in *Tetrahymena Thermophila* (known as the IVS, or L-19 IVS RNA) and which has been extensively described by Thomas Cech and collaborators (International Patent Application No. WO 88/04300; Been et al., 1986, Cell, 47:207–216). As in the antisense approach, the ribozymes can be composed of modified oligonucleotides (e.g. for improved stability, targeting, and the like) and are delivered to cells that express the nectin polypeptide in vivo. A preferred method of delivery involves using a DNA construct encoding the ribozyme under the control of a strong constitutive pol III or pol II promoter, so that transfected cells will produce sufficient quantities of the ribozyme to destroy endogenous nectin mRNA and inhibit translation. Because ribozymes, unlike antisense molecules, are catalytic, a lower intracellular concentration is required for efficiency.

Alternatively, endogenous nectin-3 and/or nectin-4 gene expression can be reduced by targeting deoxyribonucleotide sequences complementary to the regulatory region of the target gene (i.e., the target gene promoter and/or enhancers) to form triple helical structures that prevent transcription of the target nectin gene. (See generally, Helene, 1991, Anticancer Drug Des. 6(6):569–584; Helene, et al., 1992, Ann. N.Y. Acad. Sci. 660, 27–36; and Maher, 1992, Bioassays 14(12):807–815).

Antisense RNA and DNA, ribozyme, and triple helix molecules of the invention may be prepared by any method known in the art for the synthesis of DNA and RNA molecules. These include techniques for chemically synthesizing DNA or RNA oligonucleotides such as, for example, solid phase phosphoramidite chemical synthesis. Oligonucleotides can be synthesized by standard methods known in the art, e.g. by use of an automated DNA synthesizer (such as are commercially available from Biosearch and Applied Biosystems). As examples, phosphorothioate oligonucleotides may be synthesized by the method of Stein et al., 1988, Nucl. Acids Res. 16:3209. Methylphosphonate oligonucleotides can be prepared by use of controlled pore glass polymer supports (Sarin et al., 1988, Proc. Natl. Acad. Sci. U.S.A. 85:7448). Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Endogenous target gene expression can also be reduced by inactivating or "knocking out" the target gene or its promoter using targeted homologous recombination (e.g., see Smithies, et al., 1985, Nature 317:230; Thomas et al., 1987, Cell 51:503; Thompson, et al., 1989, Cell 5:313). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas et al., 1987; and Thompson, 1989, supra), or in model organisms such as *Caenorhabditis elegans* where the "RNA interference" ("RNAi") technique (Grishok et al., 2000, Science 287 (5462):2494), or the introduction of transgenes (Dernburg et al., 2000, Genes Dev. 14(13):1578) are used to inhibit the expression of specific target genes. This approach can be adapted for use in humans provided the recombinant DNA constructs are directly administered or are targeted to the required site in vivo using appropriate vectors such as viral vectors.

Organisms that have enhanced, reduced, or modified expression of the gene(s) corresponding to nectin-3 and/or 4 polynucleotides are provided. The desired change in gene expression can be achieved through the use of antisense nucleic acids or ribozymes that bind and/or cleave the mRNA transcribed from the gene (Albert et al., 1994, Trends Pharmacol. Sci. 15(7):250; Lavarosky et al., 1997, Biochem. Mol. Med. 62(1):11; and Hampel, 1998, Prog. Nucleic Acid Res. Mol. Biol. 58:1). Transgenic animals that have multiple copies of the gene(s) corresponding to the polynucleotides disclosed herein, preferably produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see European Patent No. 0 649 464 B1). In addition, organisms are provided in which the gene(s) corresponding to nectin-3 and/or nectin-4 polynucleotides have been partially or completely inactivated, through insertion of extraneous sequences into the corresponding gene(s) or through deletion of all or part of the corresponding gene(s). Partial or complete gene inactivation can be accomplished through insertion, preferably followed by imprecise excision, of transposable elements (Plasterk, 1992, Bioessays 14(9):629; Zwaal et al., 1993, Proc. Natl. Acad. Sci. USA 90(16):7431; Clark et al., 1994, Proc. Natl. Acad. Sci. USA 91(2):719), or through homologous recombination, preferably detected by positive/negative genetic selection strategies (Mansour et al., 1988, Nature 336:348; U.S. Pat. Nos:. 5,464,764; 5,487,992; 5,627,059; 5,631,153; 5,614, 396; 5,616,491; and 5,679,523). These organisms with altered gene expression are preferably eukaryotes and more preferably are non-human mammals. Such organisms are useful for the development of models for the study of disorders involving nectin-3 and/or nectin-4 and for the development of assay systems for the identification of molecules that interact with the polypeptide product(s) of the corresponding gene(s).

Assays to Identify Binding Partners. Polypeptides of the invention and fragments thereof can be used to identify binding partners. For example, they can be tested for the ability to bind a candidate-binding partner in any suitable assay, such as a conventional binding assay. To illustrate, a nectin-3 or -4 polypeptide or a soluble fragment thereof can be labeled with a detectable agent (e.g., a radionuclide, chromophore, enzyme that catalyzes a colorimetric or fluorometric reaction, and the like). The labeled polypeptide is contacted with cells expressing the candidate-binding partner. The cells then are washed to remove unbound-labeled polypeptide, and the presence of cell-bound label is determined by a suitable technique, chosen according to the nature of the label.

One example of a binding assay procedure is to transfect a host cell with a recombinant expression vector containing a candidate-binding partner cDNA. The transfected cells are cultured and then split into a 24-well plate. After culturing an additional 48 hours, the transfected cells are washed and incubated for 1 hour at 37° C. with various concentrations of, for example, a soluble nectin-3 polypeptide/Fc fusion polypeptide made as set forth herein. Cells are washed and incubated with a constant saturating concentration of a $^{125}$I-mouse anti-human IgG in binding medium. After washing, cells are released via trypsinization. The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any polypeptide/Fc polypeptide that has bound to the cells. In all assays, non-specific binding of $^{125}$I-antibody is assayed in the absence of the nectin-3 polypeptide/Fc, as well as in the presence of the Fc fusion polypeptide and a 200-fold molar excess of unlabeled mouse anti-human IgG antibody. Cell-bound $^{125}$I-antibody is quantified on a Packard Autogamma counter. Affinity calculations (Scatchard, Ann. N.Y Acad. Sci. 51:660, 1949) are generated on RS/1 (BBN Software, Boston, Mass.). Binding can also be detected using methods that are well suited for high-throughput screening procedures, such as scintillation proximity assays (Udenfriend et al., 1985, Proc Natl Acad Sci USA 82:8672), homogeneous time-resolved fluorescence methods (Park et al., 1999, Anal Biochem 269:94), fluorescence resonance energy transfer (FRET) methods (Clegg, 1995, Curr Opin Biotechnol 6:103), or methods that measure any changes in surface plasmon resonance when a bound polypeptide is exposed to a potential binding partner using, for example, a biosensor such as that supplied by Biacore AB (Uppsala, Sweden). Agents that can be assayed for binding to nectin-3 polypeptides include but are not limited to small organic molecules, such as those that are commercially available—often as part of large combinatorial chemistry compound 'libraries'— from companies such as Sigma-Aldrich (St. Louis, Mo.), Arqule (Woburn, Mass.), Enzymed (Iowa City, Iowa), Maybridge Chemical Co.(Trevillett, Cornwall, UK), MDS Panlabs (Bothell, Wash.), Pharmacopeia (Princeton, N.J.), and Trega (San Diego, Calif.). Preferred small organic molecules for screening using these assays are usually less than 10K molecular weight and may possess a number of physico-chemical and pharmacological properties which enhance cell penetration, resist degradation, and/or prolong their physiological half-lives (Gibbs, 1994, Cell 79(2): 193). Agents including natural products, inorganic chemicals, and biologically active materials such as proteins and toxins can also be assayed using these methods for the ability to bind to nectin-3 and/or nectin-4 polypeptides.

Yeast Two-Hybrid or "Interaction Trap" Assays. Where the nectin-3 and/or nectin-4 polypeptide binds or potentially binds to another polypeptide (such as, for example, in a receptor-ligand interaction), a polynucleotide encoding the nectin polypeptide can also be used in interaction trap assays (such as, for example, that described in Gyuris et al., Cell 75:791–803 (1993)) to identify polynucleotides encoding the other polypeptide with which binding occurs or to identify inhibitors of the binding interaction. Polypeptides involved in these binding interactions can also be used to screen for peptide or small molecule inhibitors or agonists of the binding interaction.

Competitive Binding Assays. Another type of suitable binding assay is a competitive binding assay. To illustrate, biological activity of a variant can be determined by assaying for the variant's ability to compete with the native polypeptide for binding to the candidate-binding partner. Competitive binding assays can be performed by conventional methodology. Reagents that can be employed in competitive binding assays include radiolabeled nectin and intact cells expressing nectin (endogenous or recombinant) on the cell surface. For example, a radiolabeled solNectin-3 can be used to compete with a soluble nectin-3 variant for binding to binding partners. Alternatively, a radiolabeled solNectin-3 can be used to compete with a solNectin-4 for binding to binding partners (e.g., nectin-1). Instead of intact cells, one could substitute a soluble binding partner/Fc fusion polypeptide bound to a solid phase through the interaction of Polypeptide A or Polypeptide G (on the solid phase) with the Fc moiety. Chromatography columns that contain Polypeptide A and Polypeptide G include those available from Pharmacia Biotech, Inc., Piscataway, N.J.

Assays to Identify Modulators of Intercellular Communication, Cell Adhesion or Migration, or Immune Cell Activity. The influence of nectin on intercellular communication, cell adhesion and migration, or immune cell activity can be manipulated to control these activities in target cells. For example, the disclosed nectin-3 and/or nectin-4 polypeptides, polynucleotides, agonists, or antagonists of such polypeptides can be administered to a cell or group of cells to induce, enhance, suppress, or arrest cellular communication, cell adhesion or migration, viral protein binding, or other nectin-3 and/or nectin-4 related activities in the target cells. Identification of nectin-3 and/or nectin-4 polypeptides, agonists, or antagonists that can be used in this manner can be carried out via a variety of assays known to those skilled in the art. Included in such assays are those that evaluate the ability of a nectin polypeptide (e.g., a soluble nectin-3 or -4 polypeptide) of the invention to influence (inhibit or promote) intercellular communication, cell adhesion or migration, or viral protein binding activity. Such an assay would involve, for example, the analysis of cell interaction in the presence of a nectin-3 or nectin-4 polypeptide or soluble fragment. In such an assay, one would determine a rate of communication or cell adhesion in the presence of the nectin polypeptide and then determine if such communication or cell adhesion is altered in the presence of a candidate agonist or antagonist. Exemplary assays for this aspect of the invention includes cytokine secretion assays, T-cell adhesion assays, endothelial migration assays, and mixed lymphocyte reactions involving antigen presenting cells and T cells. These assays are known to those skilled in the art and/or are exemplified herein.

In another aspect, the invention provides a method of detecting the ability of a test agent to affect the intercellular communication, cell adhesion or migration, or viral protein binding activity of a cell. In this aspect, the method comprises contacting a first group of target cells with a test agent including a nectin-3 or nectin-4 polypeptide or fragment thereof (e.g., solNectin-3 and/or solNectin-4) under conditions appropriate to the particular assay being used; measuring the net rate of intercellular communication, cell adhesion, or cell migration among the target cells; and observing the net rate of intercellular communication or cell adhesion among control cells (e.g., in the absence of a test agent) under otherwise identical conditions as the first group of cells. In this embodiment, the net rate of intercellular communication or cell adhesion in the control cells is compared to that of the cells treated with a test agent. The comparison will provide a difference in the net rate of intercellular communication or cell adhesion such that an effector of intercellular communication, cell adhesion, or cell migration can be identified. The test agent can function as an effector by either activating or up-regulating, or by inhibiting or down-regulating intercellular communication, cell adhesion, or migration.

Cell Proliferation. Cell Death. Cell Differentiation, and Cell Adhesion Assays. A polypeptide of the invention may exhibit cell activation or stimulation, cell proliferation (either inducing or inhibiting), cell differentiation (either inducing or inhibiting) activity, or may induce cell migration in certain cell populations. Many polypeptide factors discovered to date have exhibited such activities in one or more factor-dependent cell proliferation assays, and hence the assays serve as a convenient confirmation of cell stimulatory activity. The activity of a polypeptide of the invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK. The activity of a nectin-3 or nectin-4 polypeptide or fragment thereof (e.g., solNectin-3 and/or solNectin-4) may be measured by the following methods:

Assays for cytokine production and/or proliferation of spleen cells, lymph node cells, thymocytes, or peripheral blood mononuclear cells (PBMCs) include, without limitation, those described in: Polyclonal T cell stimulation, Kruisbeek and Shevach, In Current Protocols in Immunology, Coligan et al. eds. Vol 1 pp. 3.12.1-3.12.14, John Wiley and Sons, Toronto. 1994; and Schreiber, Id. at Vol 1 pp. 6.8.1–6.8.8.

Assays for Modulation of Smooth Muscle Cell Activity, Athreosclerosis and Vascular Injury, include contacting an appropriate animal model with a nectin-1, nectin-2, nectin-3 and/or nectin-4 polypeptide or soluble fragment thereof either before, after, or simultaneously with vascular injury and determining the progression of vascular injury in the animal compared to a control that is not treated with a nectin polypeptide.

Assays for proliferation and differentiation of hematopoietic and lymphopoietic cells include, without limitation, those described in: Measurement of Human and Murine Interleukin 2 and Interleukin 4, Bottomly et al. In Current Protocols in Immunology. Coligan et al. eds. Vol 1 pp. 6.3.1–6.3.12, John Wiley and Sons, Toronto. 1991; Measurement of mouse and human interleukin 6, Nordan, Id. at pp. 6.6.1–6.6.5; Measurement of human Interleukin 11, Bennett et al. Id. at pp. 6.15.1; Measurement of mouse and human Interleukin 9, Ciarletta et al. Id. at pp. 6.13.1; deVries et al., J. Exp. Med. 173:1205–1211, 1991; Moreau et al., Nature 336:690, 1988; Greenberger et al., Proc. Natl. Acad. Sci. U.S.A. 80:2931, 1983; Smith et al., Proc. Natl. Acad. Sci. U.S.A. 83:1857, 1986.

Assays for T-cell clone responses to antigens (which will identify, e.g., polypeptides that affect APC-T cell interactions as well as direct T-cell effects by measuring proliferation and cytokine production) include, without limitation, those described in: Current Protocols in Immunology, Coligan, et al. eds., Pub. Greene Publishing Associates and Wiley-Interscience (Chapter 3; Chapter 6; Chapter 7); Weinberger et al., Proc. Natl. Acad. Sci. USA 77:6091, 1980; Weinberger et al., Eur. J. Immun. 11:405, 1981; Takai et al., J. Immunol. 137:3494, 1986; Takai et al., J. Immunol. 140:508, 1988.

Mixed lymphocyte reaction (MLR) assays (which will identify, e.g., polypeptides that generate predominantly Th1 and CTL responses) include, without limitation, those described in: Current Protocols in Immunology, Coligan et al. eds., Pub. Greene Publishing Associates and Wiley-Interscience (Chapter 3, 3.1–3.19; Chapter 7); Takai et al., J. Immunol. 137:3494, 1986; Takai et al., J. Immunol. 140:508, 1988; Bertagnolli et al., J. Immunol. 149:3778, 1992.

Dendritic cell-dependent assays (which will identify, e.g., polypeptides expressed by dendritic cells that activate naive T-cells) include, without limitation, those described in: Guery et al., J. Immunol. 134:536, 1995; Inaba et al., J. Exper. Med. 173:549, 1991; Macatonia et al., J. Immunol. 154:5071, 1995; Porgador et al. J. Exper. Med. 182:255, 1995; Nair et al., J. Virol. 67:4062, 1993; Huang et al., Science 264:961, 1994; Macatonia et al., J. Exper. Med. 169:1255, 1989; Bhardwaj et al., J. Clin. Invest. 94:797, 1994; and Inaba et al., J. Exper. Med. 172:631,1990.

Assays for lymphocyte survival/apoptosis (which will identify, e.g., polypeptides that prevent apoptosis after superantigen induction and polypeptides that regulate lymphocyte homeostasis) include, without limitation, those described in: Darzynkiewicz et al., Cytometry 13:795, 1992; Gorczyca et al., Leukemia 7:659, 1993; Gorczyca et al., Cancer Research 53:1945, 1993; Itoh et al., Cell 66:233, 1991; Zacharchuk, J. Immunol. 145:4037, 1990; Zamai et al., Cytometry 14:891, 1993; Gorczyca et al., Int. J. Oncol. 1:639, 1992.

Assays for polypeptides that influence early steps of T-cell commitment and development include, without limitation, those described in: Antica et al., Blood 84:111, 1994; Fine et al., Cell. Immunol. 155:111, 1994; Galy et al., Blood 85:2770, 1995; Toki et al., Proc. Nat. Acad Sci. USA 88:7548, 1991.

Assays for embryonic stem cell differentiation (which will identify, e.g., polypeptides that influence embryonic differentiation hematopoiesis) include, without limitation, those described in: Johansson et al. Cell. Biol. 15:141, 1995; Keller et al., Mol. Cell. Biol. 13:473, 1993; McClanahan et al., Blood 81:2903, 1993.

Assays for stem cell survival and differentiation (which will identify, e.g., polypeptides that regulate lympho-hematopoiesis) include, without limitation, those described in: Methylcellulose colony forming assays, Freshney, M. G. In Culture of Hematopoietic Cells. R. I. Freshney, et al. eds. Vol pp. $^{2}$65-$^{2}$68, Wiley-Liss, Inc., New York, N.Y. 1994; Primitive hematopoietic colony forming cells with high proliferative potential, McNiece et al., Id. at Vol pp. 23–39; Cobblestone area forming cell assay, Ploemacher, Id. at Vol pp. 1–21; Long term bone marrow cultures in the presence of stromal cells, Spooncer, et al. Id. at Vol pp. 163–179; Long term culture initiating cell assay, Sutherland, Id. at Vol pp. 139–162; Hirayama et al., Proc. Natl. Acad. Sci. USA 89:5907, 1992; Neben et al., Exp. Hematol. 22:353, 1994.

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium). Assays for wound healing activity include, without limitation, those described in: Winter, Epidermal Wound Healing, pps. 71–112 (Maibach and Rovee, eds.), Year Book Medical Publishers, Inc., Chicago, as modified by Eaglstein and Mertz, J. Invest. Dermatol 71:382 (1978).

Assays for activin/inhibin activity include, without limitation, those described in: Vale et al., Endocrinol. 91:562, 1972; Ling et al., Nature 321:779, 1986; Vale et al., Nature 321:776, 1986; Mason et al., Nature 318:659, 1985; Forage et al., Proc. Natl. Acad. Sci. USA 83:3091, 1986.

Assays for cell movement and adhesion include, without limitation, those described in: Current Protocols in Immunology, Coligan et al. eds., Pub. Greene Publishing Associates and Wiley-Interscience (Chapter 6, 6.12.1-6.12.28); Taub et al. J. Clin. Invest. 95:1370, 1995; Lind et al. APMIS 103:140, 1995; Muller et al. Eur. J. Immunol. 25: 1744; Gruber et al. J. Immunol. 152:5860, 1994; Johnston et al. J. Immunol. 153: 1762, 1994.

Assay for hemostatic and thrombolytic activity includes, without limitation, those described in: Linet et al., J. Clin. Pharmacol. 26:131, 1986; Burdick et al., Thrombosis Res. 45:413,1987; Humphrey et al., Fibrinolysis 5:71 (1991); Schaub, Prostaglandins 35:467, 1988.

Assays for receptor-ligand activity include, without limitation, those described in: Current Protocols in Immunology, Coligan et al., eds., Pub. Greene Publishing Associates and Wiley-Interscience (Chapter 7, 7.28.1-7.28.22); Takai et al., Proc. Natl. Acad. Sci. USA 84:6864, 1987; Bierer et al., J. Exp. Med. 168:1145, 1988; Rosenstein et al., J. Exp. Med. 169:149, 1989; Stoltenborg et al., J. Immunol. Methods 175:59, 1994; Stitt et al., Cell 80:661, 1995.

Assays for cadherin adhesive and invasive suppressor activity include, without limitation, those described in: Hortsch et al. J. Biol. Chem. 270(32):18809, 1995; Miyaki et al. Oncogene 11:2547, 1995; Ozawa et al. Cell 63:1033, 1990.

Methods of Screening for Binding Partners. The nectin-3 ($\alpha$, $\beta$, or $\gamma$) polypeptides and/or nectin-4 polypeptides of the invention each can be used alone or in combination as reagents in methods to screen for or identify binding partners. For example, the nectin-3 polypeptides can be attached to a solid support material and may bind to their binding partners in a manner similar to affinity chromatography. As one example, chromatography columns containing functional groups that will react with functional groups on amino acid side chains of polypeptides are available (Pharmacia Biotech, Inc., Piscataway, N.J.). In an alternative, a nectin-3 (or nectin-4)-polypeptide/Fc fusion construct (as discussed above) is attached to Polypeptide A- or Polypeptide G-containing chromatography columns through interaction with the Fc moiety. The nectin-3 and -4 polypeptides also find use in identifying cells that express a binding partner, such as nectin-1, on the cell surface. For example, magnetic microspheres can be coated with the polypeptides and held in an incubation vessel through a magnetic field. Suspensions of cell mixtures containing potential binding-partner-expressing cells are contacted with the solid phase having the polypeptides thereon. Cells expressing the binding partner on the cell surface bind to the fixed polypeptides, and unbound cells are washed away. Alternatively, a nectin polypeptide of the invention can be conjugated to a detectable moiety, then incubated with cells to be tested for binding partner expression. After incubation, unbound-labeled matter is removed and the presence or absence of the detectable moiety on the cells is determined. In a further alternative, mixtures of cells suspected of expressing the binding partner are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.*, 10D:239, 1986). Washing to remove unbound material, and the release of the bound cells, are performed using conventional methods. In some instances, the above methods for screening for or identifying binding partners may also be used or modified to isolate or purify such binding partner molecules or cells expressing them.

Measuring Biological Activity. Polypeptides also find use in measuring the biological activity of nectin-binding polypeptides in terms of their binding affinity. The polypeptides thus can be employed by those conducting "quality assurance" studies, e.g., to monitor shelf life and stability of polypeptide under different conditions. For example, the polypeptides can be employed in a binding affinity study to measure the biological activity of a binding partner polypeptide (e.g., nectin-1 or nectin-2) that has been stored at different temperatures, or produced in different cell types. The polypeptides also can be used to determine whether biological activity is retained after modification of a binding partner polypeptide (e.g., chemical modification, truncation, mutation, and the like). The binding affinity of the modified polypeptide is compared to that of an unmodified binding polypeptide to detect any adverse impact of the modifications on its biological activity.

Carriers and Delivery Agents. The polypeptides also find use as carriers for delivering agents attached thereto to cells bearing identified binding partners. The polypeptides thus can be used to deliver diagnostic or therapeutic agents to such cells (or to other cell types found to express binding partners, such as nectin-1 or -2, on the cell surface) in in vitro or in vivo procedures. Detectable (diagnostic) and therapeutic agents that can be attached to a polypeptide include, but are not limited to, toxins, other cytotoxic agents, drugs, radionuclides, chromophores, enzymes that catalyze a colorimetric or fluorometric reaction, and the like, with the particular agent being chosen according to the intended application. Examples of toxins are ricin, abrin, diphtheria toxin, *Pseudomonas aeruginosa* exotoxin A, ribosomal inactivating polypeptides, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{67}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu. Such agents can be attached to a polypeptide by any suitable conventional procedure. The polypeptide comprises functional groups on amino acid side chains that can be reacted with functional groups on a desired agent to form covalent bonds, for example. Alternatively, the polypeptide or agent can be derivatized to generate or attach a desired reactive functional group. The derivatization can involve attachment of one of the bifunctional coupling reagents available for attaching various molecules to polypeptides (Pierce Chemical Company, Rockford, Ill.). A number of techniques for radiolabeling polypeptides are known. Radionuclide metals can be attached to polypeptides by using a suitable bifunctional chelating agent, for example. The conjugates are administered or otherwise employed in an amount appropriate for the particular application.

The nectin-3 and nectin-4 polypeptides, fragments (including soluble fragments), variants, antibodies, and binding partners of the invention are useful for treating medical conditions and diseases including, but not limited to, conditions related to cell adhesion, cell migration, or herpesvirus receptor activity. The therapeutic molecule or molecules to be used will depend on the etiology of the condition to be treated and the biological pathways involved. Variants, fragments, and binding partners of nectin-3 and/or nectin-4 polypeptides may have effects similar to or different from native nectin-3 and nectin-4 polypeptides. For example, solNectin-3 and/or solNectin-4 can be used to inhibit cell adhesion/migration activity and may be selected for treatment of conditions involving cell adhesion or cell-cell interactions. A soluble fragment of nectin-3 or nectin-4, for example, may itself act as an effective dominant negative modulator of that activity. Therefore, in the following paragraphs "nectin polypeptides" includes full-length, mature forms, and fragments of nectin-3 or nectin-4 polypeptides. As used herein, a "soluble fragments" specifically includes, among others, soluble fragments of nectin-3 or nectin-4 polypeptides, more preferably soluble fragments of the extracellular domain of a nectin-3 or a nectin-4 polypeptide, and most preferably fusion constructs comprising a soluble extracellular domain of nectin-3 and/or nectin-4 linked to, for example, an Fc polypeptide. It is understood that a specific molecule or molecules can be selected from those provided as embodiments of the invention by individuals of skill in the art, according to the biological and therapeutic considerations described herein.

The disclosed nectin polypeptides or soluble fragments, compositions and combination therapies described herein are useful in medicines for treating bacterial, viral or protozoal infections, and complications resulting therefrom. One such disease is *Mycoplasma pneumonia*. In addition, provided herein is the use of nectin polypeptides or soluble fragments to treat AIDS and related conditions. Provided herein is the use of nectin polypeptides or soluble fragments for treating protozoal diseases, including malaria and schistosomiasis. Additionally provided is the use of nectin polypeptides or soluble fragments to treat erythema nodosum leprosum; bacterial or viral meningitis; tuberculosis, including pulmonary tuberculosis; and pneumonitis secondary to a bacterial or viral infection. The nectin polypeptides or soluble fragments of the invention can also be used to prepare a therapeutic composition for treating conditions caused by Herpes viruses, such as herpetic stromal keratitis, corneal lesions, and virus-induced corneal disorders. In addition, nectin polypeptides or soluble fragments can be used in treating human papillomavirus infections. The nectin polypeptides or soluble fragments of the invention are used to prepare therapeutic compositions to treat influenza.

Cardiovascular disorders are treatable with the disclosed nectin polypeptides or soluble fragments, pharmaceutical compositions or combination therapies, including aortic aneurisms; arteritis; vascular occlusion, including cerebral artery occlusion; complications of coronary by-pass surgery; ischemia/reperfusion injury; heart disease, including atherosclerotic heart disease, myocarditis, including chronic autoimmune myocarditis and viral myocarditis; heart failure, including chronic heart failure, cachexia of heart failure; myocardial infarction; restenosis after surgery; silent myocardial ischemia.

Provided also are methods for using nectin polypeptides or soluble fragments, compositions or combination therapies to treat various disorders of the endocrine system. For example, the nectin polypeptides or soluble fragments are used to treat juvenile onset diabetes (both autoimmune and insulin-dependent types) and also to treat mature onset diabetes (both non-insulin dependent and obesity-mediated), as well as secondary conditions associated with diabetes (e.g., diabetic retinopathy, kidney transplant rejection, obesity-mediated insulin resistance, and renal failure).

Conditions of the gastrointestinal system also are treatable with nectin polypeptides or soluble fragments, compositions or combination therapies, including coeliac disease; Crohn's disease; ulcerative colitis; idiopathic gastroparesis; pancreatitis, including chronic pancreatitis and lung injury associated with acute pancreatitis; and ulcers, including gastric and duodenal ulcers.

Included also are methods for using the nectin polypeptides or soluble fragments, compositions, or combination therapies for treating disorders of the genitourinary system, such as glomerulonephritis, including autoimmune, glomerulonephritis due to exposure to toxins or glomerulonephritis secondary to infections with haemolytic streptococci or other infectious agents.

Also provided herein are methods for using nectin polypeptides or soluble fragments, compositions, or combination therapies to treat various hematologic and oncologic disorders. For example, nectin polypeptides or soluble fragments are used to treat various forms of cancer, including leukemia, including acute myelogenous leukemia, chronic or acute lymphoblastic leukemia and hairy cell leukemia; Epstein-Barr virus-positive nasopharyngeal carcinoma, glioma, colon, stomach, prostate, renal cell, cervical and ovarian cancers, lung cancer (SCLC and NSCLC). Various lymphoproliferative disorders also are treatable with the disclosed nectin polypeptides or soluble fragments, antagonists, compositions, or combination therapies. These include, but are not limited to, autoimmune lymphoproliferative syndrome (ALPS), peripheral T-cell lymphoma, small lymphocytic lymphoma, mantle cell lymphoma, follicular lymphoma, Burkitt's lymphoma, Epstein-Barr virus-positive T cell lymphoma, histiocytic lymphoma, Hodgkin's disease, diffuse aggressive lymphoma, acute lymphatic leukemias, T-γ-lymphoproliferative disease, cutaneous B cell lymphoma, cutaneous T cell lymphoma (i.e., mycosis fungoides) and Sézary syndrome.

Additional diseases treatable with the subject nectin polypeptides or soluble fragments, compositions, or combination therapies are solid tumors, including sarcoma, osteosarcoma, and carcinoma, such as adenocarcinoma (e.g., breast cancer) and squamous cell carcinoma. Other malignancies that can be treated with the subject compounds, compositions and combination therapies, include multiple myeloma.

Combination therapies for treating disorders associated with angiogenesis include a combination of at least one anti-angiogenic nectin polypeptide or soluble fragment (e.g., solNectin-3 and/or solNectin-4) and one or more other anti-angiogenesis factors or other therapeutic agent(s). The additional therapeutic agent(s) may be administered prior to, concurrently with, or following the administration of the nectin polypeptide or soluble fragment of the invention. The use of more than one therapeutic agent is particularly advantageous when the subject being treated has a solid tumor. In some embodiments of the invention, the treatment further comprises treating the subject with radiation. Radiation, including brachytherapy and teletherapy, may be administered prior to, concurrently with, or following the administration of a nectin polypeptide or soluble fragment and/or additional therapeutic agent(s).

In some embodiments, the method includes the administration of, in addition to a nectin polypeptide or soluble fragment, one or more therapeutics selected from the group consisting of alkylating agents, antimetabolites, vinca alkaloids and other plant-derived chemotherapeutics, antitumor antibiotics, antitumor enzymes, topoisomerase inhibitors, platinum analogs, adrenocortical suppressants, hormones and antihormones, antibodies, immunotherapeutics, radiotherapeutics, and biological response modifiers.

In some embodiments, the method includes administration of, in addition to a nectin polypeptide or soluble fragment, one or more therapeutics selected from the group consisting of cisplatin, cyclophosphamide, mechloretamine, melphalan, bleomycin, carboplatin, fluorouracil, 5-fluorodeoxyuridine, methotrexate, taxol, asparaginase, vincristine, and vinblastine, lymphokines and cytokines such as interleukins, interferons ($\alpha,\beta$. or $\delta$.) and TNF, chlorambucil, busulfan, carmustine, lomustine, semustine, streptozocin, dacarbazine, cytarabine, mercaptopurine, thioguanine, vindesine, etoposide, teniposide, dactinomycin, daunorubicin, doxorubicin, bleomycin, plicamycin, mitomycin, L-asparaginase, hydroxyurea, methylhydrazine, mitotane, tamoxifen, fluoxymesterone, IL-8 inhibitors, angiostatin, endostatin, kringle 5, angiopoietin-2 or other antagonists of angiopoietin-1, antagonists of platelet-activating factor, antagonists of basic fibroblast growth factor, and COX-2 inhibitors.

In some embodiments, the method includes administration of, in addition to a nectin polypeptide or soluble fragment, one or more therapeutic polypeptides, including soluble forms thereof, selected from the group consisting of Flt3 ligand (see, U.S. Pat. No. 5,554,512), CD40 ligand (see, U.S. Pat. No. 5,716,805), IL-2, IL-12, 4-1BB ligand (see, U.S. Pat. No. 5,674,704), anti-4-1BB antibodies, TRAIL (see, U.S. Pat. No. 5,763,223), TNF antagonists and TNF receptor (TNFR) antagonists including TNFR/Fc, Tek antagonists (see, PCT Publication No. WO 00/75323), TWEAK antagonists and TWEAK-R (see, U.S. Ser. No. 60/172,878 and 601203,347, and Feng et al., Am. J. Pathol. 156(4):1253) antagonists including TWEAK-R/Fc, VEGF antagonists including anti-VEGF antibodies, VEGF receptor (including VEGF-R1 and VEGF-R2, also known as Flt1 and Flk1 or KDR) antagonists, CD148 (also referred to as DEP-1, ECRTβ, and PTPRJ, see Takahashi et al., J. Am. Soc. Nephrol. 10:2135–45, 1999; and PCT Publication No. WO 00/15258) binding proteins.

In some embodiments, a nectin polypeptide or soluble fragment is used as a component of, or in combination with, "metronomic therapy," such as that described by Browder et al. and Klement et al. (Cancer Research 60:1878, 2000; J. Clin. Invest. 105(8):R15, 2000) (see also Barinaga, Science 288:245, 2000). The use of an anti-angiogenic in combination with a nectin polypeptide or soluble fragment of the invention reduces the vascularization that nourishes a tumor tissue.

Other conditions treatable by the disclosed nectin polypeptides or soluble fragments, compositions, and combination therapies include those resulting from injuries to the head or spinal cord, and including subdural hematoma due to trauma to the head.

The disclosed nectin polypeptides or soluble fragments, compositions and combination therapies can be used to treat conditions of the liver such as hepatitis, including alcohol, drug-induced or viral hepatitis, hepatitis A, B and C, sclerosing cholangitis and inflammation of the liver.

In other aspects of the invention, the nectin polypeptides or soluble fragments, compositions, and combination therapies are used to treat pulmonary disorders including chronic obstructive pulmonary disease (COPD) associated with chronic bronchitis or emphysema; fibrotic lung diseases, such as cystic fibrosis, idiopathic pulmonary fibrosis and radiation-induced pulmonary fibrosis; pulmonary sarcoidosis; and allergies, including allergic rhinitis, contact dermatitis, atopic dermatitis and asthma.

Other embodiments provide methods for using the disclosed nectin polypeptides or soluble fragments, compositions, or combination therapies to treat a variety of rheumatic disorders. These include adult and juvenile rheumatoid arthritis; systemic lupus erythematosus; gout; osteoarthritis; polymyalgia rheumatica; seronegative spondylarthropathies (e.g., ankylosing spondylitis); and Reiter's disease. The nectin polypeptides or soluble fragments, compositions, and combination therapies can be used to treat psoriatic arthritis and chronic Lyme arthritis, as well as Still's disease and uveitis associated with rheumatoid arthritis. In addition, the compounds, compositions and combination therapies of the invention can be used to treat disorders resulting in inflammation of muscle tissue (e.g., dermatomyositis and polymyositis).

The nectin polypeptides or soluble fragments, compositions and combination therapies of the invention may be used to inhibit hypertrophic scarring, The nectin polypeptides or soluble fragments of the invention may be administered alone or concurrently with other agents that inhibit hypertrophic scarring, such as inhibitors of TNFα.

The nectin polypeptides or soluble fragments, compositions, and combination therapies of the invention are useful for treating primary and secondary amyloidosis. Such conditions include, for example, Alzheimer's disease; secondary reactive amyloidosis; Down's syndrome; and dialysis-associated amyloidosis.

Disorders associated with transplantation also are treatable with the disclosed nectin polypeptides or soluble fragments, compositions, or combination therapies, such as graft-versus-host disease, and complications resulting from solid organ transplantation, including transplantation of heart, liver, lung, skin, kidney or other organs.

Ocular disorders also are treatable with the disclosed nectin polypeptides or soluble fragments, compositions, or combination therapies including, for example, rhegmatogenous retinal detachment, inflammatory eye disease, diabetic retinopathy, and macular degeneration.

The nectin polypeptides or soluble fragments of the invention and the disclosed compositions and combination therapies also are useful for treating disorders that affect the female reproductive system. Examples include, but are not limited to, multiple implant failure/infertility; fetal loss syndrome or IV embryo loss (spontaneous abortion); preeclamptic pregnancies or eclampsia; and endometriosis.

Disorders involving the skin or mucous membranes also are treatable using the disclosed nectin polypeptides or soluble fragments, compositions, or combination therapies. Such disorders include acantholytic diseases, including Darier's disease, keratosis follicularis and pemphigus vulgaris. Also treatable with the subject nectin polypeptides or soluble fragments, compositions and combination therapies are acne; acne rosacea; alopecia areata; aphthous stomatitis; bullous pemphigoid; burns; eczema; erythema, including erythema multiforme and erythema multiforme bullosum (Stevens-Johnson syndrome); inflammatory skin disease; lichen planus; linear IgA bullous disease (chronic bullous dermatosis of childhood); loss of skin elasticity; mucosal surface ulcers; neutrophilic dermatitis (Sweet's syndrome); pityriasis rubra pilaris; psoriasis; pyoderma gangrenosum; and toxic epidermal necrolysis.

This invention provides compounds, compositions, and methods for treating a subject, preferably a mammalian subject, and most preferably a human subject, who is suffering from a medical disorder, a disorder or disease associated with nectin-3α, β, or γ, or nectin-4, in some instances the disease or disorder may be associated with other nectins such as nectin-1 and nectin-2. Such nectin-associated disorders include conditions caused (directly or indirectly) or exacerbated by binding between nectin-3 and/or nectin-4 polypeptide and a binding partner (e.g., nectin-1 or -2). For example, afadin (AF-6), which has been shown to alter RAS signaling, and SH3/PDZ have been shown to interact with nectins via their PDZ binding domain by bridging the nectin's interaction with ponsin. Both afadin and ponsin have been shown to play a role in activation through RTK receptors, most notably the insulin receptor and the bidirectional ephrin-ephrin receptor system. Alpha-catenin has been shown to bind to the nectins via afadin. Alpha-catenin has been implicated as playing a role in signaling through the RAS-MAPK pathway in skin in the absence of altering the beta-catenin signaling pathway. RAS-MAPK is activated in migrating endothelial cells via RTK interaction with their ligands (e.g., VEGF, ANG, EGF, and beta-FGF) that promote angiogenesis. Adherens junction recruitment of RTKs greatly increases their signaling ability. This has been demonstrated in particular for relevant RTKs such as the EGFR, the EPHRs, and the VEGFRs. Accordingly, RAS-MAPK pathway is activated in stimulated cells and that nectin-1 binding of solNectin3-Fc (or solNectin4-Fc) leads to inhibition of this pathway and thus can modulate a hyperproliferative state.

The terms "illness," "disease," "medical condition," "abnormal condition," and "medical disorder," and the like are used interchangeably. The terms "treat", "treating", and "treatment" used herein include curative, preventative (e.g., prophylactic) and palliative or ameliorative treatment. For such therapeutic uses, nectin-3 and/or nectin-4 polypeptides and soluble fragments, nectin-3 and/or nectin-4 polynucleotides, and/or agonists or antagonists of the nectin-3 and nectin-4 polypeptide (e.g., an antibody to nectin-3 or nectin-4) can be administered to the subject through known methods of administration. Compositions of the invention can contain a polypeptide in any form described herein, such as native polypeptides, variants, derivatives, oligomers, and biologically active fragments. In particular embodiments, the composition comprises a soluble polypeptide or an oligomer comprising soluble nectin-3 and/or soluble nectin-4 polypeptide.

In practicing a method of treatment or use of the invention, a therapeutically effective amount of a therapeutic agent of the invention is administered to a subject having a condition to be treated, preferably to treat or ameliorate diseases associated with the activity of a nectin-3 and/or nectin-4 polypeptide. "Therapeutic agent" includes without limitation any of the nectin-3 or nectin-4 polypeptides, fragments, and variants; nectin-3 or nectin-4 polynucleotides, fragments, and variants; soluble forms of the nectin-3 or nectin-4 polypeptides; antibodies to a nectin-3 or nectin-4 polypeptide or fragment; nectin-3 or nectin-4 polypeptide binding partners (e.g., nectin-1 and nectin-2); complexes formed from the nectin-3 or 4 polypeptides, fragments, variants, and binding partners, and the like. As used herein, the term "therapeutically effective amount" means the total amount of each therapeutic agent or other active component of the pharmaceutical composition or method that is sufficient to show a meaningful subject benefit, e.g., treatment, healing, prevention or amelioration of the relevant medical condition, or an increase in rate of treatment, healing, prevention or amelioration of such conditions. When applied to an individual therapeutic agent or active ingredient, administered alone, the term refers to that ingredient alone. When applied to a combination, the term refers to combined amounts of the ingredients that result in the therapeutic effect, whether administered in combination, serially or simultaneously. As used herein, the phrase "administering a therapeutically effective amount" of a therapeutic agent means that the subject is treated with the therapeutic agent in an amount and for a time sufficient to induce an improvement, and preferably a sustained improvement, in at least one indicator that reflects the severity of the disorder. An improvement is considered "sustained" if the subject exhibits the improvement on at least two occasions separated by one or more weeks. The degree of improvement is determined based on signs or symptoms, and determinations may also employ questionnaires that are administered to a human subject, such as quality-of-life questionnaires. Various indicators that reflect the extent of the subject's illness may be assessed for determining whether the amount and time of the treatment is sufficient. The baseline value for the chosen indicator or indicators is established by examination of the subject prior to administration of the first dose of the therapeutic agent. Preferably, the baseline examination is done within about 60 days of administering the first dose. If the therapeutic agent is being administered to treat acute symptoms, the first dose is administered as soon as practically possible after the injury has occurred. Improvement is induced by administering therapeutic agents such as nectin-3 polypeptides, nectin-4 polypeptides, or soluble fragments thereof until the subject manifests an improvement over baseline for the chosen indicator or indicators. In treating chronic conditions, this degree of improvement is obtained by repeatedly administering this therapeutic composition over a period of at least a month or more, e.g., for one, two, or three months or longer, or indefinitely. A period of one to six weeks, or even a single dose, often is sufficient for treating acute conditions. For injuries or acute conditions, a single dose may be sufficient. Although the extent of the subject's illness after treatment may appear improved according to one or more indicators, treatment may be continued indefinitely at the same level or at a reduced dose or frequency. Once treatment has been reduced or discontinued, it later may be resumed at the original level if symptoms should reappear.

One skilled in the pertinent art will recognize that suitable dosages will vary, depending upon such factors as the nature and severity of the disorder to be treated, the subject's body weight, age, general condition, and prior illnesses and/or treatments, and the route of administration. Preliminary doses can be determined according to animal tests, and the scaling of dosages for human administration is performed according to art-accepted practices such as standard dosing trials. For example, the therapeutically effective dose can be estimated initially from cell culture assays. The dosage will depend on the specific activity of the agent and can be readily determined by routine experimentation. A dose may be formulated in animal models to achieve a circulating plasma concentration range that includes the $IC_{50}$ (i.e., the concentration of test agent that achieves a half-maximal inhibition of symptoms) as determined in cell culture, while minimizing toxicities. Such information can be used to more accurately determine useful doses in humans. Ultimately, the attending physician will decide the amount of the polypeptide (e.g., solNectin3 or solNectin4) or antibody of the invention to treat each individual subject. Doses of the polypeptide, soluble fragment, or antibody of the invention may be administered until the optimal therapeutic effect is obtained for the subject. It is contemplated that the various pharmaceutical compositions used to practice the method of the invention should contain about 0.01 ng to about 100 mg (preferably about 0.1 ng to about 10 mg, more preferably about 0.1 microgram to about 1 mg) of polypeptide, soluble fragment or antibody of the invention per kg body weight. In one embodiment of the invention, nectin polypeptides or soluble fragments are administered one time per week to treat the various medical disorders disclosed herein, in another embodiment is administered at least two times per week, and in another embodiment is administered at least three times per week. If injected, the effective amount of nectin polypeptides or soluble fragments per adult dose ranges from 1–20 $mg/m^2$, and preferably is about 5–12 $mg/m^2$. Alternatively, a flat dose may be administered whose amount may range from 5–100 mg/dose. Exemplary dose ranges for a flat dose to be administered by subcutaneous injection are 5–25 mg/dose, 25–50 mg/dose and 50–100 mg/dose. In one embodiment, the various indications described herein are treated by administering a preparation acceptable for injection containing nectin polypeptides or soluble fragments at 25 mg/dose, or alternatively, containing 50 mg per dose. The 25 mg or 50 mg dose may be administered repeatedly, particularly for chronic conditions. If a route of administration other than injection is used, the dose is appropriately adjusted in accord with standard medical practices. In many instances, an improvement in a subject's condition will be obtained by injecting a dose of about 25 mg of nectin polypeptides or soluble fragments one to three times per week over a period of at least three weeks, or a dose of 50 mg of nectin polypeptides or soluble fragments one or two times per week for at least three weeks, though treatment for longer periods may be necessary to induce the desired degree of improvement. For incurable chronic conditions, the regimen may be continued indefinitely, with adjustments being made to dose and frequency if such are deemed necessary by the subject's physician. The foregoing doses are examples for an adult subject who is a person who is 18 years of age or older. For pediatric subjects (age 4–17), a suitable regimen involves the subcutaneous injection of 0.4 mg/kg, up to a maximum dose of 25 mg of nectin polypeptides or soluble fragments, administered by subcutaneous injection one or more times per week. If an antibody against a nectin polypeptide is used as the nectin polypeptide antagonist, a preferred dose range is 0.1 to 20 mg/kg, and more preferably is 1–10 mg/kg. Another preferred dose range for an anti-nectin polypeptide antibody is 0.75 to 7.5 mg/kg of body weight. Humanized antibodies are preferred. Such antibodies may be injected or administered intravenously.

Compositions comprising an effective amount of a nectin polypeptide or soluble fragment (e.g., a solNectin-3, a solNectin-4, or oligomer thereof) of the invention (from whatever source derived, e.g., recombinant and non-recombinant sources), in combination with other components such as a physiologically acceptable diluent, carrier, or excipient, are provided herein. The term "pharmaceutically acceptable" means a non-toxic material that does not interfere with the effectiveness of the biological activity of the active ingredient(s). Formulations suitable for administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa. In addition, such compositions can be complexed with polyethylene glycol (PEG), metal ions, or incorporated into polymeric compounds such as polyacetic acid, polyglycolic acid, hydrogels, dextran, and the like, or incorporated into liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations are within the level of skill in the art, as disclosed, for example, in U.S. Pat. Nos. 4,235,871; 4,501,728; 4,837,028; and 4,737,323. Such compositions will influence the physical state, solubility, stability, rate of in vivo release, or rate of in vivo clearance, and are thus chosen according to the intended application, so that the characteristics of the carrier will depend on the selected route of administration. In a preferred embodiment of the invention, sustained-release forms of nectin polypeptides or soluble fragments are used. Sustained-release forms suitable for use in the disclosed methods include, but are not limited to, nectin polypeptides or soluble fragments that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

A nectin polypeptide of the invention (including soluble fragments) may be active in multimers (e.g., heterodimers or homodimers) or complexes with itself or other polypeptides (e.g., nectin-1, nectin-2, nectin-3 complexed with nectin-4, and the like). As a result, pharmaceutical compositions of the invention may comprise a polypeptide of the invention in such multimeric or complexed form. Such compositions contemplate the preparation of soluble fragments of nectin-1, nectin-2, nectin-3, and nectin-4 in any combination thereof as oligomers (e.g., nectin-1-Fc, nectin-2-Fc, nectin-3-Fc, nectin-4-Fc, solNectin3-Fc, solNectin4-Fc, and the like). The pharmaceutical composition of the invention may be in the form of a complex of the polypeptide(s) of invention along with polypeptide or peptide antigens. The invention further includes the administration of nectin polypeptides or soluble fragments concurrently with one or more other drugs that are administered to the same subject, each drug being administered according to a regimen suitable for that therapeutic composition. "Concurrent administration" encompasses simultaneous or sequential treatment with the components of the combination, as well as regimens in which the drugs are alternated, or wherein one component is administered long-term and the other(s) are administered intermittently. Components may be administered in the same or in separate compositions, and by the same or different routes of administration. Examples of components that may be included in the pharmaceutical composition of the invention are: cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-17, IL-18, IFN, TNF0, TNF1, TNF2, G-CSF, Meg-CSF, thrombopoietin stem cell factor, and erythropoietin. The pharmaceutical composition may further contain other agents that either enhance the activity of the polypeptide or compliment its activity or use in treatment. Such additional factors and/or agents may be included in the pharmaceutical composition to produce a synergistic effect with nectin polypeptides or soluble fragments of the invention, or to minimize side effects. Conversely, a nectin polypeptide or soluble fragment of the invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent. Examples of drugs to be administered concurrently include, but are not limited to, antivirals, antibiotics, analgesics, corticosteroids, antagonists of inflammatory cytokines, non-steroidal anti-inflammatories, pentoxifylline, thalidomide, and disease-modifying anti-rheumatic drugs (DMARDs) such as azathioprine, cyclophosphamide, cyclosporine, hydroxychloroquine sulfate, methotrexate, leflunomide, minocycline, penicillamine, sulfasalazine and gold compounds such as oral gold, gold sodium thiomalate, and aurothioglucose. Additionally, nectin polypeptides or soluble fragments of the invention may be combined with a second nectin polypeptide/antagonist, including an antibody against a nectin polypeptide, or a nectin polypeptide-derived peptide that acts as a competitive inhibitor of a native nectin polypeptide.

Any efficacious route of administration may be used to therapeutically administer nectin polypeptides or soluble fragments of the invention, including those compositions comprising polynucleotides. Parenteral administration includes injection, for example, via intra-articular, intravenous, intramuscular, intralesional, intraperitoneal, or subcutaneous routes by bolus injection or by continuous infusion., and also includes localized administration, e.g., at a site of disease or injury. Other suitable means of administration include sustained release from implants; aerosol inhalation and/or insufflation; eyedrops; vaginal or rectal suppositories; buccal preparations; oral preparations, including pills, syrups, lozenges or chewing gum; and topical preparations such as lotions, gels, sprays, ointments or other suitable techniques. Alternatively, nectin polypeptides or soluble fragments of the invention may be administered by implanting recombinant or host cells that express the polypeptide or soluble fragment. Cells may also be cultured ex vivo in the presence of polypeptides of the invention in order to proliferate or to produce a desired effect on the activity in such cells. Treated cells can then be introduced in vivo for therapeutic purposes. In another embodiment, the subject's own cells are induced to produce nectin polypeptides or soluble fragments of the invention by transfection in vivo or ex vivo with DNA that encodes a nectin polypeptide or soluble fragment of the invention. The DNA can be introduced into the subject's cells, for example, by injecting naked DNA or liposome-encapsulated DNA that encodes a nectin polypeptide or soluble fragment, or by other means of transfection. Polynucleotides of the invention may also be administered to subjects by other known methods for introduction of nucleic acids into a cell or organism (including, without limitation, in the form of viral vectors or naked DNA). When nectin polypeptides or soluble fragments of the invention are administered in combination with one or more other biologically active compounds, these may be administered by the same or by different routes, and may be administered simultaneously, separately or sequentially.

When a therapeutically effective amount of nectin polypeptide or soluble fragment of the invention is administered orally, the polypeptide will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% a polypeptide or soluble fragment of the invention, and preferably from about 25 to 90% a polypeptide of soluble fragment of the invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of polypeptide or soluble fragment of the invention, and preferably from about 1 to 50% polypeptide of the invention.

When a therapeutically effective amount of a nectin polypeptide or soluble fragment of the invention is administered by intravenous, cutaneous or subcutaneous injection, a nectin polypeptide or soluble fragment will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to a nectin polypeptide or soluble fragment, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the invention may also contain stabilizers, preservatives, buffers, antioxidants, or other additives known to those of skill in the art. The duration of intravenous therapy using the pharmaceutical composition of the invention will vary, depending on the severity of the disease being treated and the condition and potential idiosyncratic response of each individual subject. It is contemplated that the duration of each application of a nectin polypeptide or soluble fragment will be in the range of 12 to 24 hours of continuous intravenous administration. Ultimately the attending physician will decide on the appropriate duration of intravenous therapy using the pharmaceutical composition of the invention.

For compositions of the invention which are useful in treating bone, cartilage, tendon or ligament disorders, the therapeutic method includes administering the composition topically, systematically, or locally as an implant or device. When administered, the therapeutic composition for use in the invention is in a pyrogen-free, physiologically acceptable form. Further, the composition may desirably be encapsulated or injected in a viscous form for delivery to the site of bone, cartilage, or tissue damage. Topical administration may be suitable for wound healing and tissue repair.

In addition to human subjects, nectin polypeptides or soluble fragments are useful in the treatment of disease conditions in non-human animals, such as pets (canine, feline, avian, primates species, and the like), domestic farm animals (equine, bovine, procine, avian species, and the like). In such instances, an appropriate dose may be determined according to the animal's body weight. For example, a dose of 0.2–1 mg/kg may be used. Alternatively, the dose is determined according to the animal's surface area, an exemplary dose ranging from 0.1–20 mg/m$^2$, or more preferably, from 5–12 mg/m$^2$. For small animals, such as dogs or cats, a suitable dose mg/kg. In a preferred embodiment, a nectin polypeptide or soluble fragment (preferably constructed from genes derived from the same species as the subject), is administered by injection or other suitable route one or more times per week until the animal's condition is improved, or it may be administered indefinitely.

The invention also relates to the use of any of the nectin-3 or nectin-4 polypeptides, fragments, and variants; nectin-3 or nectin-4 polynucleotides, fragments, and variants; soluble forms of the nectin-3 or nectin-4 polypeptides; antibodies to a nectin-3 or nectin-4 polypeptide or fragment; nectin-3 or nectin-4 polypeptide binding partners (e.g., nectin-1 and nectin-2); complexes formed from the nectin-3 or 4 polypeptides, fragments, variants, and binding partners, and the like, in the manufacture of a therapeutic composition for the prevention or therapeutic treatment of medical disorder including those disclosed herein.

Unless otherwise defined, all technical and scientific terms used herein have the same meaning as commonly understood by one of ordinary skill in the art to which this invention belongs. All headings and subheading provided herein are solely for ease of reading and should not be construed to limit the invention. The terms "a", "an" and "the" as used herein are meant to encompass the plural unless the context clearly dictates the singular form. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. The following examples are intended to illustrate particular embodiments and not to limit the scope of the invention.

EXAMPLES

Example 1

Identification, Cloning and Chromosome Mapping

In a search for novel B7 family members that might be duplicated and clustered in the human genome with known members, the Radiation Hybrid map position of CD86 (B7-2) was examined. ESTs were identified that mapped near this position, and IMAGE clones for these ESTs were obtained and the complete nucleotide sequence of the EST determined by standard methods. One IMAGE clone, H05999, was found to encode a portion of a nectin-3 product. Additional polynucleotides encoding nectin-3 polypeptides were identified by rapid amplification of cDNA ends (RACE) analysis. All RACE products were cloned into vectors and sequenced. Sequence analysis of the RACE products identified a number of clones having substantially identical sequences. RACE Analysis kits are available from a number of companies including Roche Molecular Systems. Primers were designed based upon consensus sequences found by RACE product comparison.

Through a combination of RACE PCR and cDNA library screens with radioactively labeled nucleic acid probes derived from the nectin-3 sequences, the entire nectin-3 α and β coding sequence were isolated except for amino acids 1–6. By database comparison with a mouse nectin-3, a DNA for a chimeric polypeptide containing the first 6 amino acids of the mouse protein was designed. The first 6 amino acids of the mouse sequence were fused to a coding region for a nectin-3 (α or β) or DNA coding for the extracellular region (including a portion of the signal sequence) of nectin-3 (α or β) and this was further fused to a human IgG1 Fc coding region. Transfection of these DNAs into mammalian cells resulted in cleavage of the chimeric signal sequence and secretion of the complete mature cell bound nectin-3 or the mature soluble Fc fusion into the media.

A dataset from Celera Genomics (Rockville, Md.) containing a set of amino acid sequences predicted to be encoded by the human genome was searched using nectin consensus sequences and nectin-3 sequences to identify further members of the nectin family. Additional searches were performed in the GenBank databases. Using computer algorithm searches to identify molecules with a threshold percent identity, a molecule with significant homology to nectin-3 and nectin-1 was identified and designated nectin-4. cDNAs for this new nectin molecule were isolated by RT-PCR using specific primers and human placental cDNA as a template.

One identified clone (SEQ ID NO:33) was cloned into a vector and was subsequently used for sequencing and to construct Nectin-4-Fc fusion constructs. The point mutation causing a proline in the signal sequence (see e.g., SEQ ID NO:34 at amino acid 18) was clipped from the mature polypeptide.

The gene encoding the α, β, and γ splice forms of human nectin-3 was localized to human chromosome 3 on Gene Map 98: Marker stSG2552, Interval D3S1302-D3S1610. Radiation Hybrid (RH) mapping results were obtained from the Sanger Centre (Cambridge, UK) for stSG2552 on GB4 Map: Chromosome 3; reference interval D3S1302-D3S1610 (125.5–130.1 cM); physical position 395.26 cR3000 (P>3.00). RHdb RH12011.

The gene encoding the disclosed forms forms of nectin-4 were localized to human crhomosome 1 between bases 325001 and 375000 of contig GA_X54KRE8DBC7 (which is incorporated herein by reference).

Example 2

Expression of Human Nectin-3 Transcripts and Regulation of Human Nectin-3 Expression Northern blots of RNA molecules from various tissue sources were prepared and probed with sequences hybridizing to the coding sequence of human nectin-3α, including the extracellular domain that is present in both the α and β splice variants, so that both α and β transcripts were detected. Probe sequences and hybridization conditions were selected to exclude cross-hybridization to other human nectin transcripts. Multiple (at least two and as many as five) hybridizing bands corresponding to multiple human nectin-3 splice forms were detected in each of the tissues listed in the following Table 6.

TABLE 6

| Fetal Tissues: | Adult Tissues:[†] |
|---|---|
| fetal brain** | brain** including: cerebellum, medulla , occipital pole, frontal lobe, temporal lobe, putamen |
| fetal lung | Lung |
| fetal liver | Liver |
| fetal kidney | Kidney |
| fetal heart** | heart** including: aorta, left atrium, right atrium, left ventricle, right ventricle |
| | spinal cord |
| | Thymus |
| | Esophagus |
| | Stomach |
| | Spleen |
| | small intestine** including: duodenum, jejunum, ileum |
| | colon** including: ascending, descending, transverse |
| | Rectum |
| | Placenta |
| | peripheral blood lymphocytes (PBL) |

[†]: Partial ESTs corresponding to human nectin-3α have been isolated by others from prostate, uterus, and testes.
**: Higher levels of mRNA expression were detected in brain, heart, and the gastrointestinal tract.

Reverse transcriptase-polymerase chain reaction (RT-PCR) experiments were also performed to detect expression of human nectin-3α in certain cell types and cell lines. In addition, some of these cells were treated with cytokines or other cell-stimulatory molecules to test for changes in expression of human nectin-3 transcripts in response to these treatments. The results of the experiments are shown in Table 7 below.

TABLE 7

| Expression was detected in the following cell types or cell lines: | Regulation in response to treatment: |
|---|---|
| HUVEC (human umbilical vein endothelial cells) | |
| Colon epithelial lines T84 and Caco | Slightly down-regulated in T84 cells treated with IFN γ. |
| Lung epithelial line (Calu-3) | IFN-γ treated cells had a 2-fold decrease in nectins 1 and 3 expression as measured by Affymetrix Array. IL-4 treatment had no effect on nectin expression in these cells. |

TABLE 7-continued

| Expression was detected in the following cell types or cell lines: | Regulation in response to treatment: |
|---|---|
| Dendritic cells (DCs) derived from PB cells by GM-CSF + FTL3L + TNF treatment or by GM-CSF + FLT3L + IL-4 treatment | Up-regulated in GM-CSF + FLT3L + IL-4-derived DCs further treated with CD40L stimulation. In DCs derived by both cocktails there may also be up-regulation with RANKL treatment. |
| PBL | May be up-regulated by PHA or anti-CD3 stimulation of peripheral blood T cells |

Example 3

Expression and Purification of Human Nectin-3 Polypeptides

A vector containing a nectin-3 insert (e.g., SEQ ID NO:1, 3, 5, 7, 9, or 11) operably linked to the HIVTAT promoter was transfected into CV1EBNA/mannose receptor cells by the DEAE dextran technique. Cells were incubated under standard mammalian cell culture conditions in low IgG or serum-free conditions to lower contamination of the expressed product with serum polypeptides.

For soluble polypeptides, weekly harvests of the supernatant are pooled, and for transmembrane nectin polypeptides, membrane fractions from cultured cells are obtained, followed by purification of the polypeptides. Alternatively, CHO cell clone CS-9 is transfected with the region encoding the soluble fusion polypeptide inserted beside the CMViep of pDC314. After amplification with methotrexate the amplified cell pool or clones are incubated in suspension in serum-free media containing IGF-1. Cells may be induced with 0.2–1.0 mM Nabutyrate and the incubation period would be up to 12 days at 35° C.

To construct a polynucleotide encoding a solNectin-3-Fc, the nucleotide sequence encoding the extracellular domain (including the signal sequence) comprising amino acids 1–404 of SEQ ID NO:6 or 1–366 of SEQ ID NO:12 were fused to a nucleic acid encoding an Fc portion from human IgG1. A fusion construct lacking the signal sequence (e.g., amino acids 1 to 57 of SEQ ID NO:6, 12, and 31 may be excluded) would comprise amino acids 58–404 or 58–366 of SEQ ID NO:6 and 12, respectively. Alternatively, the first 7 amino acid from the murine nectin-3 can be used at the very N-terminal of the human nectin-3 molecule replacing the N-terminal 7 amino acid of the human molecule. Accordingly, the solNectin-3-Fc (α or β) encoded by these constructs comprised a sequence as set forth in SEQ ID NO:13 and 14 (solNectin-3α-Fc and solNectin-3β-Fc, respectively). The soluble form of the molecule is then predicted to start at amino acid 58 of SEQ ID NO:13 or 14. The Fc sequence begins at amino acid 404 (SEQ ID NO:13) or 366 (SEQ ID NO:14).

To construct a polynucleotide encoding a solNectin-4-Fc (e.g., SEQ ID NO:36), the nucleotide sequence encoding the extracellular domain (including the signal sequence) comprising amino acids 1–349 of SEQ ID NO:34 are fused to a nucleic acid encoding an Fc portion from human IgG1. A fusion construct lacking the signal sequence (e.g., amino acids 1 to 26 of SEQ ID NO:24) may be excluded in the fusion construct and accordingly would comprise amino acids 27–349 SEQ ID NO:34. Accordingly, an example of a solNectin-4-Fc polynucleotide comprises SEQ ID NO:35 and encodes a solNectin-4-Fc comprising a sequence as set forth in SEQ ID NO:36. The soluble form of the molecule is then predicted to start at amino acid 27 of SEQ ID NO:36. The Fc sequence begins at amino acid 350 of SEQ ID NO:36.

For purification of an Fc-fusion polypeptide, generated as above, the cell culture supernatant was passed over a Protein A Poros resin. The bound Fc-fusion polypeptide was eluted with 50 mM Citrate pH 3 and immediately neutralized with 1.4M Hepes pH 11 and the peak fractions were pooled and dialyzed against PBS. For purification of a polyHis-tagged polypeptide, the supernatant was concentrated and buffer exchanged into 20 mM NaPO4 pH 7.4+300 mM NaCl+5 mM Imidazole using a Millipore Tangential Flow Filter unit and was then passed over a $Co^{2+}$ chelated column (TALON Superflow). The bound polypeptide was eluted using 500 mM Imidazole and the peak fractions were pooled and dialyzed against PBS. The purity and integrity of the eluted recombinant polypeptide is monitored by SDS-PAGE of an aliquot as well as by N-terminal sequencing and amino acid analysis (AAA). The determination of endotoxin contamination is tested by the LAL assay. The polypeptide is aliquoted and stored frozen.

Example 4

Binding of Soluble Human Nectin-3 to Human Endothelial Cells

Human umbilical vein endothelial cells (HUVEC) that had been cultured overnight in medium alone (EGM-1), medium+human TNF-α (20 ng/ml), or PMA (50 ng/ml) were gently removed from tissue culture vessels using trypsin/EDTA and were resuspended in binding media (2% FBS, 2% normal rabbit serum, 10% normal goat serum, 0.1% sodium azide plus PBS) for flow cytometry. A control Fc polypeptide or human solNectin-3α-Fc (SEQ ID NO:13) at a concentration of 5 micrograms/ml was added to cells in binding media and incubated at 4° C. for 30 minutes. After washing the cells in binding medium, bound Fc-containing polypeptide was detected by incubating the cells in binding medium containing 10 micrograms/ml biotinylated goat anti-human-Fc specific antibody (Jackson Immunoresearch; West Grove, Pa.) for 30 minutes at 4° C. After washing the cells in binding medium, bound biotinylated anti-human-Fc specific antibody was detected by incubating the cells in binding medium containing a streptavidin-PE conjugate (Molecular Probes; Eugene, Oreg.) for 30 minutes at 4° C. Binding of human nectin-3α-Fc to HUVEC was analyzed by flow cytometry using Cell Quest Software and a FACSCAN apparatus (Becton Dickinson; San Jose, Calif.). The results of the experiment are shown in the table below and binding is expressed as MFI (mean fluorescence intensity) which is a direct measure of the amount of molecule binding to the cell.

| CULTURE CONDITIONS | Polypeptides Tested (results expressed as MFI) | | |
|---|---|---|---|
| | Control Fc (p7.5) | CD54 (activation marker) | Human Nectin-3-α-Fc |
| MEDIA | 7.2 | 160.7 | 210.2 |
| MEDIA + TNF-α | 6.0 | 500.7 | 123.0 |
| MEDIA + PMA | 7.4 | 542.9 | 50.2 |

The results show that nectin-3α-Fc binds with high intensity to proliferating HUVEC. Further activation of HUVEC by TNFα results in a 40% decrease in nectin-3α-Fc binding. HUVEC activation by PMA results in a more than 75% decrease in nectin-3α-Fc binding. The significant decreases in nectin-3α-Fc binding observed on HUVEC activated by TNFα or PMA, is in stark contrast to the HUVEC expression of the integrin CD54 which markedly increases after HUVEC exposure to inflammatory cytokines such as TNFα. Regulation of nectin-3α-Fc binding to counterstructure(s) on endothelial cells by inflammatory signals suggests that nectin-3α-Fc may play a significant biological role in endothelial cell function, motility/recruitment, and extravasation during inflammatory immune response, tissue remodeling, and ischemia/reperfusion conditions.

The nectin-3α-Fc also binds with high intensity to cultured human dermal microvascular endothelial cells and to the human colon carcinoma cell line T84. Additional experiments showed that the addition of exogenous nectin-3-Fc to PMA stimulated MVECs can inhibit the migration of these cells. It was also determined that recombinant nectin-3-Fc can inhibit PMA induced kidney endothelial cell migration in wound healing assays.

Studies with transient transfections show that soluble nectin-3-Fc (solNectin3-Fc) binds strongly to nectin-1 transfected cells and weakly, if at all, to nectin-2 transfectants. SolNectin3-Fc fails to bind to nectin-3 and nectin-4 transfectants. In addition, soluble nectin-1-Fc binds strongly to nectin-3 transfectants but not nectin-1 or nectin-2 transfectants. However, soluble nectin-1-Fc binds strongly to nectin-4 transfectants. In contrast, soluble nectin-2-Fc does not appear to bind to nectin-1, nectin-2, or nectin-4 transfectants it does, however, to nectin-3 transfectants. Soluble nectin-4-Fc (solNectin4-Fc) binds well to nectin-1 transfectants.

Studies with endothelial cells show that nectin-1 and nectin-2 are present on the cell surface. Nectin-3 is either not present or present at very low levels. Endothelial cells do not appear to express nectin-4. Antibodies to nectin-1 and nectin-2 show that nectin-1 is a major binding partner on endothelial cells since the increased or decreased levels of solNectin3-Fc binding found after various treatments parallel the increase and decrease of nectin-1 on the cell surface, while nectin-2 levels appear unchanged by the treatment. Accordingly, nectin-1 is the strongest candidate for a cell surface molecule mediating the anti-angiogenic effects seen with soluble nectin-3-Fc. The following Table 8 provides a summary of the interaction data.

TABLE 8

| Transfected molecule | SolNectin1-Fc | SolNectin2-Fc | SolNectin3-Fc | SolNectin4-Fc |
|---|---|---|---|---|
| Nectin1 | N/D | N/D | high | high |
| Nectin2 | N/D | N/D | low | N/D |
| Nectin3 | high | moderate | N/D | N/D |
| Nectin4 | high | N/D | N/D | N/D |

| Molecule | Presence on Endothelial Cells | Presence on aortic smooth muscle cells | Binds as Fc to aortic smooth muscle cells | Binds as Fc to Endothelial Cells |
|---|---|---|---|---|
| Nectin1 | low | low | moderate | N/D |
| Nectin2 | high | high | N/D | N/D |
| Nectin3 | very low | moderate* | N/D | moderate |
| Nectin4 | N/D | moderate* | N/D | moderate |

N/D - not detected;
*nectin1Fc binds specifically to nectin3 and nectin4 one or both molecules is present on aotic smooth muscle cells.

Example 5

Modulation of Endothelial Cell Migration by Soluble Human Nectin-3

Figure 2:
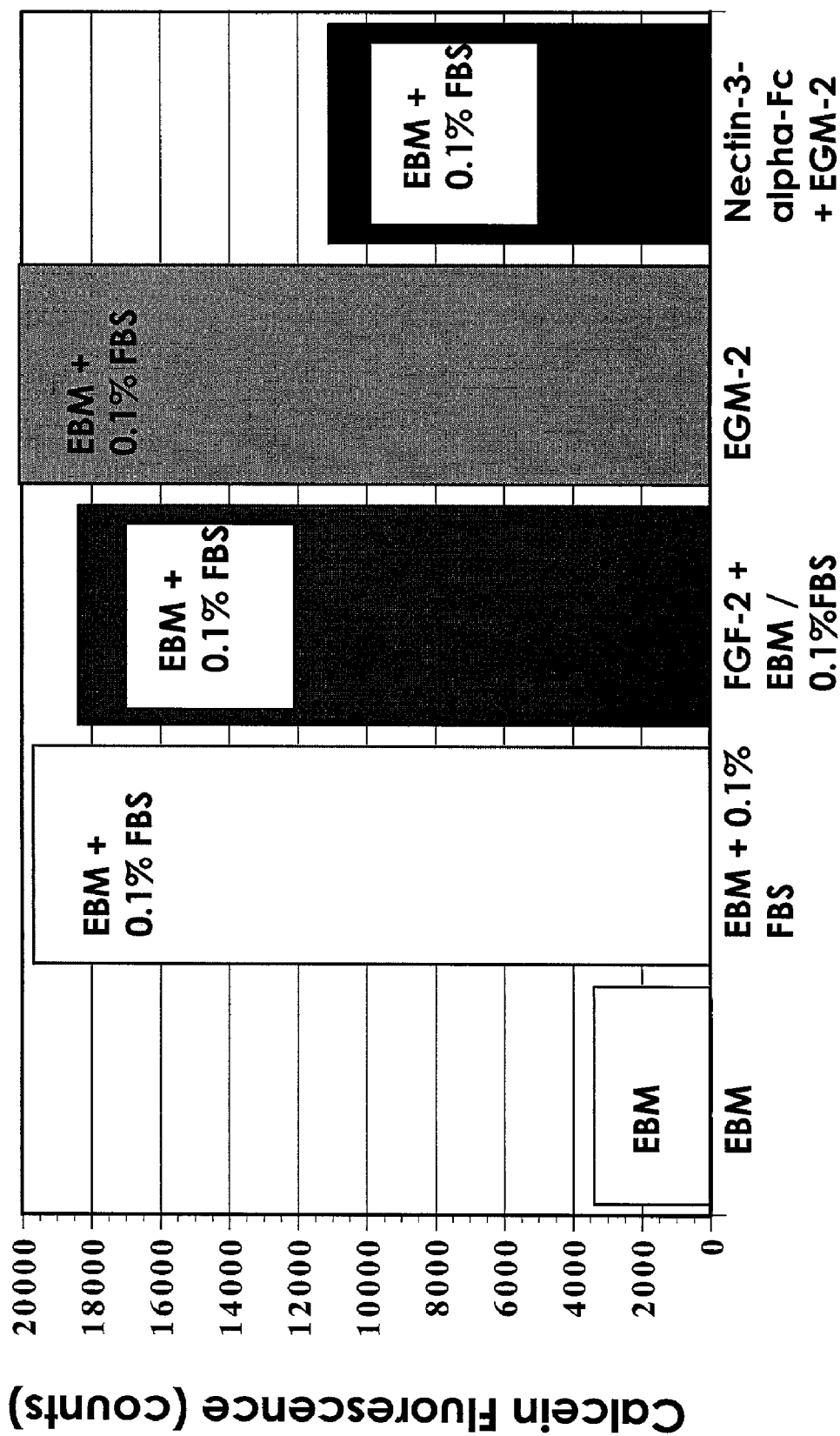
FIG. 2 shows that nectin-3α-Fc inhibits the migration of PMA-stimulated endothelial cells.

Human dermal microvascular endothelial cells (HMVEC-d) were cultured overnight (18 hours) in medium (e.g., EGM-2 media, Clonetics; Walkersville, Md.) and in the presence or absence of PMA (50 ng/ml), and then the cells were washed and labeled in PBS containing 4 microM calcein dye for two hours. After calcein labeling the cells fluoresce after excitation at 488 nm and were washed in PBS, resuspended in basal medium (EBM+/−0.1% FBS), and placed into culture in 3 micron pore size fluoroblock inserts for 24-well plates (Becton Dickinson; Franklin Lakes, N.J.). Fifty thousand HMVEC-d cells were cultured in 300 microliters of basal medium in the fluorblock insert and the inserts containing the cells were placed into 24-well sterile culture plates containing 1 ml of medium with cytokines and/or serum having the potential to cause migration or movement (haptotaxis) of the HMVEC-d through the opaque 3 micron filter of the insert into the 24-well plate. Migration of cells through the filter was detected by measuring the level of fluorescence emission observed at 530 nm in the bottom well using a Wallac Victor II multilabel counter (Perkin-Elmer Life Sciences; Wellesley, Mass.). The migration results are expressed as fluorescence counts. The level of fluorescence detected in the lower well is a direct measure of the number of endothelial cells that have moved through the filter. In this migration assay, addition of nectin-3α-Fc at a concentration of 25 micrograms/ml to HMVEC-d cultured in basal medium in the fluoroblock insert inhibited migration/haptotaxis induced by an EGM-2 gradient (contains serum+FGF-2+VEGF) by 42% compared to EGM-2 gradient induced migration of HMVEC-d cultured in basal medium (FIG. 1). The nectin-3α-Fc inhibition of migration was calculated as (migration in EGM-2—migration in EGM-2 plus the nectin-3α-Fc)/(migration in EGM-2—migration in EBM basal medium)×100%. Addition of nectin-3α-Fc at concentration of 25 micrograms/ml to the EGM-2 media gradient in the bottom well inhibited the migration of PMA-stimulated HMVEC-d by 55% compared to migration of PMA-stimulated HMVEC-d cultured in an EGM-2 gradient alone (FIG. 2). The data show that nectin-3α-Fc can decrease endothelial cell migration/haptotaxis in vitro, and indicate that nectin-3α may play a role in endothelial cell movement and vessel formation/angiogenesis in vivo.

Example 6

Activity of Soluble Human Nectin-3 in a Wound-Closure Assay

Figure 3:
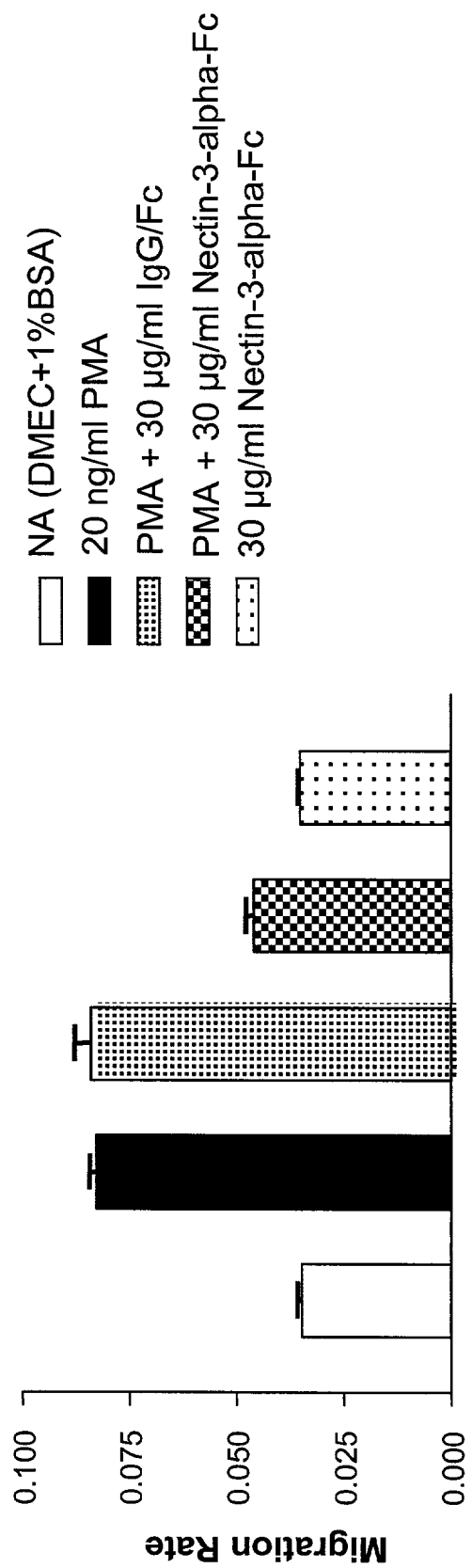
FIG. 3 shows that nectin-3α-Fc inhibits endothelial cell interaction in a wound-closure assay.
Figure 4:
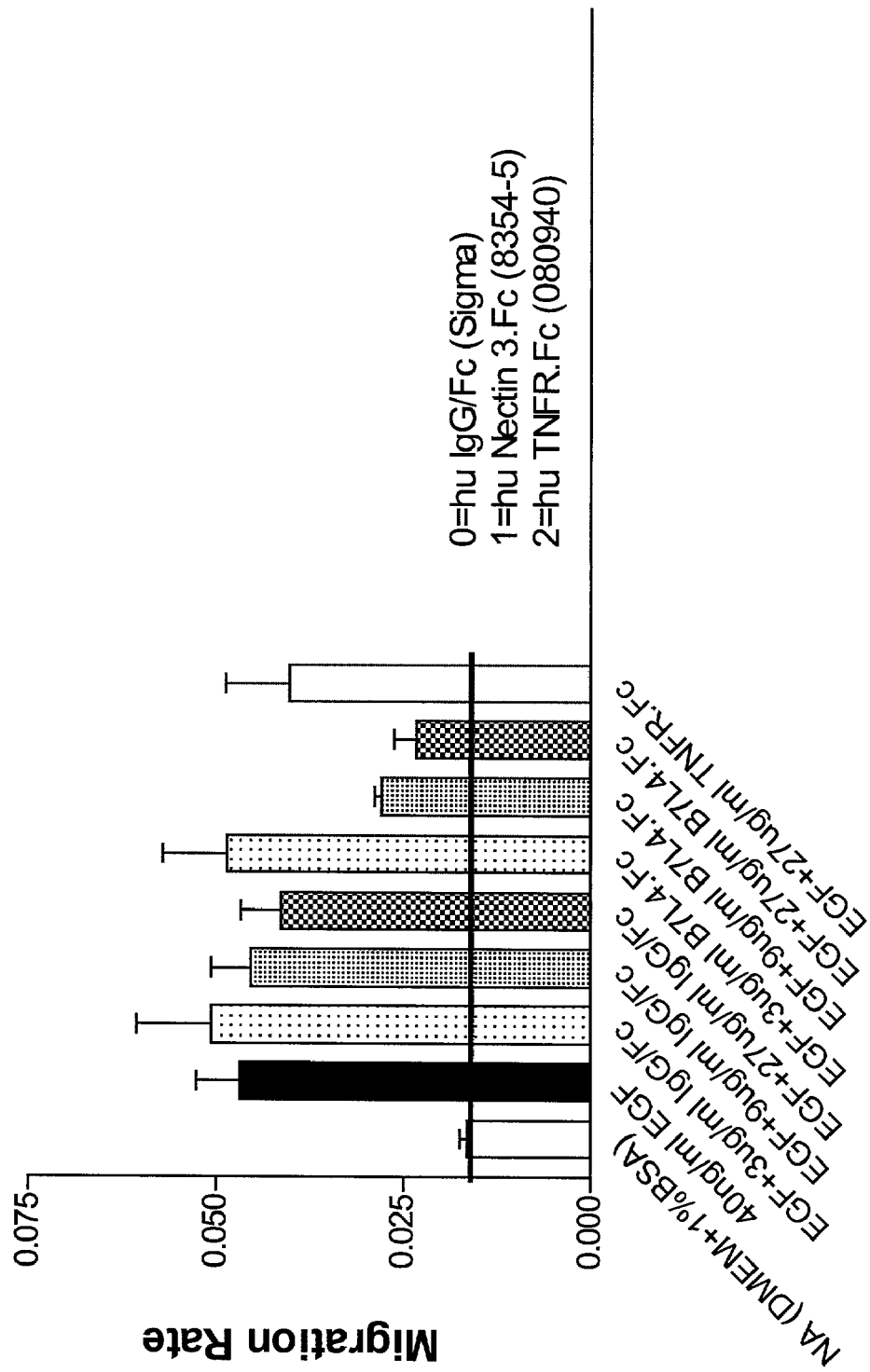
FIG. 4 shows that nectin-3α-Fc inhibits EGF-induced endothelial cell migration.

A planar endothelial cell migration (wound closure) assay was used to quantitate the inhibition of angiogenesis by nectin-3α-Fc in vitro. In this assay, endothelial cell migration is measured as the rate of closure of a circular wound in a cultured cell monolayer. The rate of wound closure is linear, and is dynamically regulated by agents that stimulate and inhibit angiogenesis in vivo. Primary human renal microvascular endothelial cells, HRMEC, were isolated, cultured, and used at the third passage after thawing, as described in Martin et al., 1997, *In Vitro Cell Dev Biol* 33: 261. Replicate circular lesions, "wounds" (600–800 micron diameter), were generated in confluent HRMEC monolayers using a silicon-tipped drill press. At the time of wounding the medium (DMEM+1% BSA) was supplemented with 20 ng/ml PMA (phorbol-12-myristate-13-acetate), 30 micrograms/ml nectin-3α-Fc, combinations of 20 ng/ml PMA and 30 micrograms/ml nectin-3α-Fc, 40 ng/ml EGF or combinations of 40 ng/ml of EGF and increasing concentrations of nectin-3α-Fc. The residual wound area was measured as a function of time (0–12 hours) using a microscope and image analysis software (Bioquant; Nashville, Tenn.). The relative migration rate was calculated for each agent and combination of agents by linear regression of residual wound area plotted over time. The results are shown in FIG. 3. The nectin-3α-Fc at 30 micrograms/ml inhibited PMA-induced endothelial migration, reducing the rate of migration to approximately the same as observed for unstimulated cells. EGF-induced endothelial migration was inhibited by nectin-3α-Fc in a concentration dependent manner. EGF-induced endothelial cell migration was inhibited by >50% at a nectin-3α-Fc concentration of 9 micrograms/ml (FIG. 4).

Nectin-3 (B7L4) and nectin-2 (PRR2) were stained on cell monolayers along with other cell junction molecules: afadin, beta-catenin and ZO-1 following wounding of the monolayer. These molecules characteristically stain the cell junctions at the cell surface as demonstrated in epithelial cells. The result in these wound assays is the cell surface staining of nectin-3 on the edge of the cell exposed to the wound. This is the first demonstration that nectins are localized in the cell surface in structures other than the adherens junctions. It is also markedly different than the other cell junction proteins that were immunolocalized in these wound assays. Afadin is the only identified binding partner of the nectins, and it is not localized to the cell surface exposed to the wound. Additionally, both beta-catenin and VE-cadherin are specific for cell surfaces in contact with other cells (i.e. cell:cell interfaces) and completely absent from the edges of cells not in contact with other cells or exposed to the wound. This is the first indication that the nectins may play a role in the cell's activity in a capacity other than in organizing cell junctions.

Some cells displayed interesting staining patterns for nectin-3 and nectin-2 at the presumptive leading edge of cells that had migrated away from the edges of the wounded monolayer. It is apparent that nectin-2 and nectin-3 are not only found on the cell surface of the cells exposed to the wound, but they also accumulate at the leading edge of migrating cells. This staining appears punctate or condensed in areas at the leading edge. It also appears that the staining of nectin-2 and nectin-3 overlap each other at this surface which may indicate an overlapping functions.

Example 7

The Effect of Soluble Nectins on Lymphocyte Interactions with Endothelial Cells To determine the effects of soluble nectins on the interaction of lymphocytes with vascular endothelial cells, mouse lymphocytes are collected, washed, and fluorescently labeled with calcein dye generally as described above for HMVEC-d cells above. The interaction of these cells with vascular endothelial cells is then assayed by intravital microscopy and image analysis as described by Frenette et al. (1995, Proc. Natl. Acad. Sci. USA. 92: 7450–7454; 1998, Blood 91: 1318–1324; 2000, J Exp Med 191(8): 1413–1422). Briefly, fluorescently labeled lymphocytes are incubated at room temperature for 10 minutes with either soluble nectin polypeptide such as nectin-Fc (0.5–2 mg/kg, weight of recipient mouse) or IgG Fc control. The suspension of lymphocytes with each Fc polypeptide is injected through the tail vein into wild-type (for example, C57BL/6×129Sv F1) recipient mice. Mice are anesthetized with 2.5% tribromoethanol 0.15 ml/10 g and prepared for intravital microscopy of the mesentery as described in Frenette et al.; 1998, Blood 91: 1318–1324. Venules are activated by superfusion of calcium ionophore A23187 (30 microliters of 10 microM solution in PBS). One venule per animal is recorded for 20 minutes. Centerline erythrocyte velocity, venular shear rates, and critical velocities (Vcrit) are determined as described in Frenette et al.; 1998, Blood 91: 1318–1324. Quantitation of lymphocyte-endothelial interactions is done by an investigator blind to the studied groups. Lymphocytes traveling for a distance 30 microns at a velocity slower than Vcrit are scored as "rolling." Any interaction of a lymphocyte with the endothelium occurring at a velocity slower than Vcrit is considered to be "tethering." The average number of tethering or rolling platelets per minute over a venular segment of 250 microns is determined by taking the average of 10 counts of 1 minute (five in each half of filming). The number of lymphocytes that are captured but not rolling on the venular wall is obtained by subtracting "rolling" from "tethering."

Alternatively, the interactions of lymphocytes with the endothelium may be assayed by electron microscopy as described in Thompson et al., 2000, *J Immunol* 165(1): 426–434. Optionally following a dynamic quantification of lymphocyte responses as described above, a portion of mesentery containing the test vessels is excised and fixed in buffer containing 2.5% glutaraldehyde (50 mM sodium cacodylate, 4 mM HCl, and 0.18 mM CaCl2). Samples are then postfixed in 1% osmium VIII oxide and, following dehydration in methanol, are embedded in araldite resin before sectioning. Thin sections (1 µm) are stained with toluidine blue to allow location of venules. Ultrathin sections (0.1 µm) are mounted on copper mesh grids and stained with uranyl acetate and lead citrate before viewing on a transmission electron microscope (Hitachi 7000, Hitachi U.K., Hayes, U.K.). The total number of lymphocytes associated with each vessel was counted, and their positions, according to the following classification, were noted: A, within lumen of the venule; B, crossing the endothelium; C, between the endothelium and perivascular basement membrane; D, crossing the basement membrane; and E, outside the venule, but within 50 µm of it. For each venule, the fraction of lymphocytes that had crossed the endothelium but were still inside the basement membrane is calculated according to the following equation C/(C+D+E). In each series of experiments, tissue samples from at least three control animals and three animals treated with soluble nectin polypeptides are analyzed, and from each animal at least three vessels are studied in detail.

Additionally, the effects of soluble nectin polypeptides on the activation of lymphocytes such as polymorphonuclear leukocytes, their interaction with endothelial cell sheets, and the resulting changes in endothelial barrier function are assayed according to the various methods described in Gautam et al., 2000, J Exp Med 191(11): 1829–1839.

Example 8

The Effect of Soluble Nectins on Formation of Endothelial Structures

The effects of nectin3-Fc or other soluble nectin polypeptides on the ability of endothelial cells to form tubular structures in response to VEGF are assayed by the method of Ergun et al., 2000, *Mol Cell* 5(2): 311–320. Three-dimensional type I collagen gels (Vitrogen 100; Collagen Corp.; Palo Alto, Calif.) are prepared in 48-well cluster tissue culture dishes (Costar; Cambridge, Mass.) as described in Pepper et al. (1992, Biochem. Biophys. Res. Commun. 189: 824–831). Human dermal microvascular endothelial cells are seeded onto solidified gels at a concentration of $2 \times 10^4$/well in 300 microliters of MV medium containing 5% FCS. At confluence, the medium is replaced by basal medium containing 2% FCS without further supplements. After 24 hours, angiogenic factors such as VEGF, FGF-2, and CEACAM alone or in combination are added to the cells in the presence or absence of nectin-Fc or IgG Fc control polypeptide. Factors and/or Fc polypeptides are renewed every 3 days after taking photographs by phase contrast microscopy (Zeiss; Jena, Germany). Endothelial tube formation is assayed visually as shown in Ergün et al., 2000, *Mol Cell* 5(2): 311–320. If nectin activity is necessary for the formation of these endothelial structures, inhibiting nectin binding interactions by adding soluble nectin-Fc polypeptides is likely to prevent endothelial tube formation, indicating a role for such nectin polypeptides in angiogenesis and vasculogenesis.

Example 9

The Effect of Nectin Polypeptides on Vascular Tissue Remodeling in Response to Injury The effects of nectin3-Fc or other soluble nectin polypeptides on the recovery of the endothelium after injury are assayed in an arterial injury model by the method of Hayashi et al., 2000, Circulation 102(14): 1710-1717. Rats are obtained and provided with care guided by the National Institutes of Health (Guide for the Care and Use of Laboratory Animals, NIH publication No. 86–23, revised 1985). These rats are anesthetized with pentobarbital sodium (50 mg/kg EP) and their left common carotid arteries are injured by 3 passages of an inflated 2F Fogarty embolectomy catheter (Baxter Healthcare). To attain a constant degree of vessel wall injury for each of the animals, the diameter of the balloon and the resistance during withdrawal is kept constant and the same for each of the animals. The sham operation involves simple ligation of the left external carotid arteries without balloon injury.

Rats in the soluble nectin polypeptide treatment group receive 4 mg/kg of soluble nectin interperitoneally, and those in the control group receive the same dose of control polypeptide such as IgG Fc, 30 minutes before arterial injury and for 7 consecutive days after balloon injury. At various time intervals, the animals are humanely killed with a lethal dose of pentobarbital sodium. The injured and contralateral uninjured carotids are perfused with cold 0.1 mol/L PBS (pH 7.4) under physiological pressure followed by careful excision of the carotid arteries. The existence of endothelial denudation is evaluated by staining with Evans blue dye (60 mg/kg IV) injected 30 minutes before death. The central portion of the injured left carotids which stains blue is regarded as the nonreendothelialized area. Fourteen days and 56 days after balloon injury, the injured and uninjured contralateral carotids are harvested as described above, and the middle parts of both arteries are divided into 2 rings. One of them is fixed in 4% paraformaldehyde and embedded in paraffin for light microscopy; and the other is prepared for scanning electron microscopy (SEM). Five sections from each carotid artery are stained with van Gieson's elastin stain and examined morphometrically by videomicroscopy (HC-300i, Nikon) with a computerized digital image analysis system (NIH Image) in a blind manner. The areas within the external elastic lamina (EEL area), the internal elastic lamina (IEL area), and the lumen area are measured. Other areas are calculated as follows: medial area=EEL area−IEL area; neointimal area=IEL area−lumen area; neointima-to-media ratio (I/M)=neointimal area/medial area. The circumferences (lengths) of the EEL, IEL, and lumen are also measured to determine vascular shrinking. Thrombogenicity of the injured arterial luminal surface at day 14 after injury is evaluated by SEM. The injured and contralateral uninjured carotid rings, prepared as described above, are fixed with 2.5% glutaraldehyde in 0.1 moll phosphate buffer (pH 7.2), sliced into longitudinal strips, and then postfixed with 1% osmium tetroxide. They are dehydrated through a graded alcohol series, critical-point-dried with CO2, and splatter-coated with platinum-palladium. They are then examined with a JSM-6000 (JEOL) SEM at 5 kV. Thrombogenicity is quantitatively assessed by counting the number of platelets adhering to the injured luminal surface in both groups. SEM pictures of 15 randomly selected visual fields are taken at a magnification of ×2500. The total number of platelets adhering to the injured surface is then counted in each of the pictures in a blind manner. In addition, immunohistochemistry is performed using adjacent sections embedded in paraffin to confirm that the luminal surface is covered with luminal smooth muscle cells. Monoclonal antibodies against smooth muscle myosin heavy chain isoform (SM1)18 is used to identify smooth muscle cells and polyclonal antibodies against factor VIII-related antigen to identify endothelial cells.

Example 10

Monoclonal Antibodies That Bind Nectin Polypeptides of the Invention

This example illustrates a method for preparing monoclonal antibodies that bind nectin polypeptides. Suitable immunogens that may be employed in generating such antibodies include, but are not limited to, purified nectin-3 polypeptide, purified nectin-4 polypeptide, or immunogenic fragments thereof.

Purified nectin-3 polypeptide can be used to generate monoclonal antibodies immunoreactive therewith, using conventional techniques such as those described in U.S. Pat. No. 4,411,993. Briefly, mice are immunized with a nectin-3 polypeptide immunogen emulsified in complete Freund's adjuvant, and injected in amounts ranging from 10–100 micrograms subcutaneously or intraperitoneally. Ten to twelve days later, the immunized animals are boosted with additional nectin polypeptide emulsified in incomplete Freund's adjuvant. Mice are periodically boosted thereafter on a weekly to bi-weekly immunization schedule. Serum samples are periodically taken by retro-orbital bleeding or tail-tip excision to test for nectin-3 polypeptide antibodies by dot blot assay, ELISA (Enzyme-Linked Immunosorbent Assay) or inhibition of binding of nectin-3 polypeptide to a nectin-3 polypeptide binding partner.

Following detection of an appropriate antibody titer, positive animals are provided one last intravenous injection of nectin polypeptide in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified nectin polypeptide by adaptations of the techniques disclosed in Engvall et al., (Immunochem. 8:871, 1971) and in U.S. Pat. No. 4,703,004. A preferred screening technique is the antibody capture technique described in Beckmann et al., (J. Immunol. 144:4212, 1990). Positive hybridoma cells can be injected intraperitoneally into syngeneic BALB/c mice to produce ascites containing high concentrations of anti-nectin polypeptide monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to Polypeptide A or Polypeptide G can also be used, as can affinity chromatography based upon binding to nectin polypeptide.

Example 11

Activity of Soluble Nectin-3-Fc (solNectin3-Fc) Polypeptides In a Corneal Pocket Assay A mouse corneal pocket assay was used to quantitate the inhibition of angiogenesis by nectin-3-Fc polypeptides in vivo. In this assay, agents to be tested for angiogenic or anti-angiogenic activity were immobilized in a slow release form in a hydron pellet, which was implanted into micropockets created in the corneal epithelium of anesthetized mice. Vascularization was measured as the appearance, density, and extent of vessel in growth from the vascularized corneal limbus into the normally avascular cornea.

Hydron pellets, as described in Kenyon et al., Invest Opthamol. & Visual Science 37:1625, 1996, incorporated sucralfate with bFGF (90 ng/pellet), bFGF and IgG (11 µg/pellet, control), or bFGF and a range of concentrations of the agent to be tested (e.g., solNectin3-Fc polypeptide). The pellets were surgically implanted into corneal stromal micropockets created by micro-dissection 1 mm medial to the lateral corneal limbus of 6–8 week old male C57BL mice. After five days, at the peak of neovascular response to bFGF, the corneas were photographed using a Zeiss slit lamp at an incipient angle of 35–50° from the polar axis in the meridian containing the pellet. Images were digitized and processed by subtractive color filters (Adobe Photoshop 4.0) to delineate established microvessels by hemoglobin content. Image analysis software (Bioquant, Nashville, Tenn.) was used to calculate the fraction of the corneal image that was vascularized, the vessel density within the vascularized area, and the vessel density within the total cornea. The inhibition of bFGF-induced corneal angiogenesis, as a function of the dose of solNectin3-Fc polypeptide, was determined.

The data demonstrated that solNectin3-Fc (α or β) as show in SEQ ID NO:13 or 14, respectively, blocked FGF-induced angiogenesis in the mouse corneal assay.

Example 12

Inhibition of Neovascularization by Soluble Nectin-3-Fc Polypeptides in a Murine Transplant Model Survival of heterotopically transplanted cardiac tissue from one mouse donor to the ear skin of another genetically similar mouse requires adequate neovascularization by the transplanted heart and the surrounding tissue, to promote survival and energy for cardiac muscle function. Inadequate vasculature at the site of transplant causes excessive ischemia to the heart, tissue damage, and failure of the tissue to engraft. Agents that antagonize factors involved in endothelial cell migration and vessel formation can decrease angiogenesis at the site of transplant, thereby limiting graft tissue function and ultimately engraftment itself. A murine heterotopic cardiac isograft model is used to demonstrate the inhibitory effects of solNectin3-Fc polypeptides on neovascularization.

Female BALB/c (≈12 weeks of age) recipients are given neonatal heart grafts from donor mice of the same strain. The donor heart tissue is grafted into the left ear pinnae of the recipient on day 0 and the mice are divided into two groups. The control group receives human IgG (Hu IgG) while the other group receives solNectin3-Fc, both intraperitoneally. The treatments are continued for five consecutive days. The functionality of the grafts is determined by monitoring visible pulsatile activity on days 7 and 14 post-engraftment. The inhibition of functional engraftment, as a function of the dose of solNectin3-Fc, is determined. The histology of the transplanted hearts is examined in order to visualize the effects of solNectin3-Fc on edema at the site of transplant and host and donor tissue vasculature (using, e.g., Factor VIII staining).

Example 13

Treatment of Tumors with Soluble Nectin-3-Fc Polypeptides

SolNectin3-Fc is tested in animal models of solid tumors. The effect of the SolNectin3-Fc is determined by measuring tumor frequency and tumor growth. The biological activity of SolNectin3-Fc is also demonstrated in other in vitro, ex vivo, and in vivo assays known in the art, such as calcium mobilization assays and assays to measure platelet activation, recruitment, or aggregation.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE OF SEQUENCES:

| | |
|---|---|
| SEQ ID NO: 1 and 2 | human nectin-3α polynucleotide and polypeptide (deletion of 7 N-terminal amino acids) |
| SEQ ID NO: 3 and 4 | nectin-3α polynucleotide and polypeptide (codons/amino acids 1-7 from mouse) |
| SEQ ID NO: 5 and 6 | human nectin-3α polynucleotide and polypeptide |
| SEQ ID NO: 7 and 8 | human nectin-3β polynucleotide and polylpeptide (deletion of 6 N-terminal amino acids) |
| SEQ ID NO: 9 and 10 | nectin-3β polynucleotide and polypeptide (codons/amino acids 1-6 from mouse) |
| SEQ ID NO: 11 and 12 | human nectin-3β polynucleotide and polypeptide |
| SEQ ID NO: 13 | nectin-3α-Fc polypeptide |
| SEQ ID NO: 14 | nectin-3β-Fc polypeptide |
| SEQ ID NO: 15 | nectin-3α-FLAGpolyHis polypeptide |
| SEQ ID NO: 16 | nectin-3α-FLAGpolyHis polypeptide |
| SEQ ID NO: 17 | mouse nectin-3α polypeptide |
| SEQ ID NO: 18 | mouse nectin-3β polypeptide |
| SEQ ID NO: 19 | mouse nectin-3γ polypeptide |
| SEQ ID NO: 20 | human nectin 1α polypeptide |
| SEQ ID NO: 21 | human nectin 1β polypeptide |
| SEQ ID NO: 22 | human nectin 2α polypeptide |
| SEQ ID NO: 23 | human nectin 2δ polypeptide |
| SEQ ID NO: 24 | human LNIR |
| SEQ ID NO: 25 | human PVRα |
| SEQ ID NOs: 26–29 | primer sequences |
| SEQ ID NO: 30 and 31 | human nectin-3γ polynucleotide and polypeptide |
| SEQ ID NO: 32 | LNIR polynucleotide sequence coding for SEQ ID NO: 24 |
| SEQ ID NO: 33 and 34 | human nectin-4 polynucleotide and polypeptide |
| SEQ ID NO: 35 and 36 | nectin-4-Fc polynucleotide and polypeptide |
| SEQ ID NO: 37–39 | nectin-4 polypeptide |

What is claimed is:

1. A substantially purified polypeptide comprising amino acids 58 through 404 of SEQ ID NO:4 or 6, wherein said polypeptide inhibits endothelial cell migration.

2. The polypeptide of claim 1 in non-glycosylated form.

3. The polypeptide of claim 1 further comprising a leucine zipper polypeptide.

4. The polypeptide of claim 1 further comprising an Fc polypeptide.

5. The polypeptide of claim 1 further comprising a peptide linker.

6. A composition comprising the polypeptide of claim 1 and a pharmaceutically acceptable carrier.

7. A substantially purified polypeptide comprising amino acids 74 through 365 of SEQ ID NO:10, 12, or 31, wherein said polypeptide inhibits endothelial cell migration.

8. The polypeptide of claim 7 in non-glycosylated form.

9. The polypeptide of claim 7 further comprising a leucine zipper polypeptide.

10. The polypeptide of claim 7 further comprising an Fc polypeptide.

11. The polypeptide of claim 7 further comprising a peptide linker.

12. A composition comprising the polypeptide of claim 7 and a pharmaceutically acceptable carrier.

13. A substantially purified nectin 3 polypeptide comprising an amino acid sequence selected from the group consisting of:
- (a) amino acids 58 through 342 of SEQ ID NO:4, 6, 10, 12, or 31;
- (b) amino acids 74 through 342 of SEQ ID NO:4, 6, 10, 12, or 31;
- (c) amino acids 74 through 404 of SEQ ID NO:4 or 6; and
- (d) amino acids 74 through 365 of SEQ ID NO:10, 12, or 31;

wherein said polypeptide inhibits endothelial cell migration.

14. The polypeptide of claim 13 in non-glycosylated form.

15. The polypeptide of claim 13 further comprising a leucine zipper polypeptide.

16. The polypeptide of claim 13 further comprising an Fc polypeptide.

17. The polypeptide of claim 13 further comprising a peptide linker.

18. A composition comprising the polypeptide of claim 13 and a pharmaceutically acceptable carrier.

19. The isolated polypeptide of claims 1, 7 or 13 produced by a process comprising:
- (a) culturing a recombinant host cell comprising a polynucleotide having a nucleotide sequence encoding said polypeptide; and
- (b) isolating said polypeptide.

20. The polypeptide of claim 19, wherein said polypeptide is produced by a process comprising substantially purifying said polypeptide.

21. The polypeptide of claim 19, wherein said polypeptide is produced by a process comprising culturing a recombinant host cell comprising a polynucleotide having a nucleotide sequence encoding said polyp eptide, wherein said nucleotide sequence is selected from the group consisting of nucleotides 172 to 1026 of SEQ ID NO:3, 5, 9, or 11; nucleotides 172 to 1212 of SEQ ID NO:3 or 5; and nucleotides 172 to 1098 of SEQ ID NO:9 or 11.

22. The polypeptide of claim 19, wherein said polypeptide is produced by a process comprising culturing a recombinant host cell comprising a polynucleotide having a nucleotide sequence encoding said polypeptide, wherein said nucleotide sequence is selected from the group consisting of SEQ ID NO:1, 3, 7, 9, 11, and 30.

23. The polypeptide of claim 19, wherein said polypeptide is produced by a process comprising culturing a recombinant host cell comprising a polynucleotide having a nucleotide sequence encoding said polypeptide, wherein said nucleotide sequence encodes a polypeptide selected from the group consisting of SEQ ID NO:13, 14, 15, and 16.

24. The polypeptide of claim 19, wherein said polypeptide comprises an amino acid sequence selected from the group consisting of:
- (a) amino acids 58 through 342 of SEQ ID NO:4, 6, 10, 12, or 31;
- (b) amino acids 58 through 404 of SEQ ID NO:4 or 6;
- (c) amino acids 74 through 342 of SEQ ID NO:4, 6, 10, 12, or 31;
- (d) amino acids 74 through 404 of SEQ ID NO:4 or 6;
- (e) amino acids 58 through 365 of SEQ ID NO:10, 12, or 31; and
- (f) amino acids 74 through 365 of SEQ ID NO:10, 12, or 31.

25. The polypeptide of claim 19 in non-glycosylated form.

26. The polypeptide of claim 19 further comprising a leucine zipper polypeptide.

27. The polypeptide of claim 19 further comprising an Fc polypeptide.

28. The polypeptide of claim 19 further comprising a peptide linker.

29. A composition comprising the polypeptide of claim 19 and a pharmaceutically acceptable carrier.

30. The polypeptide of claim 19, wherein said polypeptide is produced by a process comprising culturing a recombinant host cell into which a polynucleotide comprising a nucleotide sequence encoding said polypeptide has been introduced.

31. A substantially purified polypeptide of claim 1 wherein said polypeptide comprises an amino acid sequence selected from the group consisting of:
- (a) the polyp eptide sequence of SEQ ID NO: 2;
- (b) the polypeptide sequence of SEQ ID NO: 13; and
- (c) the polypeptide sequence of SEQ ID NO: 15.

32. A substantially purified polypeptide of claim 7 wherein said polypeptide comprises an amino acid sequence selected from the group consisting of:
- (a) the polypeptide sequence of SEQ ID NO: 8;
- (b) the polypeptide sequence of SEQ ID NO: 14; and
- (c) the polypeptide sequence of SEQ ID NO:16.

* * * * *

SEQUENCE LISTING

```
<160> NUMBER OF SEQ ID NOS: 39

<210> SEQ ID NO 1
<211> LENGTH: 3147
<212> TYPE: DNA
<213> ORGANISM: homo sapiens
<220> FEATURE:
<221> NAME/KEY: CDS
<222> LOCATION: (1)..(1626)
<223> OTHER INFORMATION:

<400> SEQUENCE: 1 tcc ccg ctg tgt cct gga ggc ggc aaa gca caa ctt tcc tcc gct tct        48
Ser Pro Leu Cys Pro Gly Gly Gly Lys Ala Gln Leu Ser Ser Ala Ser
 1               5                  10                  15 ctc ctc gga gcc ggg ctc ctg cag ccc ccg acg cca cct ccg ctg        96
Leu Leu Gly Ala Gly Leu Leu Leu Gln Pro Pro Thr Pro Pro Pro Leu
            20                  25                  30
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctg | ctg | ctg | ctc | ttc | ccg | ctg | ctg | ctc | ttc | tcc | agg | ctc | tgt | ggt | gcc | 144  |
| Leu | Leu | Leu | Leu | Phe | Pro | Leu | Leu | Leu | Phe | Ser | Arg | Leu | Cys | Gly | Ala |      |
|     |     | 35  |     |     |     | 40  |     |     |     |     | 45  |     |     |     |     |      |
| tta | gct | gga | cca | att | att | gtg | gag | cca | cat | gtc | aca | gca | gta | tgg | gga | 192  |
| Leu | Ala | Gly | Pro | Ile | Ile | Val | Glu | Pro | His | Val | Thr | Ala | Val | Trp | Gly |      |
| 50  |     |     |     |     | 55  |     |     |     |     | 60  |     |     |     |     |     |      |
| aag | aat | gtt | tca | tta | aag | tgt | tta | att | gaa | gta | aat | gaa | acc | ata | aca | 240  |
| Lys | Asn | Val | Ser | Leu | Lys | Cys | Leu | Ile | Glu | Val | Asn | Glu | Thr | Ile | Thr |      |
| 65  |     |     |     | 70  |     |     |     |     | 75  |     |     |     |     | 80  |     |      |
| cag | att | tca | tgg | gag | aag | ata | cat | ggc | aaa | agt | tca | cag | act | gtt | gca | 288  |
| Gln | Ile | Ser | Trp | Glu | Lys | Ile | His | Gly | Lys | Ser | Ser | Gln | Thr | Val | Ala |      |
|     |     |     |     | 85  |     |     |     |     | 90  |     |     |     |     | 95  |     |      |
| gtt | cac | cat | ccc | caa | tat | gga | ttc | tct | gtt | caa | gga | gaa | tat | cag | gga | 336  |
| Val | His | His | Pro | Gln | Tyr | Gly | Phe | Ser | Val | Gln | Gly | Glu | Tyr | Gln | Gly |      |
|     |     |     | 100 |     |     |     |     | 105 |     |     |     |     | 110 |     |     |      |
| aga | gtc | ttg | ttt | aaa | aat | tac | tca | ctt | aat | gat | gca | aca | att | act | ctg | 384  |
| Arg | Val | Leu | Phe | Lys | Asn | Tyr | Ser | Leu | Asn | Asp | Ala | Thr | Ile | Thr | Leu |      |
|     |     | 115 |     |     |     |     | 120 |     |     |     |     | 125 |     |     |     |      |
| cat | aac | ata | gga | ttc | tct | gat | tct | gga | aaa | tac | atc | tgc | aaa | gct | gtt | 432  |
| His | Asn | Ile | Gly | Phe | Ser | Asp | Ser | Gly | Lys | Tyr | Ile | Cys | Lys | Ala | Val |      |
| 130 |     |     |     |     | 135 |     |     |     |     | 140 |     |     |     |     |     |      |
| aca | ttc | ccg | ctt | gga | aat | gcc | cag | tcc | tct | aca | act | gta | act | gtg | tta | 480  |
| Thr | Phe | Pro | Leu | Gly | Asn | Ala | Gln | Ser | Ser | Thr | Thr | Val | Thr | Val | Leu |      |
| 145 |     |     |     |     | 150 |     |     |     |     | 155 |     |     |     |     | 160 |      |
| gtt | gaa | ccc | act | gtg | agc | ctg | ata | aaa | ggg | cca | gat | tct | tta | att | gat | 528  |
| Val | Glu | Pro | Thr | Val | Ser | Leu | Ile | Lys | Gly | Pro | Asp | Ser | Leu | Ile | Asp |      |
|     |     |     |     | 165 |     |     |     |     | 170 |     |     |     |     | 175 |     |      |
| gga | gga | aat | gaa | aca | gta | gca | gcc | att | tgc | atc | gca | gcc | act | gga | aaa | 576  |
| Gly | Gly | Asn | Glu | Thr | Val | Ala | Ala | Ile | Cys | Ile | Ala | Ala | Thr | Gly | Lys |      |
|     |     |     | 180 |     |     |     |     | 185 |     |     |     |     | 190 |     |     |      |
| ccc | gtt | gca | cat | att | gac | tgg | gaa | ggt | gat | ctt | ggt | gaa | atg | gaa | tcc | 624  |
| Pro | Val | Ala | His | Ile | Asp | Trp | Glu | Gly | Asp | Leu | Gly | Glu | Met | Glu | Ser |      |
|     |     | 195 |     |     |     |     | 200 |     |     |     |     | 205 |     |     |     |      |
| act | aca | act | tct | ttt | cca | aat | gaa | acg | gca | acg | att | atc | agc | cag | tac | 672  |
| Thr | Thr | Thr | Ser | Phe | Pro | Asn | Glu | Thr | Ala | Thr | Ile | Ile | Ser | Gln | Tyr |      |
|     | 210 |     |     |     |     | 215 |     |     |     |     | 220 |     |     |     |     |      |
| aag | cta | ttt | cca | acc | aga | ttt | gct | aga | gga | agg | cga | att | act | tgt | gtt | 720  |
| Lys | Leu | Phe | Pro | Thr | Arg | Phe | Ala | Arg | Gly | Arg | Arg | Ile | Thr | Cys | Val |      |
| 225 |     |     |     |     | 230 |     |     |     |     | 235 |     |     |     |     | 240 |      |
| gta | aaa | cat | cca | gcc | ttg | gaa | aag | gac | atc | cga | tac | tct | ttc | ata | tta | 768  |
| Val | Lys | His | Pro | Ala | Leu | Glu | Lys | Asp | Ile | Arg | Tyr | Ser | Phe | Ile | Leu |      |
|     |     |     |     | 245 |     |     |     |     | 250 |     |     |     |     | 255 |     |      |
| gac | ata | cag | tat | gct | cct | gaa | gtt | tcg | gta | aca | gga | tat | gat | gga | aat | 816  |
| Asp | Ile | Gln | Tyr | Ala | Pro | Glu | Val | Ser | Val | Thr | Gly | Tyr | Asp | Gly | Asn |      |
|     |     | 260 |     |     |     |     | 265 |     |     |     |     | 270 |     |     |     |      |
| tgg | ttt | gta | gga | aga | aaa | ggt | gtt | aat | ctc | aaa | tgt | aat | gct | gat | gca | 864  |
| Trp | Phe | Val | Gly | Arg | Lys | Gly | Val | Asn | Leu | Lys | Cys | Asn | Ala | Asp | Ala |      |
|     |     | 275 |     |     |     |     | 280 |     |     |     |     | 285 |     |     |     |      |
| aat | cca | cca | ccc | ttc | aaa | tct | gtg | tgg | agc | agg | ttg | gat | gga | caa | tgg | 912  |
| Asn | Pro | Pro | Pro | Phe | Lys | Ser | Val | Trp | Ser | Arg | Leu | Asp | Gly | Gln | Trp |      |
|     | 290 |     |     |     |     | 295 |     |     |     |     | 300 |     |     |     |     |      |
| cct | gat | ggt | tta | ttg | gct | tca | gac | aat | act | ctt | cat | ttt | gtc | cat | cca | 960  |
| Pro | Asp | Gly | Leu | Leu | Ala | Ser | Asp | Asn | Thr | Leu | His | Phe | Val | His | Pro |      |
| 305 |     |     |     |     | 310 |     |     |     |     | 315 |     |     |     |     | 320 |      |
| ttg | act | ttc | aat | tat | tct | ggt | gtt | tat | atc | tgt | aaa | gtg | acc | aat | tcc | 1008 |
| Leu | Thr | Phe | Asn | Tyr | Ser | Gly | Val | Tyr | Ile | Cys | Lys | Val | Thr | Asn | Ser |      |
|     |     |     |     | 325 |     |     |     |     | 330 |     |     |     |     | 335 |     |      |
| ctt | ggt | caa | aga | agt | gac | caa | aaa | gtc | atc | tac | att | tca | gat | cct | cct | 1056 |
| Leu | Gly | Gln | Arg | Ser | Asp | Gln | Lys | Val | Ile | Tyr | Ile | Ser | Asp | Pro | Pro |      |

```
                    340             345             350
act act acc acc ctt cag cct aca att cag tgg cat ccc tca act gct    1104
Thr Thr Thr Thr Leu Gln Pro Thr Ile Gln Trp His Pro Ser Thr Ala
            355                 360                 365 gac atc gag gat cta gca aca gaa cct aaa aaa ttg ccc ttc cca ttg    1152
Asp Ile Glu Asp Leu Ala Thr Glu Pro Lys Lys Leu Pro Phe Pro Leu
    370                 375                 380 tca act ttg gca aca att aag gat gac aca att gcc acg atc att gct    1200
Ser Thr Leu Ala Thr Ile Lys Asp Asp Thr Ile Ala Thr Ile Ile Ala
385                 390                 395                 400 agt gta gtg ggt ggg gct ctc ttc ata gta ctt gta agt gtt ttg gct    1248
Ser Val Val Gly Gly Ala Leu Phe Ile Val Leu Val Ser Val Leu Ala
                405                 410                 415 gga ata ttc tgc tat agg aga aga cgg acg ttt cgt gga gac tac ttt    1296
Gly Ile Phe Cys Tyr Arg Arg Arg Arg Thr Phe Arg Gly Asp Tyr Phe
            420                 425                 430 gcc aag aac tac att cca cca tca gat atg caa aaa gaa tca caa ata    1344
Ala Lys Asn Tyr Ile Pro Pro Ser Asp Met Gln Lys Glu Ser Gln Ile
        435                 440                 445 gat gtt ctt caa caa gat gag ctt gat tct tac cca gac agt gta aaa    1392
Asp Val Leu Gln Gln Asp Glu Leu Asp Ser Tyr Pro Asp Ser Val Lys
    450                 455                 460 aaa gaa aac aaa aat cca gtg aac aat cta ata cgt aaa gac tat tta    1440
Lys Glu Asn Lys Asn Pro Val Asn Asn Leu Ile Arg Lys Asp Tyr Leu
465                 470                 475                 480 gaa gag cct gaa aaa act cag tgg aac aat gta gaa aat ctc aat agg    1488
Glu Glu Pro Glu Lys Thr Gln Trp Asn Asn Val Glu Asn Leu Asn Arg
                485                 490                 495 ttt gaa aga cca atg gat tat tat gaa gat cta aaa atg gga atg aag    1536
Phe Glu Arg Pro Met Asp Tyr Tyr Glu Asp Leu Lys Met Gly Met Lys
            500                 505                 510 ttt gtc agt gat gaa cat tat gat gaa aac gaa gat gac tta gtt tca    1584
Phe Val Ser Asp Glu His Tyr Asp Glu Asn Glu Asp Asp Leu Val Ser
        515                 520                 525 cat gta gat ggt tcc gta att tcc agg agg gag tgg tat gtt              1626
His Val Asp Gly Ser Val Ile Ser Arg Arg Glu Trp Tyr Val
    530                 535                 540 tagcaaccac tgaatgtgac ttaactatgt acaatgttca ttcacactag ttgatcattt    1686
tcagattgtt catactttt cttgaggaag aataagcttt ttcaagttga ttttcaagct    1746
tactttttat attctaatct gacaaatgaa aatgtaaaat ctgagttcag tgtatctaag    1806
ctgctttaca atttttttc aatgctgtac tactgtctca agatttaaat tttaatgcag     1866
agtactttat tggtgtgagg cacacaggta agaagaaatg tcaacattaa atgtatgact    1926
tacttggtac aaaaatttt taaaaaggga actaccttga cattgtgtat taaatgttta    1986
cctaagacta taatctcaag tatgatgttt gtttaacata tacctctcaa aatttatcac    2046
cactcaatga cactgcatca aaattgacta taaaactaat tcaagaaata tttatatata    2106 tttttttaata tacaaaaaat atttagcctg atggaatggc tttccttttc aaacattatt   2166
ttctaagttt ctatacaaat gaatctttta cctctgcata ttaatgagcc ttgccataat    2226
tactgtagag tggctttca aagatatttt gttgcactaa aactgtggta gtaaactcag    2286
tgaacatgat gtgtggaaga gcataattag ctggtcaata ttttttgtcca aaatacctgc   2346 aagagtaata aaatacatac ctttcaaaca tgataattat tagttttttt tttccttttct   2406 ggaacatgga ttttggtaca ttagcagtag cctttatttta atgctttatg tcctaaacat    2466
actaatagaa atgaaaagac gcagagagag catttcggaa tactgaagta ctagttttag    2526
```

-continued

```
aaatgagact tcagccaac aatctataga aagaatttta tggaccatct tgttttagtt      2586
atttaatgtt gatgttgttc aaatgggtaa atgtacagaa agaaaatttt agagtaaact      2646
tggaactttg gatataacta gaaaaaacta gattatagaa ttagtcggta acacttgcta      2706
atggacattg gcattcatct cctttttcct cctaagtgta tgtatgtgtt ttaagatttc      2766 tgttttacg  attaaaactg gaaacatgag gttttttgtt tttgttttt tacataatta      2826 catatattcc ttctgaatca tttatctttt gagaaagaaa tgttacctaa acttcaaatg      2886 tgcttttgt  tgtgaggta  attaaattgc ttctacagtg gaggcttaca aaattattgt      2946
gacaactatt tgaagctga  aaggatagtt tttctattgc taagtcattt gaaaaagtga      3006 ccatttgcc  agtgaaatga agtggaagtt agtaggagaa tcataaatta aatatattat      3066
tttgttaata aaaggcaaa  gtagtaggta cttttaaac  cctcccaacc agcctttct       3126 caatattcat caaatctaaa a                                                 3147
```

<210> SEQ ID NO 2
<211> LENGTH: 542
<212> TYPE: PRT
<213> ORGANISM: homo sapiens

<400> SEQUENCE: 2

```
Ser Pro Leu Cys Pro Gly Gly Lys Ala Gln Leu Ser Ser Ala Ser
1               5                  10                  15

Leu Leu Gly Ala Gly Leu Leu Gln Pro Thr Pro Pro Pro Leu
            20                  25                  30

Leu Leu Leu Leu Phe Pro Leu Leu Phe Ser Arg Leu Cys Gly Ala
        35                  40                  45

Leu Ala Gly Pro Ile Ile Val Glu Pro His Val Thr Ala Val Trp Gly
    50                  55                  60

Lys Asn Val Ser Leu Lys Cys Leu Ile Glu Val Asn Glu Thr Ile Thr
65                  70                  75                  80

Gln Ile Ser Trp Glu Lys Ile His Gly Lys Ser Ser Gln Thr Val Ala
                85                  90                  95

Val His His Pro Gln Tyr Gly Phe Ser Val Gln Gly Glu Tyr Gln Gly
            100                 105                 110

Arg Val Leu Phe Lys Asn Tyr Ser Leu Asn Asp Ala Thr Ile Thr Leu
        115                 120                 125

His Asn Ile Gly Phe Ser Asp Ser Gly Lys Tyr Ile Cys Lys Ala Val
    130                 135                 140

Thr Phe Pro Leu Gly Asn Ala Gln Ser Ser Thr Thr Val Thr Val Leu
145                 150                 155                 160

Val Glu Pro Thr Val Ser Leu Ile Lys Gly Pro Asp Ser Leu Ile Asp
                165                 170                 175

Gly Gly Asn Glu Thr Val Ala Ala Ile Cys Ile Ala Ala Thr Gly Lys
            180                 185                 190

Pro Val Ala His Ile Asp Trp Glu Gly Asp Leu Gly Glu Met Glu Ser
        195                 200                 205

Thr Thr Thr Ser Phe Pro Asn Glu Thr Ala Thr Ile Ile Ser Gln Tyr
    210                 215                 220

Lys Leu Phe Pro Thr Arg Phe Ala Arg Gly Arg Ile Thr Cys Val
225                 230                 235                 240

Val Lys His Pro Ala Leu Glu Lys Asp Ile Arg Tyr Ser Phe Ile Leu
                245                 250                 255
```

-continued

```
Asp Ile Gln Tyr Ala Pro Glu Val Ser Val Thr Gly Tyr Asp Gly Asn
            260                 265                 270

Trp Phe Val Gly Arg Lys Gly Val Asn Leu Lys Cys Asn Ala Asp Ala
        275                 280                 285

Asn Pro Pro Phe Lys Ser Val Trp Ser Arg Leu Asp Gly Gln Trp
    290                 295                 300

Pro Asp Gly Leu Leu Ala Ser Asp Asn Thr Leu His Phe Val His Pro
305                 310                 315                 320

Leu Thr Phe Asn Tyr Ser Gly Val Tyr Ile Cys Lys Val Thr Asn Ser
                325                 330                 335

Leu Gly Gln Arg Ser Asp Gln Lys Val Ile Tyr Ile Ser Asp Pro Pro
            340                 345                 350

Thr Thr Thr Thr Leu Gln Pro Thr Ile Gln Trp His Pro Ser Thr Ala
        355                 360                 365

Asp Ile Glu Asp Leu Ala Thr Glu Pro Lys Lys Leu Pro Phe Pro Leu
    370                 375                 380

Ser Thr Leu Ala Thr Ile Lys Asp Asp Thr Ile Ala Thr Ile Ile Ala
385                 390                 395                 400

Ser Val Val Gly Gly Ala Leu Phe Ile Val Leu Val Ser Val Leu Ala
                405                 410                 415

Gly Ile Phe Cys Tyr Arg Arg Arg Thr Phe Arg Gly Asp Tyr Phe
            420                 425                 430

Ala Lys Asn Tyr Ile Pro Pro Ser Asp Met Gln Lys Glu Ser Gln Ile
        435                 440                 445

Asp Val Leu Gln Gln Asp Glu Leu Asp Ser Tyr Pro Asp Ser Val Lys
    450                 455                 460

Lys Glu Asn Lys Asn Pro Val Asn Asn Leu Ile Arg Lys Asp Tyr Leu
465                 470                 475                 480

Glu Glu Pro Glu Lys Thr Gln Trp Asn Val Glu Asn Leu Asn Arg
                485                 490                 495

Phe Glu Arg Pro Met Asp Tyr Tyr Glu Asp Leu Lys Met Gly Met Lys
            500                 505                 510

Phe Val Ser Asp Glu His Tyr Asp Glu Asn Glu Asp Asp Leu Val Ser
        515                 520                 525

His Val Asp Gly Ser Val Ile Ser Arg Arg Glu Trp Tyr Val
    530                 535                 540
```

<210> SEQ ID NO 3
<211> LENGTH: 1650
<212> TYPE: DNA
<213> ORGANISM: Artificial Sequence
<220> FEATURE:
<223> OTHER INFORMATION: nucleotides 1-21 are from Mus musculus
      Nectin-3, the rest are from human Nectin-3 alpha
<221> NAME/KEY: CDS
<222> LOCATION: (1)..(1650)
<223> OTHER INFORMATION:

<400> SEQUENCE: 3

```
atg gcc cgg acc ccc ggc ccg tcc ccg ctg tgt cct gga ggc ggc aaa    48
Met Ala Arg Thr Pro Gly Pro Ser Pro Leu Cys Pro Gly Gly Gly Lys
1               5                   10                  15 gca caa ctt tcc tcc gct tct ctc ctc gga gcc ggg ctc ctg ctg cag    96
Ala Gln Leu Ser Ser Ala Ser Leu Leu Gly Ala Gly Leu Leu Leu Gln
            20                  25                  30 ccc ccg acg cca cct ccg ctg ctg ctg ctc ttc ccg ctg ctg ctc       144
Pro Pro Thr Pro Pro Pro Leu Leu Leu Leu Leu Phe Pro Leu Leu Leu
        35                  40                  45
```

```
                                                    -continued ttc tcc agg ctc tgt ggt gcc tta gct gga cca att att gtg gag cca      192
Phe Ser Arg Leu Cys Gly Ala Leu Ala Gly Pro Ile Ile Val Glu Pro
 50                  55                  60 cat gtc aca gca gta tgg gga aag aat gtt tca tta aag tgt tta att      240
His Val Thr Ala Val Trp Gly Lys Asn Val Ser Leu Lys Cys Leu Ile
 65                  70                  75                  80 gaa gta aat gaa acc ata aca cag att tca tgg gag aag ata cat ggc      288
Glu Val Asn Glu Thr Ile Thr Gln Ile Ser Trp Glu Lys Ile His Gly
                 85                  90                  95 aaa agt tca cag act gtt gca gtt cac cat ccc caa tat gga ttc tct      336
Lys Ser Ser Gln Thr Val Ala Val His His Pro Gln Tyr Gly Phe Ser
            100                 105                 110 gtt caa gga gaa tat cag gga aga gtc ttg ttt aaa aat tac tca ctt      384
Val Gln Gly Glu Tyr Gln Gly Arg Val Leu Phe Lys Asn Tyr Ser Leu
        115                 120                 125 aat gat gca aca att act ctg cat aac ata gga ttc tct gat tct gga      432
Asn Asp Ala Thr Ile Thr Leu His Asn Ile Gly Phe Ser Asp Ser Gly
130                 135                 140 aaa tac atc tgc aaa gct gtt aca ttc ccg ctt gga aat gcc cag tcc      480
Lys Tyr Ile Cys Lys Ala Val Thr Phe Pro Leu Gly Asn Ala Gln Ser
145                 150                 155                 160 tct aca act gta act gtg tta gtt gaa ccc act gtg agc ctg ata aaa      528
Ser Thr Thr Val Thr Val Leu Val Glu Pro Thr Val Ser Leu Ile Lys
                165                 170                 175 ggg cca gat tct tta att gat gga gga aat gaa aca gta gca gcc att      576
Gly Pro Asp Ser Leu Ile Asp Gly Gly Asn Glu Thr Val Ala Ala Ile
            180                 185                 190 tgc atc gca gcc act gga aaa ccc gtt gca cat att gac tgg gaa ggt      624
Cys Ile Ala Ala Thr Gly Lys Pro Val Ala His Ile Asp Trp Glu Gly
        195                 200                 205 gat ctt ggt gaa atg gaa tcc act aca act tct ttt cca aat gaa acg      672
Asp Leu Gly Glu Met Glu Ser Thr Thr Thr Ser Phe Pro Asn Glu Thr
210                 215                 220 gca acg att atc agc cag tac aag cta ttt cca acc aga ttt gct aga      720
Ala Thr Ile Ile Ser Gln Tyr Lys Leu Phe Pro Thr Arg Phe Ala Arg
225                 230                 235                 240 gga agg cga att act tgt gtt gta aaa cat cca gcc ttg gaa aag gac      768
Gly Arg Arg Ile Thr Cys Val Val Lys His Pro Ala Leu Glu Lys Asp
                245                 250                 255 atc cga tac tct ttc ata tta gac ata cag tat gct cct gaa gtt tcg      816
Ile Arg Tyr Ser Phe Ile Leu Asp Ile Gln Tyr Ala Pro Glu Val Ser
            260                 265                 270 gta aca gga tat gat gga aat tgg ttt gta gga aga aaa ggt gtt aat      864
Val Thr Gly Tyr Asp Gly Asn Trp Phe Val Gly Arg Lys Gly Val Asn
        275                 280                 285 ctc aaa tgt aat gct gat gca aat cca cca ccc ttc aaa tct gtg tgg      912
Leu Lys Cys Asn Ala Asp Ala Asn Pro Pro Pro Phe Lys Ser Val Trp
290                 295                 300 agc agg ttg gat gga caa tgg cct gat ggt tta ttg gct tca gac aat      960
Ser Arg Leu Asp Gly Gln Trp Pro Asp Gly Leu Leu Ala Ser Asp Asn
305                 310                 315                 320 act ctt cat ttt gtc cat cca ttg act ttc aat tat tct ggt gtt tat     1008
Thr Leu His Phe Val His Pro Leu Thr Phe Asn Tyr Ser Gly Val Tyr
                325                 330                 335 atc tgt aaa gtg acc aat tcc ctt ggt caa aga agt gac caa aaa gtc     1056
Ile Cys Lys Val Thr Asn Ser Leu Gly Gln Arg Ser Asp Gln Lys Val
            340                 345                 350 atc tac att tca gat cct cct act act acc acc ctt cag cct aca att     1104
Ile Tyr Ile Ser Asp Pro Pro Thr Thr Thr Thr Leu Gln Pro Thr Ile
```

```
cag tgg cat ccc tca act gct gac atc gag gat cta gca aca gaa cct    1152
Gln Trp His Pro Ser Thr Ala Asp Ile Glu Asp Leu Ala Thr Glu Pro
        370                 375                 380 aaa aaa ttg ccc ttc cca ttg tca act ttg gca aca att aag gat gac    1200
Lys Lys Leu Pro Phe Pro Leu Ser Thr Leu Ala Thr Ile Lys Asp Asp
385                 390                 395                 400 aca att gcc acg atc att gct agt gta gtg ggt ggg gct ctc ttc ata    1248
Thr Ile Ala Thr Ile Ile Ala Ser Val Val Gly Gly Ala Leu Phe Ile
                405                 410                 415 gta ctt gta agt gtt ttg gct gga ata ttc tgc tat agg aga aga cgg    1296
Val Leu Val Ser Val Leu Ala Gly Ile Phe Cys Tyr Arg Arg Arg Arg
            420                 425                 430 acg ttt cgt gga gac tac ttt gcc aag aac tac att cca cca tca gat    1344
Thr Phe Arg Gly Asp Tyr Phe Ala Lys Asn Tyr Ile Pro Pro Ser Asp
                435                 440                 445 atg caa aaa gaa tca caa ata gat gtt ctt caa caa gat gag ctt gat    1392
Met Gln Lys Glu Ser Gln Ile Asp Val Leu Gln Gln Asp Glu Leu Asp
        450                 455                 460 tct tac cca gac agt gta aaa aaa gaa aac aaa aat cca gtg aac aat    1440
Ser Tyr Pro Asp Ser Val Lys Lys Glu Asn Lys Asn Pro Val Asn Asn
465                 470                 475                 480 cta ata cgt aaa gac tat tta gaa gag cct gaa aaa act cag tgg aac    1488
Leu Ile Arg Lys Asp Tyr Leu Glu Glu Pro Glu Lys Thr Gln Trp Asn
                485                 490                 495 aat gta gaa aat ctc aat agg ttt gaa aga cca atg gat tat tat gaa    1536
Asn Val Glu Asn Leu Asn Arg Phe Glu Arg Pro Met Asp Tyr Tyr Glu
            500                 505                 510 gat cta aaa atg gga atg aag ttt gtc agt gat gaa cat tat gat gaa    1584
Asp Leu Lys Met Gly Met Lys Phe Val Ser Asp Glu His Tyr Asp Glu
        515                 520                 525 aac gaa gat gac tta gtt tca cat gta gat ggt tcc gta att tcc agg    1632
Asn Glu Asp Asp Leu Val Ser His Val Asp Gly Ser Val Ile Ser Arg
    530                 535                 540 agg gag tgg tat gtt tag                                            1650
Arg Glu Trp Tyr Val
545
```

<210> SEQ ID NO 4
<211> LENGTH: 549
<212> TYPE: PRT
<213> ORGANISM: Artificial Sequence
<220> FEATURE:
<223> OTHER INFORMATION: nucleotides 1-21 are from Mus musculus
      Nectin-3, the rest are from human Nectin-3 alpha

<400> SEQUENCE: 4

Met Ala Arg Thr Pro Gly Pro Ser Pro Leu Cys Pro Gly Gly Gly Lys
1               5                   10                  15

Ala Gln Leu Ser Ser Ala Ser Leu Leu Gly Ala Gly Leu Leu Leu Gln
            20                  25                  30

Pro Pro Thr Pro Pro Leu Leu Leu Leu Phe Pro Leu Leu Leu
        35                  40                  45

Phe Ser Arg Leu Cys Gly Ala Leu Ala Gly Pro Ile Ile Val Glu Pro
    50                  55                  60

His Val Thr Ala Val Trp Gly Lys Asn Val Ser Leu Lys Cys Leu Ile
65                  70                  75                  80

Glu Val Asn Glu Thr Ile Thr Gln Ile Ser Trp Glu Lys Ile His Gly
                85                  90                  95

-continued

```
Lys Ser Ser Gln Thr Val Ala Val His His Pro Gln Tyr Gly Phe Ser
            100                 105                 110
Val Gln Gly Glu Tyr Gln Gly Arg Val Leu Phe Lys Asn Tyr Ser Leu
        115                 120                 125
Asn Asp Ala Thr Ile Thr Leu His Asn Ile Gly Phe Ser Asp Ser Gly
    130                 135                 140
Lys Tyr Ile Cys Lys Ala Val Thr Phe Pro Leu Gly Asn Ala Gln Ser
145                 150                 155                 160
Ser Thr Thr Val Thr Val Leu Val Glu Pro Thr Val Ser Leu Ile Lys
                165                 170                 175
Gly Pro Asp Ser Leu Ile Asp Gly Gly Asn Glu Thr Val Ala Ala Ile
            180                 185                 190
Cys Ile Ala Ala Thr Gly Lys Pro Val Ala His Ile Asp Trp Glu Gly
        195                 200                 205
Asp Leu Gly Glu Met Glu Ser Thr Thr Thr Ser Phe Pro Asn Glu Thr
    210                 215                 220
Ala Thr Ile Ile Ser Gln Tyr Lys Leu Phe Pro Thr Arg Phe Ala Arg
225                 230                 235                 240
Gly Arg Arg Ile Thr Cys Val Val Lys His Pro Ala Leu Glu Lys Asp
                245                 250                 255
Ile Arg Tyr Ser Phe Ile Leu Asp Ile Gln Tyr Ala Pro Glu Val Ser
            260                 265                 270
Val Thr Gly Tyr Asp Gly Asn Trp Phe Val Gly Arg Lys Gly Val Asn
        275                 280                 285
Leu Lys Cys Asn Ala Asp Ala Asn Pro Pro Pro Phe Lys Ser Val Trp
    290                 295                 300
Ser Arg Leu Asp Gly Gln Trp Pro Asp Gly Leu Leu Ala Ser Asp Asn
305                 310                 315                 320
Thr Leu His Phe Val His Pro Leu Thr Phe Asn Tyr Ser Gly Val Tyr
                325                 330                 335
Ile Cys Lys Val Thr Asn Ser Leu Gly Gln Arg Ser Asp Gln Lys Val
            340                 345                 350
Ile Tyr Ile Ser Asp Pro Pro Thr Thr Thr Leu Gln Pro Thr Ile
            355                 360                 365
Gln Trp His Pro Ser Thr Ala Asp Ile Glu Asp Leu Ala Thr Glu Pro
    370                 375                 380
Lys Lys Leu Pro Phe Pro Leu Ser Thr Leu Ala Thr Ile Lys Asp Asp
385                 390                 395                 400
Thr Ile Ala Thr Ile Ile Ala Ser Val Val Gly Gly Ala Leu Phe Ile
                405                 410                 415
Val Leu Val Ser Val Leu Ala Gly Ile Phe Cys Tyr Arg Arg Arg Arg
            420                 425                 430
Thr Phe Arg Gly Asp Tyr Phe Ala Lys Asn Tyr Ile Pro Pro Ser Asp
        435                 440                 445
Met Gln Lys Glu Ser Gln Ile Asp Val Leu Gln Gln Asp Glu Leu Asp
    450                 455                 460
Ser Tyr Pro Asp Ser Val Lys Lys Glu Asn Lys Asn Pro Val Asn Asn
465                 470                 475                 480
Leu Ile Arg Lys Asp Tyr Leu Glu Glu Pro Glu Lys Thr Gln Trp Asn
                485                 490                 495
Asn Val Glu Asn Leu Asn Arg Phe Glu Arg Pro Met Asp Tyr Tyr Glu
            500                 505                 510
Asp Leu Lys Met Gly Met Lys Phe Val Ser Asp Glu His Tyr Asp Glu
```

-continued

```
                515                 520                 525
Asn Glu Asp Asp Leu Val Ser His Val Asp Gly Ser Val Ile Ser Arg
        530                 535                 540
Arg Glu Trp Tyr Val
545

<210> SEQ ID NO 5
<211> LENGTH: 1650
<212> TYPE: DNA
<213> ORGANISM: homo sapiens
<220> FEATURE:
<221> NAME/KEY: CDS
<222> LOCATION: (1)..(1650)
<223> OTHER INFORMATION:

<400> SEQUENCE: 5 atg gcg cgg acc ctg cgg ccg tcc ccg ctg tgt cct gga ggc ggc aaa      48
Met Ala Arg Thr Leu Arg Pro Ser Pro Leu Cys Pro Gly Gly Gly Lys
1               5                   10                  15 gca caa ctt tcc tcc gct tct ctc ctc gga gcc ggg ctc ctg ctg cag      96
Ala Gln Leu Ser Ser Ala Ser Leu Leu Gly Ala Gly Leu Leu Leu Gln
            20                  25                  30 ccc ccg acg cca cct ccg ctg ctg ctg ctc ttc ccg ctg ctg ctc          144
Pro Pro Thr Pro Pro Pro Leu Leu Leu Leu Phe Pro Leu Leu Leu
        35                  40                  45 ttc tcc agg ctc tgt ggt gcc tta gct gga cca att att gtg gag cca      192
Phe Ser Arg Leu Cys Gly Ala Leu Ala Gly Pro Ile Ile Val Glu Pro
50                  55                  60 cat gtc aca gca gta tgg gga aag aat gtt tca tta aag tgt tta att      240
His Val Thr Ala Val Trp Gly Lys Asn Val Ser Leu Lys Cys Leu Ile
65                  70                  75                  80 gaa gta aat gaa acc ata aca cag att tca tgg gag aag ata cat ggc      288
Glu Val Asn Glu Thr Ile Thr Gln Ile Ser Trp Glu Lys Ile His Gly
                85                  90                  95 aaa agt tca cag act gtt gca gtt cac cat ccc caa tat gga ttc tct      336
Lys Ser Ser Gln Thr Val Ala Val His His Pro Gln Tyr Gly Phe Ser
            100                 105                 110 gtt caa gga gaa tat cag gga aga gtc ttg ttt aaa aat tac tca ctt      384
Val Gln Gly Glu Tyr Gln Gly Arg Val Leu Phe Lys Asn Tyr Ser Leu
        115                 120                 125 aat gat gca aca att act ctg cat aac ata gga ttc tct gat tct gga      432
Asn Asp Ala Thr Ile Thr Leu His Asn Ile Gly Phe Ser Asp Ser Gly
    130                 135                 140 aaa tac atc tgc aaa gct gtt aca ttc ccg ctt gga aat gcc cag tcc      480
Lys Tyr Ile Cys Lys Ala Val Thr Phe Pro Leu Gly Asn Ala Gln Ser
145                 150                 155                 160 tct aca act gta act gtg tta gtt gaa ccc act gtg agc ctg ata aaa      528
Ser Thr Thr Val Thr Val Leu Val Glu Pro Thr Val Ser Leu Ile Lys
                165                 170                 175 ggg cca gat tct tta att gat gga gga aat gaa aca gta gca gcc att      576
Gly Pro Asp Ser Leu Ile Asp Gly Gly Asn Glu Thr Val Ala Ala Ile
            180                 185                 190 tgc atc gca gcc act gga aaa ccc gtt gca cat att gac tgg gaa ggt      624
Cys Ile Ala Ala Thr Gly Lys Pro Val Ala His Ile Asp Trp Glu Gly
        195                 200                 205 gat ctt ggt gaa atg gaa tcc act aca act tct ttt cca aat gaa acg      672
Asp Leu Gly Glu Met Glu Ser Thr Thr Thr Ser Phe Pro Asn Glu Thr
    210                 215                 220 gca acg att atc agc cag tac aag cta ttt cca acc aga ttt gct aga      720
Ala Thr Ile Ile Ser Gln Tyr Lys Leu Phe Pro Thr Arg Phe Ala Arg
225                 230                 235                 240
```

-continued

| | | |
|---|---|---|
| gga agg cga att act tgt gtt gta aaa cat cca gcc ttg gaa aag gac<br>Gly Arg Arg Ile Thr Cys Val Val Lys His Pro Ala Leu Glu Lys Asp<br>                          245                            250                            255 | 768 |
| atc cga tac tct ttc ata tta gac ata cag tat gct cct gaa gtt tcg<br>Ile Arg Tyr Ser Phe Ile Leu Asp Ile Gln Tyr Ala Pro Glu Val Ser<br>                          260                            265                            270 | 816 |
| gta aca gga tat gat gga aat tgg ttt gta gga aga aaa ggt gtt aat<br>Val Thr Gly Tyr Asp Gly Asn Trp Phe Val Gly Arg Lys Gly Val Asn<br>                          275                            280                            285 | 864 |
| ctc aaa tgt aat gct gat gca aat cca cca ccc ttc aaa tct gtg tgg<br>Leu Lys Cys Asn Ala Asp Ala Asn Pro Pro Pro Phe Lys Ser Val Trp<br>       290                           295                            300 | 912 |
| agc agg ttg gat gga caa tgg cct gat ggt tta ttg gct tca gac aat<br>Ser Arg Leu Asp Gly Gln Trp Pro Asp Gly Leu Leu Ala Ser Asp Asn<br>305                          310                            315                            320 | 960 |
| act ctt cat ttt gtc cat cca ttg act ttc aat tat tct ggt gtt tat<br>Thr Leu His Phe Val His Pro Leu Thr Phe Asn Tyr Ser Gly Val Tyr<br>                          325                            330                            335 | 1008 |
| atc tgt aaa gtg acc aat tcc ctt ggt caa aga agt gac caa aaa gtc<br>Ile Cys Lys Val Thr Asn Ser Leu Gly Gln Arg Ser Asp Gln Lys Val<br>                          340                            345                            350 | 1056 |
| atc tac att tca gat cct cct act act acc ctt cag cct aca att<br>Ile Tyr Ile Ser Asp Pro Pro Thr Thr Thr Leu Gln Pro Thr Ile<br>                        355                            360                            365 | 1104 |
| cag tgg cat ccc tca act gct gac atc gag gat cta gca aca gaa cct<br>Gln Trp His Pro Ser Thr Ala Asp Ile Glu Asp Leu Ala Thr Glu Pro<br>       370                           375                            380 | 1152 |
| aaa aaa ttg ccc ttc cca ttg tca act ttg gca aca att aag gat gac<br>Lys Lys Leu Pro Phe Pro Leu Ser Thr Leu Ala Thr Ile Lys Asp Asp<br>385                          390                            395                            400 | 1200 |
| aca att gcc acg atc att gct agt gta gtg ggt ggg gct ctc ttc ata<br>Thr Ile Ala Thr Ile Ile Ala Ser Val Val Gly Gly Ala Leu Phe Ile<br>                          405                            410                            415 | 1248 |
| gta ctt gta agt gtt ttg gct gga ata ttc tgc tat agg aga aga cgg<br>Val Leu Val Ser Val Leu Ala Gly Ile Phe Cys Tyr Arg Arg Arg Arg<br>                        420                            425                            430 | 1296 |
| acg ttt cgt gga gac tac ttt gcc aag aac tac att cca cca tca gat<br>Thr Phe Arg Gly Asp Tyr Phe Ala Lys Asn Tyr Ile Pro Pro Ser Asp<br>                          435                            440                            445 | 1344 |
| atg caa aaa gaa tca caa ata gat gtt ctt caa caa gat gag ctt gat<br>Met Gln Lys Glu Ser Gln Ile Asp Val Leu Gln Gln Asp Glu Leu Asp<br>       450                           455                            460 | 1392 |
| tct tac cca gac agt gta aaa aaa gaa aac aaa aat cca gtg aac aat<br>Ser Tyr Pro Asp Ser Val Lys Lys Glu Asn Lys Asn Pro Val Asn Asn<br>465                          470                            475                            480 | 1440 |
| cta ata cgt aaa gac tat tta gaa gag cct gaa aaa act cag tgg aac<br>Leu Ile Arg Lys Asp Tyr Leu Glu Glu Pro Glu Lys Thr Gln Trp Asn<br>                        485                            490                            495 | 1488 |
| aat gta gaa aat ctc aat agg ttt gaa aga cca atg gat tat tat gaa<br>Asn Val Glu Asn Leu Asn Arg Phe Glu Arg Pro Met Asp Tyr Tyr Glu<br>                 500                            505                            510 | 1536 |
| gat cta aaa atg gga atg aag ttt gtc agt gat gaa cat tat gat gaa<br>Asp Leu Lys Met Gly Met Lys Phe Val Ser Asp Glu His Tyr Asp Glu<br>             515                          520                            525 | 1584 |
| aac gaa gat gac tta gtt tca cat gta gat ggt tcc gta att tcc agg<br>Asn Glu Asp Asp Leu Val Ser His Val Asp Gly Ser Val Ile Ser Arg<br>       530                           535                            540 | 1632 |
| agg gag tgg tat gtt tag<br>Arg Glu Trp Tyr Val | 1650 |

545

<210> SEQ ID NO 6
<211> LENGTH: 549
<212> TYPE: PRT
<213> ORGANISM: homo sapiens

<400> SEQUENCE: 6

```
Met Ala Arg Thr Leu Arg Pro Ser Pro Leu Cys Pro Gly Gly Lys
 1               5                  10                  15

Ala Gln Leu Ser Ser Ala Ser Leu Leu Gly Ala Gly Leu Leu Leu Gln
            20                  25                  30

Pro Pro Thr Pro Pro Leu Leu Leu Leu Phe Pro Leu Leu Leu
            35                  40                  45

Phe Ser Arg Leu Cys Gly Ala Leu Ala Gly Pro Ile Ile Val Glu Pro
 50                  55                  60

His Val Thr Ala Val Trp Gly Lys Asn Val Ser Leu Lys Cys Leu Ile
 65                  70                  75                  80

Glu Val Asn Glu Thr Ile Thr Gln Ile Ser Trp Glu Lys Ile His Gly
                    85                  90                  95

Lys Ser Ser Gln Thr Val Ala Val His His Pro Gln Tyr Gly Phe Ser
                100                 105                 110

Val Gln Gly Glu Tyr Gln Gly Arg Val Leu Phe Lys Asn Tyr Ser Leu
            115                 120                 125

Asn Asp Ala Thr Ile Thr Leu His Asn Ile Gly Phe Ser Asp Ser Gly
130                 135                 140

Lys Tyr Ile Cys Lys Ala Val Thr Phe Pro Leu Gly Asn Ala Gln Ser
145                 150                 155                 160

Ser Thr Thr Val Thr Val Leu Val Glu Pro Thr Val Ser Leu Ile Lys
                165                 170                 175

Gly Pro Asp Ser Leu Ile Asp Gly Gly Asn Glu Thr Val Ala Ala Ile
                180                 185                 190

Cys Ile Ala Ala Thr Gly Lys Pro Val Ala His Ile Asp Trp Glu Gly
            195                 200                 205

Asp Leu Gly Glu Met Glu Ser Thr Thr Thr Ser Phe Pro Asn Glu Thr
210                 215                 220

Ala Thr Ile Ile Ser Gln Tyr Lys Leu Phe Pro Thr Arg Phe Ala Arg
225                 230                 235                 240

Gly Arg Arg Ile Thr Cys Val Val Lys His Pro Ala Leu Glu Lys Asp
                245                 250                 255

Ile Arg Tyr Ser Phe Ile Leu Asp Ile Gln Tyr Ala Pro Glu Val Ser
                260                 265                 270

Val Thr Gly Tyr Asp Gly Asn Trp Phe Val Gly Arg Lys Gly Val Asn
            275                 280                 285

Leu Lys Cys Asn Ala Asp Ala Asn Pro Pro Phe Lys Ser Val Trp
            290                 295                 300

Ser Arg Leu Asp Gly Gln Trp Pro Asp Gly Leu Leu Ala Ser Asp Asn
305                 310                 315                 320

Thr Leu His Phe Val His Pro Leu Thr Phe Asn Tyr Ser Gly Val Tyr
                325                 330                 335

Ile Cys Lys Val Thr Asn Ser Leu Gly Gln Arg Ser Asp Gln Lys Val
            340                 345                 350

Ile Tyr Ile Ser Asp Pro Pro Thr Thr Thr Thr Leu Gln Pro Thr Ile
            355                 360                 365
```

```
Gln Trp His Pro Ser Thr Ala Asp Ile Glu Asp Leu Ala Thr Glu Pro
    370                 375                 380
Lys Lys Leu Pro Phe Pro Leu Ser Thr Leu Ala Thr Ile Lys Asp Asp
385                 390                 395                 400
Thr Ile Ala Thr Ile Ile Ala Ser Val Val Gly Gly Ala Leu Phe Ile
                405                 410                 415
Val Leu Val Ser Val Leu Ala Gly Ile Phe Cys Tyr Arg Arg Arg Arg
            420                 425                 430
Thr Phe Arg Gly Asp Tyr Phe Ala Lys Asn Tyr Ile Pro Pro Ser Asp
        435                 440                 445
Met Gln Lys Glu Ser Gln Ile Asp Val Leu Gln Gln Asp Glu Leu Asp
    450                 455                 460
Ser Tyr Pro Asp Ser Val Lys Lys Glu Asn Lys Asn Pro Val Asn Asn
465                 470                 475                 480
Leu Ile Arg Lys Asp Tyr Leu Glu Glu Pro Glu Lys Thr Gln Trp Asn
                485                 490                 495
Asn Val Glu Asn Leu Asn Arg Phe Glu Arg Pro Met Asp Tyr Tyr Glu
            500                 505                 510
Asp Leu Lys Met Gly Met Lys Phe Val Ser Asp Glu His Tyr Asp Glu
        515                 520                 525
Asn Glu Asp Asp Leu Val Ser His Val Asp Gly Ser Val Ile Ser Arg
    530                 535                 540
Arg Glu Trp Tyr Val
545

<210> SEQ ID NO 7
<211> LENGTH: 2603
<212> TYPE: DNA
<213> ORGANISM: homo sapiens
<220> FEATURE:
<221> NAME/KEY: CDS
<222> LOCATION: (1)..(1512)
<223> OTHER INFORMATION:

<400> SEQUENCE: 7 ccg tcc ccg ctg tgt cct gga ggc ggc aaa gca caa ctt tcc tcc gct      48
Pro Ser Pro Leu Cys Pro Gly Gly Gly Lys Ala Gln Leu Ser Ser Ala
1               5                   10                  15 tct ctc ctc gga gcc ggg ctc ctg ctg cag ccc ccg acg cca cct ccg      96
Ser Leu Leu Gly Ala Gly Leu Leu Leu Gln Pro Pro Thr Pro Pro Pro
            20                  25                  30 ctg ctg ctg ctg ctc ttc ccg ctg ctc ttc tcc agg ctc tgt ggt          144
Leu Leu Leu Leu Leu Phe Pro Leu Leu Phe Ser Arg Leu Cys Gly
        35                  40                  45 gcc tta gct gga cca att att gtg gag cca cat gtc aca gca gta tgg     192
Ala Leu Ala Gly Pro Ile Ile Val Glu Pro His Val Thr Ala Val Trp
    50                  55                  60 gga aag aat gtt tca tta aag tgt tta att gaa gta aat gaa acc ata     240
Gly Lys Asn Val Ser Leu Lys Cys Leu Ile Glu Val Asn Glu Thr Ile
65                  70                  75                  80 aca cag att tca tgg gag aag ata cat ggc aaa agt tca cag act gtt     288
Thr Gln Ile Ser Trp Glu Lys Ile His Gly Lys Ser Ser Gln Thr Val
                85                  90                  95 gca gtt cac cat ccc caa tat gga ttc tct gtt caa gga gaa tat cag     336
Ala Val His His Pro Gln Tyr Gly Phe Ser Val Gln Gly Glu Tyr Gln
            100                 105                 110 gga aga gtc ttg ttt aaa aat tac tca ctt aat gat gca aca att act     384
Gly Arg Val Leu Phe Lys Asn Tyr Ser Leu Asn Asp Ala Thr Ile Thr
        115                 120                 125
```

```
ctg cat aac ata gga ttc tct gat tct gga aaa tac atc tgc aaa gct    432
Leu His Asn Ile Gly Phe Ser Asp Ser Gly Lys Tyr Ile Cys Lys Ala
    130                 135                 140 gtt aca ttc ccg ctt gga aat gcc cag tcc tct aca act gta act gtg    480
Val Thr Phe Pro Leu Gly Asn Ala Gln Ser Ser Thr Thr Val Thr Val
145                 150                 155                 160 tta gtt gaa ccc act gtg agc ctg ata aaa ggg cca gat tct tta att    528
Leu Val Glu Pro Thr Val Ser Leu Ile Lys Gly Pro Asp Ser Leu Ile
                165                 170                 175 gat gga gga aat gaa aca gta gca gcc att tgc atc gca gcc act gga    576
Asp Gly Gly Asn Glu Thr Val Ala Ala Ile Cys Ile Ala Ala Thr Gly
            180                 185                 190 aaa ccc gtt gca cat att gac tgg gaa ggt gat ctt ggt gaa atg gaa    624
Lys Pro Val Ala His Ile Asp Trp Glu Gly Asp Leu Gly Glu Met Glu
        195                 200                 205 tcc act aca act tct ttt cca aat gaa acg gca acg att atc agc cag    672
Ser Thr Thr Thr Ser Phe Pro Asn Glu Thr Ala Thr Ile Ile Ser Gln
    210                 215                 220 tac aag cta ttt cca acc aga ttt gct aga gga agg cga att act tgt    720
Tyr Lys Leu Phe Pro Thr Arg Phe Ala Arg Gly Arg Arg Ile Thr Cys
225                 230                 235                 240 gtt gta aaa cat cca gcc ttg gaa aag gac atc cga tac tct ttc ata    768
Val Val Lys His Pro Ala Leu Glu Lys Asp Ile Arg Tyr Ser Phe Ile
                245                 250                 255 tta gac ata cag tat gct cct gaa gtt tcg gta aca gga tat gat gga    816
Leu Asp Ile Gln Tyr Ala Pro Glu Val Ser Val Thr Gly Tyr Asp Gly
            260                 265                 270 aat tgg ttt gta gga aga aaa ggt gtt aat ctc aaa tgt aat gct gat    864
Asn Trp Phe Val Gly Arg Lys Gly Val Asn Leu Lys Cys Asn Ala Asp
        275                 280                 285 gca aat cca cca ccc ttc aaa tct gtg tgg agc agg ttg gat gga caa    912
Ala Asn Pro Pro Pro Phe Lys Ser Val Trp Ser Arg Leu Asp Gly Gln
    290                 295                 300 tgg cct gat ggt tta ttg gct tca gac aat act ctt cat ttt gtc cat    960
Trp Pro Asp Gly Leu Leu Ala Ser Asp Asn Thr Leu His Phe Val His
305                 310                 315                 320 cca ttg act ttc aat tat tct ggt gtt tat atc tgt aaa gtg acc aat    1008
Pro Leu Thr Phe Asn Tyr Ser Gly Val Tyr Ile Cys Lys Val Thr Asn
                325                 330                 335 tcc ctt ggt caa aga agt gac caa aaa gtc atc tac att tca gat gtt    1056
Ser Leu Gly Gln Arg Ser Asp Gln Lys Val Ile Tyr Ile Ser Asp Val
            340                 345                 350 cca ttt aag cag acc tct tcc ata gct gta gct gga gcg gta att gga    1104
Pro Phe Lys Gln Thr Ser Ser Ile Ala Val Ala Gly Ala Val Ile Gly
        355                 360                 365 gct gtt ctt gcc ctt ttc atc att gct atc ttt gtg act gtg ctg ctg    1152
Ala Val Leu Ala Leu Phe Ile Ile Ala Ile Phe Val Thr Val Leu Leu
    370                 375                 380 act cct cga aaa aaa aga cca tcc tat ctt gac aaa gtg att gac ctt    1200
Thr Pro Arg Lys Lys Arg Pro Ser Tyr Leu Asp Lys Val Ile Asp Leu
385                 390                 395                 400 cca ccc aca cat aaa cca cct cct ctg tat gaa gaa cga tcc cca cct    1248
Pro Pro Thr His Lys Pro Pro Pro Leu Tyr Glu Glu Arg Ser Pro Pro
                405                 410                 415 ttg cct cag aaa gac cta ttt cag cct gaa cac ttg cct ttg cag act    1296
Leu Pro Gln Lys Asp Leu Phe Gln Pro Glu His Leu Pro Leu Gln Thr
            420                 425                 430 cag ttc aaa gaa aga gaa gtt ggc aat ctt cag cac tct aat gga cta    1344
Gln Phe Lys Glu Arg Glu Val Gly Asn Leu Gln His Ser Asn Gly Leu
```

-continued

```
          435                 440                 445
aat agc agg agt ttt gac tat gaa gat gag aat cca gtt ggg gaa gat        1392
Asn Ser Arg Ser Phe Asp Tyr Glu Asp Glu Asn Pro Val Gly Glu Asp
        450                 455                 460 ggc att cag cag atg tac ccc ctt tac aat caa atg tgc tac caa gac        1440
Gly Ile Gln Gln Met Tyr Pro Leu Tyr Asn Gln Met Cys Tyr Gln Asp
465                 470                 475                 480 cgg agc cct ggc aaa cat cat caa aat aac gac cct aag aga gtc tac        1488
Arg Ser Pro Gly Lys His His Gln Asn Asn Asp Pro Lys Arg Val Tyr
                485                 490                 495 atc gac cca cga gaa cat tat gtg tgatttttct cttttccaa tgggcgttct        1542
Ile Asp Pro Arg Glu His Tyr Val
                500 aacaaatgtt tattcttaga ttggggagag aagctaaggc caatagttat tttactgtct      1602 ctcatataag aacagtccca ctctaagggt attggaagtc ttaatgaatg acgtaaagcc      1662 aatagcaaat ttcttttctt cattaagcgt ttcttaacca ccagctgtgt ttgtgaactt      1722 gactatagct ttgtgtgttt ctgtgatgat ggtatttaac tgctaacatt tggcctacaa      1782 tggcattttc atttaacagt acagcatctg cctgtgataa ctgcagtgat ctccagaaa       1842 gaaaggcccc agctgatact attaacctcg ttgggtctca ggcatgctag cctgttcatc      1902 tgtaattcac acaggcataa aaatgagttc agaatctatt tcactaatta tttagctggg      1962 atttggattt ccctgacatg cttaatacaa ttacaatacc tgtgtacaaa cagaggcctg      2022 aggaaagagg caaatttgc ttttcatcca acagcaaca aaaggcagtt gaaaccttca        2082 agcctgttgg ttgcttttaa acctttgtgt tattatgata tatattcttt gttgagcact      2142 gaggtcctga gggatacata tctcttgctg ttttctgcct acttttgact agctgtatgt      2202 aacaaaggct ctacttttgc tctgtcactg ttcctacagt cctgttcttt actagctaga     2262 ttagcctatt ttgcacctat taaattctaa aaaccttgtt taaatggtgt acagccttta      2322 accttgttcc tcttttctct agtattgtac atgacaggct cagcttttcac ttctgaaatt    2382 tctttcaaac taatcccagc cacacagtct tcacctcccc ttctgcattc ttcagactac      2442 ttatcatcca tgttttatct acctcagaaa agcctgctgg aaagtcacca tgaaataact      2502 tctgctctta aaagccaggt gaaaatttag aaaacttaaa agaaaaggca cttcaatatg     2562 gcacgtatgt taaactgaca tgttttttat cccttctccc c                         2603
```

<210> SEQ ID NO 8
<211> LENGTH: 504
<212> TYPE: PRT
<213> ORGANISM: homo sapiens

<400> SEQUENCE: 8

```
Pro Ser Pro Leu Cys Pro Gly Gly Gly Lys Ala Gln Leu Ser Ser Ala
1               5                   10                  15

Ser Leu Leu Gly Ala Gly Leu Leu Gln Pro Thr Pro Pro
            20                  25                  30

Leu Leu Leu Leu Leu Phe Pro Leu Leu Phe Ser Arg Leu Cys Gly
            35                  40                  45

Ala Leu Ala Gly Pro Ile Ile Val Glu Pro His Val Thr Ala Val Trp
        50                  55                  60

Gly Lys Asn Val Ser Leu Lys Cys Leu Ile Glu Val Asn Glu Thr Ile
65                  70                  75                  80

Thr Gln Ile Ser Trp Glu Lys Ile His Gly Lys Ser Ser Gln Thr Val
                85                  90                  95
```

```
Ala Val His His Pro Gln Tyr Gly Phe Ser Val Gln Gly Glu Tyr Gln
            100                 105                 110

Gly Arg Val Leu Phe Lys Asn Tyr Ser Leu Asn Asp Ala Thr Ile Thr
        115                 120                 125

Leu His Asn Ile Gly Phe Ser Asp Ser Gly Lys Tyr Ile Cys Lys Ala
    130                 135                 140

Val Thr Phe Pro Leu Gly Asn Ala Gln Ser Ser Thr Val Thr Val
145                 150                 155                 160

Leu Val Glu Pro Thr Val Ser Leu Ile Lys Gly Pro Asp Ser Leu Ile
                165                 170                 175

Asp Gly Gly Asn Glu Thr Val Ala Ala Ile Cys Ile Ala Ala Thr Gly
            180                 185                 190

Lys Pro Val Ala His Ile Asp Trp Glu Gly Asp Leu Gly Glu Met Glu
        195                 200                 205

Ser Thr Thr Thr Ser Phe Pro Asn Glu Thr Ala Thr Ile Ile Ser Gln
    210                 215                 220

Tyr Lys Leu Phe Pro Thr Arg Phe Ala Arg Gly Arg Arg Ile Thr Cys
225                 230                 235                 240

Val Val Lys His Pro Ala Leu Glu Lys Asp Ile Arg Tyr Ser Phe Ile
                245                 250                 255

Leu Asp Ile Gln Tyr Ala Pro Glu Val Ser Val Thr Gly Tyr Asp Gly
            260                 265                 270

Asn Trp Phe Val Gly Arg Lys Gly Val Asn Leu Lys Cys Asn Ala Asp
        275                 280                 285

Ala Asn Pro Pro Pro Phe Lys Ser Val Trp Ser Arg Leu Asp Gly Gln
    290                 295                 300

Trp Pro Asp Gly Leu Leu Ala Ser Asp Asn Thr Leu His Phe Val His
305                 310                 315                 320

Pro Leu Thr Phe Asn Tyr Ser Gly Val Tyr Ile Cys Lys Val Thr Asn
                325                 330                 335

Ser Leu Gly Gln Arg Ser Asp Gln Lys Val Ile Tyr Ile Ser Asp Val
            340                 345                 350

Pro Phe Lys Gln Thr Ser Ser Ile Ala Val Ala Gly Ala Val Ile Gly
        355                 360                 365

Ala Val Leu Ala Leu Phe Ile Ile Ala Ile Phe Val Thr Val Leu Leu
    370                 375                 380

Thr Pro Arg Lys Lys Arg Pro Ser Tyr Leu Asp Lys Val Ile Asp Leu
385                 390                 395                 400

Pro Pro Thr His Lys Pro Pro Leu Tyr Glu Glu Arg Ser Pro Pro
                405                 410                 415

Leu Pro Gln Lys Asp Leu Phe Gln Pro Glu His Leu Pro Leu Gln Thr
            420                 425                 430

Gln Phe Lys Glu Arg Glu Val Gly Asn Leu Gln His Ser Asn Gly Leu
        435                 440                 445

Asn Ser Arg Ser Phe Asp Tyr Glu Asp Glu Asn Pro Val Gly Glu Asp
    450                 455                 460

Gly Ile Gln Gln Met Tyr Pro Leu Tyr Asn Gln Met Cys Tyr Gln Asp
465                 470                 475                 480

Arg Ser Pro Gly Lys His His Gln Asn Asn Asp Pro Lys Arg Val Tyr
                485                 490                 495

Ile Asp Pro Arg Glu His Tyr Val
                500
```

-continued

```
<210> SEQ ID NO 9
<211> LENGTH: 1533
<212> TYPE: DNA
<213> ORGANISM: Artificial Sequence
<220> FEATURE:
<223> OTHER INFORMATION: nucleotides 1-18 are from Mus musculus Nectin-3
      DNA, the rest are from human Nectin-3 beta
<221> NAME/KEY: CDS
<222> LOCATION: (1)..(1533)
<223> OTHER INFORMATION:

<400> SEQUENCE: 9 atg gcc cgg acc ccc ggc ccg tcc ccg ctg tgt cct gga ggc ggc aaa      48
Met Ala Arg Thr Pro Gly Pro Ser Pro Leu Cys Pro Gly Gly Gly Lys
1               5                   10                  15 gca caa ctt tcc tcc gct tct ctc ctc gga gcc ggg ctc ctg ctg cag      96
Ala Gln Leu Ser Ser Ala Ser Leu Leu Gly Ala Gly Leu Leu Leu Gln
            20                  25                  30 ccc ccg acg cca cct ccg ctg ctg ctg ctc ttc ccg ctg ctg ctc         144
Pro Pro Thr Pro Pro Pro Leu Leu Leu Leu Phe Pro Leu Leu Leu
        35                  40                  45 ttc tcc agg ctc tgt ggt gcc tta gct gga cca att att gtg gag cca     192
Phe Ser Arg Leu Cys Gly Ala Leu Ala Gly Pro Ile Ile Val Glu Pro
50                  55                  60 cat gtc aca gca gta tgg gga aag aat gtt tca tta aag tgt tta att     240
His Val Thr Ala Val Trp Gly Lys Asn Val Ser Leu Lys Cys Leu Ile
65                  70                  75                  80 gaa gta aat gaa acc ata aca cag att tca tgg gag aag ata cat ggc     288
Glu Val Asn Glu Thr Ile Thr Gln Ile Ser Trp Glu Lys Ile His Gly
                85                  90                  95 aaa agt tca cag act gtt gca gtt cac cat ccc caa tat gga ttc tct     336
Lys Ser Ser Gln Thr Val Ala Val His His Pro Gln Tyr Gly Phe Ser
            100                 105                 110 gtt caa gga gaa tat cag gga aga gtc ttg ttt aaa aat tac tca ctt     384
Val Gln Gly Glu Tyr Gln Gly Arg Val Leu Phe Lys Asn Tyr Ser Leu
        115                 120                 125 aat gat gca aca att act ctg cat aac ata gga ttc tct gat tct gga     432
Asn Asp Ala Thr Ile Thr Leu His Asn Ile Gly Phe Ser Asp Ser Gly
130                 135                 140 aaa tac atc tgc aaa gct gtt aca ttc ccg ctt gga aat gcc cag tcc     480
Lys Tyr Ile Cys Lys Ala Val Thr Phe Pro Leu Gly Asn Ala Gln Ser
145                 150                 155                 160 tct aca act gta act gtg tta gtt gaa ccc act gtg agc ctg ata aaa     528
Ser Thr Thr Val Thr Val Leu Val Glu Pro Thr Val Ser Leu Ile Lys
                165                 170                 175 ggg cca gat tct tta att gat gga gga aat gaa aca gta gca gcc att     576
Gly Pro Asp Ser Leu Ile Asp Gly Gly Asn Glu Thr Val Ala Ala Ile
            180                 185                 190 tgc atc gca gcc act gga aaa ccc gtt gca cat att gac tgg gaa ggt     624
Cys Ile Ala Ala Thr Gly Lys Pro Val Ala His Ile Asp Trp Glu Gly
        195                 200                 205 gat ctt ggt gaa atg gaa tcc act aca act tct ttt cca aat gaa acg     672
Asp Leu Gly Glu Met Glu Ser Thr Thr Thr Ser Phe Pro Asn Glu Thr
210                 215                 220 gca acg att atc agc cag tac aag cta ttt cca acc aga ttt gct aga     720
Ala Thr Ile Ile Ser Gln Tyr Lys Leu Phe Pro Thr Arg Phe Ala Arg
225                 230                 235                 240 gga agg cga att act tgt gtt gta aaa cat cca gcc ttg gaa aag gac     768
Gly Arg Arg Ile Thr Cys Val Val Lys His Pro Ala Leu Glu Lys Asp
                245                 250                 255 atc cga tac tct ttc ata tta gac ata cag tat gct cct gaa gtt tcg     816
```

-continued

```
Ile Arg Tyr Ser Phe Ile Leu Asp Ile Gln Tyr Ala Pro Glu Val Ser
            260                 265                 270 gta aca gga tat gat gga aat tgg ttt gta gga aga aaa ggt gtt aat      864
Val Thr Gly Tyr Asp Gly Asn Trp Phe Val Gly Arg Lys Gly Val Asn
            275                 280                 285 ctc aaa tgt aat gct gat gca aat cca cca ccc ttc aaa tct gtg tgg      912
Leu Lys Cys Asn Ala Asp Ala Asn Pro Pro Pro Phe Lys Ser Val Trp
            290                 295                 300 agc agg ttg gat gga caa tgg cct gat ggt tta ttg gct tca gac aat      960
Ser Arg Leu Asp Gly Gln Trp Pro Asp Gly Leu Leu Ala Ser Asp Asn
305                 310                 315                 320 act ctt cat ttt gtc cat cca ttg act ttc aat tat tct ggt gtt tat     1008
Thr Leu His Phe Val His Pro Leu Thr Phe Asn Tyr Ser Gly Val Tyr
            325                 330                 335 atc tgt aaa gtg acc aat tcc ctt ggt caa aga agt gac caa aaa gtc     1056
Ile Cys Lys Val Thr Asn Ser Leu Gly Gln Arg Ser Asp Gln Lys Val
            340                 345                 350 atc tac att tca gat gtt cca ttt aag cag acc tct tcc ata gct gta     1104
Ile Tyr Ile Ser Asp Val Pro Phe Lys Gln Thr Ser Ser Ile Ala Val
            355                 360                 365 gct gga gcg gta att gga gct gtt ctt gcc ctt ttc atc att gct atc     1152
Ala Gly Ala Val Ile Gly Ala Val Leu Ala Leu Phe Ile Ile Ala Ile
            370                 375                 380 ttt gtg act gtg ctg ctg act cct cga aaa aaa aga cca tcc tat ctt     1200
Phe Val Thr Val Leu Leu Thr Pro Arg Lys Lys Arg Pro Ser Tyr Leu
385                 390                 395                 400 gac aaa gtg att gac ctt cca ccc aca cat aaa cca cct cct ctg tat     1248
Asp Lys Val Ile Asp Leu Pro Pro Thr His Lys Pro Pro Pro Leu Tyr
            405                 410                 415 gaa gaa cga tcc cca cct ttg cct cag aaa gac cta ttt cag cct gaa     1296
Glu Glu Arg Ser Pro Pro Leu Pro Gln Lys Asp Leu Phe Gln Pro Glu
            420                 425                 430 cac ttg cct ttg cag act cag ttc aaa gaa aga gaa gtt ggc aat ctt     1344
His Leu Pro Leu Gln Thr Gln Phe Lys Glu Arg Glu Val Gly Asn Leu
            435                 440                 445 cag cac tct aat gga cta aat agc agg agt ttt gac tat gaa gat gag     1392
Gln His Ser Asn Gly Leu Asn Ser Arg Ser Phe Asp Tyr Glu Asp Glu
        450                 455                 460 aat cca gtt ggg gaa gat ggc att cag cag atg tac ccc ctt tac aat     1440
Asn Pro Val Gly Glu Asp Gly Ile Gln Gln Met Tyr Pro Leu Tyr Asn
465                 470                 475                 480 caa atg tgc tac caa gac cgg agc cct ggc aaa cat cat caa aat aac     1488
Gln Met Cys Tyr Gln Asp Arg Ser Pro Gly Lys His His Gln Asn Asn
            485                 490                 495 gac cct aag aga gtc tac atc gac cca cga gaa cat tat gtg tga         1533
Asp Pro Lys Arg Val Tyr Ile Asp Pro Arg Glu His Tyr Val
            500                 505                 510
```

<210> SEQ ID NO 10
<211> LENGTH: 510
<212> TYPE: PRT
<213> ORGANISM: Artificial Sequence
<220> FEATURE:
<223> OTHER INFORMATION: nucleotides 1-18 are from Mus musculus Nectin-3
      DNA, the rest are from human Nectin-3 beta

<400> SEQUENCE: 10

```
Met Ala Arg Thr Pro Gly Pro Ser Pro Leu Cys Pro Gly Gly Gly Lys
1               5                   10                  15

Ala Gln Leu Ser Ser Ala Ser Leu Leu Gly Ala Gly Leu Leu Leu Gln
            20                  25                  30
```

-continued

```
Pro Pro Thr Pro Pro Leu Leu Leu Leu Phe Pro Leu Leu Leu
        35              40              45

Phe Ser Arg Leu Cys Gly Ala Leu Ala Gly Pro Ile Ile Val Glu Pro
    50              55              60

His Val Thr Ala Val Trp Gly Lys Asn Val Ser Leu Lys Cys Leu Ile
65              70              75              80

Glu Val Asn Glu Thr Ile Thr Gln Ile Ser Trp Glu Lys Ile His Gly
                85              90              95

Lys Ser Ser Gln Thr Val Ala Val His His Pro Gln Tyr Gly Phe Ser
            100             105             110

Val Gln Gly Glu Tyr Gln Gly Arg Val Leu Phe Lys Asn Tyr Ser Leu
        115             120             125

Asn Asp Ala Thr Ile Thr Leu His Asn Ile Gly Phe Ser Asp Ser Gly
    130             135             140

Lys Tyr Ile Cys Lys Ala Val Thr Phe Pro Leu Gly Asn Ala Gln Ser
145             150             155             160

Ser Thr Thr Val Thr Val Leu Val Glu Pro Thr Val Ser Leu Ile Lys
                165             170             175

Gly Pro Asp Ser Leu Ile Asp Gly Gly Asn Glu Thr Val Ala Ala Ile
            180             185             190

Cys Ile Ala Ala Thr Gly Lys Pro Val Ala His Ile Asp Trp Glu Gly
        195             200             205

Asp Leu Gly Glu Met Glu Ser Thr Thr Thr Ser Phe Pro Asn Glu Thr
    210             215             220

Ala Thr Ile Ile Ser Gln Tyr Lys Leu Phe Pro Thr Arg Phe Ala Arg
225             230             235             240

Gly Arg Arg Ile Thr Cys Val Val Lys His Pro Ala Leu Glu Lys Asp
                245             250             255

Ile Arg Tyr Ser Phe Ile Leu Asp Ile Gln Tyr Ala Pro Glu Val Ser
            260             265             270

Val Thr Gly Tyr Asp Gly Asn Trp Phe Val Gly Arg Lys Gly Val Asn
        275             280             285

Leu Lys Cys Asn Ala Asp Ala Asn Pro Pro Pro Phe Lys Ser Val Trp
    290             295             300

Ser Arg Leu Asp Gly Gln Trp Pro Asp Gly Leu Leu Ala Ser Asp Asn
305             310             315             320

Thr Leu His Phe Val His Pro Leu Thr Phe Asn Tyr Ser Gly Val Tyr
                325             330             335

Ile Cys Lys Val Thr Asn Ser Leu Gly Gln Arg Ser Asp Gln Lys Val
            340             345             350

Ile Tyr Ile Ser Asp Val Pro Phe Lys Gln Thr Ser Ser Ile Ala Val
        355             360             365

Ala Gly Ala Val Ile Gly Ala Val Leu Ala Leu Phe Ile Ile Ala Ile
    370             375             380

Phe Val Thr Val Leu Leu Thr Pro Arg Lys Lys Arg Pro Ser Tyr Leu
385             390             395             400

Asp Lys Val Ile Asp Leu Pro Pro Thr His Lys Pro Pro Leu Tyr
                405             410             415

Glu Glu Arg Ser Pro Pro Leu Pro Gln Lys Asp Leu Phe Gln Pro Glu
            420             425             430

His Leu Pro Leu Gln Thr Gln Phe Lys Glu Arg Glu Val Gly Asn Leu
        435             440             445
```

```
Gln His Ser Asn Gly Leu Asn Ser Arg Ser Phe Asp Tyr Glu Asp Glu
    450                 455                 460

Asn Pro Val Gly Glu Asp Gly Ile Gln Gln Met Tyr Pro Leu Tyr Asn
465                 470                 475                 480

Gln Met Cys Tyr Gln Asp Arg Ser Pro Gly Lys His His Gln Asn Asn
            485                 490                 495

Asp Pro Lys Arg Val Tyr Ile Asp Pro Arg Glu His Tyr Val
            500                 505                 510

<210> SEQ ID NO 11
<211> LENGTH: 1533
<212> TYPE: DNA
<213> ORGANISM: homo sapiens
<220> FEATURE:
<221> NAME/KEY: CDS
<222> LOCATION: (1)..(1533)
<223> OTHER INFORMATION:

<400> SEQUENCE: 11 atg gcg cgg acc ctg cgg ccg tcc ccg ctg tgt cct gga ggc ggc aaa      48
Met Ala Arg Thr Leu Arg Pro Ser Pro Leu Cys Pro Gly Gly Gly Lys
1               5                   10                  15 gca caa ctt tcc tcc gct tct ctc ctc gga gcc ggg ctc ctg ctg cag      96
Ala Gln Leu Ser Ser Ala Ser Leu Leu Gly Ala Gly Leu Leu Leu Gln
            20                  25                  30 ccc ccg acg cca cct ccg ctg ctg ctg ctc ttc ccg ctg ctg ctc           144
Pro Pro Thr Pro Pro Pro Leu Leu Leu Leu Leu Phe Pro Leu Leu Leu
        35                  40                  45 ttc tcc agg ctc tgt ggt gcc tta gct gga cca att att gtg gag cca      192
Phe Ser Arg Leu Cys Gly Ala Leu Ala Gly Pro Ile Ile Val Glu Pro
50                  55                  60 cat gtc aca gca gta tgg gga aag aat gtt tca tta aag tgt tta att      240
His Val Thr Ala Val Trp Gly Lys Asn Val Ser Leu Lys Cys Leu Ile
65                  70                  75                  80 gaa gta aat gaa acc ata aca cag att tca tgg gag aag ata cat ggc      288
Glu Val Asn Glu Thr Ile Thr Gln Ile Ser Trp Glu Lys Ile His Gly
                85                  90                  95 aaa agt tca cag act gtt gca gtt cac cat ccc caa tat gga ttc tct      336
Lys Ser Ser Gln Thr Val Ala Val His His Pro Gln Tyr Gly Phe Ser
            100                 105                 110 gtt caa gga gaa tat cag gga aga gtc ttg ttt aaa aat tac tca ctt      384
Val Gln Gly Glu Tyr Gln Gly Arg Val Leu Phe Lys Asn Tyr Ser Leu
        115                 120                 125 aat gat gca aca att act ctg cat aac ata gga ttc tct gat tct gga      432
Asn Asp Ala Thr Ile Thr Leu His Asn Ile Gly Phe Ser Asp Ser Gly
130                 135                 140 aaa tac atc tgc aaa gct gtt aca ttc ccg ctt gga aat gcc cag tcc      480
Lys Tyr Ile Cys Lys Ala Val Thr Phe Pro Leu Gly Asn Ala Gln Ser
145                 150                 155                 160 tct aca act gta act gtg tta gtt gaa ccc act gtg agc ctg ata aaa      528
Ser Thr Thr Val Thr Val Leu Val Glu Pro Thr Val Ser Leu Ile Lys
                165                 170                 175 ggg cca gat tct tta att gat gga gga aat gaa aca gta gca gcc att      576
Gly Pro Asp Ser Leu Ile Asp Gly Gly Asn Glu Thr Val Ala Ala Ile
            180                 185                 190 tgc atc gca gcc act gga aaa ccc gtt gca cat att gac tgg gaa ggt      624
Cys Ile Ala Ala Thr Gly Lys Pro Val Ala His Ile Asp Trp Glu Gly
        195                 200                 205 gat ctt ggt gaa atg gaa tcc act aca act tct ttt cca aat gaa acg      672
Asp Leu Gly Glu Met Glu Ser Thr Thr Thr Ser Phe Pro Asn Glu Thr
210                 215                 220
```

```
gca acg att atc agc cag tac aag cta ttt cca acc aga ttt gct aga       720
Ala Thr Ile Ile Ser Gln Tyr Lys Leu Phe Pro Thr Arg Phe Ala Arg
225                 230                 235                 240 gga agg cga att act tgt gtt gta aaa cat cca gcc ttg gaa aag gac       768
Gly Arg Arg Ile Thr Cys Val Val Lys His Pro Ala Leu Glu Lys Asp
                245                 250                 255 atc cga tac tct ttc ata tta gac ata cag tat gct cct gaa gtt tcg       816
Ile Arg Tyr Ser Phe Ile Leu Asp Ile Gln Tyr Ala Pro Glu Val Ser
            260                 265                 270 gta aca gga tat gat gga aat tgg ttt gta gga aga aaa ggt gtt aat       864
Val Thr Gly Tyr Asp Gly Asn Trp Phe Val Gly Arg Lys Gly Val Asn
        275                 280                 285 ctc aaa tgt aat gct gat gca aat cca cca ccc ttc aaa tct gtg tgg       912
Leu Lys Cys Asn Ala Asp Ala Asn Pro Pro Pro Phe Lys Ser Val Trp
290                 295                 300 agc agg ttg gat gga caa tgg cct gat ggt tta ttg gct tca gac aat       960
Ser Arg Leu Asp Gly Gln Trp Pro Asp Gly Leu Leu Ala Ser Asp Asn
305                 310                 315                 320 act ctt cat ttt gtc cat cca ttg act ttc aat tat tct ggt gtt tat      1008
Thr Leu His Phe Val His Pro Leu Thr Phe Asn Tyr Ser Gly Val Tyr
                325                 330                 335 atc tgt aaa gtg acc aat tcc ctt ggt caa aga agt gac caa aaa gtc      1056
Ile Cys Lys Val Thr Asn Ser Leu Gly Gln Arg Ser Asp Gln Lys Val
            340                 345                 350 atc tac att tca gat gtt cca ttt aag cag acc tct tcc ata gct gta      1104
Ile Tyr Ile Ser Asp Val Pro Phe Lys Gln Thr Ser Ser Ile Ala Val
        355                 360                 365 gct gga gcg gta att gga gct gtt ctt gcc ctt ttc atc att gct atc      1152
Ala Gly Ala Val Ile Gly Ala Val Leu Ala Leu Phe Ile Ile Ala Ile
370                 375                 380 ttt gtg act gtg ctg ctg act cct cga aaa aaa aga cca tcc tat ctt      1200
Phe Val Thr Val Leu Leu Thr Pro Arg Lys Lys Arg Pro Ser Tyr Leu
385                 390                 395                 400 gac aaa gtg att gac ctt cca ccc aca cat aaa cca cct cct ctg tat      1248
Asp Lys Val Ile Asp Leu Pro Pro Thr His Lys Pro Pro Pro Leu Tyr
                405                 410                 415 gaa gaa cga tcc cca cct ttg cct cag aaa gac cta ttt cag cct gaa      1296
Glu Glu Arg Ser Pro Pro Leu Pro Gln Lys Asp Leu Phe Gln Pro Glu
            420                 425                 430 cac ttg cct ttg cag act cag ttc aaa gaa aga gaa gtt ggc aat ctt      1344
His Leu Pro Leu Gln Thr Gln Phe Lys Glu Arg Glu Val Gly Asn Leu
        435                 440                 445 cag cac tct aat gga cta aat agc agg agt ttt gac tat gaa gat gag      1392
Gln His Ser Asn Gly Leu Asn Ser Arg Ser Phe Asp Tyr Glu Asp Glu
450                 455                 460 aat cca gtt ggg gaa gat ggc att cag cag atg tac ccc ctt tac aat      1440
Asn Pro Val Gly Glu Asp Gly Ile Gln Gln Met Tyr Pro Leu Tyr Asn
465                 470                 475                 480 caa atg tgc tac caa gac cgg agc cct ggc aaa cat cat caa aat aac      1488
Gln Met Cys Tyr Gln Asp Arg Ser Pro Gly Lys His His Gln Asn Asn
                485                 490                 495 gac cct aag aga gtc tac atc gac cca cga gaa cat tat gtg tga          1533
Asp Pro Lys Arg Val Tyr Ile Asp Pro Arg Glu His Tyr Val
                500                 505                 510

<210> SEQ ID NO 12
<211> LENGTH: 510
<212> TYPE: PRT
<213> ORGANISM: homo sapiens
```

<400> SEQUENCE: 12

```
Met Ala Arg Thr Leu Arg Pro Ser Pro Leu Cys Pro Gly Gly Gly Lys
1               5                   10                  15

Ala Gln Leu Ser Ser Ala Ser Leu Leu Gly Ala Gly Leu Leu Leu Gln
            20                  25                  30

Pro Pro Thr Pro Pro Leu Leu Leu Leu Phe Pro Leu Leu Leu
        35                  40                  45

Phe Ser Arg Leu Cys Gly Ala Leu Ala Gly Pro Ile Ile Val Glu Pro
    50                  55                  60

His Val Thr Ala Val Trp Gly Lys Asn Val Ser Leu Lys Cys Leu Ile
65                  70                  75                  80

Glu Val Asn Glu Thr Ile Thr Gln Ile Ser Trp Glu Lys Ile His Gly
                85                  90                  95

Lys Ser Ser Gln Thr Val Ala Val His His Pro Gln Tyr Gly Phe Ser
            100                 105                 110

Val Gln Gly Glu Tyr Gln Gly Arg Val Leu Phe Lys Asn Tyr Ser Leu
        115                 120                 125

Asn Asp Ala Thr Ile Thr Leu His Asn Ile Gly Phe Ser Asp Ser Gly
130                 135                 140

Lys Tyr Ile Cys Lys Ala Val Thr Phe Pro Leu Gly Asn Ala Gln Ser
145                 150                 155                 160

Ser Thr Thr Val Thr Val Leu Val Glu Pro Thr Val Ser Leu Ile Lys
                165                 170                 175

Gly Pro Asp Ser Leu Ile Asp Gly Gly Asn Glu Thr Val Ala Ala Ile
            180                 185                 190

Cys Ile Ala Ala Thr Gly Lys Pro Val Ala His Ile Asp Trp Glu Gly
        195                 200                 205

Asp Leu Gly Glu Met Glu Ser Thr Thr Thr Ser Phe Pro Asn Glu Thr
210                 215                 220

Ala Thr Ile Ile Ser Gln Tyr Lys Leu Phe Pro Thr Arg Phe Ala Arg
225                 230                 235                 240

Gly Arg Arg Ile Thr Cys Val Val Lys His Pro Ala Leu Glu Lys Asp
                245                 250                 255

Ile Arg Tyr Ser Phe Ile Leu Asp Ile Gln Tyr Ala Pro Glu Val Ser
            260                 265                 270

Val Thr Gly Tyr Asp Gly Asn Trp Phe Val Gly Arg Lys Gly Val Asn
        275                 280                 285

Leu Lys Cys Asn Ala Asp Ala Asn Pro Pro Phe Lys Ser Val Trp
290                 295                 300

Ser Arg Leu Asp Gly Gln Trp Pro Asp Gly Leu Leu Ala Ser Asp Asn
305                 310                 315                 320

Thr Leu His Phe Val His Pro Leu Thr Phe Asn Tyr Ser Gly Val Tyr
                325                 330                 335

Ile Cys Lys Val Thr Asn Ser Leu Gly Gln Arg Ser Asp Gln Lys Val
            340                 345                 350

Ile Tyr Ile Ser Asp Val Pro Phe Lys Gln Thr Ser Ser Ile Ala Val
        355                 360                 365

Ala Gly Ala Val Ile Gly Ala Val Leu Ala Leu Phe Ile Ile Ala Ile
370                 375                 380

Phe Val Thr Val Leu Leu Thr Pro Arg Lys Lys Arg Pro Ser Tyr Leu
385                 390                 395                 400

Asp Lys Val Ile Asp Leu Pro Pro Thr His Lys Pro Pro Pro Leu Tyr
                405                 410                 415
```

```
Glu Glu Arg Ser Pro Pro Leu Pro Gln Lys Asp Leu Phe Gln Pro Glu
            420                 425                 430

His Leu Pro Leu Gln Thr Gln Phe Lys Glu Arg Glu Val Gly Asn Leu
            435                 440                 445

Gln His Ser Asn Gly Leu Asn Ser Arg Ser Phe Asp Tyr Glu Asp Glu
            450                 455                 460

Asn Pro Val Gly Glu Asp Gly Ile Gln Gln Met Tyr Pro Leu Tyr Asn
465                 470                 475                 480

Gln Met Cys Tyr Gln Asp Arg Ser Pro Gly Lys His His Gln Asn Asn
            485                 490                 495

Asp Pro Lys Arg Val Tyr Ile Asp Pro Arg Glu His Tyr Val
            500                 505                 510

<210> SEQ ID NO 13
<211> LENGTH: 634
<212> TYPE: PRT
<213> ORGANISM: Artificial Sequence
<220> FEATURE:
<223> OTHER INFORMATION: fusion protein:  human Nectin-3-alpha-Fc

<400> SEQUENCE: 13

Met Ala Arg Thr Pro Gly Pro Ser Pro Leu Cys Pro Gly Gly Gly Lys
1               5                   10                  15

Ala Gln Leu Ser Ser Ala Ser Leu Leu Gly Ala Gly Leu Leu Leu Gln
            20                  25                  30

Pro Pro Thr Pro Pro Pro Leu Leu Leu Leu Phe Pro Leu Leu Leu
            35                  40                  45

Phe Ser Arg Leu Cys Gly Ala Leu Ala Gly Pro Ile Ile Val Glu Pro
50                  55                  60

His Val Thr Ala Val Trp Gly Lys Asn Val Ser Leu Lys Cys Leu Ile
65                  70                  75                  80

Glu Val Asn Glu Thr Ile Thr Gln Ile Ser Trp Glu Lys Ile His Gly
            85                  90                  95

Lys Ser Ser Gln Thr Val Ala Val His His Pro Gln Tyr Gly Phe Ser
            100                 105                 110

Val Gln Gly Glu Tyr Gln Gly Arg Val Leu Phe Lys Asn Tyr Ser Leu
            115                 120                 125

Asn Asp Ala Thr Ile Thr Leu His Asn Ile Gly Phe Ser Asp Ser Gly
            130                 135                 140

Lys Tyr Ile Cys Lys Ala Val Thr Phe Pro Leu Gly Asn Ala Gln Ser
145                 150                 155                 160

Ser Thr Thr Val Thr Val Leu Val Glu Pro Thr Val Ser Leu Ile Lys
            165                 170                 175

Gly Pro Asp Ser Leu Ile Asp Gly Gly Asn Glu Thr Val Ala Ala Ile
            180                 185                 190

Cys Ile Ala Ala Thr Gly Lys Pro Val Ala His Ile Asp Trp Glu Gly
            195                 200                 205

Asp Leu Gly Glu Met Glu Ser Thr Thr Thr Ser Phe Pro Asn Glu Thr
            210                 215                 220

Ala Thr Ile Ile Ser Gln Tyr Lys Leu Phe Pro Thr Arg Phe Ala Arg
225                 230                 235                 240

Gly Arg Arg Ile Thr Cys Val Val Lys His Pro Ala Leu Glu Lys Asp
            245                 250                 255

Ile Arg Tyr Ser Phe Ile Leu Asp Ile Gln Tyr Ala Pro Glu Val Ser
            260                 265                 270
```

```
Val Thr Gly Tyr Asp Gly Asn Trp Phe Val Gly Arg Lys Gly Val Asn
        275                 280                 285

Leu Lys Cys Asn Ala Asp Ala Asn Pro Pro Phe Lys Ser Val Trp
    290                 295                 300

Ser Arg Leu Asp Gly Gln Trp Pro Asp Gly Leu Leu Ala Ser Asp Asn
305                 310                 315                 320

Thr Leu His Phe Val His Pro Leu Thr Phe Asn Tyr Ser Gly Val Tyr
                    325                 330                 335

Ile Cys Lys Val Thr Asn Ser Leu Gly Gln Arg Ser Asp Gln Lys Val
                340                 345                 350

Ile Tyr Ile Ser Asp Pro Pro Thr Thr Thr Leu Gln Pro Thr Ile
            355                 360                 365

Gln Trp His Pro Ser Thr Ala Asp Ile Glu Asp Leu Ala Thr Glu Pro
    370                 375                 380

Lys Lys Leu Pro Phe Pro Leu Ser Thr Leu Ala Thr Ile Lys Asp Asp
385                 390                 395                 400

Thr Ile Ala Thr Arg Ser Cys Asp Lys Thr His Thr Cys Pro Pro Cys
                405                 410                 415

Pro Ala Pro Glu Ala Glu Gly Ala Pro Ser Val Phe Leu Phe Pro Pro
                420                 425                 430

Lys Pro Lys Asp Thr Leu Met Ile Ser Arg Thr Pro Glu Val Thr Cys
            435                 440                 445

Val Val Val Asp Val Ser His Glu Asp Pro Glu Val Lys Phe Asn Trp
            450                 455                 460

Tyr Val Asp Gly Val Glu Val His Asn Ala Lys Thr Lys Pro Arg Glu
465                 470                 475                 480

Glu Gln Tyr Asn Ser Thr Tyr Arg Val Val Ser Val Leu Thr Val Leu
                485                 490                 495

His Gln Asp Trp Leu Asn Gly Lys Glu Tyr Lys Cys Lys Val Ser Asn
                500                 505                 510

Lys Ala Leu Pro Ala Pro Ile Glu Lys Thr Ile Ser Lys Ala Lys Gly
            515                 520                 525

Gln Pro Arg Glu Pro Gln Val Tyr Thr Leu Pro Pro Ser Arg Glu Glu
    530                 535                 540

Met Thr Lys Asn Gln Val Ser Leu Thr Cys Leu Val Lys Gly Phe Tyr
545                 550                 555                 560

Pro Ser Asp Ile Ala Val Glu Trp Glu Ser Asn Gly Gln Pro Glu Asn
                565                 570                 575

Asn Tyr Lys Thr Thr Pro Pro Val Leu Asp Ser Asp Gly Ser Phe Phe
                580                 585                 590

Leu Tyr Ser Lys Leu Thr Val Asp Lys Ser Arg Trp Gln Gln Gly Asn
            595                 600                 605

Val Phe Ser Cys Ser Val Met His Glu Ala Leu His Asn His Tyr Thr
        610                 615                 620

Gln Lys Ser Leu Ser Leu Ser Pro Gly Lys
625                 630

<210> SEQ ID NO 14
<211> LENGTH: 595
<212> TYPE: PRT
<213> ORGANISM: Artificial Sequence
<220> FEATURE:
<223> OTHER INFORMATION: fusion protein: human Nectin-3-beta-Fc

<400> SEQUENCE: 14
```

-continued

```
Met Ala Arg Thr Pro Gly Pro Ser Pro Leu Cys Pro Gly Gly Lys
1               5                   10                  15

Ala Gln Leu Ser Ser Ala Ser Leu Leu Gly Ala Gly Leu Leu Leu Gln
                20                  25                  30

Pro Pro Thr Pro Pro Leu Leu Leu Leu Phe Pro Leu Leu Leu
        35                  40                  45

Phe Ser Arg Leu Cys Gly Ala Leu Ala Gly Pro Ile Ile Val Glu Pro
    50                  55                  60

His Val Thr Ala Val Trp Gly Lys Asn Val Ser Leu Lys Cys Leu Ile
65                  70                  75                  80

Glu Val Asn Glu Thr Ile Thr Gln Ile Ser Trp Glu Lys Ile His Gly
                85                  90                  95

Lys Ser Ser Gln Thr Val Ala Val His His Pro Gln Tyr Gly Phe Ser
                100                 105                 110

Val Gln Gly Glu Tyr Gln Gly Arg Val Leu Phe Lys Asn Tyr Ser Leu
                115                 120                 125

Asn Asp Ala Thr Ile Thr Leu His Asn Ile Gly Phe Ser Asp Ser Gly
    130                 135                 140

Lys Tyr Ile Cys Lys Ala Val Thr Phe Pro Leu Gly Asn Ala Gln Ser
145                 150                 155                 160

Ser Thr Thr Val Thr Val Leu Val Glu Pro Thr Val Ser Leu Ile Lys
                165                 170                 175

Gly Pro Asp Ser Leu Ile Asp Gly Gly Asn Glu Thr Val Ala Ala Ile
                180                 185                 190

Cys Ile Ala Ala Thr Gly Lys Pro Val Ala His Ile Asp Trp Glu Gly
                195                 200                 205

Asp Leu Gly Glu Met Glu Ser Thr Thr Thr Ser Phe Pro Asn Glu Thr
    210                 215                 220

Ala Thr Ile Ile Ser Gln Tyr Lys Leu Phe Pro Thr Arg Phe Ala Arg
225                 230                 235                 240

Gly Arg Arg Ile Thr Cys Val Val Lys His Pro Ala Leu Glu Lys Asp
                245                 250                 255

Ile Arg Tyr Ser Phe Ile Leu Asp Ile Gln Tyr Ala Pro Glu Val Ser
                260                 265                 270

Val Thr Gly Tyr Asp Gly Asn Trp Phe Val Gly Arg Lys Gly Val Asn
                275                 280                 285

Leu Lys Cys Asn Ala Asp Ala Asn Pro Pro Pro Phe Lys Ser Val Trp
    290                 295                 300

Ser Arg Leu Asp Gly Gln Trp Pro Asp Gly Leu Leu Ala Ser Asp Asn
305                 310                 315                 320

Thr Leu His Phe Val His Pro Leu Thr Phe Asn Tyr Ser Gly Val Tyr
                325                 330                 335

Ile Cys Lys Val Thr Asn Ser Leu Gly Gln Arg Ser Asp Gln Lys Val
                340                 345                 350

Ile Tyr Ile Ser Asp Val Pro Phe Lys Gln Thr Ser Ser Arg Ser Cys
                355                 360                 365

Asp Lys Thr His Thr Cys Pro Pro Cys Pro Ala Pro Glu Ala Glu Gly
    370                 375                 380

Ala Pro Ser Val Phe Leu Phe Pro Pro Lys Pro Lys Asp Thr Leu Met
385                 390                 395                 400

Ile Ser Arg Thr Pro Glu Val Thr Cys Val Val Val Asp Val Ser His
                405                 410                 415
```

```
Glu Asp Pro Glu Val Lys Phe Asn Trp Tyr Val Asp Gly Val Glu Val
            420                 425                 430

His Asn Ala Lys Thr Lys Pro Arg Glu Glu Gln Tyr Asn Ser Thr Tyr
        435                 440                 445

Arg Val Val Ser Val Leu Thr Val Leu His Gln Asp Trp Leu Asn Gly
450                 455                 460

Lys Glu Tyr Lys Cys Lys Val Ser Asn Lys Ala Leu Pro Ala Pro Ile
465                 470                 475                 480

Glu Lys Thr Ile Ser Lys Ala Lys Gly Gln Pro Arg Glu Pro Gln Val
                485                 490                 495

Tyr Thr Leu Pro Pro Ser Arg Glu Glu Met Thr Lys Asn Gln Val Ser
            500                 505                 510

Leu Thr Cys Leu Val Lys Gly Phe Tyr Pro Ser Asp Ile Ala Val Glu
        515                 520                 525

Trp Glu Ser Asn Gly Gln Pro Glu Asn Asn Tyr Lys Thr Thr Pro Pro
    530                 535                 540

Val Leu Asp Ser Asp Gly Ser Phe Phe Leu Tyr Ser Lys Leu Thr Val
545                 550                 555                 560

Asp Lys Ser Arg Trp Gln Gln Gly Asn Val Phe Ser Cys Ser Val Met
                565                 570                 575

His Glu Ala Leu His Asn His Tyr Thr Gln Lys Ser Leu Ser Leu Ser
            580                 585                 590

Pro Gly Lys
        595

<210> SEQ ID NO 15
<211> LENGTH: 426
<212> TYPE: PRT
<213> ORGANISM: Artificial Sequence
<220> FEATURE:
<223> OTHER INFORMATION: fusion protein: human Nectin-3-alpha-
      FLAGpolyHis

<400> SEQUENCE: 15

Met Ala Arg Thr Pro Gly Pro Ser Pro Leu Cys Pro Gly Gly Gly Lys
1               5                   10                  15

Ala Gln Leu Ser Ser Ala Ser Leu Leu Gly Ala Gly Leu Leu Leu Gln
            20                  25                  30

Pro Pro Thr Pro Pro Leu Leu Leu Leu Leu Phe Pro Leu Leu Leu
        35                  40                  45

Phe Ser Arg Leu Cys Gly Ala Leu Ala Gly Pro Ile Ile Val Glu Pro
50                  55                  60

His Val Thr Ala Val Trp Gly Lys Asn Val Ser Leu Lys Cys Leu Ile
65                  70                  75                  80

Glu Val Asn Glu Thr Ile Thr Gln Ile Ser Trp Glu Lys Ile His Gly
                85                  90                  95

Lys Ser Ser Gln Thr Val Ala Val His His Pro Gln Tyr Gly Phe Ser
            100                 105                 110

Val Gln Gly Glu Tyr Gln Gly Arg Val Leu Phe Lys Asn Tyr Ser Leu
        115                 120                 125

Asn Asp Ala Thr Ile Thr Leu His Asn Ile Gly Phe Ser Asp Ser Gly
    130                 135                 140

Lys Tyr Ile Cys Lys Ala Val Thr Phe Pro Leu Gly Asn Ala Gln Ser
145                 150                 155                 160

Ser Thr Thr Val Thr Val Leu Val Glu Pro Thr Val Ser Leu Ile Lys
                165                 170                 175
```

```
Gly Pro Asp Ser Leu Ile Asp Gly Gly Asn Glu Thr Val Ala Ala Ile
            180                 185                 190

Cys Ile Ala Ala Thr Gly Lys Pro Val Ala His Ile Asp Trp Glu Gly
        195                 200                 205

Asp Leu Gly Glu Met Glu Ser Thr Thr Thr Ser Phe Pro Asn Glu Thr
    210                 215                 220

Ala Thr Ile Ile Ser Gln Tyr Lys Leu Phe Pro Thr Arg Phe Ala Arg
225                 230                 235                 240

Gly Arg Arg Ile Thr Cys Val Val Lys His Pro Ala Leu Glu Lys Asp
                245                 250                 255

Ile Arg Tyr Ser Phe Ile Leu Asp Ile Gln Tyr Ala Pro Glu Val Ser
            260                 265                 270

Val Thr Gly Tyr Asp Gly Asn Trp Phe Val Gly Arg Lys Gly Val Asn
        275                 280                 285

Leu Lys Cys Asn Ala Asp Ala Asn Pro Pro Pro Phe Lys Ser Val Trp
    290                 295                 300

Ser Arg Leu Asp Gly Gln Trp Pro Asp Gly Leu Leu Ala Ser Asp Asn
305                 310                 315                 320

Thr Leu His Phe Val His Pro Leu Thr Phe Asn Tyr Ser Gly Val Tyr
                325                 330                 335

Ile Cys Lys Val Thr Asn Ser Leu Gly Gln Arg Ser Asp Gln Lys Val
            340                 345                 350

Ile Tyr Ile Ser Asp Pro Pro Thr Thr Thr Thr Leu Gln Pro Thr Ile
        355                 360                 365

Gln Trp His Pro Ser Thr Ala Asp Ile Glu Asp Leu Ala Thr Glu Pro
    370                 375                 380

Lys Lys Leu Pro Phe Pro Leu Ser Thr Leu Ala Thr Ile Lys Asp Asp
385                 390                 395                 400

Thr Ile Ala Thr Arg Ser Gly Ser Ser Asp Tyr Lys Asp Asp Asp Asp
                405                 410                 415

Lys Gly Ser Ser His His His His His His
            420                 425

<210> SEQ ID NO 16
<211> LENGTH: 387
<212> TYPE: PRT
<213> ORGANISM: Artificial Sequence
<220> FEATURE:
<223> OTHER INFORMATION: fusion protein: human Nectin-3-beta-
      FLAGpolyHis

<400> SEQUENCE: 16

Met Ala Arg Thr Pro Gly Pro Ser Pro Leu Cys Pro Gly Gly Gly Lys
1               5                   10                  15

Ala Gln Leu Ser Ser Ala Ser Leu Leu Gly Ala Gly Leu Leu Leu Gln
                20                  25                  30

Pro Pro Thr Pro Pro Pro Leu Leu Leu Leu Phe Pro Leu Leu Leu
            35                  40                  45

Phe Ser Arg Leu Cys Gly Ala Leu Ala Gly Pro Ile Ile Val Glu Pro
    50                  55                  60

His Val Thr Ala Val Trp Gly Lys Asn Val Ser Leu Lys Cys Leu Ile
65                  70                  75                  80

Glu Val Asn Glu Thr Ile Thr Gln Ile Ser Trp Glu Lys Ile His Gly
                85                  90                  95

Lys Ser Ser Gln Thr Val Ala Val His His Pro Gln Tyr Gly Phe Ser
```

-continued

```
                    100                 105                 110
Val Gln Gly Glu Tyr Gln Gly Arg Val Leu Phe Lys Asn Tyr Ser Leu
                115                 120                 125

Asn Asp Ala Thr Ile Thr Leu His Asn Ile Gly Phe Ser Asp Ser Gly
            130                 135                 140

Lys Tyr Ile Cys Lys Ala Val Thr Phe Pro Leu Gly Asn Ala Gln Ser
145                 150                 155                 160

Ser Thr Thr Val Thr Val Leu Val Glu Pro Thr Val Ser Leu Ile Lys
                165                 170                 175

Gly Pro Asp Ser Leu Ile Asp Gly Gly Asn Glu Thr Val Ala Ala Ile
            180                 185                 190

Cys Ile Ala Ala Thr Gly Lys Pro Val Ala His Ile Asp Trp Glu Gly
            195                 200                 205

Asp Leu Gly Glu Met Glu Ser Thr Thr Thr Ser Phe Pro Asn Glu Thr
210                 215                 220

Ala Thr Ile Ile Ser Gln Tyr Lys Leu Phe Pro Thr Arg Phe Ala Arg
225                 230                 235                 240

Gly Arg Arg Ile Thr Cys Val Val Lys His Pro Ala Leu Glu Lys Asp
                245                 250                 255

Ile Arg Tyr Ser Phe Ile Leu Asp Ile Gln Tyr Ala Pro Glu Val Ser
                260                 265                 270

Val Thr Gly Tyr Asp Gly Asn Trp Phe Val Gly Arg Lys Gly Val Asn
                275                 280                 285

Leu Lys Cys Asn Ala Asp Ala Asn Pro Pro Phe Lys Ser Val Trp
290                 295                 300

Ser Arg Leu Asp Gly Gln Trp Pro Asp Gly Leu Leu Ala Ser Asp Asn
305                 310                 315                 320

Thr Leu His Phe Val His Pro Leu Thr Phe Asn Tyr Ser Gly Val Tyr
            325                 330                 335

Ile Cys Lys Val Thr Asn Ser Leu Gly Gln Arg Ser Asp Gln Lys Val
            340                 345                 350

Ile Tyr Ile Ser Asp Val Pro Phe Lys Gln Thr Ser Ser Arg Ser Gly
            355                 360                 365

Ser Ser Asp Tyr Lys Asp Asp Asp Lys Gly Ser His His His
    370                 375                 380

His His His
385

<210> SEQ ID NO 17
<211> LENGTH: 549
<212> TYPE: PRT
<213> ORGANISM: mus musculus

<400> SEQUENCE: 17

Met Ala Arg Thr Pro Gly Pro Ala Pro Leu Cys Pro Gly Gly Lys
1               5                   10                  15

Ala Gln Leu Ser Ser Ala Phe Pro Pro Ala Ala Gly Leu Leu Leu Pro
                20                  25                  30

Ala Pro Thr Pro Pro Leu Leu Leu Leu Ile Pro Leu Leu Leu
            35                  40                  45

Phe Ser Arg Leu Cys Gly Ala Leu Ala Gly Ser Ile Ile Val Glu Pro
        50                  55                  60

His Val Thr Ala Val Trp Gly Lys Asn Val Ser Leu Lys Cys Leu Ile
65                  70                  75                  80
```

```
Glu Val Asn Glu Thr Ile Thr Gln Ile Ser Trp Glu Lys Ile His Gly
                85                  90                  95
Lys Ser Thr Gln Thr Val Ala Val His His Pro Gln Tyr Gly Phe Ser
                100                 105                 110
Val Gln Gly Asp Tyr Gln Gly Arg Val Leu Phe Lys Asn Tyr Ser Leu
                115                 120                 125
Asn Asp Ala Thr Ile Thr Leu His Asn Ile Gly Phe Ser Asp Ser Gly
            130                 135                 140
Lys Tyr Ile Cys Lys Ala Val Thr Phe Pro Leu Gly Asn Ala Gln Ser
145                 150                 155                 160
Ser Thr Thr Val Thr Val Leu Val Glu Pro Thr Val Ser Leu Ile Lys
                165                 170                 175
Gly Pro Asp Ser Leu Ile Asp Gly Gly Asn Glu Thr Val Ala Ala Val
                180                 185                 190
Cys Val Ala Ala Thr Gly Lys Pro Val Ala Gln Ile Asp Trp Glu Gly
                195                 200                 205
Asp Leu Gly Glu Met Glu Ser Ser Thr Thr Ser Phe Pro Asn Glu Thr
            210                 215                 220
Ala Thr Ile Val Ser Gln Tyr Lys Leu Phe Pro Thr Arg Phe Ala Arg
225                 230                 235                 240
Gly Arg Arg Ile Thr Cys Val Val Lys His Pro Ala Leu Glu Lys Asp
                245                 250                 255
Ile Arg Tyr Ser Phe Ile Leu Asp Ile Gln Tyr Ala Pro Glu Val Ser
                260                 265                 270
Val Thr Gly Tyr Asp Gly Asn Trp Phe Val Gly Arg Lys Gly Val Asn
                275                 280                 285
Leu Lys Cys Asn Ala Asp Ala Asn Pro Pro Pro Phe Lys Ser Val Trp
            290                 295                 300
Ser Arg Leu Asp Gly Gln Trp Pro Asp Gly Leu Leu Ala Ser Asp Asn
305                 310                 315                 320
Thr Leu His Phe Val His Pro Leu Thr Val Asn Tyr Ser Gly Val Tyr
                325                 330                 335
Val Cys Lys Val Ser Asn Ser Leu Gly Gln Arg Ser Asp Gln Lys Val
                340                 345                 350
Ile Tyr Ile Ser Asp Pro Pro Thr Thr Thr Thr Leu Gln Pro Thr Val
                355                 360                 365
Gln Trp His Ser Ser Pro Ala Asp Val Gln Asp Ile Ala Thr Glu His
            370                 375                 380
Lys Lys Leu Pro Phe Pro Leu Ser Thr Leu Ala Thr Leu Lys Asp Asp
385                 390                 395                 400
Thr Ile Gly Thr Ile Ile Ala Ser Val Val Gly Gly Ala Leu Phe Leu
                405                 410                 415
Val Leu Val Ser Ile Leu Ala Gly Val Phe Cys Tyr Arg Arg Arg Arg
                420                 425                 430
Thr Phe Arg Gly Asp Tyr Phe Ala Lys Asn Tyr Ile Pro Pro Ser Asp
                435                 440                 445
Met Gln Lys Glu Ser Gln Ile Asp Val Leu His Gln Asp Glu Leu Asp
            450                 455                 460
Ser Tyr Pro Asp Ser Val Lys Lys Glu Asn Lys Asn Pro Val Asn Asn
465                 470                 475                 480
Leu Ile Arg Lys Asp Tyr Leu Glu Glu Pro Glu Lys Thr Gln Trp Asn
                485                 490                 495
Asn Val Glu Asn Leu Thr Arg Phe Glu Arg Pro Met Asp Tyr Tyr Glu
```

```
                500             505             510
Asp Leu Lys Met Gly Met Lys Phe Val Ser Asp Glu Arg Tyr Asn Glu
        515                 520                 525

Ser Glu Asp Gly Leu Val Ser His Val Asp Gly Ser Val Ile Ser Arg
        530                 535                 540

Arg Glu Trp Tyr Val
545

<210> SEQ ID NO 18
<211> LENGTH: 510
<212> TYPE: PRT
<213> ORGANISM: mus musculus

<400> SEQUENCE: 18

Met Ala Arg Thr Pro Gly Pro Ala Pro Leu Cys Pro Gly Gly Gly Lys
1               5                   10                  15

Ala Gln Leu Ser Ser Ala Phe Pro Pro Ala Gly Leu Leu Leu Leu Pro
            20                  25                  30

Ala Pro Thr Pro Pro Pro Leu Leu Leu Leu Ile Pro Leu Leu Leu Leu
        35                  40                  45

Phe Ser Arg Leu Cys Gly Ala Leu Ala Gly Ser Ile Ile Val Glu Pro
    50                  55                  60

His Val Thr Ala Val Trp Gly Lys Asn Val Ser Leu Lys Cys Leu Ile
65                  70                  75                  80

Glu Val Asn Glu Thr Ile Thr Gln Ile Ser Trp Glu Lys Ile His Gly
                85                  90                  95

Lys Ser Thr Gln Thr Val Ala Val His His Pro Gln Tyr Gly Phe Ser
            100                 105                 110

Val Gln Gly Asp Tyr Gln Gly Arg Val Leu Phe Lys Asn Tyr Ser Leu
        115                 120                 125

Asn Asp Ala Thr Ile Thr Leu His Asn Ile Gly Phe Ser Asp Ser Gly
    130                 135                 140

Lys Tyr Ile Cys Lys Ala Val Thr Phe Pro Leu Gly Asn Ala Gln Ser
145                 150                 155                 160

Ser Thr Thr Val Thr Val Leu Val Glu Pro Thr Val Ser Leu Ile Lys
                165                 170                 175

Gly Pro Asp Ser Leu Ile Asp Gly Gly Asn Glu Thr Val Ala Ala Val
            180                 185                 190

Cys Val Ala Ala Thr Gly Lys Pro Val Ala Gln Ile Asp Trp Glu Gly
        195                 200                 205

Asp Leu Gly Glu Met Glu Ser Ser Thr Thr Ser Phe Pro Asn Glu Thr
    210                 215                 220

Ala Thr Ile Val Ser Gln Tyr Lys Leu Phe Pro Thr Arg Phe Ala Arg
225                 230                 235                 240

Gly Arg Arg Ile Thr Cys Val Val Lys His Pro Ala Leu Glu Lys Asp
                245                 250                 255

Ile Arg Tyr Ser Phe Ile Leu Asp Ile Gln Tyr Ala Pro Glu Val Ser
            260                 265                 270

Val Thr Gly Tyr Asp Gly Asn Trp Phe Val Gly Arg Lys Gly Val Asn
        275                 280                 285

Leu Lys Cys Asn Ala Asp Ala Asn Pro Pro Pro Phe Lys Ser Val Trp
    290                 295                 300

Ser Arg Leu Asp Gly Gln Trp Pro Asp Gly Leu Leu Ala Ser Asp Asn
305                 310                 315                 320
```

```
Thr Leu His Phe Val His Pro Leu Thr Val Asn Tyr Ser Gly Val Tyr
                325                 330                 335

Val Cys Lys Val Ser Asn Ser Leu Gly Gln Arg Ser Asp Gln Lys Val
                340                 345                 350

Ile Tyr Ile Ser Asp Ile Pro Leu Thr Gln Thr Ser Ser Ile Ala Val
                355                 360                 365

Ala Gly Ala Val Ile Gly Ala Val Leu Ala Leu Phe Ile Ile Thr Val
            370                 375                 380

Phe Val Thr Val Leu Leu Thr Pro Arg Lys Arg Pro Ser Tyr Leu
385                 390                 395                 400

Asp Lys Val Ile Asp Leu Pro Pro Thr His Lys Pro Pro Val Tyr
                405                 410                 415

Glu Glu Arg Ile Pro Ser Leu Pro Gln Lys Asp Leu Leu Gly Gln Thr
                420                 425                 430

Glu His Leu Pro Leu Gln Thr Gln Phe Lys Glu Lys Gly Ala Gly Gly
            435                 440                 445

Leu Gln Pro Ser Asn Gly Pro Ile Ser Arg Arg Phe Asp Tyr Glu Asp
        450                 455                 460

Glu Ser Thr Met Gln Glu Asp Gly Thr Gln Arg Met Cys Pro Leu Tyr
465                 470                 475                 480

Ser Gln Met Cys His Gln Asp Arg Ser Pro Arg Gln His His Pro Arg
                485                 490                 495

Asn Pro Glu Arg Leu Tyr Ile Asn Pro Arg Glu His Tyr Val
                500                 505                 510

<210> SEQ ID NO 19
<211> LENGTH: 438
<212> TYPE: PRT
<213> ORGANISM: mus musculus

<400> SEQUENCE: 19

Met Ala Arg Thr Pro Gly Pro Ala Pro Leu Cys Pro Gly Gly Gly Lys
1               5                   10                  15

Ala Gln Leu Ser Ser Ala Phe Pro Pro Ala Ala Gly Leu Leu Leu Pro
                20                  25                  30

Ala Pro Thr Pro Pro Leu Leu Leu Leu Ile Pro Leu Leu Leu
            35                  40                  45

Phe Ser Arg Leu Cys Gly Ala Leu Ala Gly Ser Ile Ile Val Glu Pro
    50                  55                  60

His Val Thr Ala Val Trp Gly Lys Asn Val Ser Leu Lys Cys Leu Ile
65                  70                  75                  80

Glu Val Asn Glu Thr Ile Thr Gln Ile Ser Trp Glu Lys Ile His Gly
                85                  90                  95

Lys Ser Thr Gln Thr Val Ala Val His His Pro Gln Tyr Gly Phe Ser
                100                 105                 110

Val Gln Gly Asp Tyr Gln Gly Arg Val Leu Phe Lys Asn Tyr Ser Leu
            115                 120                 125

Asn Asp Ala Thr Ile Thr Leu His Asn Ile Gly Phe Ser Asp Ser Gly
        130                 135                 140

Lys Tyr Ile Cys Lys Ala Val Thr Phe Pro Leu Gly Asn Ala Gln Ser
145                 150                 155                 160

Ser Thr Thr Val Thr Val Leu Val Glu Pro Thr Val Ser Leu Ile Lys
                165                 170                 175

Gly Pro Asp Ser Leu Ile Asp Gly Gly Asn Glu Thr Val Ala Ala Val
            180                 185                 190
```

```
Cys Val Ala Ala Thr Gly Lys Pro Val Ala Gln Ile Asp Trp Glu Gly
            195                 200                 205

Asp Leu Gly Glu Met Glu Ser Ser Thr Thr Ser Phe Pro Asn Glu Thr
        210                 215                 220

Ala Thr Ile Val Ser Gln Tyr Lys Leu Phe Pro Thr Arg Phe Ala Arg
225                 230                 235                 240

Gly Arg Arg Ile Thr Cys Val Val Lys His Pro Ala Leu Glu Lys Asp
                245                 250                 255

Ile Arg Tyr Ser Phe Ile Leu Asp Ile Gln Tyr Ala Pro Glu Val Ser
            260                 265                 270

Val Thr Gly Tyr Asp Gly Asn Trp Phe Val Gly Arg Lys Gly Val Asn
        275                 280                 285

Leu Lys Cys Asn Ala Asp Ala Asn Pro Pro Pro Phe Lys Ser Val Trp
290                 295                 300

Ser Arg Leu Asp Gly Gln Trp Pro Asp Gly Leu Leu Ala Ser Asp Asn
305                 310                 315                 320

Thr Leu His Phe Val His Pro Leu Thr Val Asn Tyr Ser Gly Val Tyr
                325                 330                 335

Val Cys Lys Val Ser Asn Ser Leu Gly Gln Arg Ser Asp Gln Lys Val
            340                 345                 350

Ile Tyr Ile Ser Asp Ile Pro Leu Thr Gln Thr Ser Ser Ile Ala Val
        355                 360                 365

Ala Gly Ala Val Ile Gly Ala Val Leu Ala Leu Phe Ile Ile Thr Val
370                 375                 380

Phe Val Thr Val Leu Leu Thr Pro Arg Lys Lys Arg Pro Ser Tyr Leu
385                 390                 395                 400

Asp Lys Val Ile Asp Leu Pro Pro Thr His Lys Pro Pro Pro Val Tyr
                405                 410                 415

Glu Glu Arg Ile Pro Ser Leu Pro Gln Lys Asp Leu Leu Gly Gln Val
            420                 425                 430

Arg Ala Leu Glu Asp Thr
            435

<210> SEQ ID NO 20
<211> LENGTH: 517
<212> TYPE: PRT
<213> ORGANISM: homo sapiens

<400> SEQUENCE: 20

Met Ala Arg Met Gly Leu Ala Gly Ala Ala Gly Arg Trp Trp Gly Leu
1               5                   10                  15

Ala Leu Gly Leu Thr Ala Phe Phe Leu Pro Gly Val His Ser Gln Val
            20                  25                  30

Val Gln Val Asn Asp Ser Met Tyr Gly Phe Ile Gly Thr Asp Val Val
        35                  40                  45

Leu His Cys Ser Phe Ala Asn Pro Leu Pro Ser Val Lys Ile Thr Gln
    50                  55                  60

Val Thr Trp Gln Lys Ser Thr Asn Gly Ser Lys Gln Asn Val Ala Ile
65                  70                  75                  80

Tyr Asn Pro Ser Met Gly Val Ser Val Leu Ala Pro Tyr Arg Glu Arg
                85                  90                  95

Val Glu Phe Leu Arg Pro Ser Phe Thr Asp Gly Thr Ile Arg Leu Ser
            100                 105                 110

Arg Leu Glu Leu Glu Asp Glu Gly Val Tyr Ile Cys Glu Phe Ala Thr
```

```
            115                 120                 125
Phe Pro Thr Gly Asn Arg Glu Ser Gln Leu Asn Leu Thr Val Met Ala
    130                 135                 140
Lys Pro Thr Asn Trp Ile Glu Gly Thr Gln Ala Val Leu Arg Ala Lys
145                 150                 155                 160
Lys Gly Gln Asp Asp Lys Val Leu Val Ala Thr Cys Thr Ser Ala Asn
                165                 170                 175
Gly Lys Pro Pro Ser Val Val Ser Trp Glu Thr Arg Leu Lys Gly Glu
                180                 185                 190
Ala Glu Tyr Gln Glu Ile Arg Asn Pro Asn Gly Thr Val Thr Val Ile
            195                 200                 205
Ser Arg Tyr Arg Leu Val Pro Ser Arg Glu Ala His Gln Gln Ser Leu
    210                 215                 220
Ala Cys Ile Val Asn Tyr His Met Asp Arg Phe Lys Glu Ser Leu Thr
225                 230                 235                 240
Leu Asn Val Gln Tyr Glu Pro Glu Val Thr Ile Glu Gly Phe Asp Gly
                245                 250                 255
Asn Trp Tyr Leu Gln Arg Met Asp Val Lys Leu Thr Cys Lys Ala Asp
                260                 265                 270
Ala Asn Pro Pro Ala Thr Glu Tyr His Trp Thr Thr Leu Asn Gly Ser
            275                 280                 285
Leu Pro Lys Gly Val Glu Ala Gln Asn Arg Thr Leu Phe Phe Lys Gly
    290                 295                 300
Pro Ile Asn Tyr Ser Leu Ala Gly Thr Tyr Ile Cys Glu Ala Thr Asn
305                 310                 315                 320
Pro Ile Gly Thr Arg Ser Gly Gln Val Glu Val Asn Ile Thr Glu Phe
                325                 330                 335
Pro Tyr Thr Pro Ser Pro Glu His Gly Arg Arg Ala Gly Pro Val
                340                 345                 350
Pro Thr Ala Ile Ile Gly Gly Val Ala Gly Ser Ile Leu Leu Val Leu
            355                 360                 365
Ile Val Val Gly Gly Ile Val Val Ala Leu Arg Arg Arg His Thr
    370                 375                 380
Phe Lys Gly Asp Tyr Ser Thr Lys Lys His Val Tyr Gly Asn Gly Tyr
385                 390                 395                 400
Ser Lys Ala Gly Ile Pro Gln His His Pro Met Ala Gln Asn Leu
                405                 410                 415
Gln Tyr Pro Asp Asp Ser Asp Asp Glu Lys Lys Ala Gly Pro Leu Gly
                420                 425                 430
Gly Ser Ser Tyr Glu Glu Glu Glu Glu Glu Glu Gly Gly Gly Gly
                435                 440                 445
Gly Glu Arg Lys Val Gly Gly Pro His Pro Lys Tyr Asp Glu Asp Ala
    450                 455                 460
Lys Arg Pro Tyr Phe Thr Val Asp Glu Ala Glu Ala Arg Gln Asp Gly
465                 470                 475                 480
Tyr Gly Asp Arg Thr Leu Gly Tyr Gln Tyr Asp Pro Glu Gln Leu Asp
                485                 490                 495
Leu Ala Glu Asn Met Val Ser Gln Asn Asp Gly Ser Phe Ile Ser Lys
                500                 505                 510
Lys Glu Trp Tyr Val
            515
```

<210> SEQ ID NO 21

```
<211> LENGTH: 458
<212> TYPE: PRT
<213> ORGANISM: homo sapiens

<400> SEQUENCE: 21

Met Ala Arg Met Gly Leu Ala Gly Ala Ala Gly Arg Trp Trp Gly Leu
1               5                   10                  15

Ala Leu Gly Leu Thr Ala Phe Phe Leu Pro Gly Val His Ser Gln Val
            20                  25                  30

Val Gln Val Asn Asp Ser Met Tyr Gly Phe Ile Gly Thr Asp Val Val
        35                  40                  45

Leu His Cys Ser Phe Ala Asn Pro Leu Pro Ser Val Lys Ile Thr Gln
    50                  55                  60

Val Thr Trp Gln Lys Ser Thr Asn Gly Ser Lys Gln Asn Val Ala Ile
65                  70                  75                  80

Tyr Asn Pro Ser Met Gly Val Ser Val Leu Ala Pro Tyr Arg Glu Arg
                85                  90                  95

Val Glu Phe Leu Arg Pro Ser Phe Thr Asp Gly Thr Ile Arg Leu Ser
            100                 105                 110

Arg Leu Glu Leu Glu Asp Glu Gly Val Tyr Ile Cys Glu Phe Ala Thr
        115                 120                 125

Phe Pro Thr Gly Asn Arg Glu Ser Gln Leu Asn Leu Thr Val Met Ala
    130                 135                 140

Lys Pro Thr Asn Trp Ile Glu Gly Thr Gln Ala Val Leu Arg Ala Lys
145                 150                 155                 160

Lys Gly Gln Asp Asp Lys Val Leu Val Ala Thr Cys Thr Ser Ala Asn
                165                 170                 175

Gly Lys Pro Pro Ser Val Val Ser Trp Glu Thr Arg Leu Lys Gly Glu
            180                 185                 190

Ala Glu Tyr Gln Glu Ile Arg Asn Pro Asn Gly Thr Val Thr Val Ile
        195                 200                 205

Ser Arg Tyr Arg Leu Val Pro Ser Arg Glu Ala His Gln Gln Ser Leu
210                 215                 220

Ala Cys Ile Val Asn Tyr His Met Asp Arg Phe Lys Glu Ser Leu Thr
225                 230                 235                 240

Leu Asn Val Gln Tyr Glu Pro Glu Val Thr Ile Glu Gly Phe Asp Gly
                245                 250                 255

Asn Trp Tyr Leu Gln Arg Met Asp Val Lys Leu Thr Cys Lys Ala Asp
            260                 265                 270

Ala Asn Pro Pro Ala Thr Glu Tyr His Trp Thr Thr Leu Asn Gly Ser
        275                 280                 285

Leu Pro Lys Gly Val Glu Ala Gln Asn Arg Thr Leu Phe Phe Lys Gly
    290                 295                 300

Pro Ile Asn Tyr Ser Leu Ala Gly Thr Tyr Ile Cys Glu Ala Thr Asn
305                 310                 315                 320

Pro Ile Gly Thr Arg Ser Gly Gln Val Glu Val Asn Ile Thr Glu Lys
                325                 330                 335

Pro Arg Pro Gln Arg Gly Leu Gly Ser Ala Ala Arg Leu Leu Ala Gly
            340                 345                 350

Thr Val Ala Val Phe Leu Ile Leu Val Ala Val Leu Thr Val Phe Phe
        355                 360                 365

Leu Tyr Asn Arg Gln Gln Lys Ser Pro Pro Glu Thr Asp Gly Ala Gly
    370                 375                 380

Thr Asp Gln Pro Leu Ser Gln Lys Pro Glu Pro Ser Pro Ser Arg Gln
```

```
                385                 390                 395                 400
Ser Ser Leu Val Pro Glu Asp Ile Gln Val Val His Leu Asp Pro Gly
                    405                 410                 415

Arg Gln Gln Gln Glu Glu Glu Asp Leu Gln Lys Leu Ser Leu Gln
            420                 425                 430

Pro Pro Tyr Tyr Asp Leu Gly Val Ser Pro Tyr His Pro Ser Val
            435                 440                 445

Arg Thr Thr Glu Pro Arg Gly Glu Cys Pro
        450                 455

<210> SEQ ID NO 22
<211> LENGTH: 479
<212> TYPE: PRT
<213> ORGANISM: homo sapiens

<400> SEQUENCE: 22

Met Ala Arg Ala Ala Ala Leu Leu Pro Ser Arg Ser Pro Pro Thr Pro
1               5                   10                  15

Leu Leu Trp Pro Leu Leu Leu Leu Leu Leu Glu Thr Gly Ala Gln
            20                  25                  30

Asp Val Arg Val Gln Val Leu Pro Glu Val Arg Gly Gln Leu Gly Gly
        35                  40                  45

Thr Val Glu Leu Pro Cys His Leu Leu Pro Pro Val Pro Gly Leu Tyr
    50                  55                  60

Ile Ser Leu Val Thr Trp Gln Arg Pro Asp Ala Pro Ala Asn His Gln
65                  70                  75                  80

Asn Val Ala Ala Phe His Pro Lys Met Gly Pro Ser Phe Pro Ser Pro
                85                  90                  95

Lys Pro Gly Ser Glu Arg Leu Ser Phe Val Ser Ala Lys Gln Ser Thr
            100                 105                 110

Gly Gln Asp Thr Glu Ala Glu Leu Gln Asp Ala Thr Leu Ala Leu His
            115                 120                 125

Gly Leu Thr Val Glu Asp Glu Gly Asn Tyr Thr Cys Glu Phe Ala Thr
        130                 135                 140

Phe Pro Lys Gly Ser Val Arg Gly Met Thr Trp Leu Arg Val Ile Ala
145                 150                 155                 160

Lys Pro Lys Asn Gln Ala Glu Ala Gln Lys Val Thr Phe Ser Gln Asp
                165                 170                 175

Pro Thr Thr Val Ala Leu Cys Ile Ser Lys Glu Gly Arg Pro Pro Ala
            180                 185                 190

Arg Ile Ser Trp Leu Ser Ser Leu Asp Trp Glu Ala Lys Glu Thr Gln
        195                 200                 205

Val Ser Gly Thr Leu Ala Gly Thr Val Thr Val Thr Ser Arg Phe Thr
    210                 215                 220

Leu Val Pro Ser Gly Arg Ala Asp Gly Val Thr Val Thr Cys Lys Val
225                 230                 235                 240

Glu His Glu Ser Phe Glu Glu Pro Ala Leu Ile Pro Val Thr Leu Ser
                245                 250                 255

Val Arg Tyr Pro Pro Glu Val Ser Ile Ser Gly Tyr Asp Asp Asn Trp
            260                 265                 270

Tyr Leu Gly Arg Thr Asp Ala Thr Leu Ser Cys Asp Val Arg Ser Asn
        275                 280                 285

Pro Glu Pro Thr Gly Tyr Asp Trp Ser Thr Thr Ser Gly Thr Phe Pro
    290                 295                 300
```

```
Thr Ser Ala Val Ala Gln Gly Ser Gln Leu Val Ile His Ala Val Asp
305                 310                 315                 320

Ser Leu Phe Asn Thr Thr Phe Val Cys Thr Val Asn Ala Val Gly
        325                 330                 335

Met Gly Arg Ala Glu Gln Val Ile Phe Val Arg Glu Thr Pro Arg Ala
            340                 345                 350

Ser Pro Arg Asp Val Gly Pro Leu Val Trp Gly Ala Val Gly Gly Thr
        355                 360                 365

Leu Leu Val Leu Leu Leu Ala Gly Gly Ser Leu Ala Phe Ile Leu
    370                 375                 380

Leu Arg Val Arg Arg Arg Lys Ser Pro Gly Ala Gly Gly Gly
385             390                 395                 400

Ala Ser Gly Asp Gly Phe Tyr Asp Pro Lys Ala Gln Val Leu Gly
            405                 410                 415

Asn Gly Asp Pro Val Phe Trp Thr Pro Val Pro Gly Pro Met Glu
            420                 425                 430

Pro Asp Gly Lys Asp Glu Glu Glu Glu Glu Lys Ala Glu
        435                 440                 445

Lys Gly Leu Met Leu Pro Pro Pro Ala Leu Glu Asp Asp Met Glu
    450                 455                 460

Ser Gln Leu Asp Gly Ser Leu Ile Ser Arg Arg Ala Val Tyr Val
465                 470                 475

<210> SEQ ID NO 23
<211> LENGTH: 538
<212> TYPE: PRT
<213> ORGANISM: homo sapiens

<400> SEQUENCE: 23

Met Ala Arg Ala Ala Ala Leu Leu Pro Ser Arg Ser Pro Pro Thr Pro
1               5                   10                  15

Leu Leu Trp Pro Leu Leu Leu Leu Leu Glu Thr Gly Ala Gln
            20                  25                  30

Asp Val Arg Val Gln Val Leu Pro Glu Val Arg Gly Gln Leu Gly Gly
            35                  40                  45

Thr Val Glu Leu Pro Cys His Leu Leu Pro Pro Val Pro Gly Leu Tyr
    50                  55                  60

Ile Ser Leu Val Thr Trp Gln Arg Pro Asp Ala Pro Ala Asn His Gln
65                  70                  75                  80

Asn Val Ala Ala Phe His Pro Lys Met Gly Pro Ser Phe Pro Ser Pro
                85                  90                  95

Lys Pro Gly Ser Glu Arg Leu Ser Phe Val Ser Ala Lys Gln Ser Thr
            100                 105                 110

Gly Gln Asp Thr Glu Ala Glu Leu Gln Asp Ala Thr Leu Ala Leu His
        115                 120                 125

Gly Leu Thr Val Glu Asp Glu Gly Asn Tyr Thr Cys Glu Phe Ala Thr
    130                 135                 140

Phe Pro Lys Gly Ser Val Arg Gly Met Thr Trp Leu Arg Val Ile Ala
145                 150                 155                 160

Lys Pro Lys Asn Gln Ala Glu Ala Gln Lys Val Thr Phe Ser Gln Asp
                165                 170                 175

Pro Thr Thr Val Ala Leu Cys Ile Ser Lys Glu Gly Arg Pro Pro Ala
            180                 185                 190

Arg Ile Ser Trp Leu Ser Ser Leu Asp Trp Glu Ala Lys Glu Thr Gln
        195                 200                 205
```

```
Val Ser Gly Thr Leu Ala Gly Thr Val Thr Val Thr Ser Arg Phe Thr
            210                 215                 220

Leu Val Pro Ser Gly Arg Ala Asp Gly Val Thr Val Thr Cys Lys Val
225                 230                 235                 240

Glu His Glu Ser Phe Glu Pro Ala Leu Ile Pro Val Thr Leu Ser
            245                 250                 255

Val Arg Tyr Pro Pro Glu Val Ser Ile Ser Gly Tyr Asp Asp Asn Trp
            260                 265                 270

Tyr Leu Gly Arg Thr Asp Ala Thr Leu Ser Cys Asp Val Arg Ser Asn
            275                 280                 285

Pro Glu Pro Thr Gly Tyr Asp Trp Ser Thr Thr Ser Gly Thr Phe Pro
290                 295                 300

Thr Ser Ala Val Ala Gln Gly Ser Gln Leu Val Ile His Ala Val Asp
305                 310                 315                 320

Ser Leu Phe Asn Thr Thr Phe Val Cys Thr Val Thr Asn Ala Val Gly
            325                 330                 335

Met Gly Arg Ala Glu Gln Val Ile Phe Val Arg Glu Thr Pro Asn Thr
            340                 345                 350

Ala Gly Ala Gly Ala Thr Gly Gly Ile Ile Gly Gly Ile Ile Ala Ala
            355                 360                 365

Ile Ile Ala Thr Ala Val Ala Ala Thr Gly Ile Leu Ile Cys Arg Gln
            370                 375                 380

Gln Arg Lys Glu Gln Thr Leu Gln Gly Ala Glu Glu Asp Glu Asp Leu
385                 390                 395                 400

Glu Gly Pro Pro Ser Tyr Lys Pro Pro Thr Pro Lys Ala Lys Leu Glu
                    405                 410                 415

Ala Gln Glu Met Pro Ser Gln Leu Phe Thr Leu Gly Ala Ser Glu His
                420                 425                 430

Ser Pro Leu Lys Thr Pro Tyr Phe Asp Ala Gly Ala Ser Cys Thr Glu
            435                 440                 445

Gln Glu Met Pro Arg Tyr His Glu Leu Pro Thr Leu Glu Glu Arg Ser
450                 455                 460

Gly Pro Leu His Pro Gly Ala Thr Ser Leu Gly Ser Pro Ile Pro Val
465                 470                 475                 480

Pro Pro Gly Pro Pro Ala Val Glu Asp Val Ser Leu Asp Leu Glu Asp
                485                 490                 495

Glu Glu Gly Glu Glu Glu Glu Glu Tyr Leu Asp Lys Ile Asn Pro Ile
                500                 505                 510

Tyr Asp Ala Leu Ser Tyr Ser Ser Pro Ser Asp Ser Tyr Gln Gly Lys
            515                 520                 525

Gly Phe Val Met Ser Arg Ala Met Tyr Val
    530                 535

<210> SEQ ID NO 24
<211> LENGTH: 510
<212> TYPE: PRT
<213> ORGANISM: homo sapiens

<400> SEQUENCE: 24

Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala Gly
            20                  25                  30

Glu Leu Glu Thr Ser Asp Val Val Thr Val Val Leu Gly Gln Asp Ala
```

```
                35                  40                  45
Lys Leu Pro Cys Phe Tyr Arg Gly Asp Ser Gly Glu Gln Val Gly Gln
 50                  55                  60
Val Ala Trp Ala Arg Val Asp Ala Gly Glu Gly Ala Gln Glu Leu Ala
 65                  70                  75                  80
Leu Leu His Ser Lys Tyr Gly Leu His Val Ser Pro Ala Tyr Glu Gly
                 85                  90                  95
Arg Val Glu Gln Pro Pro Pro Arg Asn Pro Leu Asp Gly Ser Val
                100                 105                 110
Leu Leu Arg Asn Ala Val Gln Ala Asp Glu Gly Glu Tyr Glu Cys Arg
                115                 120                 125
Val Ser Thr Phe Pro Ala Gly Ser Phe Gln Ala Arg Leu Arg Leu Arg
            130                 135                 140
Val Met Val Pro Pro Leu Pro Ser Leu Asn Pro Gly Pro Ala Leu Glu
145                 150                 155                 160
Glu Gly Gln Gly Leu Thr Leu Ala Ala Ser Cys Thr Ala Glu Gly Ser
                165                 170                 175
Pro Ala Pro Ser Val Thr Trp Asp Thr Glu Val Lys Gly Thr Thr Ser
            180                 185                 190
Ser Arg Ser Phe Lys His Ser Arg Ser Ala Ala Val Thr Ser Glu Phe
            195                 200                 205
His Leu Val Pro Ser Arg Ser Met Asn Gly Gln Pro Leu Thr Cys Val
        210                 215                 220
Val Ser His Pro Gly Leu Leu Gln Asp Gln Arg Ile Thr His Ile Leu
225                 230                 235                 240
His Val Ser Phe Leu Ala Glu Ala Ser Val Arg Gly Leu Glu Asp Gln
                245                 250                 255
Asn Leu Trp His Ile Gly Arg Glu Gly Ala Met Leu Lys Cys Leu Ser
            260                 265                 270
Glu Gly Gln Pro Pro Ser Tyr Asn Trp Thr Arg Leu Asp Gly Pro
            275                 280                 285
Leu Pro Ser Gly Val Arg Val Asp Gly Asp Thr Leu Gly Phe Pro Pro
        290                 295                 300
Leu Thr Thr Glu His Ser Gly Ile Tyr Val Cys His Val Ser Asn Glu
305                 310                 315                 320
Phe Ser Ser Arg Asp Ser Gln Val Thr Val Asp Val Leu Asp Pro Gln
                325                 330                 335
Glu Asp Ser Gly Lys Gln Val Asp Leu Val Ser Ala Ser Val Val Val
            340                 345                 350
Val Gly Val Ile Ala Ala Leu Leu Phe Cys Leu Leu Val Val Val Val
            355                 360                 365
Val Leu Met Ser Arg Tyr His Arg Arg Lys Ala Gln Gln Met Thr Gln
        370                 375                 380
Lys Tyr Glu Glu Glu Leu Thr Leu Thr Arg Glu Asn Ser Ile Arg Arg
385                 390                 395                 400
Leu His Ser His His Thr Asp Pro Arg Ser Gln Pro Glu Glu Ser Val
                405                 410                 415
Gly Leu Arg Ala Glu Gly His Pro Asp Ser Leu Lys Asp Asn Ser Ser
            420                 425                 430
Cys Ser Val Met Ser Glu Glu Pro Glu Gly Arg Ser Tyr Ser Thr Leu
        435                 440                 445
Thr Thr Val Arg Glu Ile Glu Thr Gln Thr Glu Leu Leu Ser Pro Gly
450                 455                 460
```

```
Ser Gly Arg Ala Glu Glu Glu Asp Gln Asp Glu Gly Ile Lys Gln
465                 470                 475                 480

Ala Met Asn His Phe Val Gln Glu Asn Gly Thr Leu Arg Ala Lys Pro
            485                 490                 495

Thr Gly Asn Gly Ile Tyr Ile Asn Gly Arg Gly His Leu Val
            500                 505                 510
```

<210> SEQ ID NO 25
<211> LENGTH: 417
<212> TYPE: PRT
<213> ORGANISM: homo sapiens

<400> SEQUENCE: 25

```
Met Ala Arg Ala Met Ala Ala Trp Pro Leu Leu Leu Val Ala Leu
1               5                   10                  15

Leu Val Leu Ser Trp Pro Pro Gly Thr Gly Asp Val Val Gln
            20                  25                  30

Ala Pro Thr Gln Val Pro Gly Phe Leu Gly Asp Ser Val Thr Leu Pro
            35                  40                  45

Cys Tyr Leu Gln Val Pro Asn Met Glu Val Thr His Val Ser Gln Leu
50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
                100                 105                 110

Leu Arg Val Glu Asp Glu Gly Asn Tyr Thr Cys Leu Phe Val Thr Phe
            115                 120                 125

Pro Gln Gly Ser Arg Ser Val Asp Ile Trp Leu Arg Val Leu Ala Lys
130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
            180                 185                 190

Pro Gly Phe Leu Ser Gly Thr Val Thr Val Thr Ser Leu Trp Ile Leu
            195                 200                 205

Val Pro Ser Ser Gln Val Asp Gly Lys Asn Val Thr Cys Lys Val Glu
    210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
            260                 265                 270

Glu Pro Thr Gly Tyr Asn Trp Ser Thr Thr Met Gly Pro Leu Pro Pro
            275                 280                 285

Phe Ala Val Ala Gln Gly Ala Gln Leu Leu Ile Arg Pro Val Asp Lys
        290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
```

-continued

```
                      325                 330                 335
His Ser Gly Ile Ser Arg Asn Ala Ile Ile Phe Leu Val Leu Gly Ile
            340                 345                 350

Leu Val Phe Leu Ile Leu Leu Gly Ile Gly Ile Tyr Phe Tyr Trp Ser
            355                 360                 365

Lys Cys Ser Arg Glu Val Leu Trp His Cys His Leu Cys Pro Ser Ser
370                 375                 380

Thr Glu His Ala Ser Ala Ser Ala Asn Gly His Val Ser Tyr Ser Ala
385                 390                 395                 400

Val Ser Arg Glu Asn Ser Ser Ser Gln Asp Pro Gln Thr Glu Gly Thr
            405                 410                 415

Arg

<210> SEQ ID NO 26
<211> LENGTH: 54
<212> TYPE: DNA
<213> ORGANISM: Artificial Sequence
<220> FEATURE:
<223> OTHER INFORMATION: Oligonucleotide Primer

<400> SEQUENCE: 26
atatgtcgac gcgggcatgg cccggacccc cggcccgtcc ccgctgtgtc ctgg       54

<210> SEQ ID NO 27
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 27
atatgcggcc gcctaaacat accactccct cc                               32

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 28
ccctcaactg ctgacatcga                                             20

<210> SEQ ID NO 29
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 29
tgatcgtggc aattgtgtca t                                           21

<210> SEQ ID NO 30
<211> LENGTH: 1314
<212> TYPE: DNA
<213> ORGANISM: homo sapiens
<220> FEATURE:
<221> NAME/KEY: CDS
<222> LOCATION: (1)..(1314)
<223> OTHER INFORMATION:

<400> SEQUENCE: 30
```

-continued

| | |
|---|---|
| atg gcg cgg acc ctg cgg cct tcc ccg ctg tgt cct gga ggc ggc aaa<br>Met Ala Arg Thr Leu Arg Pro Ser Pro Leu Cys Pro Gly Gly Gly Lys<br>1                   5                   10                15 | 48 |
| gca caa ctt tcc tcc gct tct ctc ctc gga gcc ggg ctc ctg ctg cag<br>Ala Gln Leu Ser Ser Ala Ser Leu Leu Gly Ala Gly Leu Leu Leu Gln<br>                  20                  25                  30 | 96 |
| ccc ccg acg cca cct ccg ctg ctg ctg ctc ttc ccg ctg ctg ctc<br>Pro Pro Thr Pro Pro Pro Leu Leu Leu Leu Phe Pro Leu Leu Leu<br>        35                  40                  45 | 144 |
| ttc tcc agg ctc tgt ggt gcc tta gct gga cca att att gtg gag cca<br>Phe Ser Arg Leu Cys Gly Ala Leu Ala Gly Pro Ile Ile Val Glu Pro<br>50                  55                  60 | 192 |
| cat gtc aca gca gta tgg gga aag aat gtt tca tta aag tgt tta att<br>His Val Thr Ala Val Trp Gly Lys Asn Val Ser Leu Lys Cys Leu Ile<br>65                    70                  75                  80 | 240 |
| gaa gta aat gaa acc ata aca cag att tca tgg gag aag ata cat ggc<br>Glu Val Asn Glu Thr Ile Thr Gln Ile Ser Trp Glu Lys Ile His Gly<br>                        85                  90                  95 | 288 |
| aaa agt tca cag act gtt gca gtt cac cat ccc caa tat gga ttc tct<br>Lys Ser Ser Gln Thr Val Ala Val His His Pro Gln Tyr Gly Phe Ser<br>                  100                105              110 | 336 |
| gtt caa gga gaa tat cag gga aga gtc ttg ttt aaa aat tac tca ctt<br>Val Gln Gly Glu Tyr Gln Gly Arg Val Leu Phe Lys Asn Tyr Ser Leu<br>                115                120              125 | 384 |
| aat gat gca aca att act ctg cat aac ata gga ttc tct gat tct gga<br>Asn Asp Ala Thr Ile Thr Leu His Asn Ile Gly Phe Ser Asp Ser Gly<br>130                  135                140 | 432 |
| aaa tac atc tgc aaa gct gtt aca ttc ccg ctt gga aat gcc cag tcc<br>Lys Tyr Ile Cys Lys Ala Val Thr Phe Pro Leu Gly Asn Ala Gln Ser<br>145                  150                155              160 | 480 |
| tct aca act gta act gtg tta gtt gaa ccc act gtg agc ctg ata aaa<br>Ser Thr Thr Val Thr Val Leu Val Glu Pro Thr Val Ser Leu Ile Lys<br>                        165                170              175 | 528 |
| ggg cca gat tct tta att gat gga gga aat gaa aca gta gca gcc att<br>Gly Pro Asp Ser Leu Ile Asp Gly Gly Asn Glu Thr Val Ala Ala Ile<br>                180                185              190 | 576 |
| tgc atc gca gcc act gga aaa ccc gtt gca cat att gac tgg gaa ggt<br>Cys Ile Ala Ala Thr Gly Lys Pro Val Ala His Ile Asp Trp Glu Gly<br>                195                200              205 | 624 |
| gat ctt ggt gaa atg gaa tcc act aca act tct ttt cca aat gaa acg<br>Asp Leu Gly Glu Met Glu Ser Thr Thr Thr Ser Phe Pro Asn Glu Thr<br>210                  215                220 | 672 |
| gca acg att atc agc cag tac aag cta ttt cca acc aga ttt gct aga<br>Ala Thr Ile Ile Ser Gln Tyr Lys Leu Phe Pro Thr Arg Phe Ala Arg<br>225                  230                235              240 | 720 |
| gga agg cga att act tgt gtt gta aaa cat cca gcc ttg gaa aag gac<br>Gly Arg Arg Ile Thr Cys Val Val Lys His Pro Ala Leu Glu Lys Asp<br>                        245                250              255 | 768 |
| atc cga tac tct ttc ata tta gac ata cag tat gct cct gaa gtt tcg<br>Ile Arg Tyr Ser Phe Ile Leu Asp Ile Gln Tyr Ala Pro Glu Val Ser<br>                260                265              270 | 816 |
| gta aca gga tat gat gga aat tgg ttt gta gga aga aaa ggt gtt aat<br>Val Thr Gly Tyr Asp Gly Asn Trp Phe Val Gly Arg Lys Gly Val Asn<br>                275                280              285 | 864 |
| ctc aaa tgt aat gct gat gca aat cca cca ccc ttc aaa tct gtg tgg<br>Leu Lys Cys Asn Ala Asp Ala Asn Pro Pro Pro Phe Lys Ser Val Trp<br>290                  295                300 | 912 |
| agc agg ttg gat gga caa tgg cct gat ggt tta ttg gct tca gac aat<br>Ser Arg Leu Asp Gly Gln Trp Pro Asp Gly Leu Leu Ala Ser Asp Asn<br>305                  310                315              320 | 960 |

-continued

```
act ctt cat ttt gtc cat cca ttg act ttc aat tat tct ggt gtt tat    1008
Thr Leu His Phe Val His Pro Leu Thr Phe Asn Tyr Ser Gly Val Tyr
            325                 330                 335 atc tgt aaa gtg acc aat tcc ctt ggt caa aga agt gac caa aaa gtc    1056
Ile Cys Lys Val Thr Asn Ser Leu Gly Gln Arg Ser Asp Gln Lys Val
340                 345                 350 atc tac att tca gat gtt cca ttt aag cag acc tct tcc ata gct gta    1104
Ile Tyr Ile Ser Asp Val Pro Phe Lys Gln Thr Ser Ser Ile Ala Val
        355                 360                 365 gct gga gcg gta att gga gct gtt ctt gcc ctt ttc atc att gct atc    1152
Ala Gly Ala Val Ile Gly Ala Val Leu Ala Leu Phe Ile Ile Ala Ile
    370                 375                 380 ttt gtg act gtg ctg ctg act cct cga aaa aaa aga cca tcc tat ctt    1200
Phe Val Thr Val Leu Leu Thr Pro Arg Lys Lys Arg Pro Ser Tyr Leu
385                 390                 395                 400 gac aaa gtg att gac ctt cca ccc aca cat aaa cca cct cct ctg tat    1248
Asp Lys Val Ile Asp Leu Pro Pro Thr His Lys Pro Pro Pro Leu Tyr
        405                 410                 415 gaa gaa cga tcc cca cct ttg cct cag aaa gac cta ttt cag gta tgt    1296
Glu Glu Arg Ser Pro Pro Leu Pro Gln Lys Asp Leu Phe Gln Val Cys
    420                 425                 430 gtt cat gag tac act taa                                            1314
Val His Glu Tyr Thr
        435

<210> SEQ ID NO 31
<211> LENGTH: 437
<212> TYPE: PRT
<213> ORGANISM: homo sapiens

<400> SEQUENCE: 31

Met Ala Arg Thr Leu Arg Pro Ser Pro Leu Cys Pro Gly Gly Gly Lys
1               5                   10                  15

Ala Gln Leu Ser Ser Ala Ser Leu Leu Gly Ala Gly Leu Leu Leu Gln
            20                  25                  30

Pro Pro Thr Pro Pro Pro Leu Leu Leu Leu Leu Phe Pro Leu Leu Leu
        35                  40                  45

Phe Ser Arg Leu Cys Gly Ala Leu Ala Gly Pro Ile Ile Val Glu Pro
    50                  55                  60

His Val Thr Ala Val Trp Gly Lys Asn Val Ser Leu Lys Cys Leu Ile
65                  70                  75                  80

Glu Val Asn Glu Thr Ile Thr Gln Ile Ser Trp Glu Lys Ile His Gly
                85                  90                  95

Lys Ser Ser Gln Thr Val Ala Val His His Pro Gln Tyr Gly Phe Ser
            100                 105                 110

Val Gln Gly Glu Tyr Gln Gly Arg Val Leu Phe Lys Asn Tyr Ser Leu
        115                 120                 125

Asn Asp Ala Thr Ile Thr Leu His Asn Ile Gly Phe Ser Asp Ser Gly
    130                 135                 140

Lys Tyr Ile Cys Lys Ala Val Thr Phe Pro Leu Gly Asn Ala Gln Ser
145                 150                 155                 160

Ser Thr Thr Val Thr Val Leu Val Glu Pro Thr Val Ser Leu Ile Lys
                165                 170                 175

Gly Pro Asp Ser Leu Ile Asp Gly Gly Asn Glu Thr Val Ala Ala Ile
            180                 185                 190

Cys Ile Ala Ala Thr Gly Lys Pro Val Ala His Ile Asp Trp Glu Gly
        195                 200                 205
```

```
Asp Leu Gly Glu Met Glu Ser Thr Thr Thr Ser Phe Pro Asn Glu Thr
    210                 215                 220
Ala Thr Ile Ile Ser Gln Tyr Lys Leu Phe Pro Thr Arg Phe Ala Arg
225                 230                 235                 240
Gly Arg Arg Ile Thr Cys Val Val Lys His Pro Ala Leu Glu Lys Asp
                245                 250                 255
Ile Arg Tyr Ser Phe Ile Leu Asp Ile Gln Tyr Ala Pro Glu Val Ser
            260                 265                 270
Val Thr Gly Tyr Asp Gly Asn Trp Phe Val Gly Arg Lys Gly Val Asn
        275                 280                 285
Leu Lys Cys Asn Ala Asp Ala Asn Pro Pro Phe Lys Ser Val Trp
    290                 295                 300
Ser Arg Leu Asp Gly Gln Trp Pro Asp Gly Leu Ala Ser Asp Asn
305                 310                 315                 320
Thr Leu His Phe Val His Pro Leu Thr Phe Asn Tyr Ser Gly Val Tyr
                325                 330                 335
Ile Cys Lys Val Thr Asn Ser Leu Gly Gln Arg Ser Asp Gln Lys Val
            340                 345                 350
Ile Tyr Ile Ser Asp Val Pro Phe Lys Gln Thr Ser Ser Ile Ala Val
        355                 360                 365
Ala Gly Ala Val Ile Gly Ala Val Leu Ala Leu Phe Ile Ile Ala Ile
    370                 375                 380
Phe Val Thr Val Leu Leu Thr Pro Arg Lys Lys Arg Pro Ser Tyr Leu
385                 390                 395                 400
Asp Lys Val Ile Asp Leu Pro Pro Thr His Lys Pro Pro Leu Tyr
                405                 410                 415
Glu Glu Arg Ser Pro Pro Leu Pro Gln Lys Asp Leu Phe Gln Val Cys
            420                 425                 430
Val His Glu Tyr Thr
        435

<210> SEQ ID NO 32
<211> LENGTH: 1533
<212> TYPE: DNA
<213> ORGANISM: homo sapiens

<400> SEQUENCE: 32 atgccctgt ccctgggagc cgagatgtgg gggcctgagg cctggctgct gctgctgcta    60
ctgctggcat catttacagg ccggtgcccc gcgggtgagc tggagacctc agacgtggta   120
actgtggtgc tgggccagga cgcaaaactg ccctgcttct accgagggga ctccggcgag   180
caagtggggc aagtggcatg ggctcgggtg gacgcgggcg aaggcgccca ggaactagcg   240
ctactgcact ccaaatacgg gcttcatgtg agcccggctt acgagggccg cgtggagcag   300
ccgccgcccc cacgcaaccc cctggacggc tcagtgctcc tgcgcaacgc agtgcaggcg   360
gatgagggcg agtacgagtg ccgggtcagc accttccccg ccggcagctt ccaggcgcgg   420
ctgcggctcc gagtgatggt gcctccctg ccctcactga tcctggtcc agcactagaa   480
gagggccagg gcctgaccct ggcagcctcc tgcacagctg agggcagccc agcccccagc   540
gtgacctggg acacggaggt caaaggcaca acgtccagcc gttccttcaa gcactcccgc   600
tctgctgccg tcacctcaga gttccacttg gtgcctagcc gcagcatgaa tgggcagcca   660
ctgacttgtg tggtgtccca tcctggcctg ctccaggacc aaaggatcac ccacatcctc   720
cacgtgtcct tccttgctga ggcctctgtg agggcctg aagaccaaaa tctgtggcac   780
```

-continued

```
attggcagag aaggagctat gctcaagtgc ctgagtgaag ggcagccccc tccctcatac    840
aactggacac ggctggatgg gcctctgccc agtggggtac gagtggatgg ggacactttg    900
ggctttcccc cactgaccac tgagcacagc ggcatctacg tctgccatgt cagcaatgag    960
ttctcctcaa gggattctca ggtcactgtg gatgttcttg accccaggaa agactctggg   1020
aagcaggtgg acctagtgtc agcctcggtg gtggtggtgg gtgtgatcgc cgcactcttg   1080
ttctgccttc tggtggtggt ggtggtgctc atgtcccgat accatcggcg caaggcccag   1140
cagatgaccc agaaatatga ggaggagctg accctgacca gggagaactc catccggagg   1200
ctgcattccc atcacacgga ccccaggagc cagccggagg agagtgtagg gctgagagcc   1260
gagggccacc ctgatagtct caaggacaac agtagctgct ctgtgatgag tgaagagccc   1320
gagggccgca gttactccac gctgaccacg gtgagggaga tagaaacaca gactgaactg   1380
ctgtctccag gctctgggcg ggccgaggag gaggaagatc aggatgaagg catcaaacag   1440
gccatgaacc attttgttca ggagaatggg accctacggg ccaagcccac gggcaatggc   1500
atctacatca atgggcgggg acacctggtc tga                                1533
```

<210> SEQ ID NO 33
<211> LENGTH: 1660
<212> TYPE: DNA
<213> ORGANISM: homo sapiens
<220> FEATURE:
<221> NAME/KEY: CDS
<222> LOCATION: (61)..(1596)
<223> OTHER INFORMATION:

<400> SEQUENCE: 33

```
cccggccgcc atggcggccg cgggaattcg attaaacgct gggcagtctg cctttcaacc     60 atg ccc ctg tcc ctg gga gcc gag atg tgg ggg cct gag gcc tgg ctg      108
Met Pro Leu Ser Leu Gly Ala Glu Met Trp Gly Pro Glu Ala Trp Leu
1               5                   10                  15 ctg ccg ctg cta ctg ctg gca tca ttt aca ggc cgg tgc ccc gcg ggt      156
Leu Pro Leu Leu Leu Leu Ala Ser Phe Thr Gly Arg Cys Pro Ala Gly
                20                  25                  30 gag ctg gag acc tca gac gtg gta act gtg gtg ctg ggc cag gac gca      204
Glu Leu Glu Thr Ser Asp Val Val Thr Val Val Leu Gly Gln Asp Ala
            35                  40                  45 aaa ctg ccc tgc ttc tac cga ggg gac tcc ggc gag caa gtg ggg caa      252
Lys Leu Pro Cys Phe Tyr Arg Gly Asp Ser Gly Glu Gln Val Gly Gln
50                  55                  60 gtg gca tgg gct cgg gtg gac gcg ggc gaa ggc gcc cag gaa cta gcg      300
Val Ala Trp Ala Arg Val Asp Ala Gly Glu Gly Ala Gln Glu Leu Ala
65                  70                  75                  80 cta ctg cac tcc aaa tac ggg ctt cat gtg agc ccg gct tac gag ggc      348
Leu Leu His Ser Lys Tyr Gly Leu His Val Ser Pro Ala Tyr Glu Gly
                85                  90                  95 cgc gtg gag cag ccg ccg ccc cca cgc aac ccc ctg gac ggc tca gtg      396
Arg Val Glu Gln Pro Pro Pro Pro Arg Asn Pro Leu Asp Gly Ser Val
                100                 105                 110 ctc ctg cgc aac gca gtg cag gcg gat gag ggc gag tac gag tgc cgg      444
Leu Leu Arg Asn Ala Val Gln Ala Asp Glu Gly Glu Tyr Glu Cys Arg
            115                 120                 125 gtc agc acc ttc ccc gcc ggc agc ttc cag gcg cgg ctg cgg ctc cga      492
Val Ser Thr Phe Pro Ala Gly Ser Phe Gln Ala Arg Leu Arg Leu Arg
        130                 135                 140 gtg ctg gtg cct ccc ctg ccc tcg ctg aat cct ggt cca gca cta gaa      540
Val Leu Val Pro Pro Leu Pro Ser Leu Asn Pro Gly Pro Ala Leu Glu
```

-continued

```
                145                 150                 155                 160
gag ggc cag ggc ctg acc ctg gca gcc tcc tgc aca gct gag ggc agc      588
Glu Gly Gln Gly Leu Thr Leu Ala Ala Ser Cys Thr Ala Glu Gly Ser
                    165                 170                 175 cca gcc ccc agc gtg acc tgg gac acg gag gtc aaa ggc aca acg tcc      636
Pro Ala Pro Ser Val Thr Trp Asp Thr Glu Val Lys Gly Thr Thr Ser
            180                 185                 190 agc cgt tcc ttc aag cac tcc cgc tct gct gcc gtc acc tca gag ttc      684
Ser Arg Ser Phe Lys His Ser Arg Ser Ala Ala Val Thr Ser Glu Phe
        195                 200                 205 cac ttg gtg cct agc cgc agc atg aat ggg cag cca ctg act tgt gtg      732
His Leu Val Pro Ser Arg Ser Met Asn Gly Gln Pro Leu Thr Cys Val
    210                 215                 220 gtg tcc cat cct ggc ctg ctc cag gac caa agg atc acc cac atc ctc      780
Val Ser His Pro Gly Leu Leu Gln Asp Gln Arg Ile Thr His Ile Leu
225                 230                 235                 240 cac gtg tcc ttc ctt gct gag gcc tct gtg agg ggc ctt gaa gac caa      828
His Val Ser Phe Leu Ala Glu Ala Ser Val Arg Gly Leu Glu Asp Gln
                    245                 250                 255 aat ctg tgg cac att ggc aga gaa gga gct atg ctc aag tgc ctg agt      876
Asn Leu Trp His Ile Gly Arg Glu Gly Ala Met Leu Lys Cys Leu Ser
            260                 265                 270 gaa ggg cag ccc cct ccc tca tac aac tgg aca cgg ctg gat ggg cct      924
Glu Gly Gln Pro Pro Pro Ser Tyr Asn Trp Thr Arg Leu Asp Gly Pro
        275                 280                 285 ctg ccc agt ggg gta cga gtg gat ggg gac act ttg ggc ttt ccc cca      972
Leu Pro Ser Gly Val Arg Val Asp Gly Asp Thr Leu Gly Phe Pro Pro
    290                 295                 300 ctg acc act gag cac agc ggc atc tac gtc tgc cat gtc agc aat gag     1020
Leu Thr Thr Glu His Ser Gly Ile Tyr Val Cys His Val Ser Asn Glu
305                 310                 315                 320 ttc tcc tca agg gat tct cag gtc act gtg gat gtt ctt gca gac ccc     1068
Phe Ser Ser Arg Asp Ser Gln Val Thr Val Asp Val Leu Ala Asp Pro
                    325                 330                 335 cag gaa gac tct ggg aag cag gtg gac cta gtg tca gcc tcg gtg gtg     1116
Gln Glu Asp Ser Gly Lys Gln Val Asp Leu Val Ser Ala Ser Val Val
            340                 345                 350 gtg gtg ggt gtg atc gcc gca ctc ttg ttc tgc ctt ctg gtg gtg gtg     1164
Val Val Gly Val Ile Ala Ala Leu Leu Phe Cys Leu Leu Val Val Val
        355                 360                 365 gtg gtg ctc atg tcc cga tac cat cgg cgc aag gcc cag cag atg acc     1212
Val Val Leu Met Ser Arg Tyr His Arg Arg Lys Ala Gln Gln Met Thr
    370                 375                 380 cag aaa tat gag gag gag ctg acc ctg acc agg gag aac tcc atc cgg     1260
Gln Lys Tyr Glu Glu Glu Leu Thr Leu Thr Arg Glu Asn Ser Ile Arg
385                 390                 395                 400 agg ctg cat tcc cat cac acg gac ccc agg agc cag ccg gag gag agt     1308
Arg Leu His Ser His His Thr Asp Pro Arg Ser Gln Pro Glu Glu Ser
                    405                 410                 415 gta ggg ctg aga gcc gag ggc cac cct gat agt ctc aag gac aac agt     1356
Val Gly Leu Arg Ala Glu Gly His Pro Asp Ser Leu Lys Asp Asn Ser
            420                 425                 430 agc tgc tct gtg atg agt gaa gag ccc gag ggc cgc agt tac tcc acg     1404
Ser Cys Ser Val Met Ser Glu Glu Pro Glu Gly Arg Ser Tyr Ser Thr
        435                 440                 445 ctg acc acg gtg agg gag ata gaa aca cag act gaa ctg ctg tct cca     1452
Leu Thr Thr Val Arg Glu Ile Glu Thr Gln Thr Glu Leu Leu Ser Pro
    450                 455                 460 ggc tct ggg cgg gcc gag gag gag gaa gat cag gat gaa ggc atc aaa     1500
Gly Ser Gly Arg Ala Glu Glu Glu Glu Asp Gln Asp Glu Gly Ile Lys
```

```
Gly Ser Gly Arg Ala Glu Glu Glu Asp Gln Asp Glu Gly Ile Lys
465                 470                 475                 480 cag gcc atg aac cat ttt gtt cag gag aat ggg acc cta cgg gcc aag      1548
Gln Ala Met Asn His Phe Val Gln Glu Asn Gly Thr Leu Arg Ala Lys
                485                 490                 495 ccc acg ggc aat ggc atc tac atc aat ggg cgg gga cac ctg gtc tga      1596
Pro Thr Gly Asn Gly Ile Tyr Ile Asn Gly Arg Gly His Leu Val
            500                 505                 510 ccgcggccgc atataatcac tagtgaattc gcggccgcct gcaggtcgac catatgggag    1656
agct                                                                 1660

<210> SEQ ID NO 34
<211> LENGTH: 511
<212> TYPE: PRT
<213> ORGANISM: homo sapiens

<400> SEQUENCE: 34

Met Pro Leu Ser Leu Gly Ala Glu Met Trp Gly Pro Glu Ala Trp Leu
1               5                   10                  15

Leu Pro Leu Leu Leu Leu Ala Ser Phe Thr Gly Arg Cys Pro Ala Gly
            20                  25                  30

Glu Leu Glu Thr Ser Asp Val Val Thr Val Val Leu Gly Gln Asp Ala
        35                  40                  45

Lys Leu Pro Cys Phe Tyr Arg Gly Asp Ser Gly Glu Gln Val Gly Gln
    50                  55                  60

Val Ala Trp Ala Arg Val Asp Ala Gly Glu Gly Ala Gln Glu Leu Ala
65                  70                  75                  80

Leu Leu His Ser Lys Tyr Gly Leu His Val Ser Pro Ala Tyr Glu Gly
                85                  90                  95

Arg Val Glu Gln Pro Pro Pro Arg Asn Pro Leu Asp Gly Ser Val
            100                 105                 110

Leu Leu Arg Asn Ala Val Gln Ala Asp Glu Gly Glu Tyr Glu Cys Arg
            115                 120                 125

Val Ser Thr Phe Pro Ala Gly Ser Phe Gln Ala Arg Leu Arg Leu Arg
130                 135                 140

Val Leu Val Pro Pro Leu Pro Ser Leu Asn Pro Gly Pro Ala Leu Glu
145                 150                 155                 160

Glu Gly Gln Gly Leu Thr Leu Ala Ala Ser Cys Thr Ala Glu Gly Ser
                165                 170                 175

Pro Ala Pro Ser Val Thr Trp Asp Thr Glu Val Lys Gly Thr Thr Ser
            180                 185                 190

Ser Arg Ser Phe Lys His Ser Arg Ser Ala Ala Val Thr Ser Glu Phe
        195                 200                 205

His Leu Val Pro Ser Arg Ser Met Asn Gly Gln Pro Leu Thr Cys Val
    210                 215                 220

Val Ser His Pro Gly Leu Leu Gln Asp Gln Arg Ile Thr His Ile Leu
225                 230                 235                 240

His Val Ser Phe Leu Ala Glu Ala Ser Val Arg Gly Leu Glu Asp Gln
                245                 250                 255

Asn Leu Trp His Ile Gly Arg Glu Gly Ala Met Leu Lys Cys Leu Ser
            260                 265                 270

Glu Gly Gln Pro Pro Pro Ser Tyr Asn Trp Thr Arg Leu Asp Gly Pro
        275                 280                 285

Leu Pro Ser Gly Val Arg Val Asp Gly Asp Thr Leu Gly Phe Pro Pro
    290                 295                 300
```

```
Leu Thr Thr Glu His Ser Gly Ile Tyr Val Cys His Val Ser Asn Glu
305                 310                 315                 320

Phe Ser Ser Arg Asp Ser Gln Val Thr Val Asp Val Leu Ala Asp Pro
            325                 330                 335

Gln Glu Asp Ser Gly Lys Gln Val Asp Leu Val Ser Ala Ser Val Val
            340                 345                 350

Val Val Gly Val Ile Ala Ala Leu Leu Phe Cys Leu Leu Val Val Val
            355                 360                 365

Val Val Leu Met Ser Arg Tyr His Arg Arg Lys Ala Gln Gln Met Thr
370                 375                 380

Gln Lys Tyr Glu Glu Glu Leu Thr Leu Thr Arg Glu Asn Ser Ile Arg
385                 390                 395                 400

Arg Leu His Ser His His Thr Asp Pro Arg Ser Gln Pro Glu Glu Ser
                405                 410                 415

Val Gly Leu Arg Ala Glu Gly His Pro Asp Ser Leu Lys Asp Asn Ser
            420                 425                 430

Ser Cys Ser Val Met Ser Glu Glu Pro Glu Gly Arg Ser Tyr Ser Thr
            435                 440                 445

Leu Thr Thr Val Arg Glu Ile Glu Thr Gln Thr Glu Leu Leu Ser Pro
450                 455                 460

Gly Ser Gly Arg Ala Glu Glu Glu Asp Gln Asp Glu Gly Ile Lys
465                 470                 475                 480

Gln Ala Met Asn His Phe Val Gln Glu Asn Gly Thr Leu Arg Ala Lys
                485                 490                 495

Pro Thr Gly Asn Gly Ile Tyr Ile Asn Gly Arg Gly His Leu Val
            500                 505                 510

<210> SEQ ID NO 35
<211> LENGTH: 1838
<212> TYPE: DNA
<213> ORGANISM: Artificial Sequence
<220> FEATURE:
<223> OTHER INFORMATION: Fusion Construct
<221> NAME/KEY: CDS
<222> LOCATION: (58)..(1800)
<223> OTHER INFORMATION:

<400> SEQUENCE: 35
tcggaaaacc tctcgagggc cacgcgttta acgtcgacg cagtctgcct ttcaacc        57 atg ccc ctg tcc ctg gga gcc gag atg tgg ggg cct gag gcc tgg ctg    105
Met Pro Leu Ser Leu Gly Ala Glu Met Trp Gly Pro Glu Ala Trp Leu
1               5                   10                  15 ctg ccg ctg cta ctg ctg gca tca ttt aca ggc cgg tgc ccc gcg ggt    153
Leu Pro Leu Leu Leu Leu Ala Ser Phe Thr Gly Arg Cys Pro Ala Gly
            20                  25                  30 gag ctg gag acc tca gac gtg gta act gtg gtg ctg ggc cag gac gca    201
Glu Leu Glu Thr Ser Asp Val Val Thr Val Val Leu Gly Gln Asp Ala
        35                  40                  45 aaa ctg ccc tgc ttc tac cga ggg gac tcc ggc gag caa gtg ggg caa    249
Lys Leu Pro Cys Phe Tyr Arg Gly Asp Ser Gly Glu Gln Val Gly Gln
    50                  55                  60 gtg gca tgg gct cgg gtg gac gcg ggc gaa ggc gcc cag gaa cta gcg    297
Val Ala Trp Ala Arg Val Asp Ala Gly Glu Gly Ala Gln Glu Leu Ala
65                  70                  75                  80 cta ctg cac tcc aaa tac ggg ctt cat gtg agc ccg gct tac gag ggc    345
Leu Leu His Ser Lys Tyr Gly Leu His Val Ser Pro Ala Tyr Glu Gly
                85                  90                  95
```

-continued

| | |
|---|---|
| cgc gtg gag cag ccg ccg ccc cca cgc aac ccc ctg gac ggc tca gtg<br>Arg Val Glu Gln Pro Pro Pro Pro Arg Asn Pro Leu Asp Gly Ser Val<br>                  100                        105                    110 | 393 |
| ctc ctg cgc aac gca gtg cag gcg gat gag ggc gag tac gag tgc cgg<br>Leu Leu Arg Asn Ala Val Gln Ala Asp Glu Gly Glu Tyr Glu Cys Arg<br>          115                        120                        125 | 441 |
| gtc agc acc ttc ccc gcc ggc agc ttc cag gcg cgg cta cgg ctc cga<br>Val Ser Thr Phe Pro Ala Gly Ser Phe Gln Ala Arg Leu Arg Leu Arg<br>130                         135                        140 | 489 |
| gtg ctg gtg cct ccc ctg ccc tcg ctg aat cct ggt cca gca cta gaa<br>Val Leu Val Pro Pro Leu Pro Ser Leu Asn Pro Gly Pro Ala Leu Glu<br>145                       150                       155                    160 | 537 |
| gag ggc cag ggc ctg acc ctg gca gcc tcc tgc aca gct gag ggc agc<br>Glu Gly Gln Gly Leu Thr Leu Ala Ala Ser Cys Thr Ala Glu Gly Ser<br>                  165                        170                        175 | 585 |
| cca gcc ccc agc gtg acc tgg gac acg gag gtc aaa ggc aca acg tcc<br>Pro Ala Pro Ser Val Thr Trp Asp Thr Glu Val Lys Gly Thr Thr Ser<br>                  180                        185                        190 | 633 |
| agc cgt tcc ttc aag cac tcc cgc tct gct gcc gtc acc tca gag ttc<br>Ser Arg Ser Phe Lys His Ser Arg Ser Ala Ala Val Thr Ser Glu Phe<br>          195                        200                        205 | 681 |
| cac ttg gtg cct agc cgc agc atg aat ggg cag cca ctg act tgt gtg<br>His Leu Val Pro Ser Arg Ser Met Asn Gly Gln Pro Leu Thr Cys Val<br>                  210                        215                        220 | 729 |
| gtg tcc cat cct ggc ctg ctc cag gac caa agg atc acc cac atc ctc<br>Val Ser His Pro Gly Leu Leu Gln Asp Gln Arg Ile Thr His Ile Leu<br>225                       230                       235                        240 | 777 |
| cac gtg tcc ttc ctt gct gag gcc tct gtg agg ggc ctt gaa gac caa<br>His Val Ser Phe Leu Ala Glu Ala Ser Val Arg Gly Leu Glu Asp Gln<br>                       245                        250                        255 | 825 |
| aat ctg tgg cac att ggc aga gaa gga gct atg ctc aag tgc ctg agt<br>Asn Leu Trp His Ile Gly Arg Glu Gly Ala Met Leu Lys Cys Leu Ser<br>                      260                        265                        270 | 873 |
| gaa ggg cag ccc cct ccc tca tac aac tgg aca cgg ctg gat ggg cct<br>Glu Gly Gln Pro Pro Pro Ser Tyr Asn Trp Thr Arg Leu Asp Gly Pro<br>                  275                        280                        285 | 921 |
| ctg ccc agt ggg gta cga gtg gat ggg gac act ttg ggc ttt ccc cca<br>Leu Pro Ser Gly Val Arg Val Asp Gly Asp Thr Leu Gly Phe Pro Pro<br>          290                        295                        300 | 969 |
| ctg acc act gag cac agc ggc atc tac gtc tgc cat gtc agc aat gag<br>Leu Thr Thr Glu His Ser Gly Ile Tyr Val Cys His Val Ser Asn Glu<br>305                       310                       315                        320 | 1017 |
| ttc tcc tca agg gat tct cag gtc act gtg gat gtt ctt gca gac ccc<br>Phe Ser Ser Arg Asp Ser Gln Val Thr Val Asp Val Leu Ala Asp Pro<br>                       325                        330                        335 | 1065 |
| cag gaa gac tct ggg aag cag gtg gac cta gtg tca gcc tcg aga tct<br>Gln Glu Asp Ser Gly Lys Gln Val Asp Leu Val Ser Ala Ser Arg Ser<br>                  340                        345                        350 | 1113 |
| tgt gac aaa act cac aca tgc cca ccg tgc cca gca cct gaa gcc gag<br>Cys Asp Lys Thr His Thr Cys Pro Pro Cys Pro Ala Pro Glu Ala Glu<br>          355                        360                        365 | 1161 |
| ggc gcg ccg tca gtc ttc ctc ttc ccc cca aaa ccc aag gac acc ctc<br>Gly Ala Pro Ser Val Phe Leu Phe Pro Pro Lys Pro Lys Asp Thr Leu<br>370                       375                       380 | 1209 |
| atg atc tcc cgg acc cct gag gtc aca tgc gtg gtg gtg gac gtg agc<br>Met Ile Ser Arg Thr Pro Glu Val Thr Cys Val Val Val Asp Val Ser<br>385                       390                       395                        400 | 1257 |
| cac gaa gac cct gag gtc aag ttc aac tgg tac gtg gac ggc gtg gag<br>His Glu Asp Pro Glu Val Lys Phe Asn Trp Tyr Val Asp Gly Val Glu<br>                       405                        410                        415 | 1305 |

```
gtg cat aat gcc aag aca aag ccg cgg gag gag cag tac aac agc acg      1353
Val His Asn Ala Lys Thr Lys Pro Arg Glu Glu Gln Tyr Asn Ser Thr
            420                 425                 430 tac cgt gtg gtc agc gtc ctc acc gtc ctg cac cag gac tgg ctg aat      1401
Tyr Arg Val Val Ser Val Leu Thr Val Leu His Gln Asp Trp Leu Asn
        435                 440                 445 ggc aag gag tac aag tgc aag gtc tcc aac aaa gcc ctc cca gcc ccc      1449
Gly Lys Glu Tyr Lys Cys Lys Val Ser Asn Lys Ala Leu Pro Ala Pro
    450                 455                 460 atc gag aaa acc atc tcc aaa gcc aaa ggg cag ccc cga gaa cca cag      1497
Ile Glu Lys Thr Ile Ser Lys Ala Lys Gly Gln Pro Arg Glu Pro Gln
465                 470                 475                 480 gtg tac acc ctg ccc cca tcc cgg gag gag atg acc aag aac cag gtc      1545
Val Tyr Thr Leu Pro Pro Ser Arg Glu Glu Met Thr Lys Asn Gln Val
                485                 490                 495 agc ctg acc tgc ctg gtc aaa ggc ttc tat ccc agc gac atc gcc gtg      1593
Ser Leu Thr Cys Leu Val Lys Gly Phe Tyr Pro Ser Asp Ile Ala Val
            500                 505                 510 gag tgg gag agc aat ggg cag ccg gag aac aac tac aag acc acg cct      1641
Glu Trp Glu Ser Asn Gly Gln Pro Glu Asn Asn Tyr Lys Thr Thr Pro
        515                 520                 525 ccc gtg ctg gac tcc gac ggc tcc ttc ttc ctc tat agc aag ctc acc      1689
Pro Val Leu Asp Ser Asp Gly Ser Phe Phe Leu Tyr Ser Lys Leu Thr
    530                 535                 540 gtg gac aag agc agg tgg cag cag ggg aac gtc ttc tca tgc tcc gtg      1737
Val Asp Lys Ser Arg Trp Gln Gln Gly Asn Val Phe Ser Cys Ser Val
545                 550                 555                 560 atg cat gag gct ctg cac aac cac tac acg cag aag agc ctc tcc ctg      1785
Met His Glu Ala Leu His Asn His Tyr Thr Gln Lys Ser Leu Ser Leu
                565                 570                 575 tct ccg ggt aaa tga actagttcta gagcggccgc ggatctgttt aaactagt        1838
Ser Pro Gly Lys
            580

<210> SEQ ID NO 36
<211> LENGTH: 580
<212> TYPE: PRT
<213> ORGANISM: Artificial Sequence
<220> FEATURE:
<223> OTHER INFORMATION: Fusion Construct

<400> SEQUENCE: 36

Met Pro Leu Ser Leu Gly Ala Glu Met Trp Gly Pro Glu Ala Trp Leu
1               5                   10                  15

Leu Pro Leu Leu Leu Leu Ala Ser Phe Thr Gly Arg Cys Pro Ala Gly
                20                  25                  30

Glu Leu Glu Thr Ser Asp Val Thr Val Val Leu Gly Gln Asp Ala
        35                  40                  45

Lys Leu Pro Cys Phe Tyr Arg Gly Asp Ser Gly Glu Gln Val Gly Gln
    50                  55                  60

Val Ala Trp Ala Arg Val Asp Ala Gly Glu Gly Ala Gln Glu Leu Ala
65                  70                  75                  80

Leu Leu His Ser Lys Tyr Gly Leu His Val Ser Pro Ala Tyr Glu Gly
                85                  90                  95

Arg Val Glu Gln Pro Pro Pro Arg Asn Pro Leu Asp Gly Ser Val
                100                 105                 110

Leu Leu Arg Asn Ala Val Gln Ala Asp Glu Gly Glu Tyr Glu Cys Arg
            115                 120                 125
```

-continued

```
Val Ser Thr Phe Pro Ala Gly Ser Phe Gln Ala Arg Leu Arg Leu Arg
    130                 135                 140

Val Leu Val Pro Pro Leu Pro Ser Leu Asn Pro Gly Pro Ala Leu Glu
145                 150                 155                 160

Glu Gly Gln Gly Leu Thr Leu Ala Ala Ser Cys Thr Ala Glu Gly Ser
                165                 170                 175

Pro Ala Pro Ser Val Thr Trp Asp Thr Glu Val Lys Gly Thr Thr Ser
            180                 185                 190

Ser Arg Ser Phe Lys His Ser Arg Ser Ala Ala Val Thr Ser Glu Phe
        195                 200                 205

His Leu Val Pro Ser Arg Ser Met Asn Gly Gln Pro Leu Thr Cys Val
    210                 215                 220

Val Ser His Pro Gly Leu Leu Gln Asp Gln Arg Ile Thr His Ile Leu
225                 230                 235                 240

His Val Ser Phe Leu Ala Glu Ala Ser Val Arg Gly Leu Glu Asp Gln
                245                 250                 255

Asn Leu Trp His Ile Gly Arg Glu Gly Ala Met Leu Lys Cys Leu Ser
            260                 265                 270

Glu Gly Gln Pro Pro Ser Tyr Asn Trp Thr Arg Leu Asp Gly Pro
        275                 280                 285

Leu Pro Ser Gly Val Arg Val Asp Gly Asp Thr Leu Gly Phe Pro Pro
    290                 295                 300

Leu Thr Thr Glu His Ser Gly Ile Tyr Val Cys His Val Ser Asn Glu
305                 310                 315                 320

Phe Ser Ser Arg Asp Ser Gln Val Thr Val Asp Val Leu Ala Asp Pro
                325                 330                 335

Gln Glu Asp Ser Gly Lys Gln Val Asp Leu Val Ser Ala Ser Arg Ser
            340                 345                 350

Cys Asp Lys Thr His Thr Cys Pro Pro Cys Pro Ala Pro Glu Ala Glu
        355                 360                 365

Gly Ala Pro Ser Val Phe Leu Phe Pro Pro Lys Pro Lys Asp Thr Leu
    370                 375                 380

Met Ile Ser Arg Thr Pro Glu Val Thr Cys Val Val Val Asp Val Ser
385                 390                 395                 400

His Glu Asp Pro Glu Val Lys Phe Asn Trp Tyr Val Asp Gly Val Glu
                405                 410                 415

Val His Asn Ala Lys Thr Lys Pro Arg Glu Glu Gln Tyr Asn Ser Thr
            420                 425                 430

Tyr Arg Val Val Ser Val Leu Thr Val Leu His Gln Asp Trp Leu Asn
        435                 440                 445

Gly Lys Glu Tyr Lys Cys Lys Val Ser Asn Lys Ala Leu Pro Ala Pro
    450                 455                 460

Ile Glu Lys Thr Ile Ser Lys Ala Lys Gly Gln Pro Arg Glu Pro Gln
465                 470                 475                 480

Val Tyr Thr Leu Pro Pro Ser Arg Glu Glu Met Thr Lys Asn Gln Val
                485                 490                 495

Ser Leu Thr Cys Leu Val Lys Gly Phe Tyr Pro Ser Asp Ile Ala Val
            500                 505                 510

Glu Trp Glu Ser Asn Gly Gln Pro Glu Asn Asn Tyr Lys Thr Thr Pro
        515                 520                 525

Pro Val Leu Asp Ser Asp Gly Ser Phe Phe Leu Tyr Ser Lys Leu Thr
    530                 535                 540

Val Asp Lys Ser Arg Trp Gln Gln Gly Asn Val Phe Ser Cys Ser Val
```

-continued

```
               545                 550                 555                 560
Met His Glu Ala Leu His Asn His Tyr Thr Gln Lys Ser Leu Ser Leu
                565                 570                 575

Ser Pro Gly Lys
            580

<210> SEQ ID NO 37
<211> LENGTH: 497
<212> TYPE: PRT
<213> ORGANISM: homo sapiens

<400> SEQUENCE: 37

Glu Leu Gln Lys Arg Trp Ala Val Cys Leu Ser Thr Met Pro Leu Ser
1               5                  10                  15

Leu Gly Ala Glu Met Trp Gly Pro Glu Ala Trp Leu Leu Leu Leu Leu
                20                  25                  30

Leu Leu Ala Ser Phe Thr Gly Arg Cys Pro Ala Gly Glu Leu Glu Thr
            35                  40                  45

Ser Asp Val Val Thr Val Val Leu Gly Gln Asp Ala Lys Leu Pro Cys
50                  55                  60

Phe Tyr Arg Gly Asp Ser Gly Glu Gln Val Gly Gln Val Ala Trp Ala
65                  70                  75                  80

Arg Val Asp Ala Gly Glu Gly Ala Gln Glu Leu Ala Leu Leu His Ser
                85                  90                  95

Lys Tyr Gly Leu His Val Ser Pro Ala Tyr Glu Gly Arg Val Glu Gln
            100                 105                 110

Pro Pro Pro Pro Arg Asn Pro Leu Asp Gly Ser Val Leu Leu Arg Asn
        115                 120                 125

Ala Val Gln Ala Asp Glu Gly Glu Tyr Glu Cys Arg Val Ser Thr Phe
130                 135                 140

Pro Ala Gly Ser Phe Gln Ala Arg Leu Arg Leu Arg Val Leu Val Pro
145                 150                 155                 160

Pro Leu Pro Ser Leu Asn Pro Gly Pro Ala Leu Glu Glu Gly Gln Gly
                165                 170                 175

Leu Thr Leu Ala Ala Ser Cys Thr Ala Glu Gly Ser Pro Ala Pro Ser
            180                 185                 190

Val Thr Trp Asp Thr Glu Val Lys Gly Thr Thr Ser Ser Arg Ser Phe
        195                 200                 205

Lys His Ser Arg Ser Ala Ala Val Thr Ser Glu Phe His Leu Val Pro
210                 215                 220

Ser Arg Ser Met Asn Gly Gln Pro Leu Thr Cys Val Val Ser His Pro
225                 230                 235                 240

Gly Leu Leu Gln Asp Gln Arg Ile Thr His Ile Leu His Val Ser Phe
                245                 250                 255

Leu Ala Glu Ala Ser Val Arg Gly Leu Glu Asp Gln Asn Leu Trp His
            260                 265                 270

Ile Gly Arg Glu Gly Ala Met Leu Lys Cys Leu Ser Glu Gly Gln Pro
        275                 280                 285

Pro Pro Ser Tyr Asn Trp Thr Arg Leu Asp Gly Pro Leu Pro Ser Gly
        290                 295                 300

Val Arg Val Asp Gly Asp Thr Leu Gly Phe Pro Pro Leu Thr Thr Glu
305                 310                 315                 320

His Ser Gly Ile Tyr Val Cys His Val Ser Asn Glu Phe Ser Ser Arg
                325                 330                 335
```

-continued

```
Asp Ser Gln Val Thr Val Asp Val Leu Asp Pro Gln Glu Asp Ser Gly
        340                 345                 350

Lys Gln Val Asp Leu Val Ser Ala Ser Val Val Val Gly Val Ile
        355                 360                 365

Ala Ala Leu Leu Phe Cys Leu Leu Val Val Val Val Leu Met Ser
        370                 375                 380

Arg Tyr His Arg Arg Lys Ala Gln Gln Met Thr Gln Lys Tyr Glu Glu
385                 390                 395                 400

Glu Leu Thr Leu Thr Arg Glu Asn Ser Ile Arg Arg Leu His Ser His
                405                 410                 415

His Thr Asp Pro Arg Ser Gln Ser Glu Glu Pro Glu Gly Arg Ser Tyr
            420                 425                 430

Ser Thr Leu Thr Thr Val Arg Glu Ile Glu Thr Gln Thr Glu Leu Leu
        435                 440                 445

Ser Pro Gly Ser Gly Arg Ala Glu Glu Glu Asp Gln Asp Glu Gly
    450                 455                 460

Ile Lys Gln Ala Met Asn His Phe Val Gln Glu Asn Gly Thr Leu Arg
465                 470                 475                 480

Ala Lys Pro Thr Gly Asn Gly Ile Tyr Ile Asn Gly Arg Gly His Leu
                485                 490                 495

Val

<210> SEQ ID NO 38
<211> LENGTH: 402
<212> TYPE: PRT
<213> ORGANISM: homo sapiens

<400> SEQUENCE: 38

Glu Leu Gln Lys Arg Trp Ala Val Cys Leu Ser Thr Met Pro Leu Ser
1               5                   10                  15

Leu Gly Ala Glu Met Trp Gly Pro Glu Ala Trp Leu Leu Leu Leu
            20                  25                  30

Leu Leu Ala Ser Phe Thr Val Pro Pro Leu Pro Ser Leu Asn Pro Gly
        35                  40                  45

Pro Ala Leu Glu Glu Gly Gln Gly Leu Thr Leu Ala Ala Ser Cys Thr
    50                  55                  60

Ala Glu Gly Ser Pro Ala Pro Ser Val Thr Trp Asp Thr Glu Val Lys
65                  70                  75                  80

Gly Thr Thr Ser Ser Arg Ser Phe Lys His Ser Arg Ser Ala Ala Val
                85                  90                  95

Thr Ser Glu Phe His Leu Val Pro Ser Arg Ser Met Asn Gly Gln Pro
            100                 105                 110

Leu Thr Cys Val Val Ser His Pro Gly Leu Leu Gln Asp Gln Arg Ile
        115                 120                 125

Thr His Ile Leu His Val Ser Phe Leu Ala Glu Ala Ser Val Arg Gly
    130                 135                 140

Leu Glu Asp Gln Asn Leu Trp His Ile Gly Arg Glu Gly Ala Met Leu
145                 150                 155                 160

Lys Cys Leu Ser Glu Gly Gln Pro Pro Ser Tyr Asn Trp Thr Arg
                165                 170                 175

Leu Asp Gly Pro Leu Pro Ser Gly Val Arg Val Asp Gly Asp Thr Leu
            180                 185                 190

Gly Phe Pro Pro Leu Thr Thr Glu His Ser Gly Ile Tyr Val Cys His
        195                 200                 205
```

-continued

```
Val Ser Asn Glu Phe Ser Ser Arg Asp Ser Gln Val Thr Val Asp Val
    210                 215                 220

Leu Asp Pro Gln Glu Asp Ser Gly Lys Gln Val Asp Leu Val Ser Ala
225                 230                 235                 240

Ser Val Val Val Gly Val Ile Ala Ala Leu Leu Phe Cys Leu Leu
                245                 250                 255

Val Val Val Val Val Leu Met Ser Arg Tyr His Arg Arg Lys Ala Gln
            260                 265                 270

Gln Met Thr Gln Lys Tyr Glu Glu Leu Thr Leu Thr Arg Glu Asn
        275                 280                 285

Ser Ile Arg Arg Leu His Ser His His Thr Asp Pro Arg Ser Gln Pro
    290                 295                 300

Glu Glu Ser Val Gly Leu Arg Ala Glu Gly His Pro Asp Ser Leu Lys
305                 310                 315                 320

Asp Asn Ser Ser Cys Ser Val Met Ser Glu Glu Pro Glu Gly Arg Ser
                325                 330                 335

Tyr Ser Thr Leu Thr Thr Val Arg Glu Ile Glu Thr Gln Thr Glu Leu
            340                 345                 350

Leu Ser Pro Gly Ser Gly Arg Ala Glu Glu Glu Asp Gln Asp Glu
        355                 360                 365

Gly Ile Lys Gln Ala Met Asn His Phe Val Gln Glu Asn Gly Thr Leu
370                 375                 380

Arg Ala Lys Pro Thr Gly Asn Gly Ile Tyr Ile Asn Gly Arg Gly His
385                 390                 395                 400

Leu Val

<210> SEQ ID NO 39
<211> LENGTH: 498
<212> TYPE: PRT
<213> ORGANISM: homo sapiens

<400> SEQUENCE: 39

Glu Leu Gln Lys Arg Trp Ala Val Cys Leu Ser Thr Met Pro Leu Ser
1               5                   10                  15

Leu Gly Ala Glu Met Trp Gly Pro Glu Ala Trp Leu Leu Leu Leu
            20                  25                  30

Leu Leu Ala Ser Phe Ala Gly Arg Cys Pro Ala Gly Glu Leu Glu Thr
        35                  40                  45

Ser Asp Val Val Thr Val Leu Gly Gln Asp Ala Lys Leu Pro Cys
50                  55                  60

Phe Tyr Arg Gly Asp Ser Gly Glu Gln Val Gly Gln Val Ala Trp Ala
65                  70                  75                  80

Arg Val Asp Ala Gly Glu Gly Ala Gln Glu Leu Ala Leu Leu His Ser
                85                  90                  95

Lys Tyr Gly Leu His Val Ser Pro Ala Tyr Glu Gly Arg Val Glu Gln
            100                 105                 110

Pro Pro Pro Pro Arg Asn Leu Leu Asp Gly Ser Val Leu Leu Arg Asn
        115                 120                 125

Ala Val Gln Ala Asp Glu Gly Glu Tyr Glu Cys Arg Val Ser Thr Phe
    130                 135                 140

Pro Ala Gly Ser Phe Gln Ala Arg Leu Arg Leu Arg Val Leu Val Pro
145                 150                 155                 160

Pro Leu Pro Ser Leu Asn Pro Gly Pro Ala Leu Glu Glu Gly Gln Gly
                165                 170                 175
```

-continued

```
Leu Thr Leu Ala Ala Ser Cys Thr Ala Glu Gly Ser Pro Ala Pro Ser
            180                 185                 190

Val Thr Trp Asp Thr Glu Val Lys Gly Thr Thr Ser Ser Arg Ser Phe
            195                 200                 205

Lys His Ser Arg Ser Ala Ala Val Thr Ser Glu Phe His Leu Val Pro
            210                 215                 220

Ser Arg Ser Met Asn Gly Gln Pro Leu Thr Cys Val Val Ser His Pro
225                 230                 235                 240

Gly Leu Leu Gln Asp Gln Arg Ile Thr His Ile Leu His Val Ser Phe
                245                 250                 255

Leu Ala Glu Ala Ser Val Arg Gly Leu Glu Asp Gln Asn Leu Trp His
            260                 265                 270

Ile Gly Arg Glu Gly Ala Met Leu Lys Cys Leu Ser Glu Gly Gln Pro
            275                 280                 285

Pro Pro Ser Tyr Asn Trp Thr Arg Leu Asp Gly Pro Leu Pro Ser Gly
            290                 295                 300

Val Arg Val Asp Gly Asp Thr Leu Gly Phe Pro Pro Leu Thr Thr Glu
305                 310                 315                 320

His Ser Gly Ile Tyr Val Cys His Val Ser Asn Glu Phe Ser Ser Arg
                325                 330                 335

Asp Ser Gln Val Thr Val Asp Val Leu Ala Asp Pro Gln Glu Asp Ser
                340                 345                 350

Gly Lys Gln Val Asp Leu Val Ser Ala Ser Val Val Val Gly Val
                355                 360                 365

Ile Ala Ala Leu Leu Phe Cys Leu Leu Val Val Val Val Leu Met
            370                 375                 380

Ser Arg Tyr His Arg Arg Lys Ala Gln Gln Met Thr Gln Lys Tyr Glu
385                 390                 395                 400

Glu Glu Leu Thr Leu Thr Arg Glu Asn Ser Ile Arg Arg Leu His Ser
            405                 410                 415

His His Thr Asp Pro Arg Ser Gln Ser Glu Glu Pro Glu Gly Arg Ser
            420                 425                 430

Tyr Ser Thr Leu Thr Thr Val Arg Glu Ile Glu Thr Gln Ala Glu Leu
            435                 440                 445

Leu Ser Pro Gly Ser Gly Arg Ala Glu Glu Glu Asp Gln Asp Glu
450                 455                 460

Gly Ile Lys Gln Ala Met Asn His Phe Val Gln Glu Asn Gly Thr Leu
465                 470                 475                 480

Arg Ala Lys Pro Thr Gly Asn Gly Ile Tyr Ile Asn Gly Arg Gly His
                485                 490                 495

Leu Val
```